(12) United States Patent
Kawakami et al.

(10) Patent No.: US 8,216,696 B2
(45) Date of Patent: Jul. 10, 2012

(54) QUINOXALINE DERIVATIVE, AND LIGHT EMITTING ELEMENT, LIGHT EMITTING DEVICE AND ELECTRONIC APPLIANCE USING THE SAME

(75) Inventors: Sachiko Kawakami, Kanagawa (JP);
Hiroko Nomura, Kanagawa (JP);
Nobuharu Ohsawa, Kanagawa (JP);
Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 769 days.

(21) Appl. No.: 12/325,608

(22) Filed: Dec. 1, 2008

(65) Prior Publication Data

US 2009/0153041 A1 Jun. 18, 2009

(30) Foreign Application Priority Data

Dec. 3, 2007 (JP) ................. 2007-312354

(51) Int. Cl.
*H01L 51/54* (2006.01)
(52) U.S. Cl. ........ 428/690; 428/917; 313/504; 313/505; 313/506; 257/40; 257/E51.05; 564/426; 564/434; 544/234
(58) Field of Classification Search .......... 428/690, 428/917; 313/504, 505; 257/40, E51.05; 564/426, 434; 544/234
See application file for complete search history.

(56) References Cited

U.S. PATENT DOCUMENTS

| | | |
|---|---|---|
| 4,760,006 A | 7/1988 | Pawlowski |
| 7,034,026 B2 | 4/2006 | Barnett et al. |
| 2005/0186446 A1 | 8/2005 | Shitagaki et al. |
| 2007/0059553 A1 | 3/2007 | Egawa et al. |
| 2007/0222374 A1 | 9/2007 | Egawa et al. |
| 2008/0306239 A1* | 12/2008 | Horiba et al. ........ 528/332 |

FOREIGN PATENT DOCUMENTS

| | | |
|---|---|---|
| JP | 64-57261 | 3/1989 |
| JP | 2000-309566 | 11/2000 |
| JP | 2006-16384 | 1/2006 |
| WO | WO 2007/108403 A1 | 9/2007 |

OTHER PUBLICATIONS

Tang, C.W. et al, "Organic Electroluminescent Diodes," Appl. Phys. Lett., vol. 51, No. 12, Sep. 21, 1987, pp. 913-915.

Adachi, C. et al, "Electroluminescence in Organic Films with Three-Layer Structure," Japanese Journal of Applied Physics, vol. 27, No. 2, Feb. 1988, pp. L269-L271.

(Continued)

*Primary Examiner* — Jennifer Chriss
*Assistant Examiner* — Gregory Clark
(74) *Attorney, Agent, or Firm* — Husch Blackwell LLP

(57) ABSTRACT

A quinoxaline-based, new bipolar organic compound is provided, and a light emitting element using the quinoxaline-based compound is demonstrated. The quinoxaline derivative of the invention has a structure in which carbon at one or both of the 2-position and the 3-position of the quinoxaline unit are bonded, via an arylene group, with an amine unit which has a substituted or unsubstituted five-membered ring or a substituted or unsubstituted condensed ring containing a five-membered ring structure. The quinoxaline-based compound was proven to possess bipolar characteristics in view of carrier transportation, which allows the fabrication of a light emitting element and an electronic appliance with a low driving voltage and low power consumption.

10 Claims, 33 Drawing Sheets

OTHER PUBLICATIONS

Thomas, K.R.J. et al, "Green and Yellow Electroluminescent Dipolar Carbazole Derivatives: Features and Benefits of Electron-Withdrawing Segments," Chem. Mater., vol. 14, No. 9, 2002, pp. 3852-3859.

Thomas, K.R.J. et al, "Quinoxalines Incorporating Triarylamines: Potential Electroluminescent Materials with Tunable Emission Characteristics," Chem. Mater., vol. 14, No. 6, 2002, pp. 2796-2802.

Huang, T-H. et al, "Quinoxalines Incorporating Triarylamines: Dipolar Electroluminescent Materials with Tunable Emission Characteristics," Journal of the Chinese Chemical Society, vol. 53, No. 1, 2006, pp. 233-242.

European Search Report re application No. EP 08019753.6, dated Apr. 22, 2009.

* cited by examiner

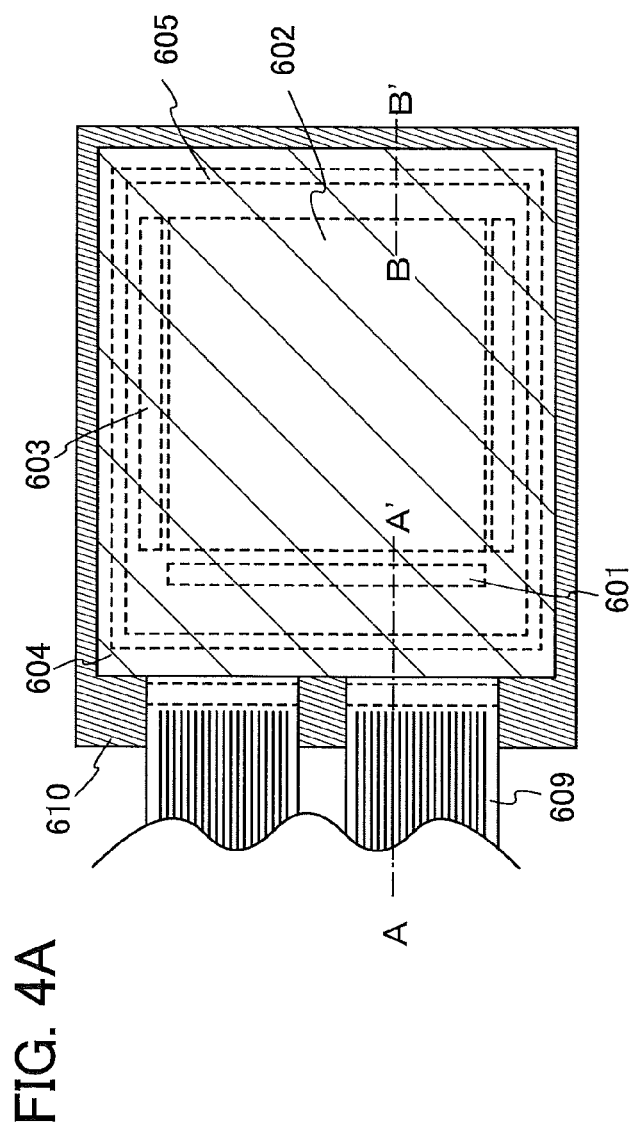
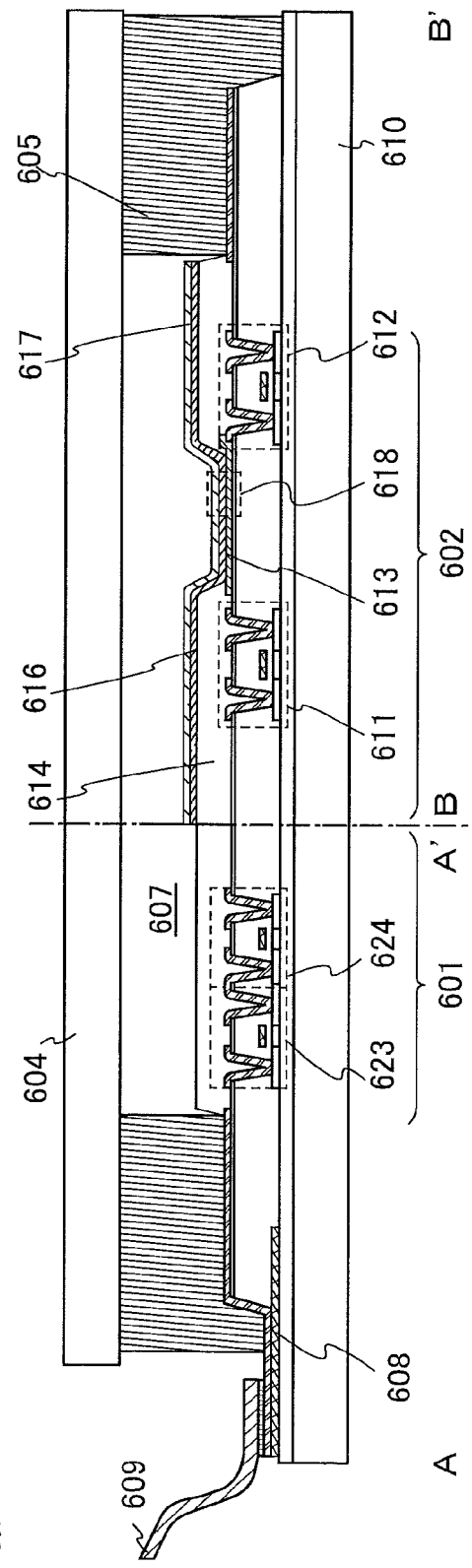
FIG. 4A
FIG. 4B

QUINOXALINE DERIVATIVE, AND LIGHT EMITTING ELEMENT, LIGHT EMITTING DEVICE AND ELECTRONIC APPLIANCE USING THE SAME

BACKGROUND OF THE INVENTION

1. Field of the Invention

The present invention relates to a quinoxaline derivative, and a light emitting element, a light emitting device and an electronic appliance using the quinoxaline derivative.

2. Description of the Related Art

Organic compounds can have a wide variety of structures as compared with inorganic compounds, and have a possibility to provide materials with various functions by appropriate molecular design. Because of these advantages, photo electronics and electronics that use a functional organic material have been attracting attention in recent years.

As examples of electronic devices using an organic compound as a functional material, there are solar cells, light emitting elements, organic transistors, and the like. These devices utilize electrical properties and optical properties of the organic compound. In particular, the light emitting elements have been significantly developed.

It is considered that the light emission mechanism of a light emitting element is as follows: when a voltage is applied between a pair of electrodes with a light emitting layer interposed therebetween, electrons injected from the cathode and holes injected from the anode are recombined in the light emission center of the light emitting layer to form molecular excitons, and energy is released to emit light when the molecular excitons relax to the ground state. A singlet excited state and a triplet excited state are known as the excited states, and it is thought that light emission can be obtained through either of the excited states.

Such a light emitting element has a lot of problems that depend on the organic materials. In order to solve these problems, improvement of an element structure, development of a material, and the like have been carried out.

As the most basic structure of a light emitting element, the following structure is known: a hole transporting layer formed of an organic compound with hole transporting properties and an electron transporting light emitting layer formed of an organic compound with electron transporting properties are stacked to form a thin film with a total thickness of about 100 nm, and this thin film is interposed between electrodes (for example, see Non-Patent Document 1: C. W. Tang et al., *Applied Physics Letters*, vol. 51, No. 12, pp. 913-915 (1987)).

When a voltage is applied to the light emitting element described in Non-Patent Document 1, light emission can be obtained from an organic compound having light emitting and electron transporting properties.

Furthermore, in the light emitting element described in Non-Patent Document 1, functions of the thin film are appropriately separated in such a manner that the hole transporting layer transports holes while the electron transporting layer transports electrons and emits light. However, various interactions (for example, exciplex formation) occur at the interface of stacked layers, which may cause a change in emission spectrum or a decrease in emission efficiency.

In order to suppress the change in emission spectrum and the decrease in emission efficiency that are caused by the interaction at the interface, a light emitting element in which functions of the thin film are further distributed has been developed. For example, proposed has been a light emitting element having such a structure that a light emitting layer is sandwiched between a hole transporting layer and an electron transporting layer (for example, see Non-Patent Document 2: Chihaya Adachi et al., *Japanese Journal of Applied Physics*, vol. 27, No. 2, L269-L271 (1988)).

In the light emitting element described in Non-Patent Document 2, in order to more effectively suppress the interaction occurring at the interface, a light emitting layer is preferably formed using a bipolar organic compound that has both electron transporting properties and hole transporting properties.

However, most organic compounds are monopolar materials in which either hole transporting properties or electron transporting properties dominate.

Therefore, a bipolar organic compound having both electron transporting properties and hole transporting properties is needed to be developed.

SUMMARY OF THE INVENTION

In view of the aforementioned problems, an object of the present invention is to provide a new bipolar organic compound.

Another object is to provide a light emitting element with a low driving voltage and low power consumption by using the bipolar organic compound of the present invention.

Still another object is to provide a light emitting device and an electronic appliance with low power consumption by using the bipolar organic compound of the present invention.

An aspect of the present invention is a quinoxaline derivative represented by the general formula (G11).

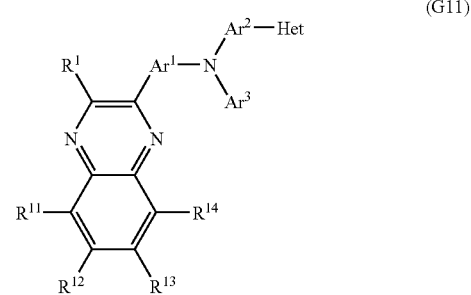

(G11)

In the formula, Het is a substituted or unsubstituted aromatic heterocycle containing a five-membered ring structure, $Ar^1$ and $Ar^2$ each are a substituted or unsubstituted arylene group having 6 to 13 carbon atoms, $Ar^3$ is a substituted or unsubstituted aryl group having 6 to 13 carbon atoms, $R^1$ is any of an alkyl group having 1 to 4 carbon atoms and a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms.

Note that, in this specification, the substituted or unsubstituted aromatic heterocycle containing a five-membered ring structure, which is represented by Het, includes not only an aromatic heterocycle consisting of one piece of five-membered aromatic heterocycle but also a condensed ring in which a five-membered aromatic heterocycle is condensed with another aromatic ring. Specifically, exemplified are substituted or unsubstituted 1,3,4-oxadiazole, substituted or unsubstituted imidazo[1,2-a]pyridine, substituted or unsubstituted imidazo[1,5-a]pyridine, substituted or unsubstituted 1,2,4-oxadiazole, substituted or unsubstituted benzoxazole, substituted or unsubstituted 1,3,4-triazole, substituted or unsubstituted imidazole, substituted or unsubstituted oxazole, substituted or unsubstituted 1,3-thiazole, substituted or unsubstituted 1,2,5-oxadiazole, substituted or unsubstituted pyrazole, substituted or unsubstituted isothiazole, substituted or unsubstituted isoxazole, substituted or unsubstituted indazole, substituted or unsubstituted purine, substituted or unsubstituted 1H-imidazo[5,1-c][1,2,4]triazole, substituted or unsubstituted 1H-tetrazole, substituted or unsubstituted 1,2,3,4-oxatriazole, substituted or unsubstituted 1,2,3,4-thiatriazole, and the like.

Another aspect of the present invention is a quinoxaline derivative represented by the general formula (G12).

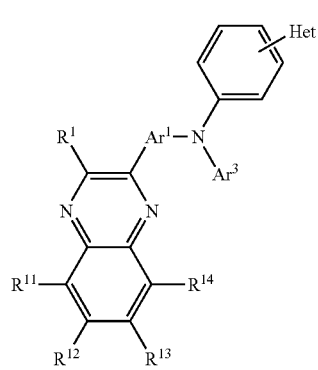
(G12)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $Ar^3$ is a substituted or unsubstituted aryl group having 6 to 13 carbon atoms, $R^1$ is any of an alkyl group having 1 to 4 carbon atoms and a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms.

Another aspect of the present invention is a quinoxaline derivative represented by the general formula (G13).

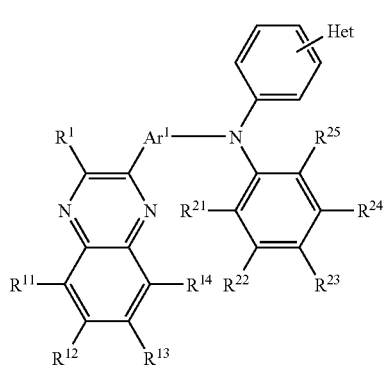
(G13)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $R^{21}$ to $R^{25}$ may be the same or different from one another, each of which represents any of hydrogen, an alkyl group having 1 to 4 carbon atoms, and a substituted or unsubstituted phenyl group, $R^1$ is any of an alkyl group having 1 to 4 carbon atoms and an aryl group having 6 to 13 carbon atoms, and $R^{11}$ to $R^{14}$ may be the same or different from one another, each of which represents any of hydrogen, an alkyl group having 1 to 4 carbon atoms, and an aryl group having 6 to 13 carbon atoms.

Another aspect of the present invention is a quinoxaline derivative represented by the general formula (G14).

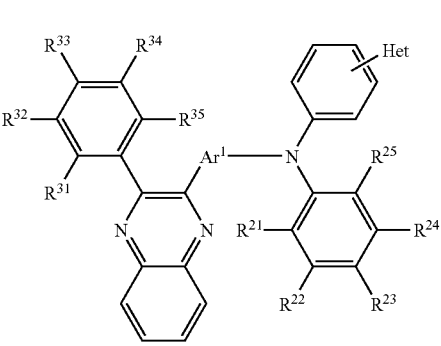
(G14)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $R^{21}$ to $R^{25}$ may be the same or different from one another, each of which represents any of hydrogen, an alkyl group having 1 to 4 carbon atoms, and a substituted or unsubstituted phenyl group, and $R^{31}$ to $R^{35}$ may be the same or different from one another, each of which represents any of hydrogen, an alkyl group having 1 to 4 carbon atoms, and a substituted or unsubstituted phenyl group.

Another aspect of the present invention is a quinoxaline derivative represented by the general formula (G15).

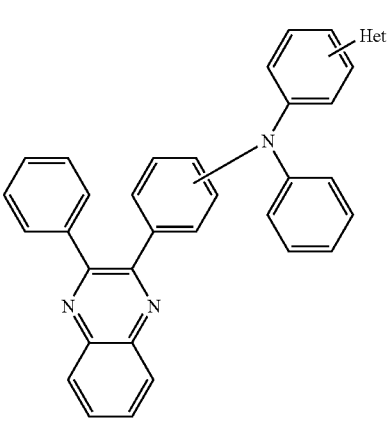
(G15)

In the formula, Het is any of substituted or unsubstituted 1,3,4-oxadiazole, substituted or unsubstituted imidazo[1,2-a]pyridine, and substituted or unsubstituted benzoxazole.

Another aspect of the present invention is a quinoxaline derivative represented by the general formula (G16).

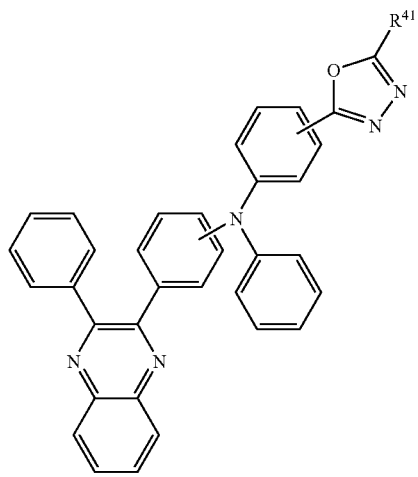

(G16)

In the formula, $R^{41}$ is any of a substituted or unsubstituted phenyl group, a substituted or unsubstituted naphthyl group, and a substituted or unsubstituted pyridyl group.

Another aspect of the present invention is a quinoxaline derivative represented by the general formula (G17).

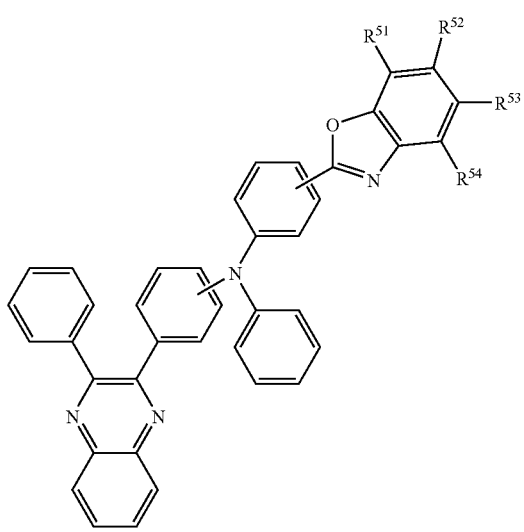

(G17)

In the formula, $R^{51}$ to $R^{54}$ may be the same or different from one another, each of which represents any of an alkyl group having 1 to 4 carbon atoms, a methoxy group, and a phenyl group.

Another aspect of the present invention is a quinoxaline derivative represented by the general formula (G18).

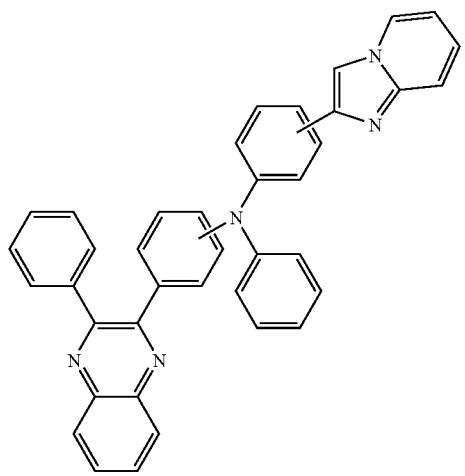

(G18)

Another aspect of the present invention is a quinoxaline derivative represented by the general formula (G21).

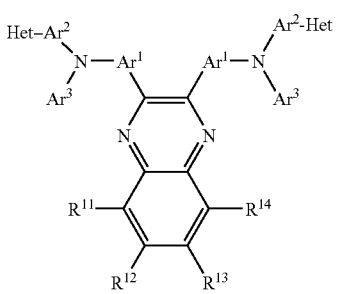

(G21)

In the formula, Het is a substituted or unsubstituted aromatic heterocycle containing a five-membered ring structure, $Ar^1$ and $Ar^2$ each are a substituted or unsubstituted arylene group having 6 to 13 carbon atoms, $Ar^3$ is a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms.

As the aromatic heterocycle containing a five-membered ring structure, which is represented by Het, there are substituted or unsubstituted 1,3,4-oxadiazole, substituted or unsubstituted imidazo[1,2-a]pyridine, substituted or unsubstituted imidazo[1,5-a]pyridine, substituted or unsubstituted 1,2,4-oxadiazole, substituted or unsubstituted benzoxazole, substituted or unsubstituted 1,3,4-triazole, substituted or unsubstituted imidazole, substituted or unsubstituted oxazole, substituted or unsubstituted 1,3-thiazole, substituted or unsubstituted 1,2,5-oxadiazole, substituted or unsubstituted pyrazole, substituted or unsubstituted isothiazole, substituted or unsubstituted isoxazole, substituted or unsubstituted indazole, substituted or unsubstituted purine, substituted or unsubstituted 1H-imidazo[5,1-c][1,2,4]triazole, substituted or unsubstituted 1H-tetrazole, substituted or unsubstituted 1,2,3,4-oxatriazole, substituted or unsubstituted 1,2,3,4-thiatriazole, and the like.

Another aspect of the present invention is a quinoxaline derivative represented by the general formula (G22).

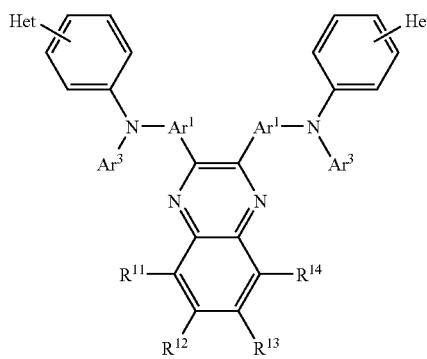

(G22)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $Ar^3$ is a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms.

Another aspect of the present invention is a quinoxaline derivative represented by the general formula (G23).

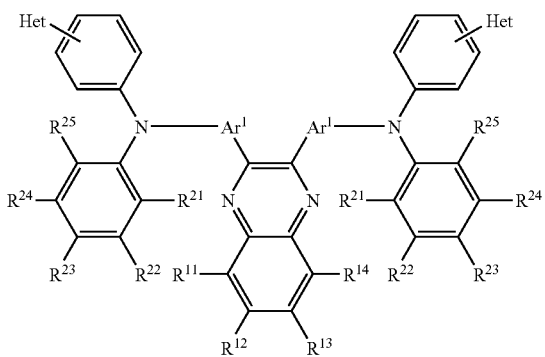

(G23)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $R^{21}$ to $R^{25}$ may be the same or different from one another, each of which represents any of hydrogen, an alkyl group having 1 to 4 carbon atoms, and a substituted or unsubstituted phenyl group, and $R^{11}$ to $R^{14}$ may be the same or different from one another, each of which represents any of hydrogen, an alkyl group having 1 to 4 carbon atoms, and an aryl group having 6 to 13 carbon atoms.

Another aspect of the present invention is a quinoxaline derivative represented by the general formula (G24).

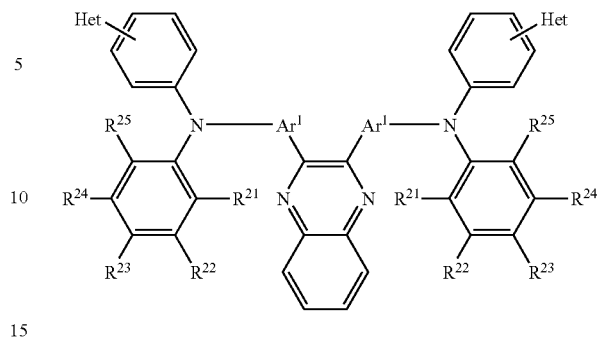

(G24)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, and $R^{21}$ to $R^{25}$ may be the same or different from one another, each of which represents any of hydrogen, an alkyl group having 1 to 4 carbon atoms, and a substituted or unsubstituted phenyl group.

Another aspect of the present invention is a quinoxaline derivative represented by the general formula (G25).

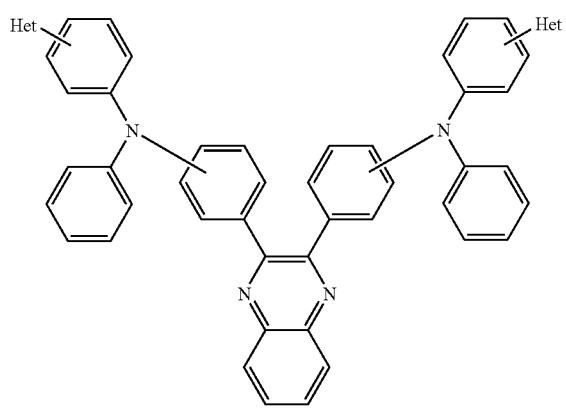

(G25)

In the formula, Het is any of substituted or unsubstituted 1,3,4-oxadiazole, substituted or unsubstituted imidazo[1,2-a]pyridine, and substituted or unsubstituted benzoxazole.

Another aspect of the present invention is a quinoxaline derivative represented by the general formula (G26).

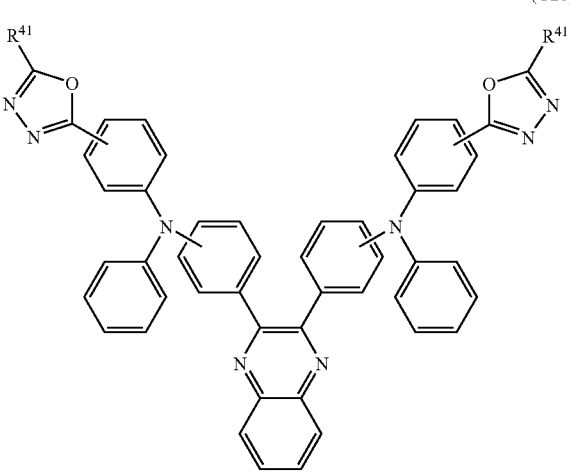

(G26)

In the formula, $R^{41}$ is any of a substituted or unsubstituted phenyl group, a substituted or unsubstituted naphthyl group, and a substituted or unsubstituted pyridyl group.

Another aspect of the present invention is a quinoxaline derivative represented by the general formula (G27).

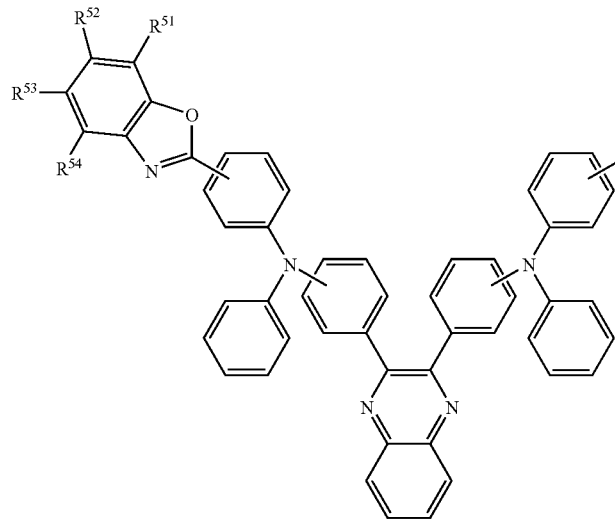

(G27)

In the formula, $R^{51}$ to $R^{54}$ may be the same or different from one another, each of which represents any of an alkyl group having 1 to 4 carbon atoms, a methoxy group, and a phenyl group.

Another aspect of the present invention is a quinoxaline derivative represented by the general formula (G28).

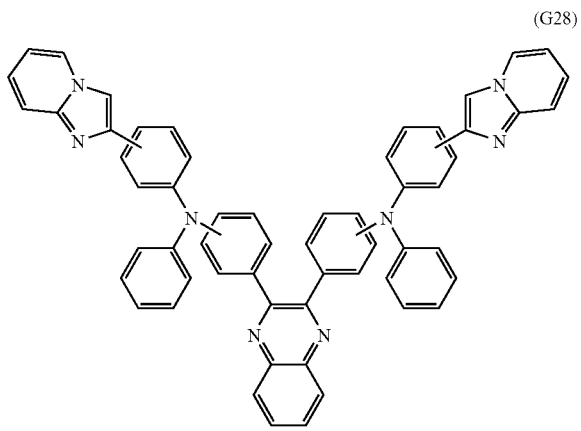

(G28)

Another aspect of the present invention is a light emitting element using any of the aforementioned quinoxaline derivatives. Specifically, a light emitting element has any of the aforementioned quinoxaline derivatives between a pair of electrodes.

Another aspect of the present invention is a light emitting element having a light emitting layer between a pair of electrodes, in which the light emitting layer has any of the aforementioned quinoxaline derivatives.

Another aspect of the present invention is a light emitting element having a light emitting layer between a pair of electrodes, in which the light emitting layer has any of the aforementioned quinoxaline derivatives and a substance emitting fluorescence.

Another aspect of the present invention is a light emitting element having a light emitting layer between a pair of electrodes, in which the light emitting layer has any of the aforementioned quinoxaline derivatives and a substance emitting phosphorescence.

A light emitting device of the present invention has a light emitting element which has a layer containing a light emitting substance between a pair of electrodes, and the layer containing the light emitting substance includes any of the aforementioned quinoxaline derivatives. The light emitting device of the present invention further has a control circuit that controls the emission of the light emitting element. Note that in this specification, a light emitting device includes an image display device, a lighting device, and a light source (including a lighting system) in its category. In addition, the light emitting device of the present invention includes in its category a module in which a panel is provided with a connector such as an FPC (flexible printed circuit), a TAB (tape automated bonding) tape, or a TCP (tape carrier package), and a module in which the tip of the TAB tape or the TCP is provided with a printed wiring board. Furthermore, the light emitting device in this specification also includes, in its category, a module in which an IC (integrated circuit) is directly mounted on a light emitting element by COG (chip on glass).

Furthermore, an electronic appliance having a display portion using the light emitting element of the present invention is also included in the scope of the present invention. Accordingly, the electronic appliance of the present invention has a display portion that is provided with any of the aforementioned light emitting elements and a control circuit for controlling the emission of the light emitting element.

The quinoxaline derivative of the present invention is bipolar and excellent in both electron transporting properties and hole transporting properties.

Furthermore, by using the quinoxaline derivative of the present invention that is bipolar, a light emitting element with a low driving voltage and low power consumption can be obtained.

In addition, by using the quinoxaline derivative of the present invention, a light emitting device and an electronic appliance with low power consumption can be obtained.

BRIEF DESCRIPTION OF THE DRAWINGS

In the accompanying drawings:

FIGS. 4A and 4B are diagrams illustrating a light emitting device of the present invention;

DETAILED DESCRIPTION OF THE INVENTION

Figure 1:
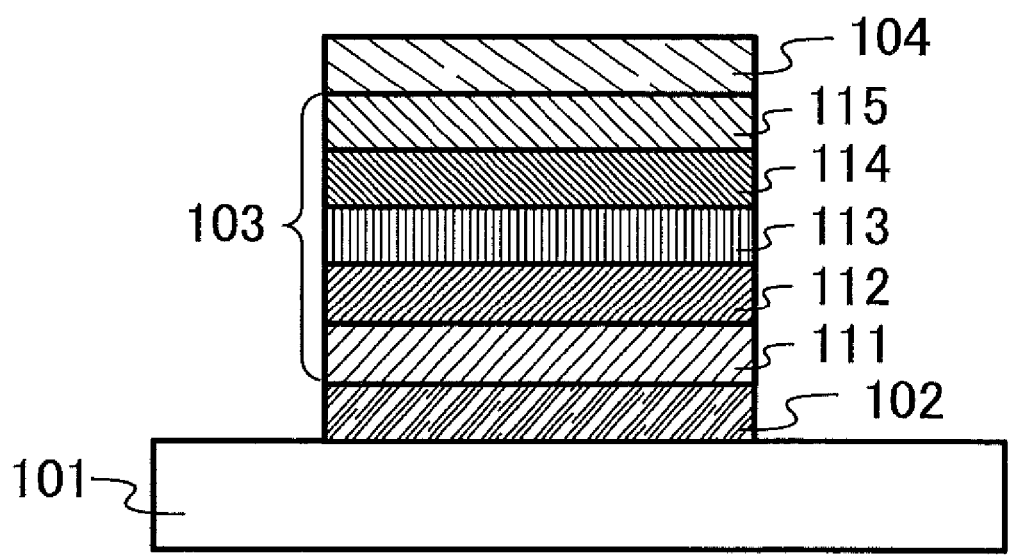
FIG. 1 is a diagram illustrating a light emitting element of the present invention.

Although the embodiment modes of the present invention will be described below with reference to the accompanying drawings, it is to be understood that various changes and modifications will be apparent to those skilled in the art. Therefore, unless such changes and modifications depart from the spirit and the scope of the present invention, they should be construed as being included therein.

Embodiment Mode 1

In this embodiment mode, a quinoxaline derivative of the present invention is described.

As a result of intensive studies, the inventors have found that a bipolar organic compound can be obtained by introducing an electron transporting skeleton and a hole transporting skeleton into one molecule. In particular, it has been found that a bipolar organic compound excellent in carrier balance can be obtained when one molecule has a quinoxaline skeleton, a substituted or unsubstituted aromatic heterocycle containing a five-membered ring structure, and an amine skeleton.

The quinoxaline derivative of the present invention has such a structure that carbon at one or both of the 2-position and the 3-position of quinoxaline and an amine unit having a substituted or unsubstituted aromatic heterocycle containing a five-membered ring structure (hereinafter referred to as a hetero ring) are bonded through an arylene group. That is, one molecule has a quinoxaline skeleton, a hetero ring, and an amine skeleton.

More specifically, the quinoxaline derivative of the present invention is a quinoxaline derivative represented by the general formula (G11).

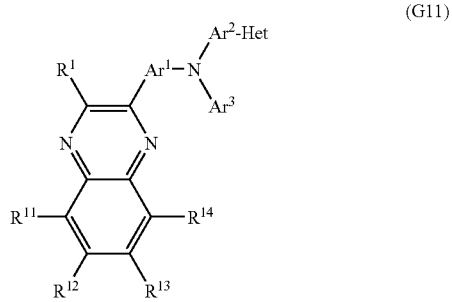

(G11)

In the formula, Het is a substituted or unsubstituted aromatic heterocycle containing a five-membered ring structure, $Ar^1$ and $Ar^2$ each are a substituted or unsubstituted arylene group having 6 to 13 carbon atoms, $Ar^3$ is a substituted or unsubstituted aryl group having 6 to 13 carbon atoms, $R^1$ is any of an alkyl group having 1 to 4 carbon atoms and a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms.

The quinoxaline derivative of the present invention is a quinoxaline derivative represented by the general formula (G21).

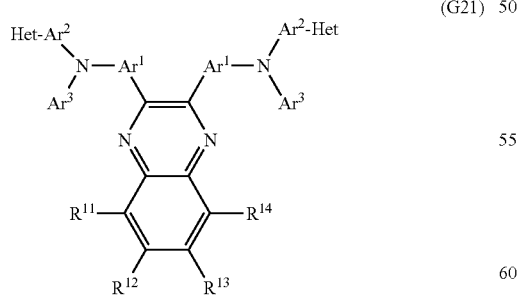

(G21)

In the formula, Het is a substituted or unsubstituted aromatic heterocycle containing a five-membered ring structure, $Ar^1$ and $Ar^2$ each are a substituted or unsubstituted arylene group having 6 to 13 carbon atoms, $Ar^3$ is a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms.

In the quinoxaline derivative represented by the general formula (G11), carbon at the 2-position of quinoxaline and an amine unit are bonded through an arylene group. In the quinoxaline derivative represented by the general formula (G21), carbons at the 2-position and 3-position of quinoxaline and an amine unit are bonded through an arylene group. The quinoxaline derivative represented by the general formula (G11) has a smaller molecular weight than the quinoxaline derivative represented by the general formula (G21), and thus sublimes more easily. Therefore, the quinoxaline derivative represented by the general formula (G11) can be purified by sublimation and is suitable for deposition by vacuum evaporation. On the other hand, the quinoxaline derivative represented by the general formula (G21) has a larger molecular weight than the quinoxaline derivative represented by the general formula (G11), and thus is excellent in heat stability.

Note that in the general formula (G11) and the general formula (G21), the substituted or unsubstituted aromatic heterocycle containing a five-membered ring structure, which is represented by Het, includes not only an aromatic heterocycle consisting of one piece of five-membered aromatic heterocycle but also a condensed ring in which a five-membered aromatic heterocycle is condensed with another aromatic ring. For instance, there are substituted or unsubstituted 1,3,4-oxadiazole, substituted or unsubstituted imidazo[1,2-a]pyridine, substituted or unsubstituted imidazo[1,5-a]pyridine, substituted or unsubstituted 1,2,4-oxadiazole, substituted or unsubstituted benzoxazole, substituted or unsubstituted 1,3,4-triazole, substituted or unsubstituted imidazole, substituted or unsubstituted oxazole, substituted or unsubstituted 1,3-thiazole, substituted or unsubstituted 1,2,5-oxadiazole, substituted or unsubstituted pyrazole, substituted or unsubstituted isothiazole, substituted or unsubstituted isoxazole, substituted or unsubstituted indazole, substituted or unsubstituted purine, substituted or unsubstituted 1H-imidazo[5,1-c][1,2,4]triazole, substituted or unsubstituted 1H-tetrazole, substituted or unsubstituted 1,2,3,4-oxatriazole, substituted or unsubstituted 1,2,3,4-thiatriazole, and the like. Specific structural examples of these substituents are shown in the structural formula (10-1) to the structural formula (11-20).

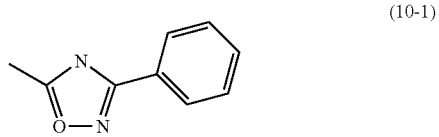

(10-1)

(10-2)

(10-3)

Above all, substituted or unsubstituted 1,3,4-oxadiazole, substituted or unsubstituted imidazo[1,2-a]pyridine, and substituted or unsubstituted benzoxazole are preferably used since they can be easily synthesized and purified (highly purified). In particular, the substituents represented by the structural formula (11-1) to the structural formula (11-16) are preferably used since they can be easily synthesized.

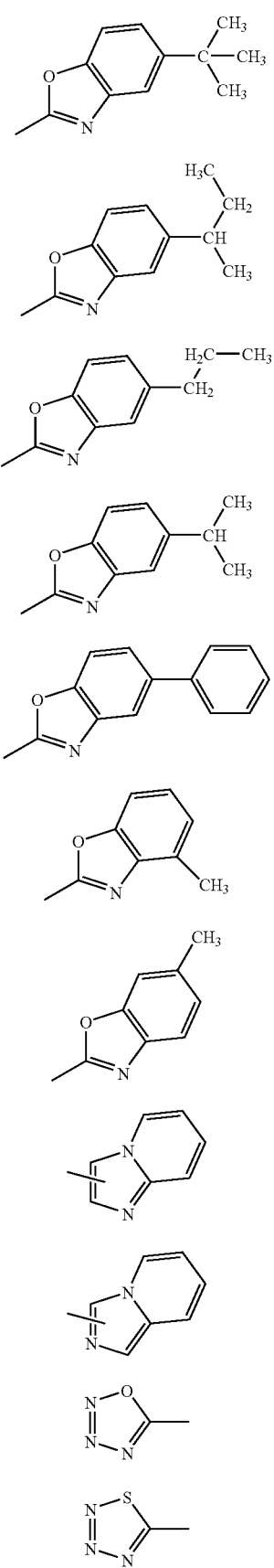

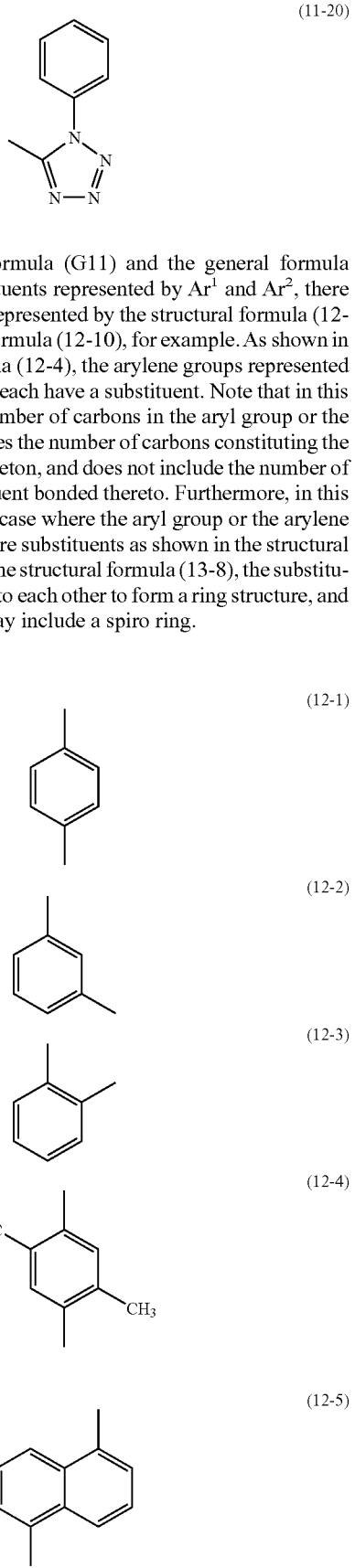

In the general formula (G11) and the general formula (G21), as the substituents represented by $Ar^1$ and $Ar^2$, there are arylene groups represented by the structural formula (12-1) to the structural formula (12-10), for example. As shown in the structural formula (12-4), the arylene groups represented by $Ar^1$ and $Ar^2$ may each have a substituent. Note that in this specification, the number of carbons in the aryl group or the arylene group denotes the number of carbons constituting the ring of the main skeleton, and does not include the number of carbons of a substituent bonded thereto. Furthermore, in this specification, in the case where the aryl group or the arylene group has two or more substituents as shown in the structural formula (12-9) and the structural formula (13-8), the substituents may be bonded to each other to form a ring structure, and the ring structure may include a spiro ring.

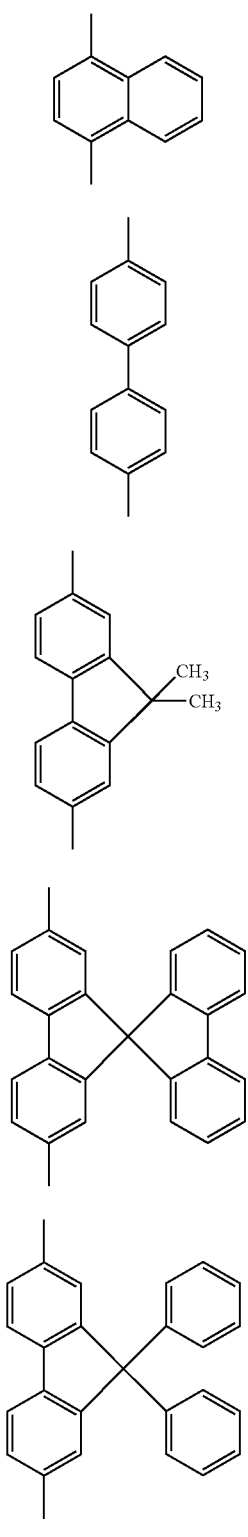
(12-6)
(12-7)
(12-8)
(12-9)
(12-10)
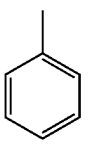
(13-1)
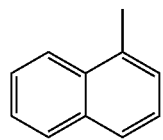
(13-2)
(13-3)
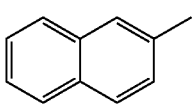
(13-4)
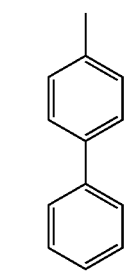
(13-5)
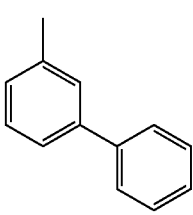
(13-6)
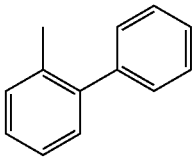
(13-7)
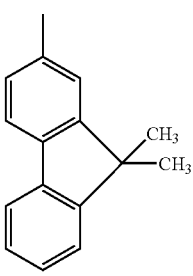
(13-8)
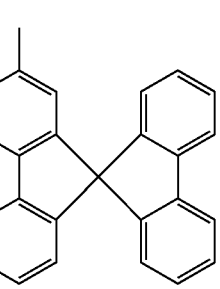
In the general formula (G11) and the general formula (G21), as the substituent represented by Ar$^3$, there are aryl groups represented by the structural formula (13-1) to the structural formula (13-13), for example. As shown in the structural formula (13-7) to the structural formula (13-13), the aryl group represented by Ar$^3$ may have a substituent.

(13-9)
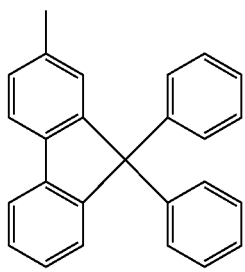
(13-10)
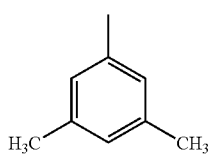
(13-11)
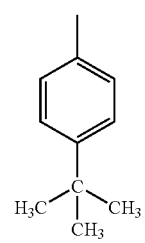
(13-12)
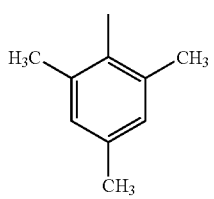
(13-13)
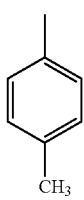
In the general formula (G11) and the general formula (G21), as the substituents represented by $R^{11}$ to $R^{14}$, there are hydrogen, alkyl groups and aryl groups represented by the structural formula (14-1) to the structural formula (14-22), for example. As shown in the structural formula (14-16) to the structural formula (14-22), the aryl groups represented by $R^{11}$ to $R^{14}$ may each have a substituent.
(14-1)
(14-2)
(14-3)
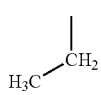
(14-4)
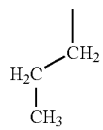
(14-5)
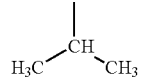
(14-6)
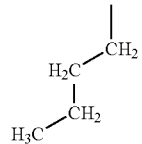
(14-7)
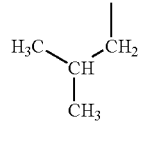
(14-8)
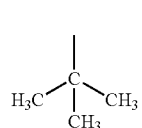
(14-9)
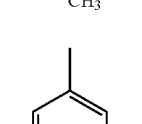
(14-10)
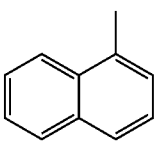
(14-11)
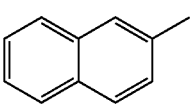
(14-12)
(14-13)
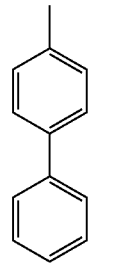

(14-14)
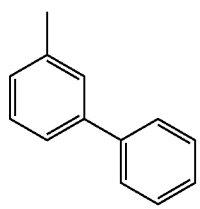
(14-15)
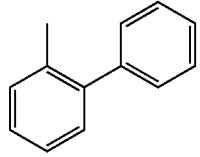
(14-16)
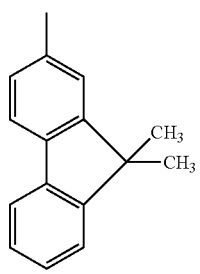
(14-17)
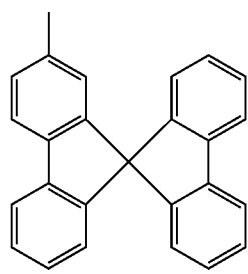
(14-18)
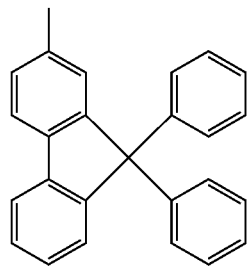
(14-19)
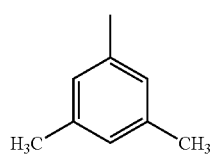
(14-20)
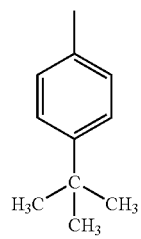
(14-21)
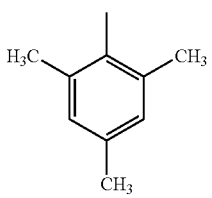
(14-22)
In the general formula (G11), as the substituent represented by $R^1$, there are alkyl groups and aryl groups represented by the structural formula (15-1) to the structural formula (15-21), for example. As shown in the structural formula (15-15) to the structural formula (15-21), the aryl group represented by $R^1$ may have a substituent.
(15-1)
(15-2)
(15-3)
(15-4)
(15-5)
(15-6)
(15-7)
(15-8)

-continued (15-9) 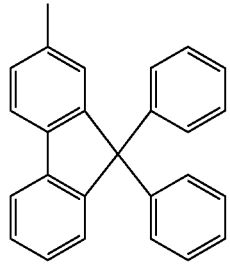

(15-10)

(15-11)

(15-12) 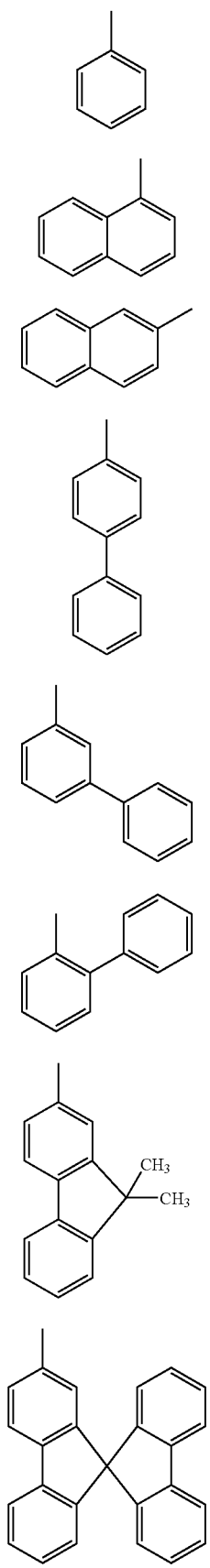

(15-13)

(15-14)

(15-15)

(15-16)

(15-17) 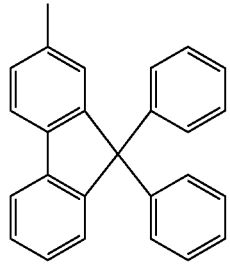

(15-18) 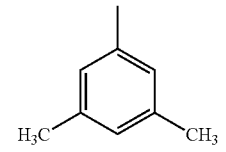

(15-19) 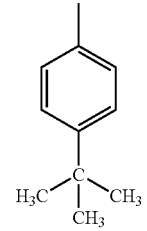

(15-20) 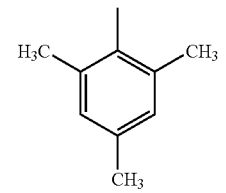

(15-21) 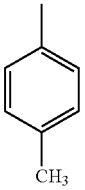

In the quinoxaline derivative represented by the general formula (G11), Ar² is preferably a phenylene group from the viewpoint of obtaining a quinoxaline derivative having appropriate triplet excitation energy as well as facility of synthesis and purification (high purification). That is, a quinoxaline derivative represented by the general formula (G12) is preferably used.

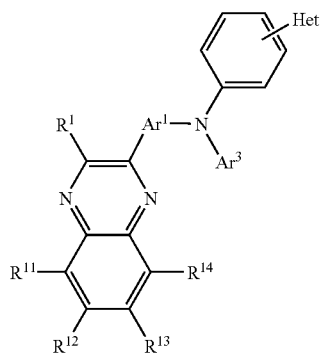

(G12)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $Ar^3$ is a substituted or unsubstituted aryl group having 6 to 13 carbon atoms, $R^1$ is any of an alkyl group having 1 to 4 carbon atoms and a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms.

Similarly, in the quinoxaline derivative represented by the general formula (G21), $Ar^2$ is preferably a phenylene group from the viewpoint of obtaining a quinoxaline derivative having appropriate triplet excitation energy as well as facility of synthesis and purification (high purification). That is, a quinoxaline derivative represented by the general formula (G22) is preferably used.

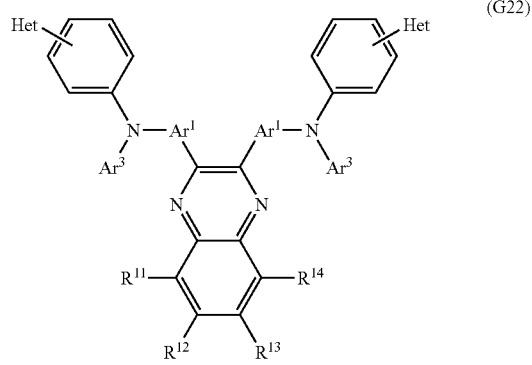

(G22)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $Ar^3$ is a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms.

More preferably, in the quinoxaline derivative represented by the general formula (G11), $Ar^3$ is a phenyl group from the viewpoint of obtaining a quinoxaline derivative having appropriate triplet excitation energy as well as facility of synthesis and purification (high purification). That is, a quinoxaline derivative represented by the general formula (G13) is preferably used.

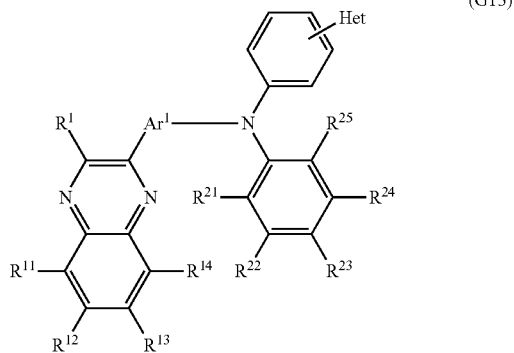

(G13)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $R^{21}$ to $R^{25}$ may be the same or different from one another, each of which represents any of hydrogen, an alkyl group having 1 to 4 carbon atoms, and a substituted or unsubstituted phenyl group, $R^1$ is any of an alkyl group having 1 to 4 carbon atoms and an aryl group having 6 to 13 carbon atoms, and $R^{11}$ to $R^{14}$ may be the same or different from one another, each of which represents any of hydrogen, an alkyl group having 1 to 4 carbon atoms, and an aryl group having 6 to 13 carbon atoms.

Similarly, in the quinoxaline derivative represented by the general formula (G21), $Ar^3$ is preferably a phenylene group from the viewpoint of obtaining a quinoxaline derivative having appropriate triplet excitation energy as well as facility of synthesis and purification (high purification). That is, a quinoxaline derivative represented by the general formula (G23) is preferably used.

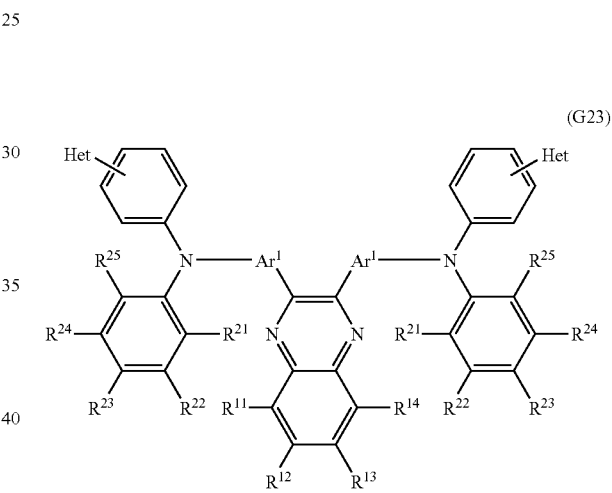

(G23)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $R^{21}$ to $R^{25}$ may be the same or different from one another, each of which represents any of hydrogen, an alkyl group having 1 to 4 carbon atoms, and a substituted or unsubstituted phenyl group, and $R^{11}$ to $R^{14}$ may be the same or different from one another, each of which represents any of hydrogen, an alkyl group having 1 to 4 carbon atoms, and an aryl group having 6 to 13 carbon atoms.

Furthermore, in the quinoxaline derivative represented by the general formula (G11), $R^1$ is preferably a phenyl group from the viewpoint of obtaining a quinoxaline derivative having appropriate triplet excitation energy as well as facility of synthesis and purification (high purification). In addition, $R^{11}$ to $R^{14}$ each are preferably hydrogen. That is, a quinoxaline derivative represented by the general formula (G14) is preferably used.

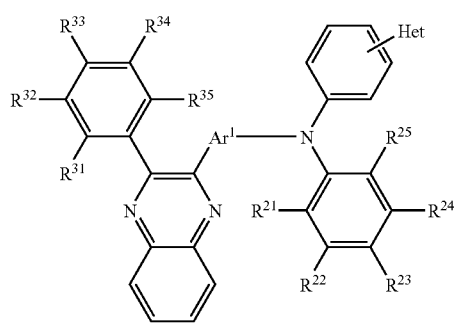

(G14)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, $R^{21}$ to $R^{25}$ may be the same or different from one another, each of which represents any of hydrogen, an alkyl group having 1 to 4 carbon atoms, and a substituted or unsubstituted phenyl group, and $R^{31}$ to $R^{35}$ may be the same or different from one another, each of which represents any of hydrogen, an alkyl group having 1 to 4 carbon atoms, and a substituted or unsubstituted phenyl group.

Similarly, in the quinoxaline derivative represented by the general formula (G21), $R^{11}$ to $R^{14}$ each are preferably hydrogen from the viewpoint of obtaining a quinoxaline derivative having appropriate triplet excitation energy as well as easy synthesis and purification (high purification). That is, a quinoxaline derivative represented by the general formula (G24) is preferably used.

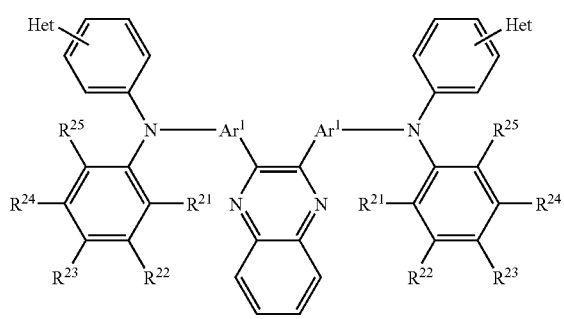

(G24)

In the formula, Het is any of substituted or unsubstituted 1,3,4-oxadiazole, substituted or unsubstituted imidazo[1,2-a]pyridine, and substituted or unsubstituted benzoxazole, $Ar^1$ is a substituted or unsubstituted arylene group having 6 to 13 carbon atoms, and $R^{21}$ to $R^{25}$ may be the same or different from one another, each of which represents any of hydrogen, an alkyl group having 1 to 4 carbon atoms, and a substituted or unsubstituted phenyl group.

Furthermore, in the quinoxaline derivative represented by the general formula (G11), $Ar^1$ is preferably a phenyl group from the viewpoint of obtaining a quinoxaline derivative having appropriate triplet excitation energy as well as facility of synthesis and purification (high purification). In addition, Het is preferably any of substituted or unsubstituted 1,3,4-oxadiazole, substituted or unsubstituted imidazo[1,2-a]pyridine, and substituted or unsubstituted benzoxazole from the viewpoint of obtaining a quinoxaline derivative having appropriate triplet excitation energy as well as facility of synthesis and purification (high purification). That is, a quinoxaline derivative represented by the general formula (G15) is preferably used.

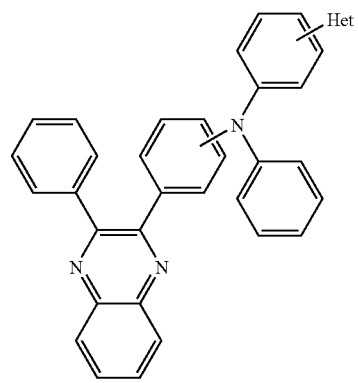

(G15)

In the formula, Het is any of substituted or unsubstituted 1,3,4-oxadiazole, substituted or unsubstituted imidazo[1,2-a]pyridine, and substituted or unsubstituted benzoxazole.

As the quinoxaline derivative represented by the general formula (G15), specifically, there are quinoxaline derivatives represented by the general formula (G16) to the general formula (G18).

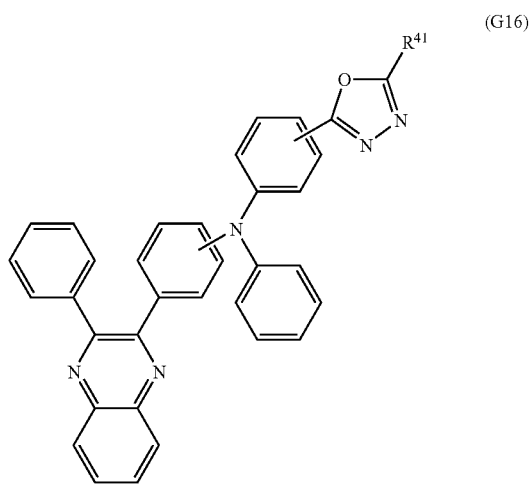

(G16)

In the formula, $R^{41}$ is any of a substituted or unsubstituted phenyl group, a substituted or unsubstituted naphthyl group, and a substituted or unsubstituted pyridyl group.

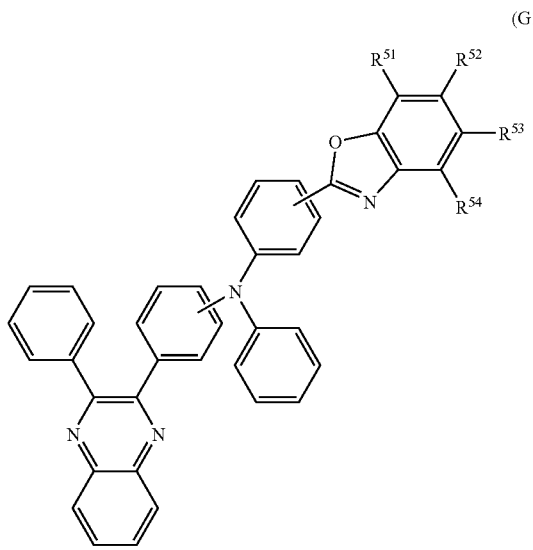

(G17)

In the formula, $R^{51}$ to $R^{54}$ may be the same or different from one another, each of which represents any of an alkyl group having 1 to 4 carbon atoms, a methoxy group, and a phenyl group.

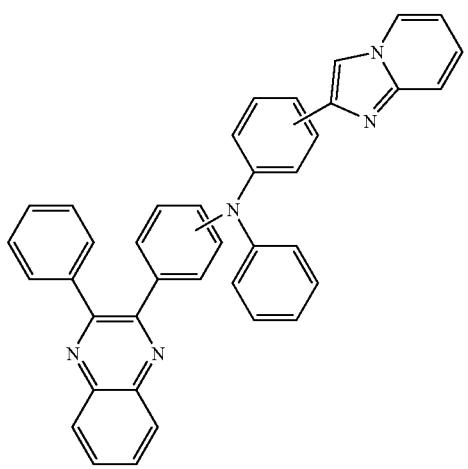

(G18)

Similarly, in the quinoxaline derivative represented by the general formula (G21), $Ar^1$ is preferably a phenyl group from the viewpoint of obtaining a quinoxaline derivative having appropriate triplet excitation energy as well as facility of synthesis and purification (high purification). In addition, Het is preferably any of substituted or unsubstituted 1,3,4-oxadiazole, substituted or unsubstituted imidazo[1,2-a]pyridine, and substituted or unsubstituted benzoxazole from the viewpoint of obtaining a quinoxaline derivative having appropriate triplet excitation energy as well as facility of synthesis and purification (high purification). That is, a quinoxaline derivative represented by the general formula (G25) is preferably used.

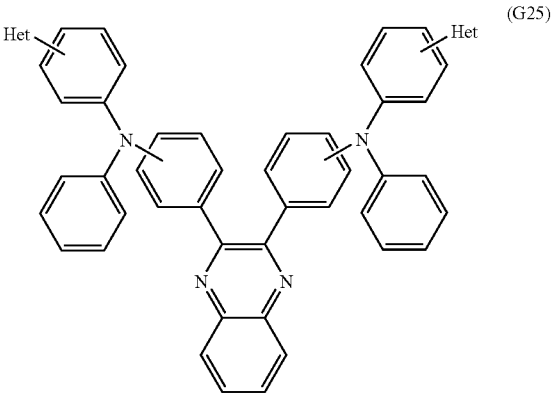

(G25)

In the formula, Het is any of substituted or unsubstituted 1,3,4-oxadiazole, substituted or unsubstituted imidazo[1,2-a]pyridine, and substituted or unsubstituted benzoxazole.

As the quinoxaline derivative represented by the general formula (G25), specifically, there are quinoxaline derivatives represented by the general formula (G26) to the general formula (G28).

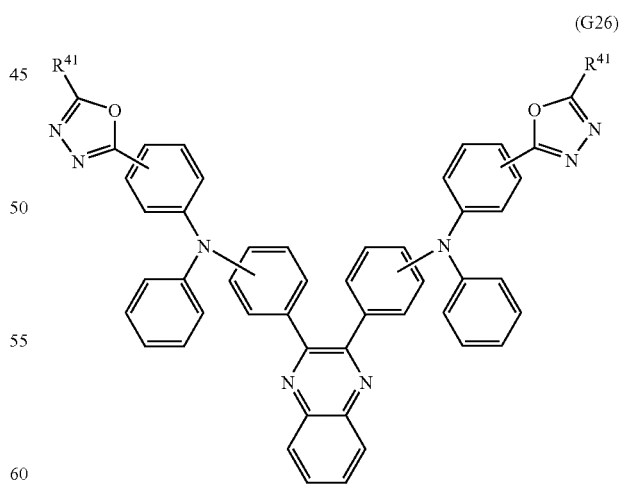

(G26)

In the formula, $R^{41}$ is any of a substituted or unsubstituted phenyl group, a substituted or unsubstituted naphthyl group, and a substituted or unsubstituted pyridyl group.

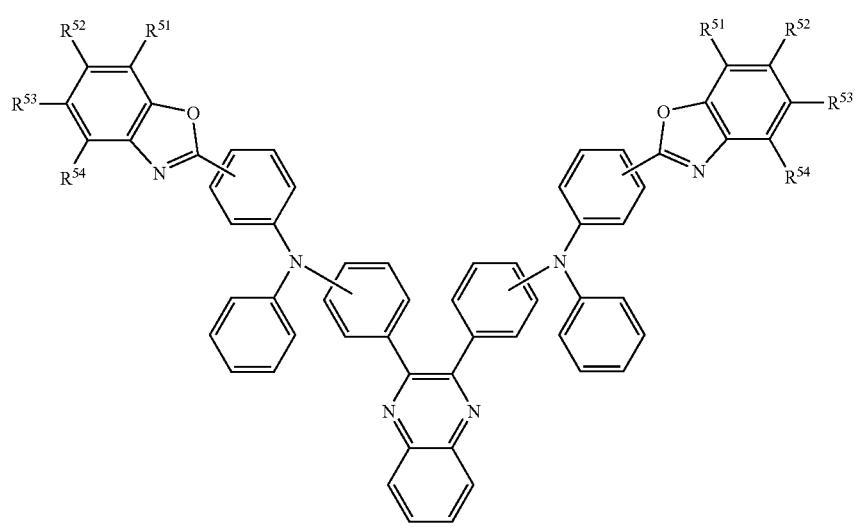
(G27)

In the formula, $R^{51}$ to $R^{54}$ may be the same or different from one another, each of which represents any of an alkyl group having 1 to 4 carbon atoms, a methoxy group, and a phenyl group.

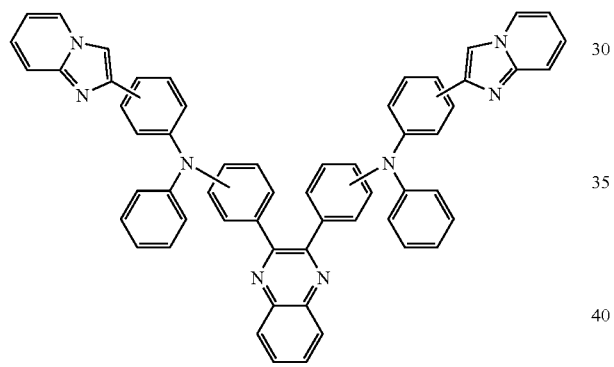
(G28)

As the quinoxaline derivative represented by the general formula (G11), for example, there are quinoxaline derivatives represented by the structural formula (101) to the structural formula (181), the structural formula (201) to the structural formula (282), and the structural formula (301) to the structural formula (373). As the quinoxaline derivative represented by the general formula (G21), for example, there are quinoxaline derivatives represented by the structural formula (401) to the structural formula (467), the structural formula (501) to the structural formula (568), and the structural formula (601) to the structural formula (659). However, the present invention is not limited to these derivatives.

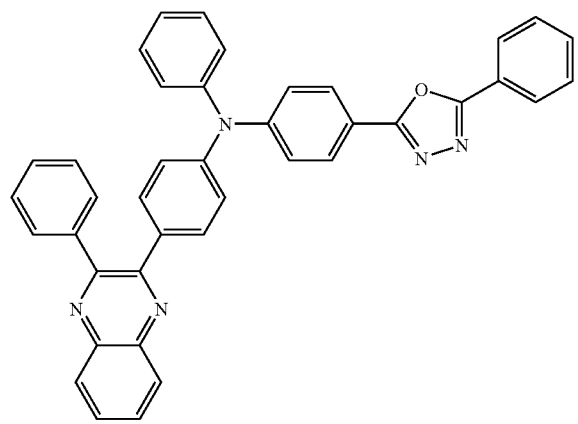
(101)

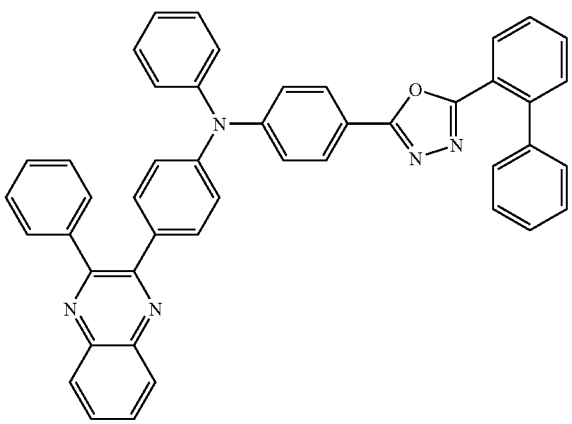
(102)

-continued
(103)
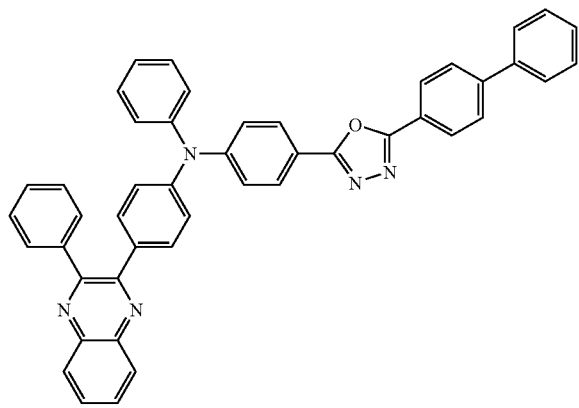
(104)
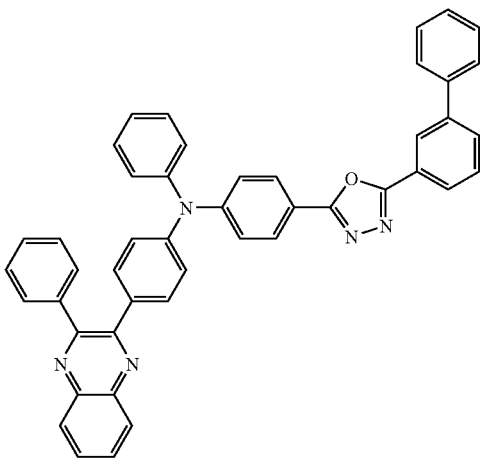
(105)
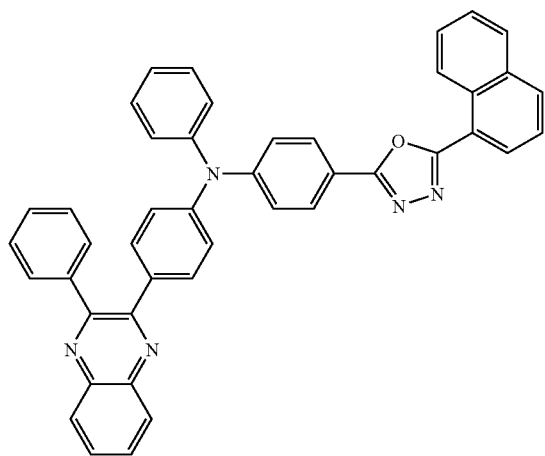
(106)
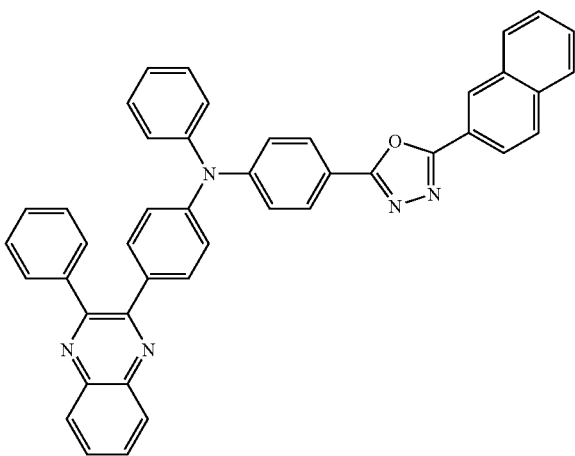
(107)
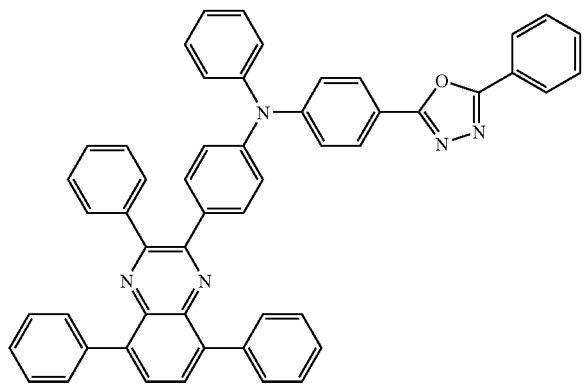
(108)
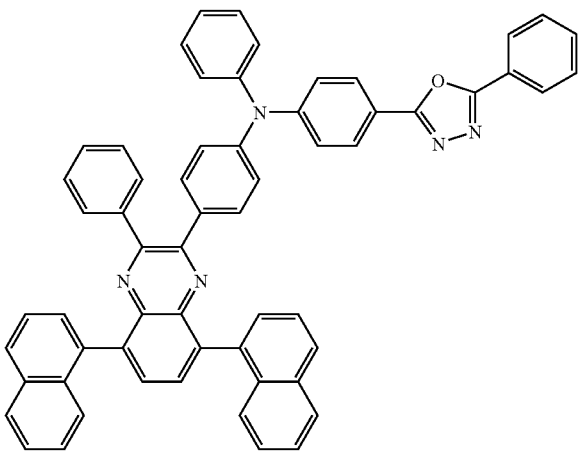

(109)
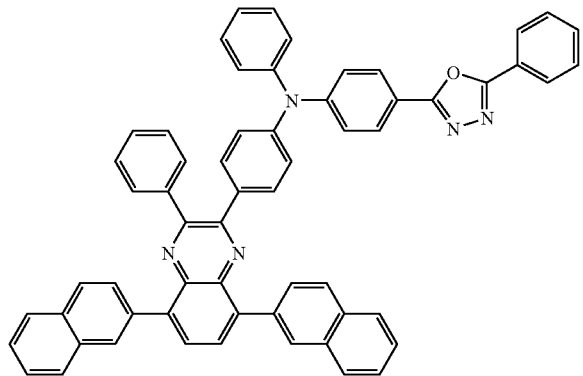
(110)
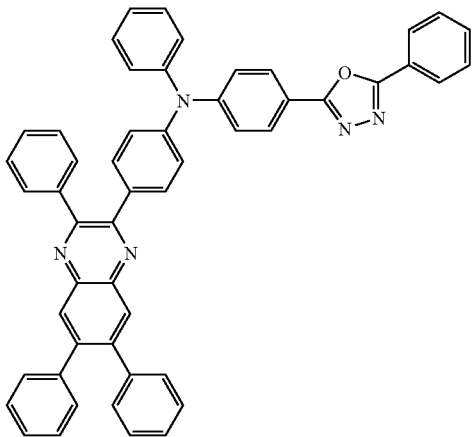
(111)
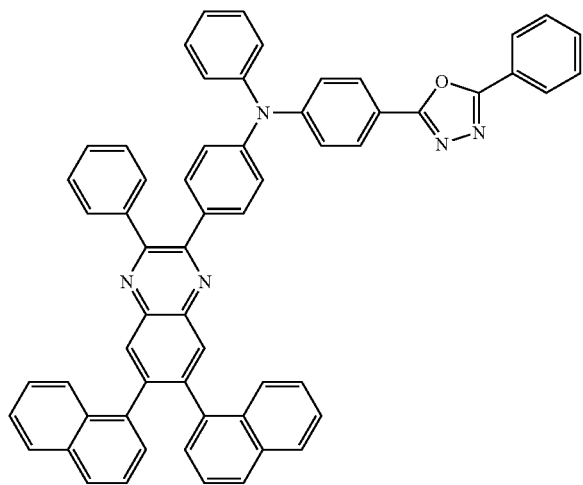
(112)
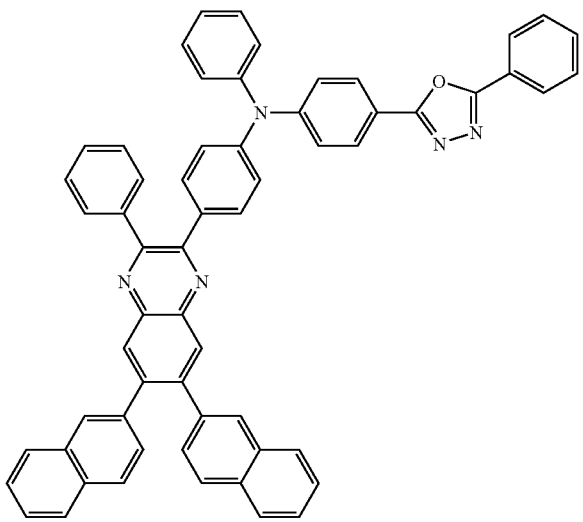
(113)
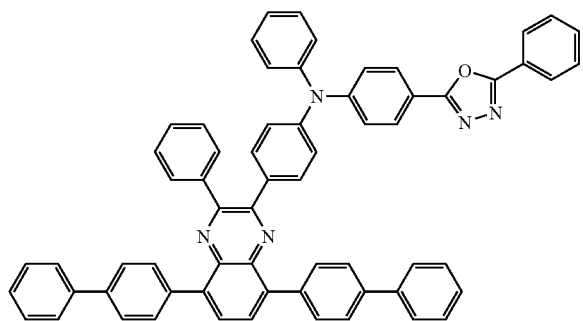
(114)
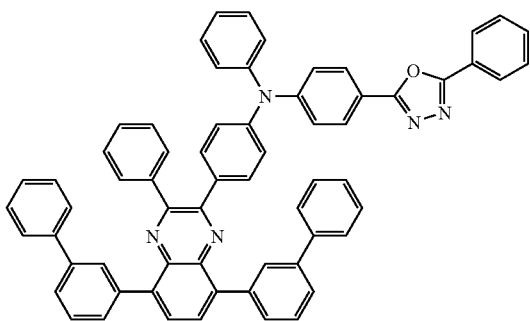

-continued
(115)
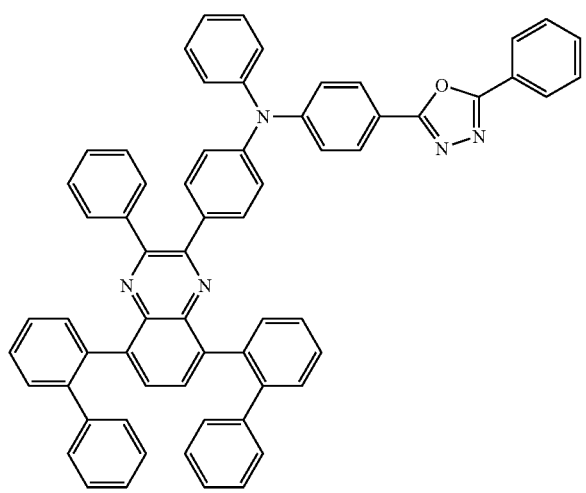
(116)
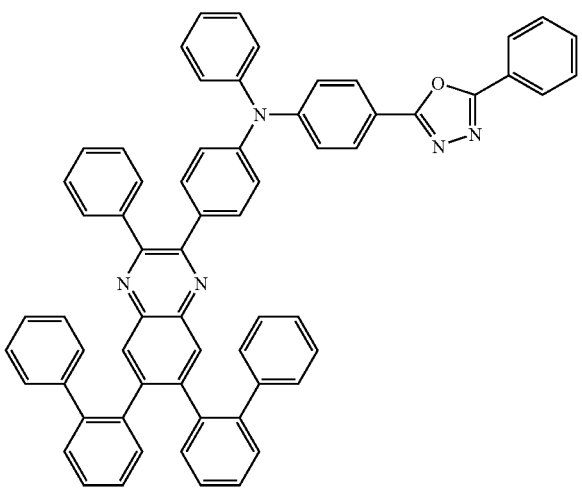
(117)
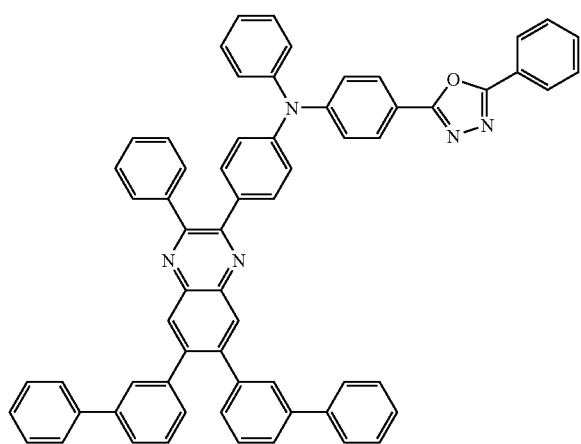
(118)
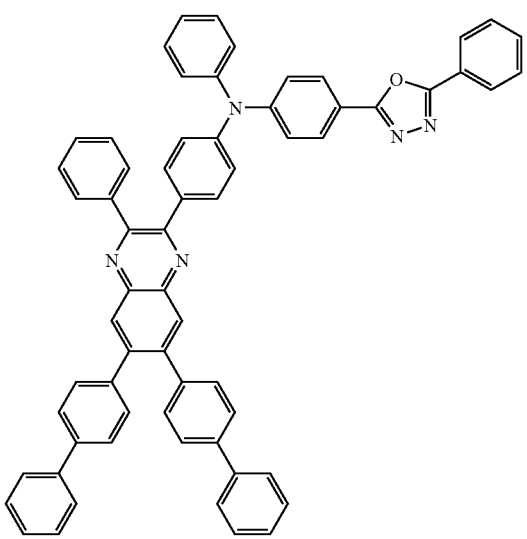
(119)
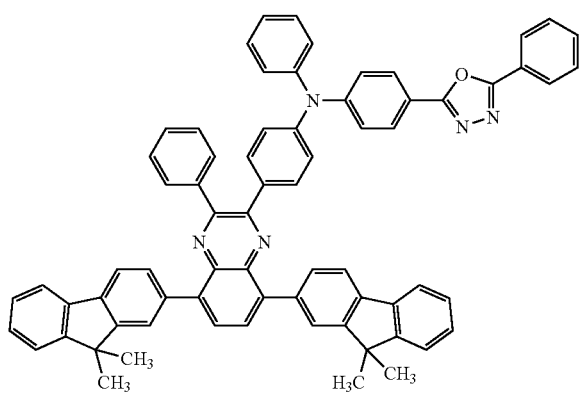
(120)
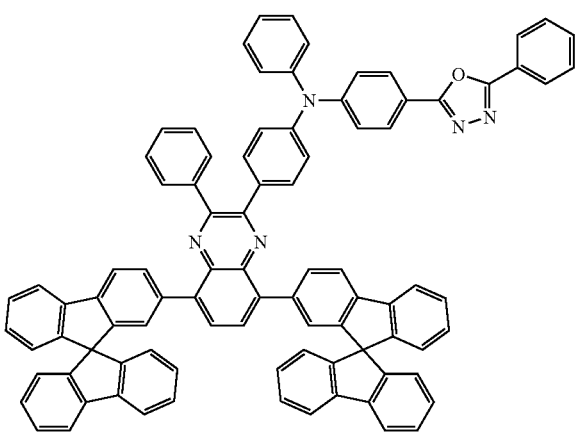

(121)
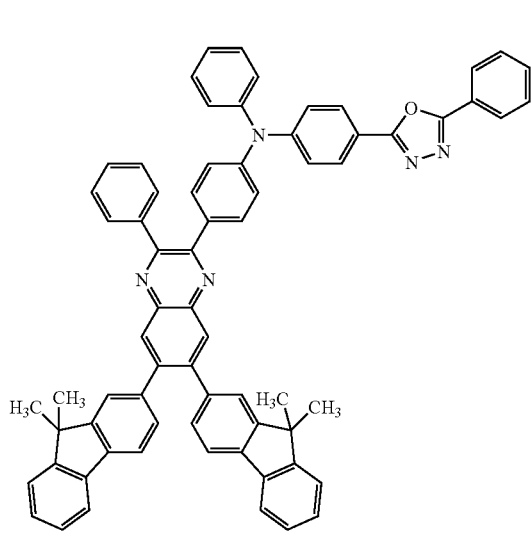
(122)
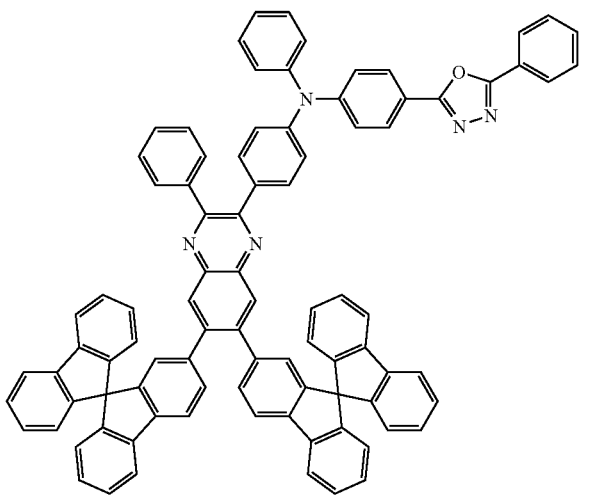
(123)
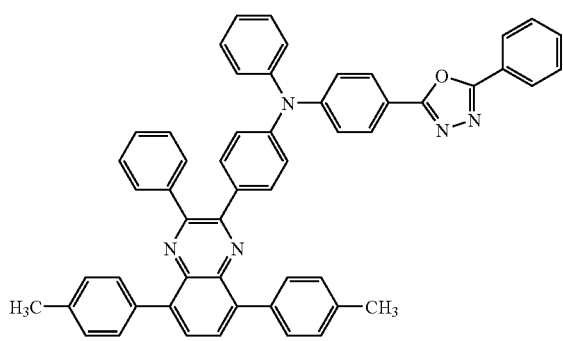
(124)
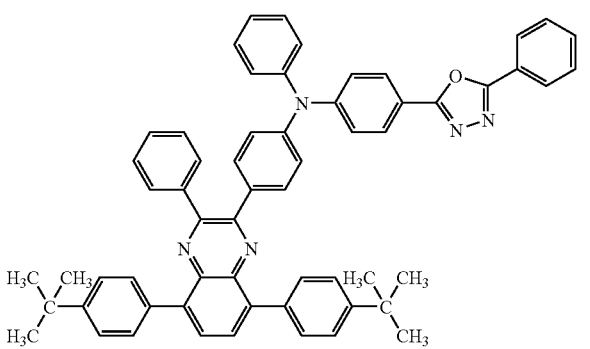
(125)
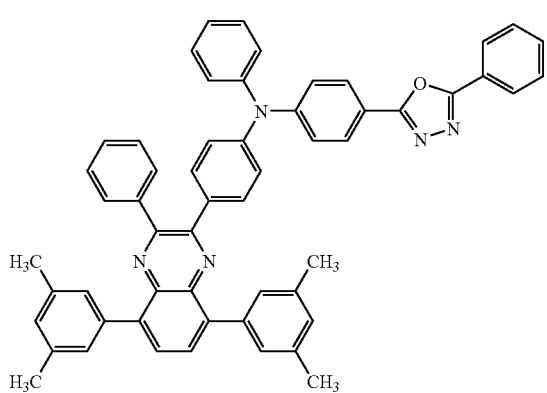
(126)
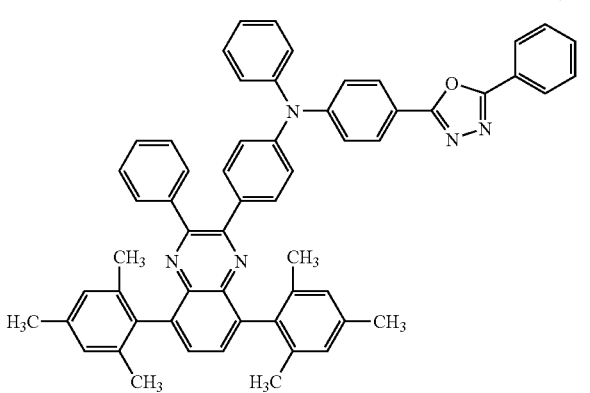

(127) 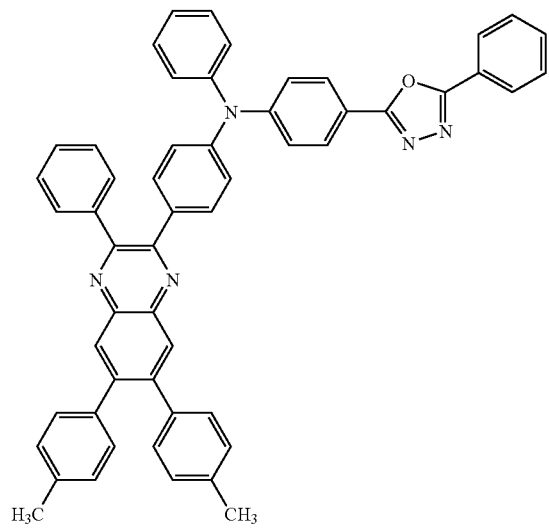
(128) 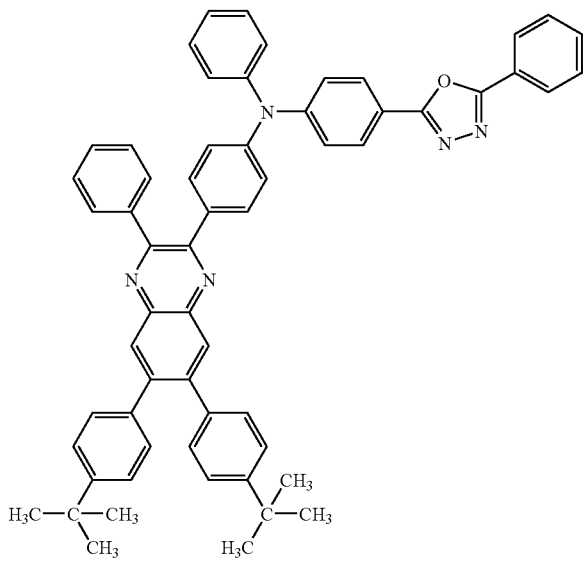
(129) 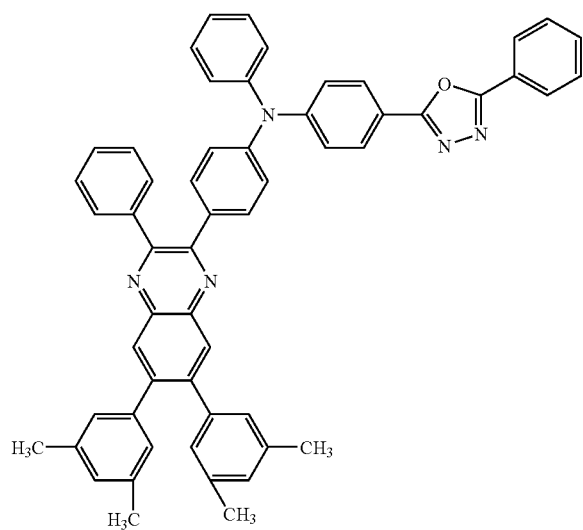
(130) 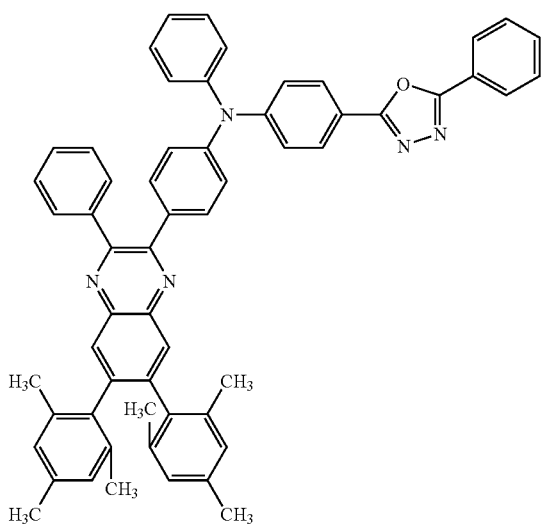
(131) 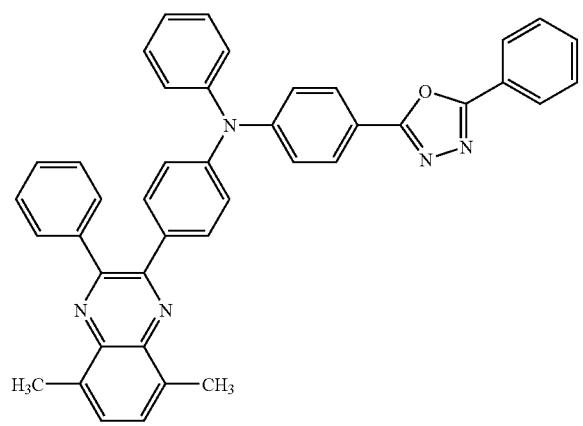
(132) 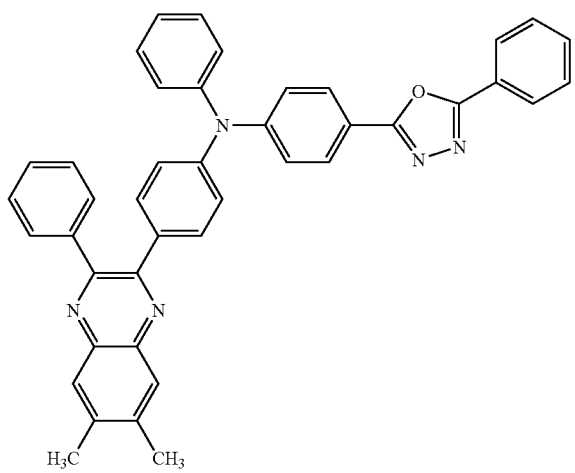

(133)
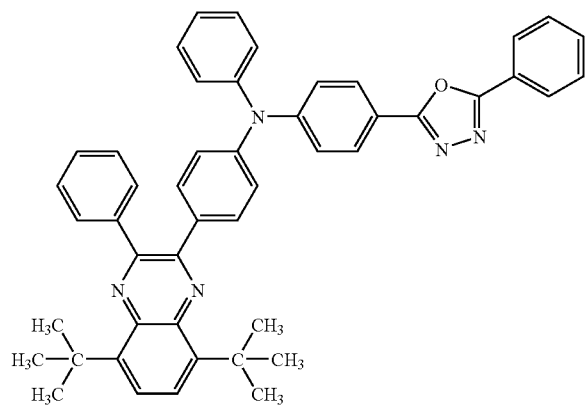
(134)
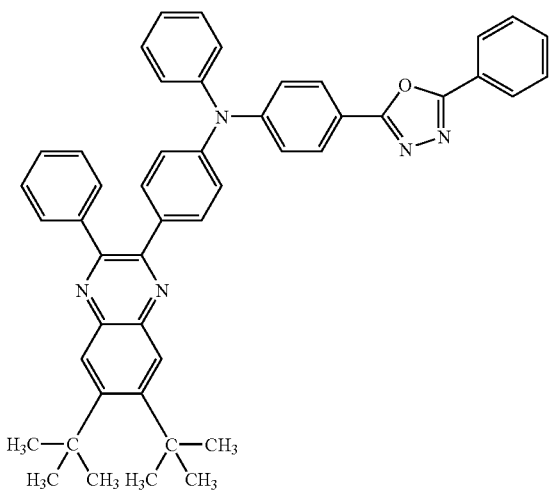
(135)
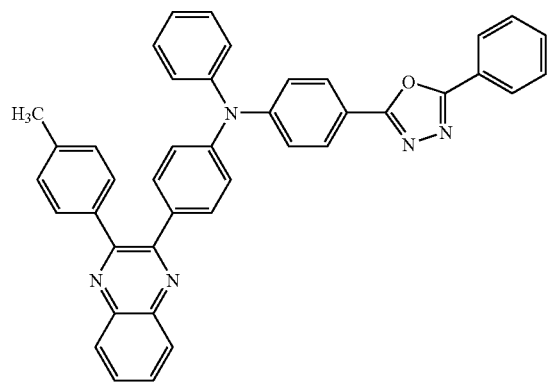
(136)
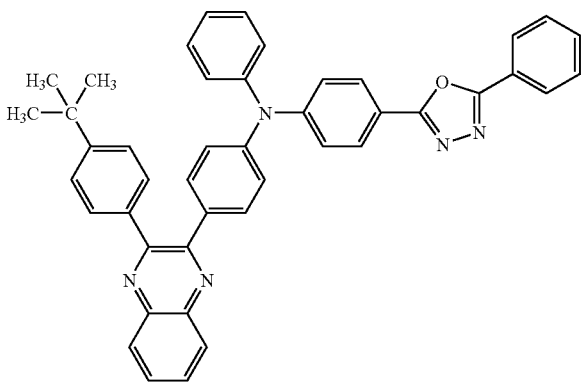
(137)
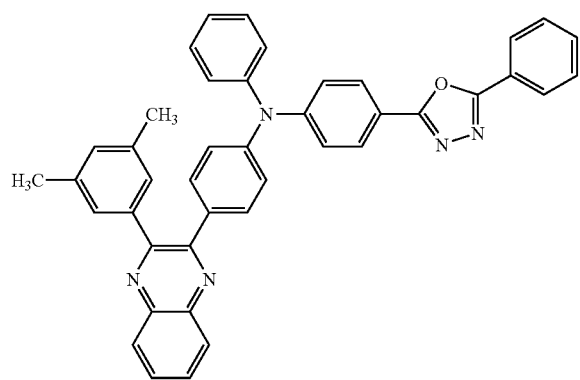
(138)
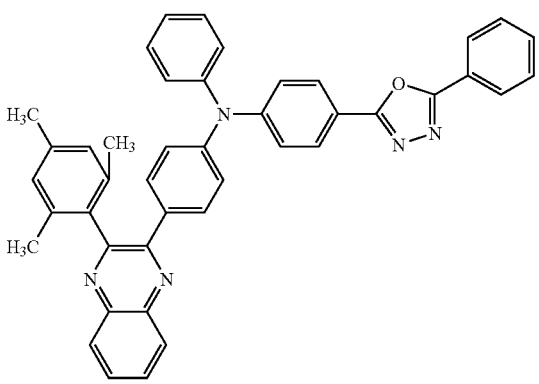

-continued
(139)
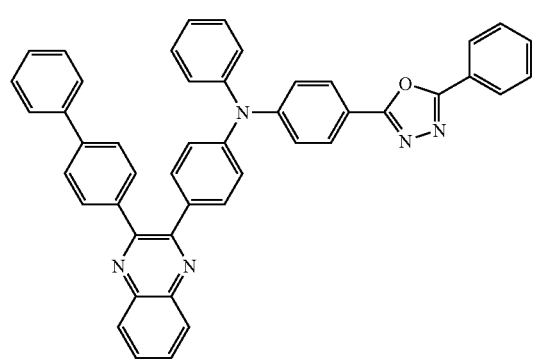
(140)
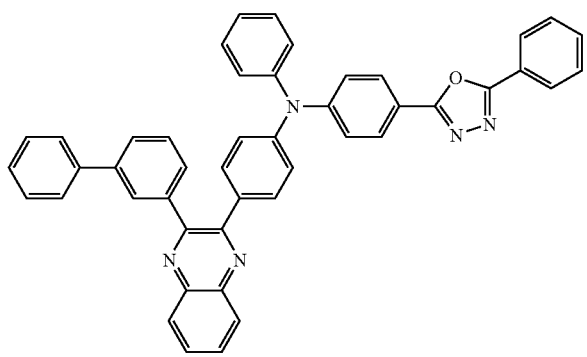
(141)
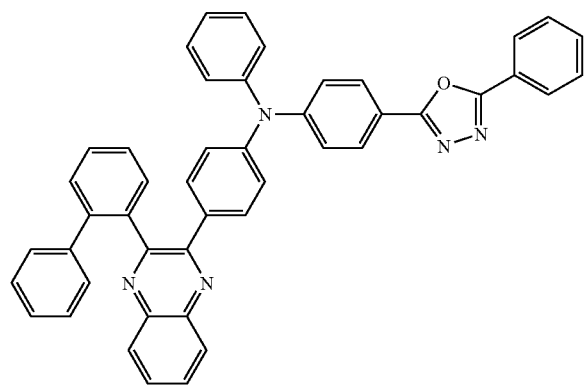
(142)
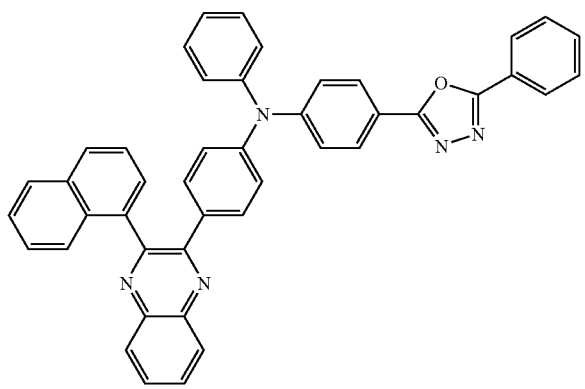
(143)
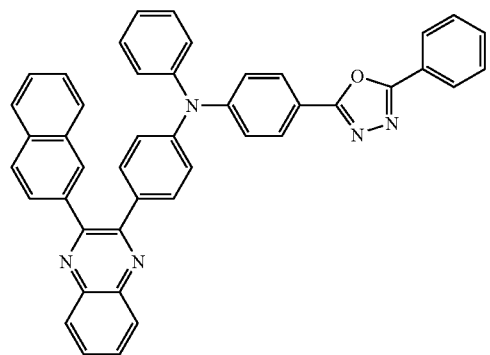
(144)
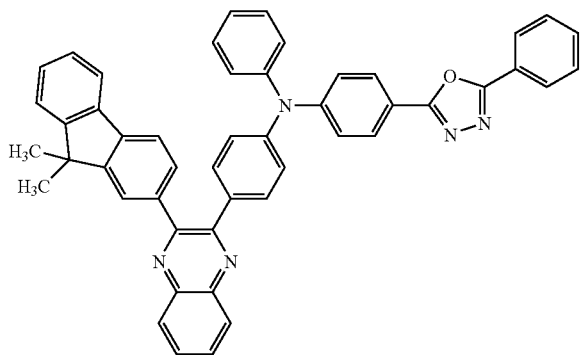
(145)
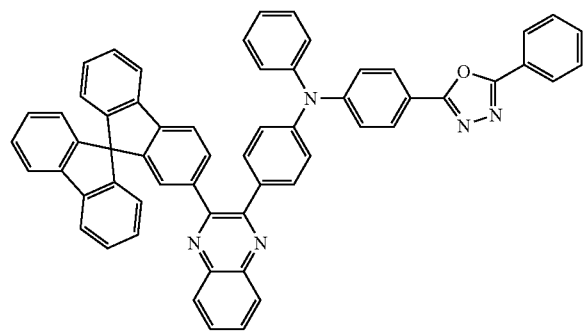
(146)
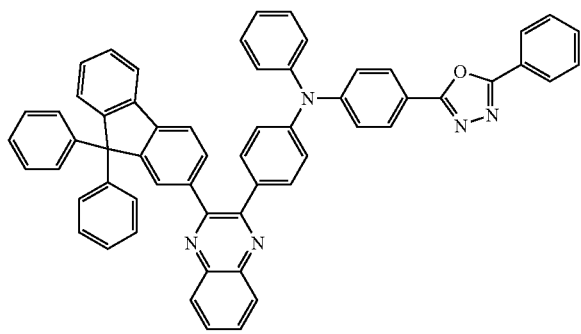

(147) 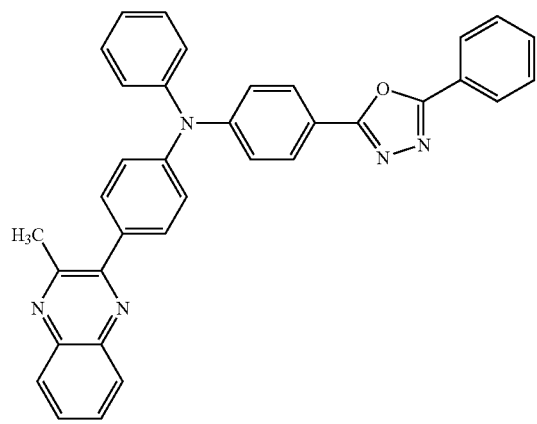
(148) 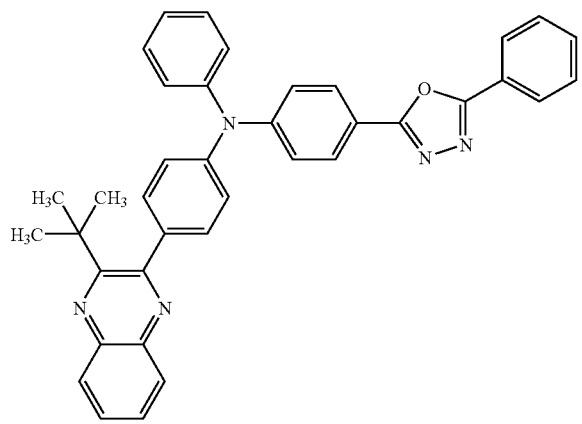
(149) 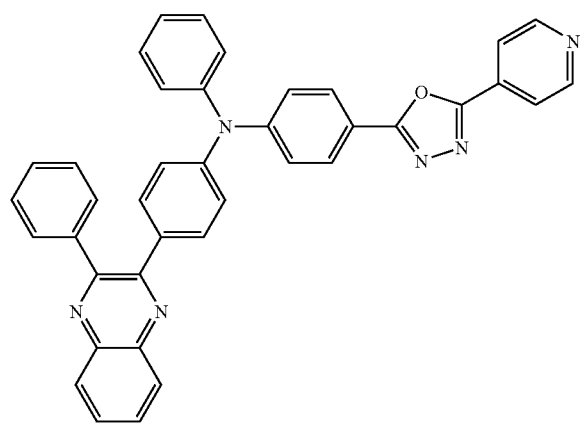
(150) 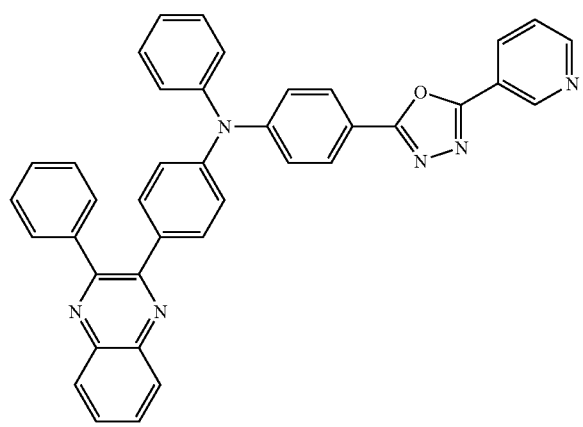
(151) 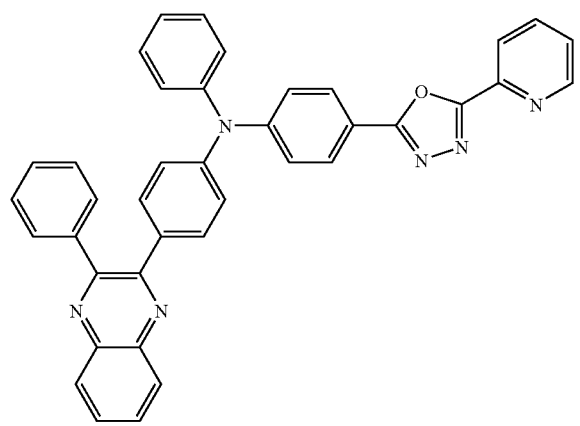
(152) 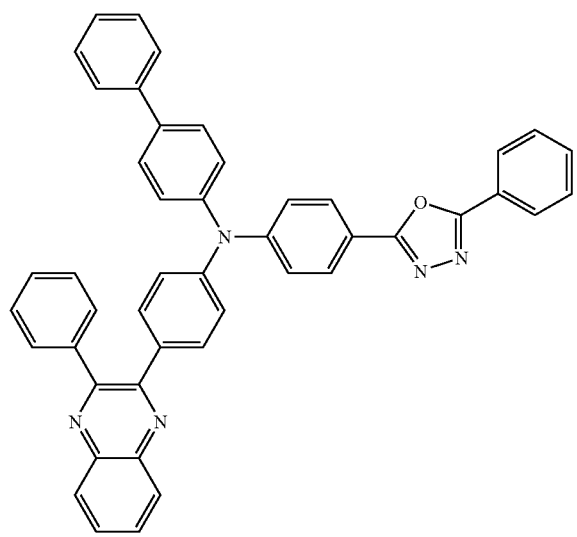

-continued
(153)
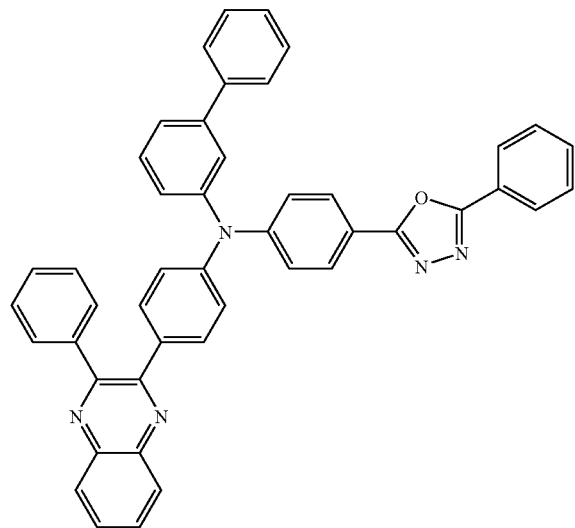
(154)
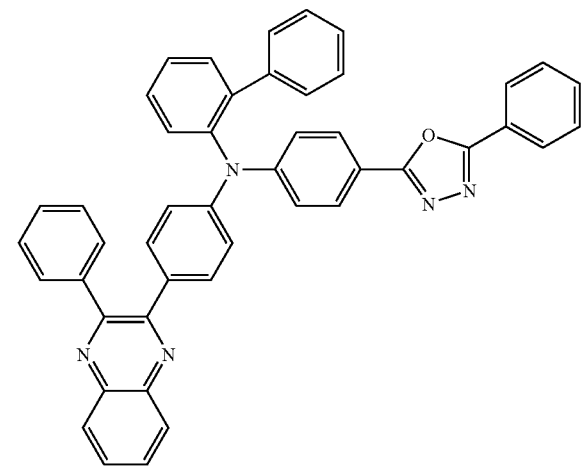
(155)
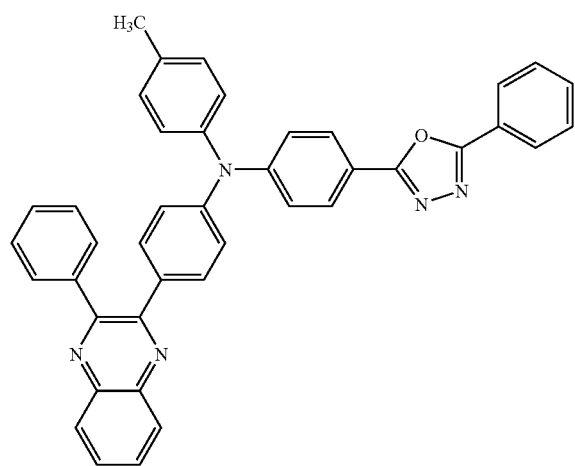
(156)
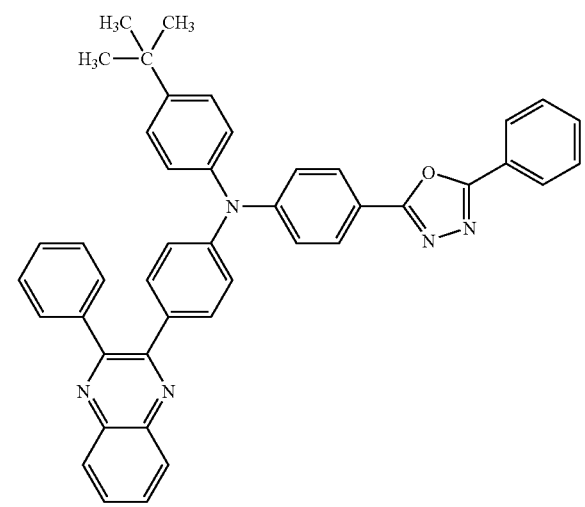
(157)
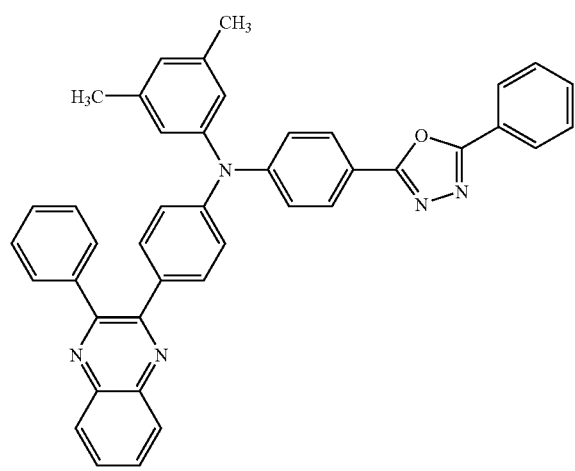
(158)
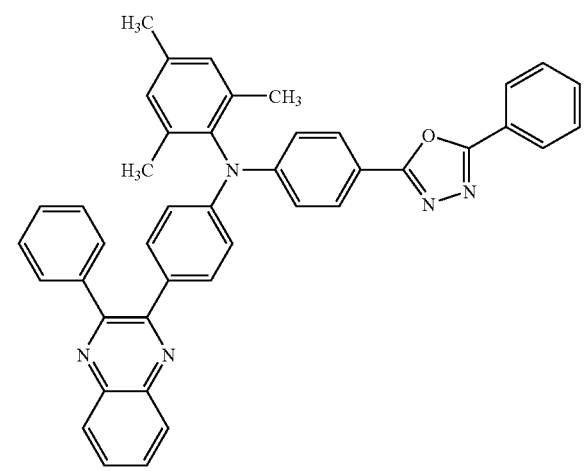

-continued
(159)
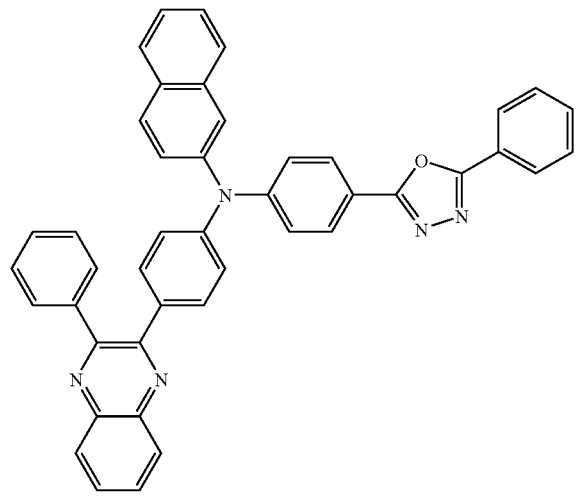
(160)
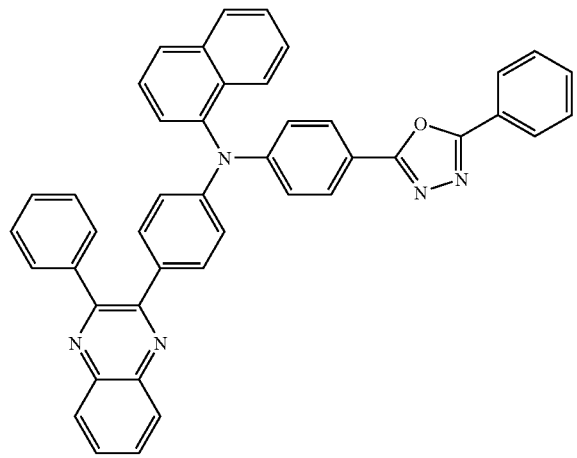
(161)
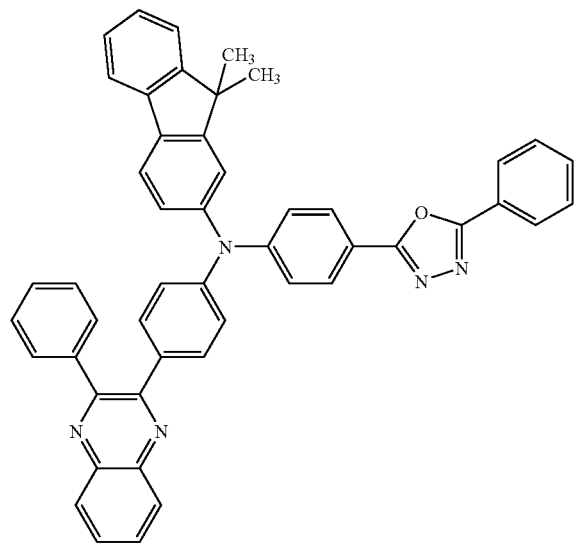
(162)
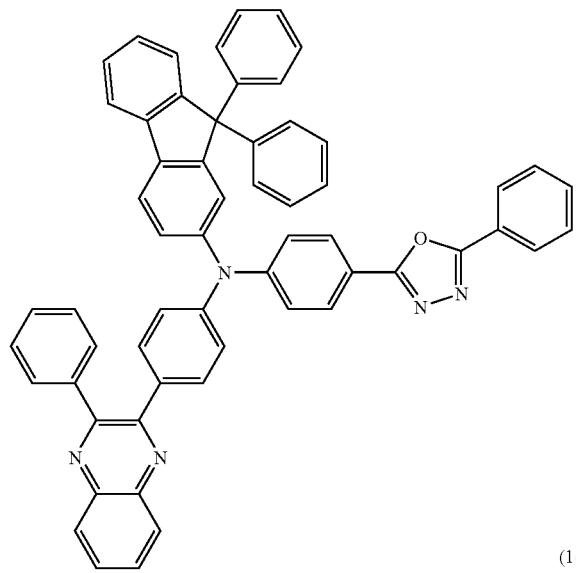
(163)
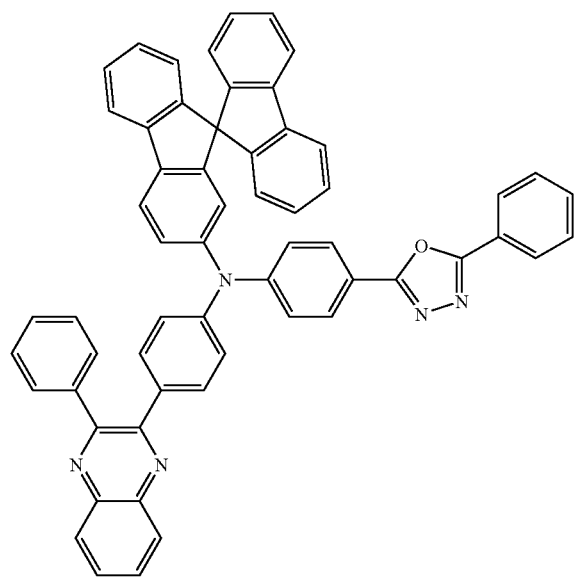
(164)
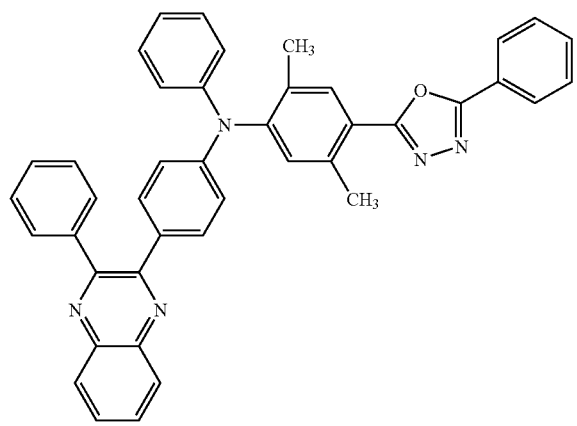

(165) 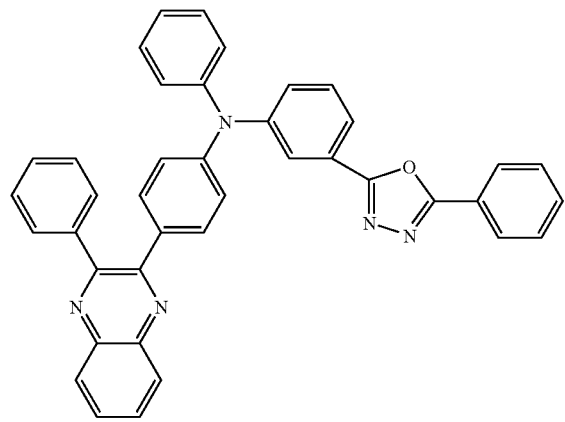
(166) 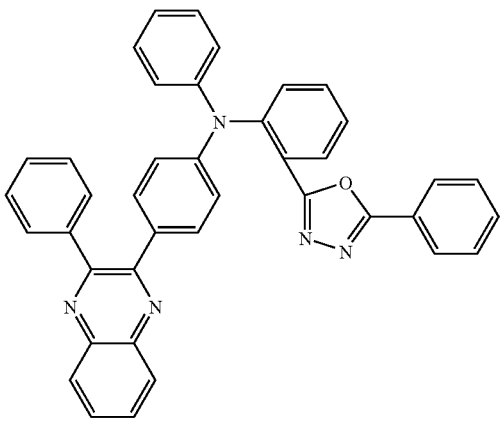
(167) 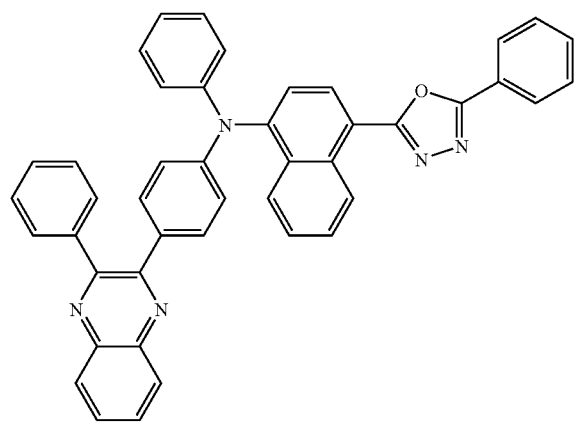
(168) 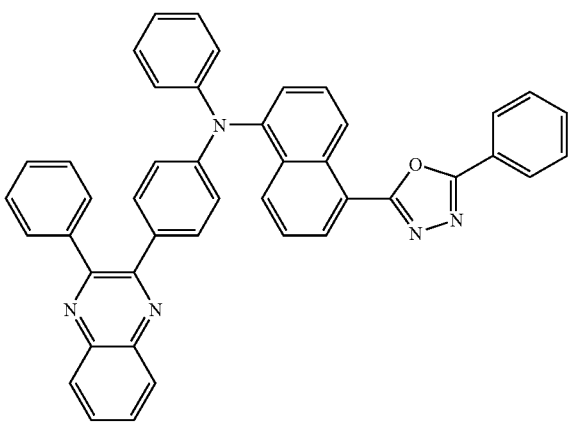
(169) 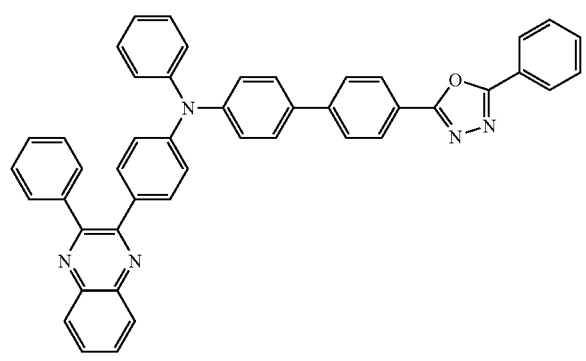
(170) 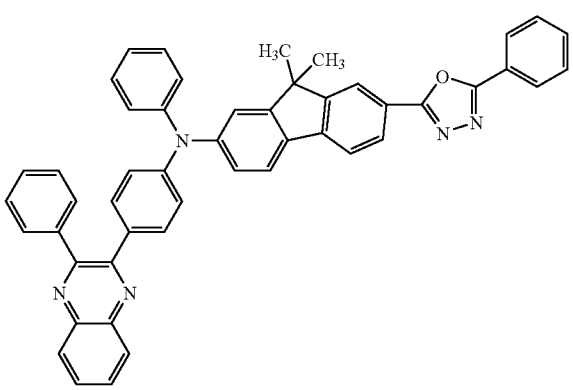

-continued
(171)
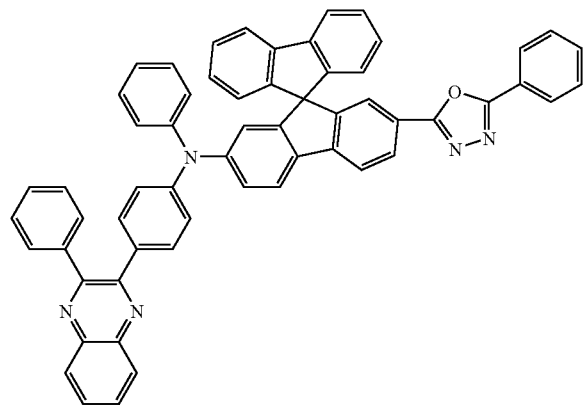
(172)
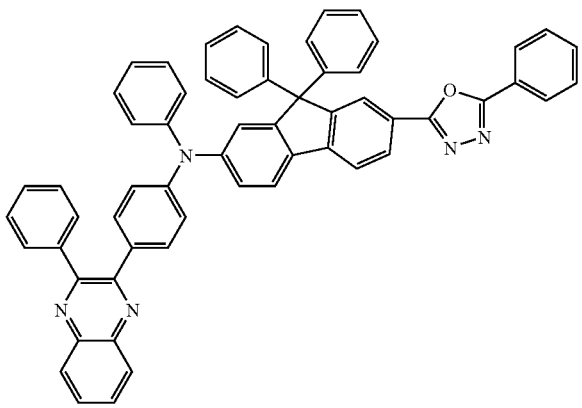
(173)
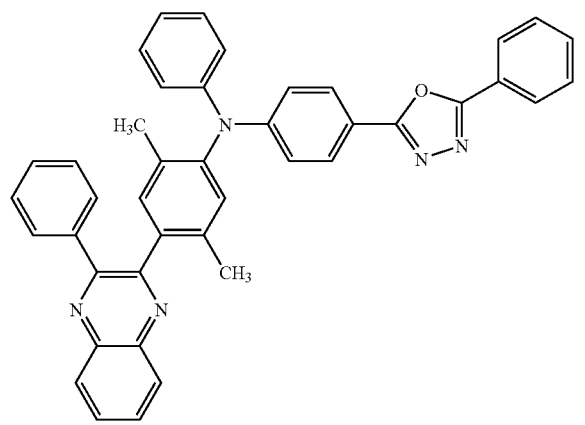
(174)
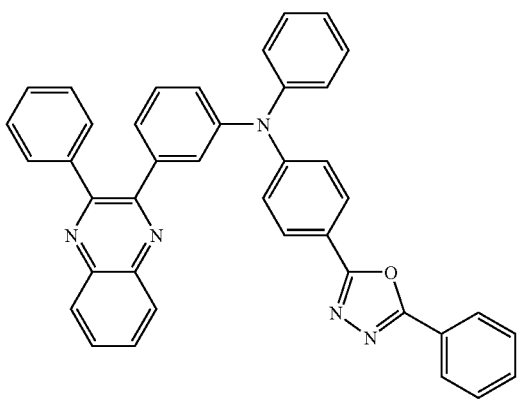
(175)
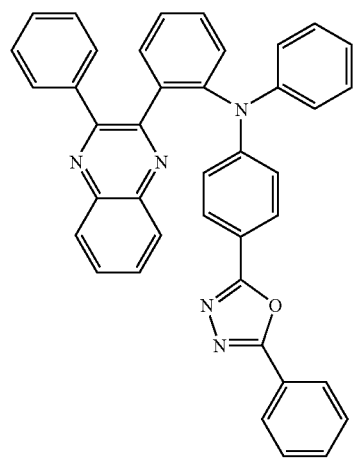
(176)
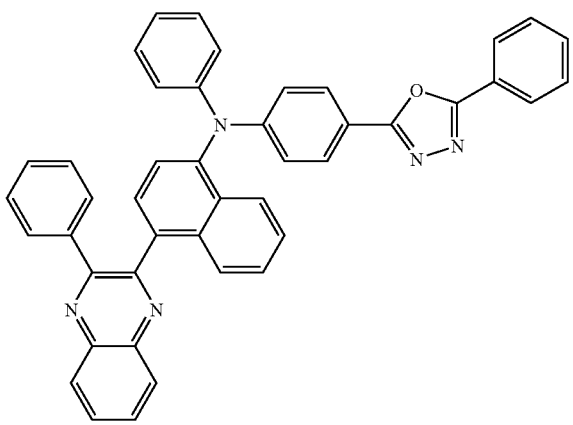

(177)
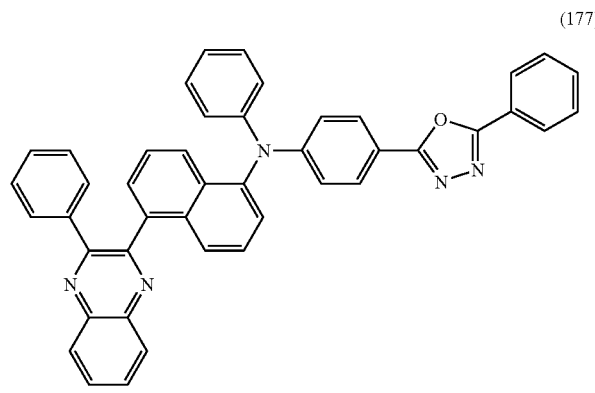
(178)
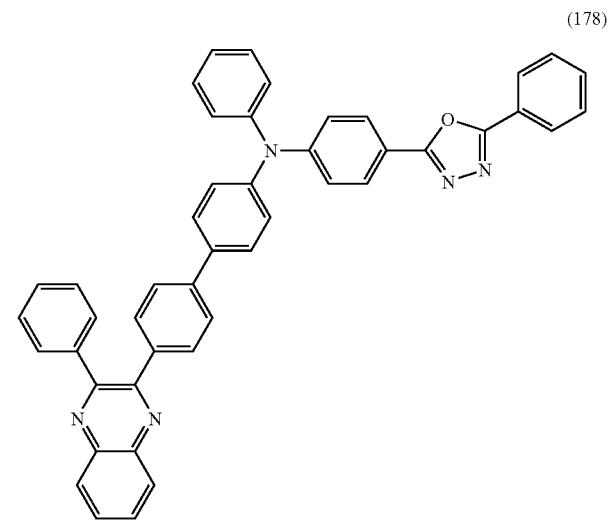
(179)
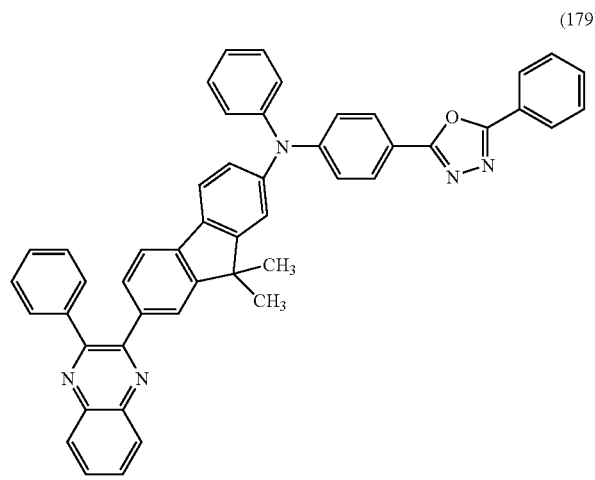
(180)
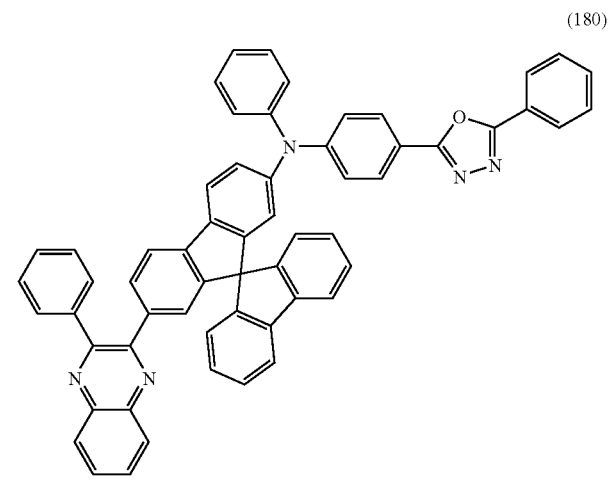
(181)
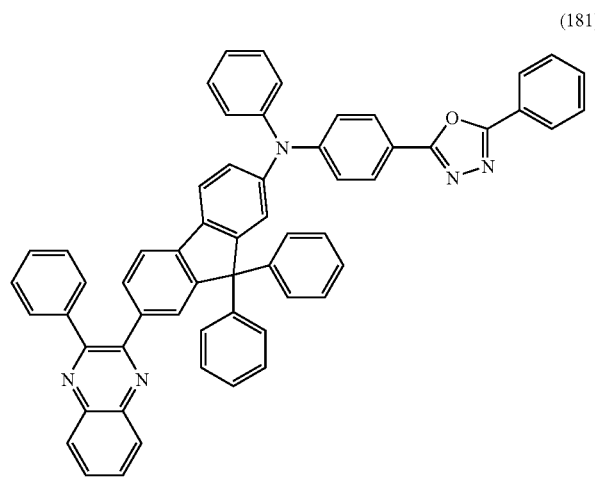
(201)
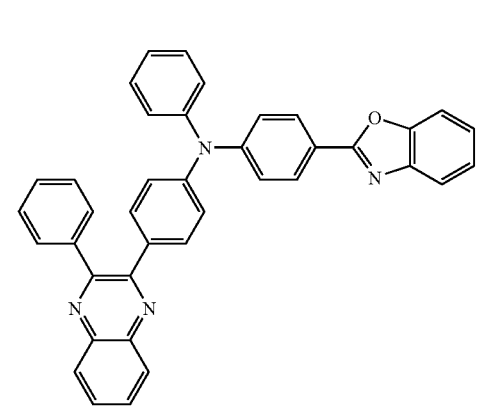

-continued
(202)
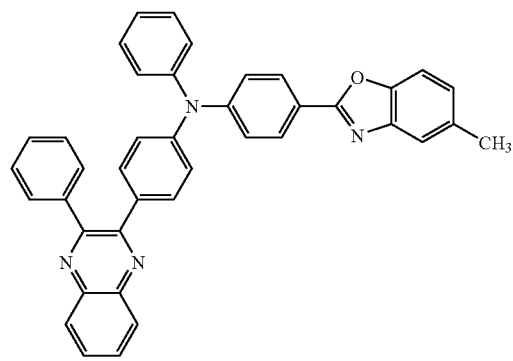
(203)
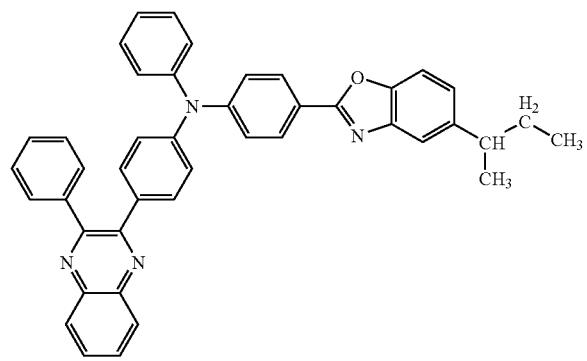
(204)
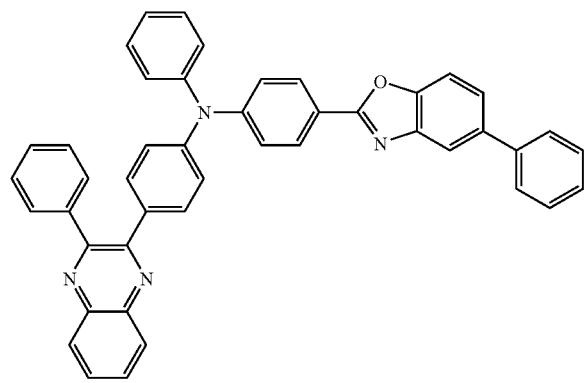
(205)
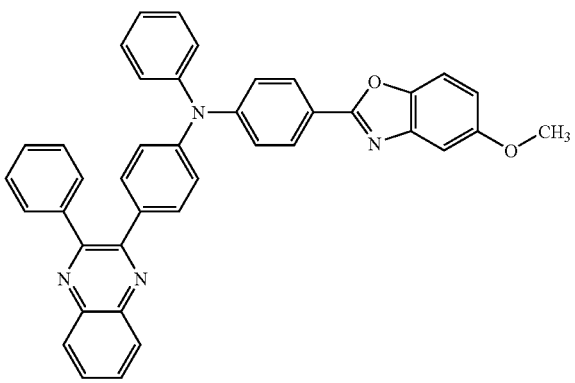
(206)
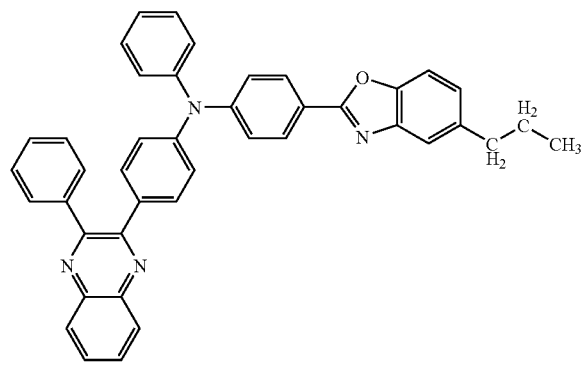
(207)
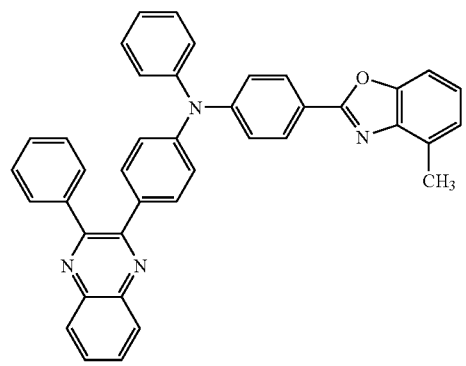
(208)
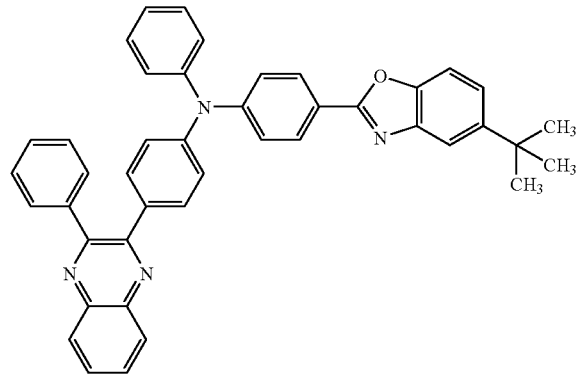
(209)
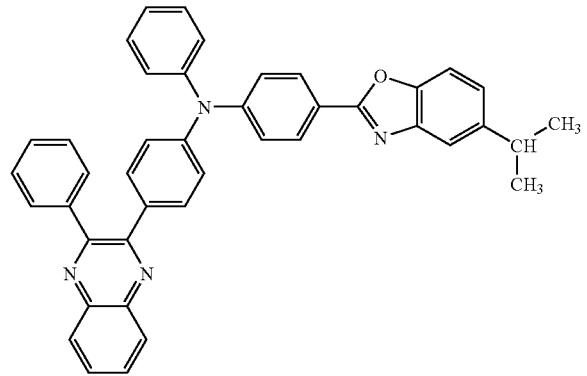

-continued
(210)
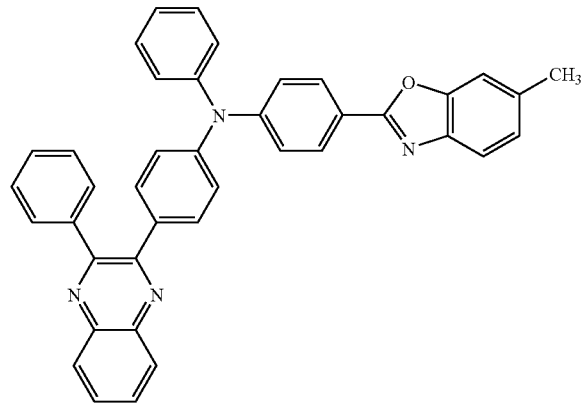
(211)
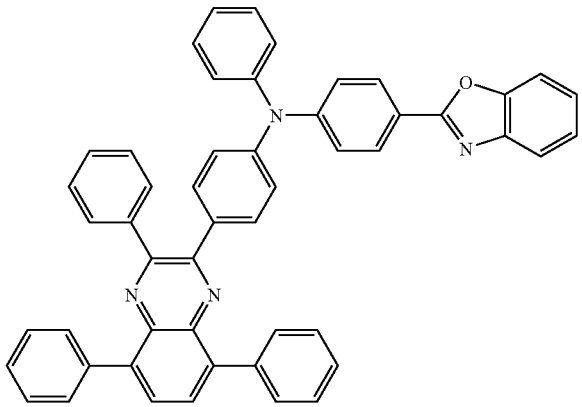
(212)
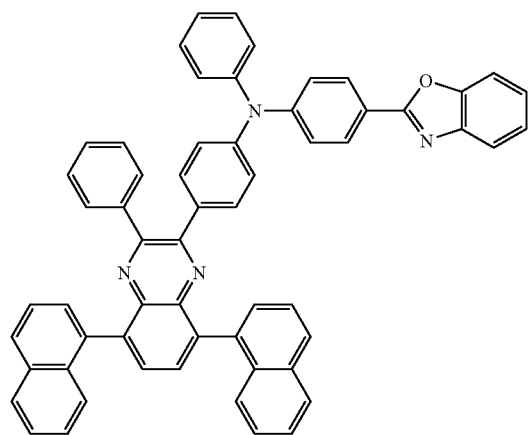
(213)
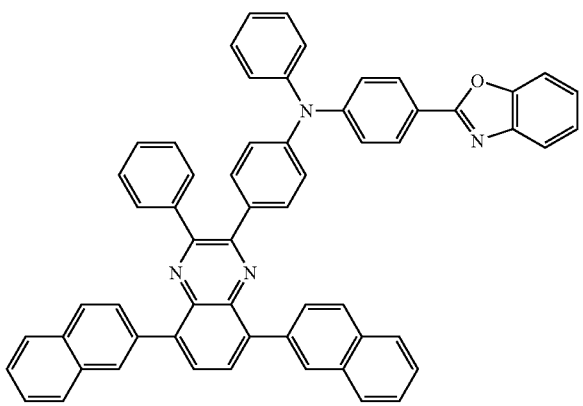
(214)
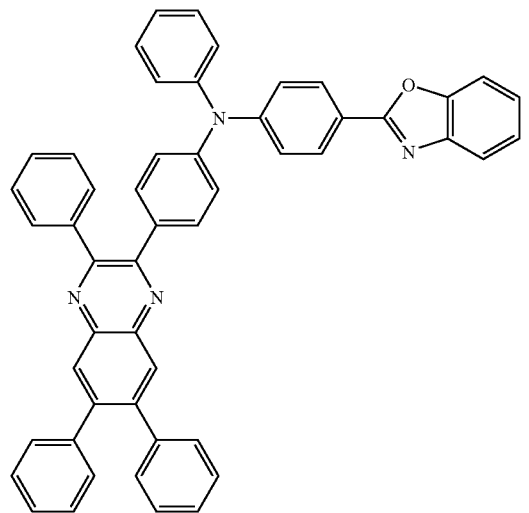
(215)
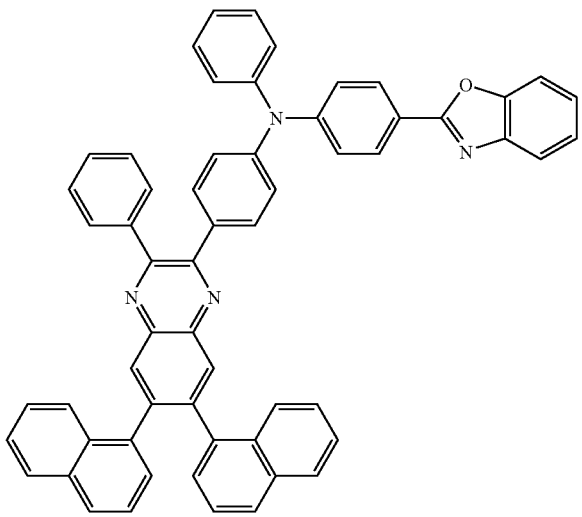

-continued
(216) 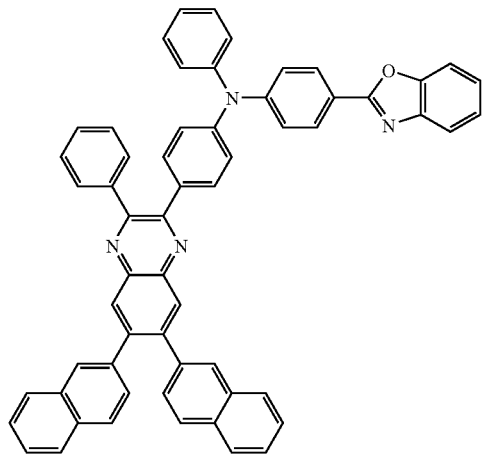
(217) 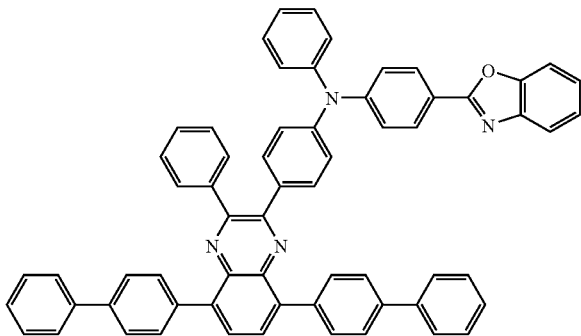
(218) 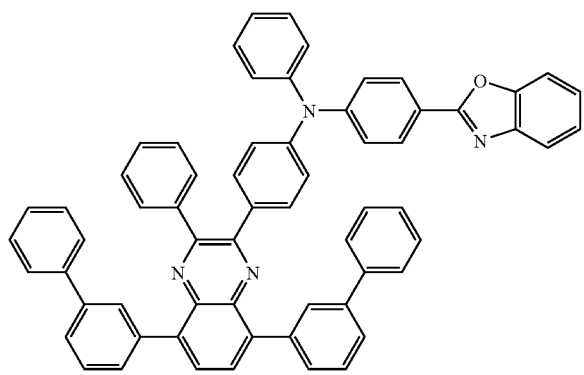
(219) 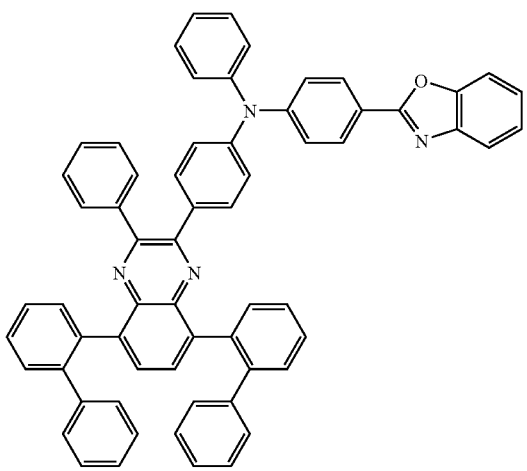
(220) 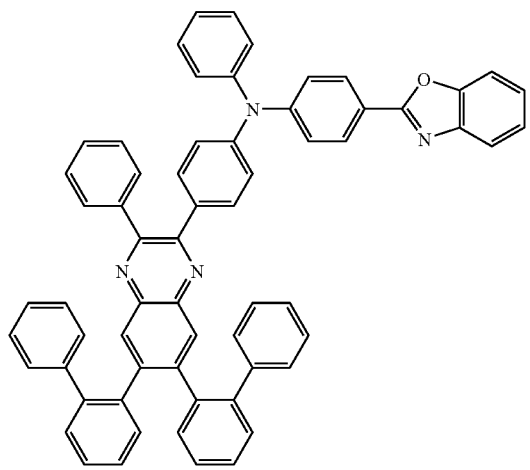
(221) 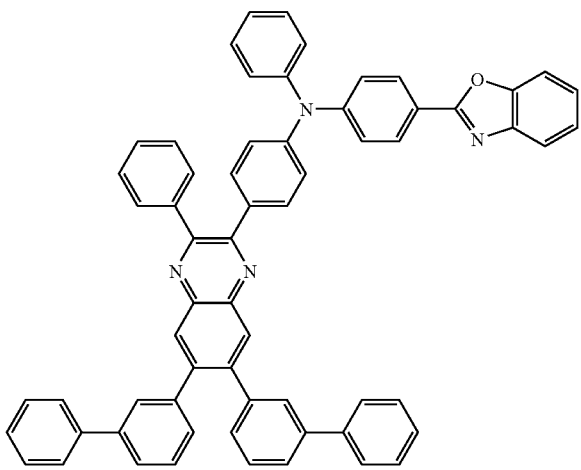

-continued
(222)
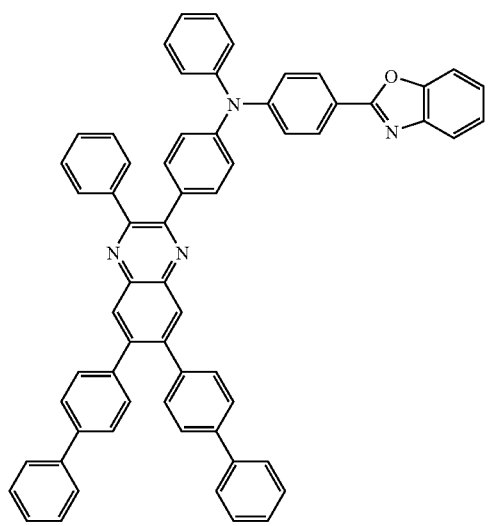
(223)
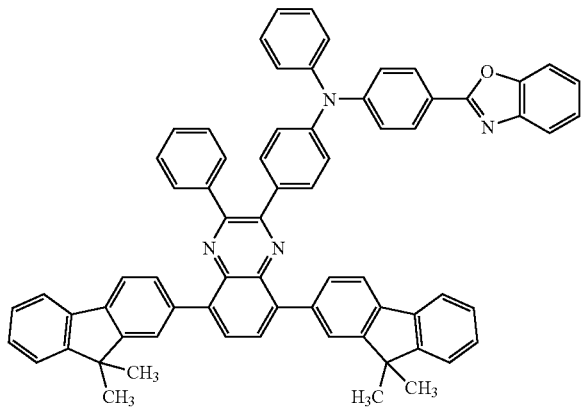
(224)
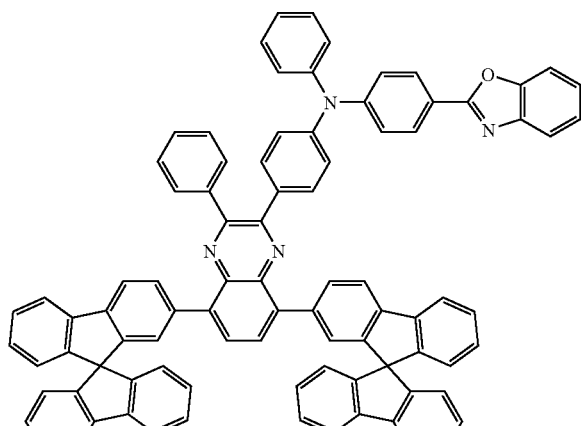
(225)
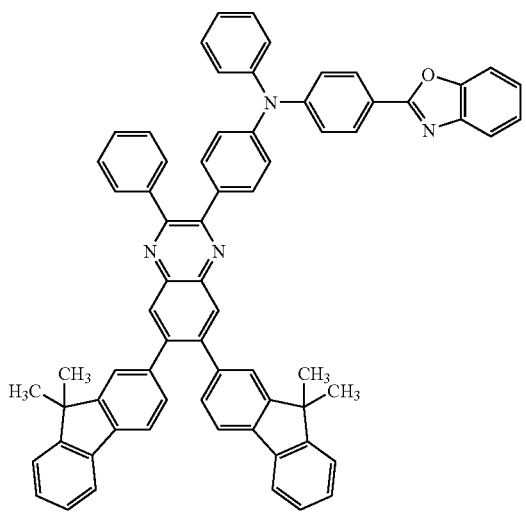
(226)
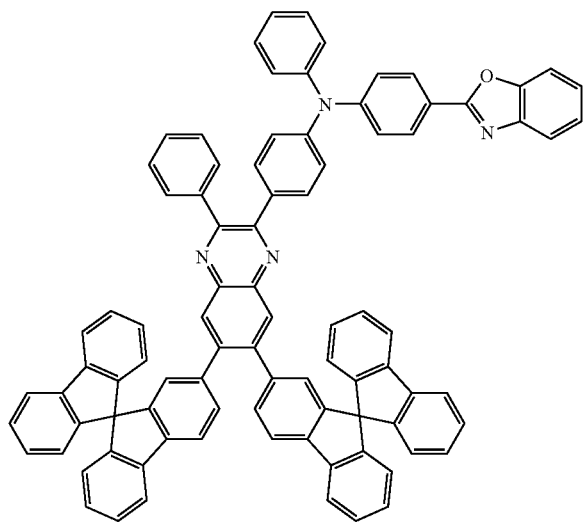
(227)
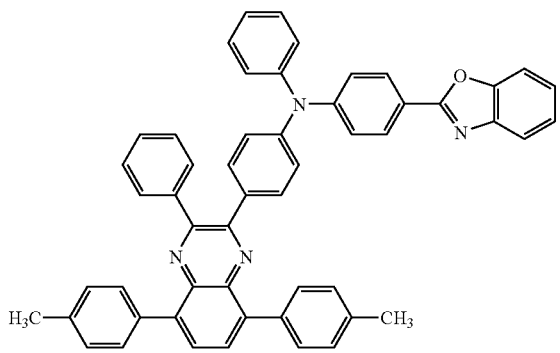

-continued
(228)
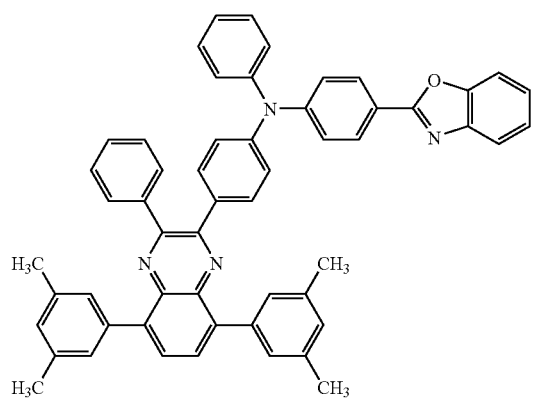
(229)
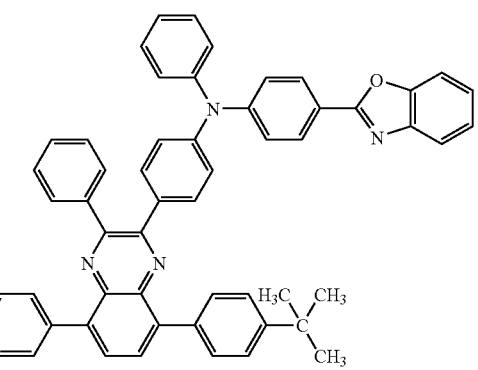
(230)
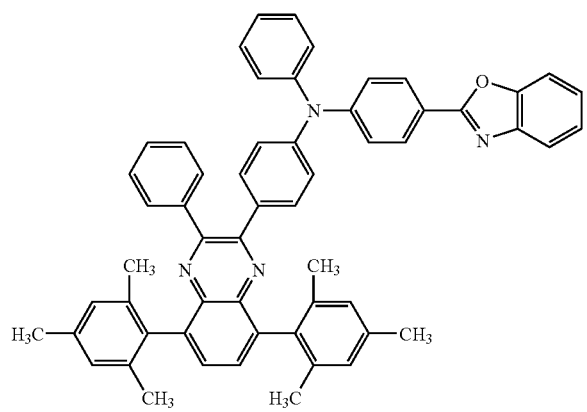
(231)
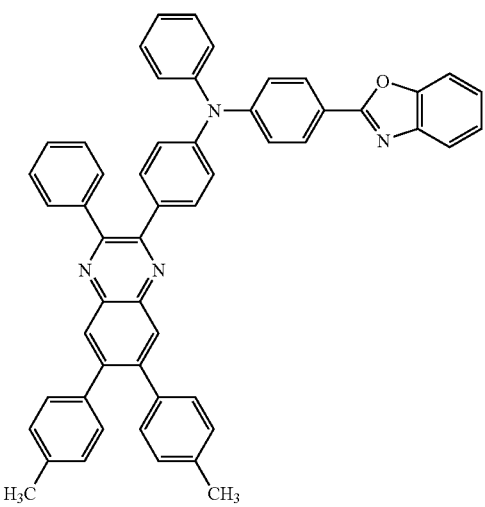
(232)
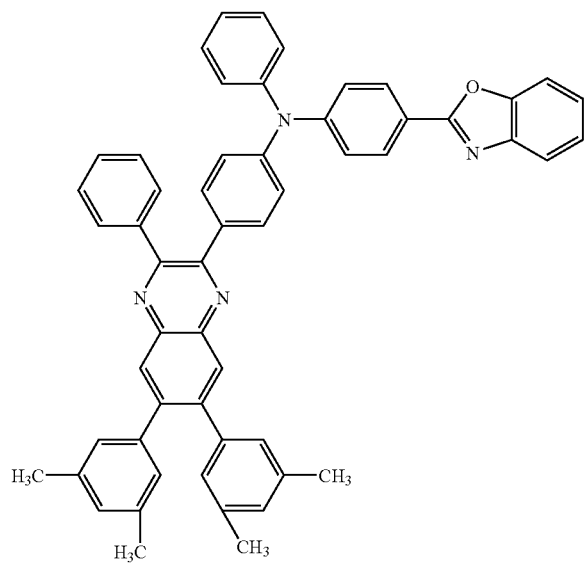
(233)
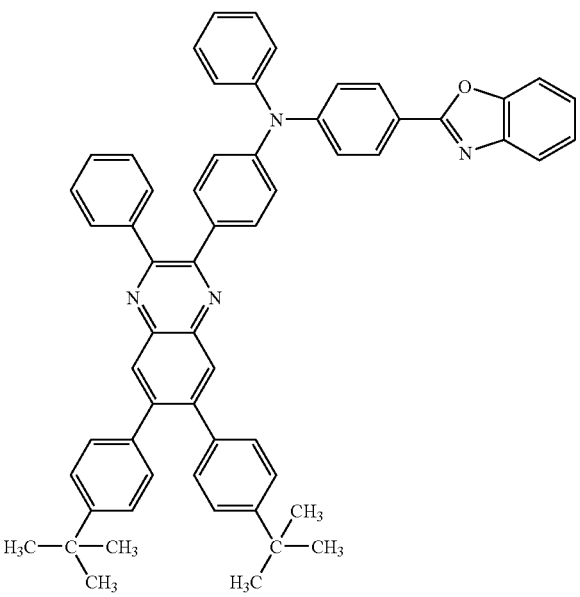

-continued
(234)
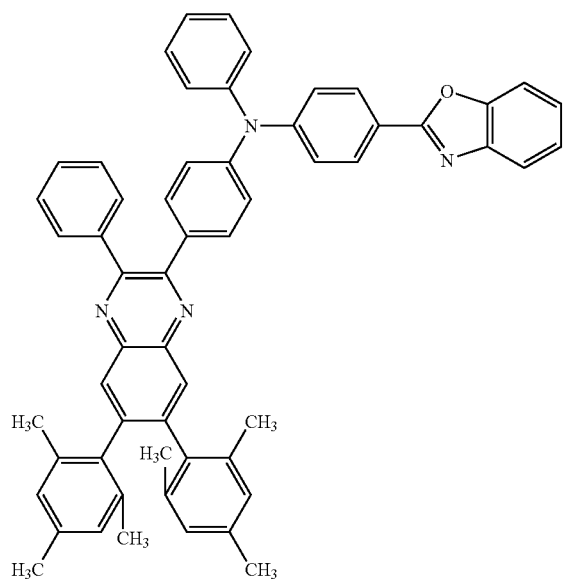
(235)
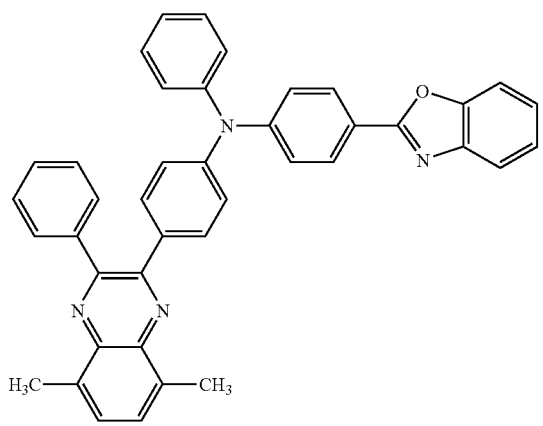
(236)
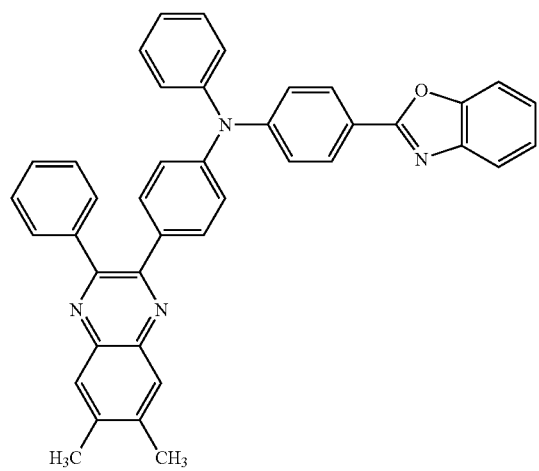
(237)
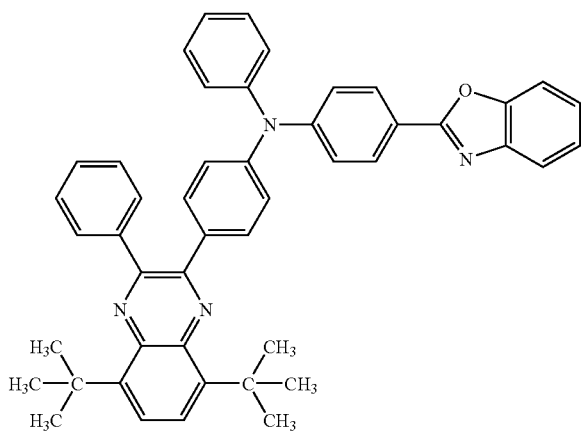
(238)
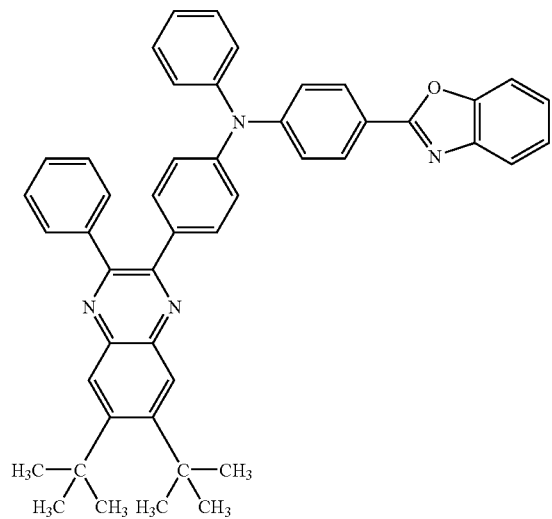
(239)
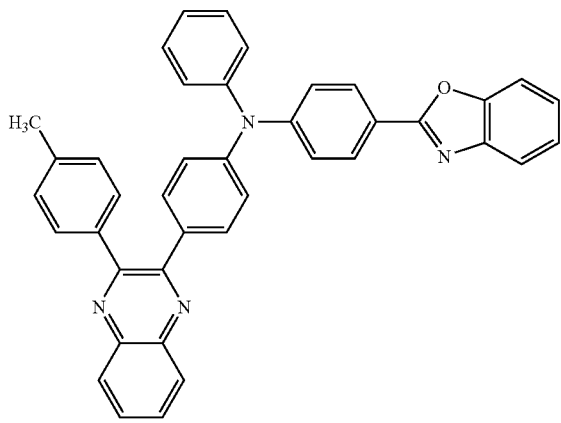

(240)
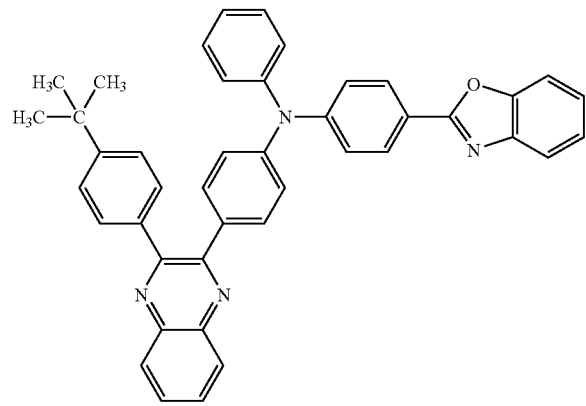
(241)
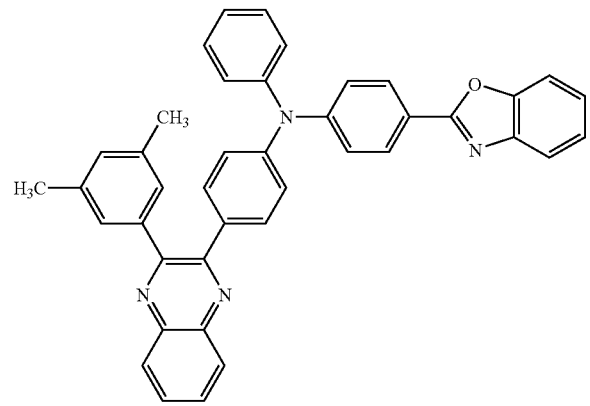
(242)
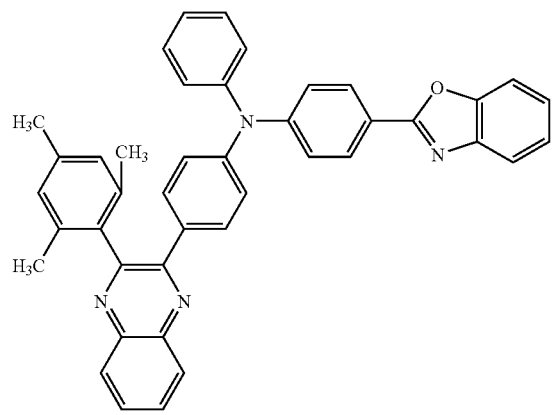
(243)
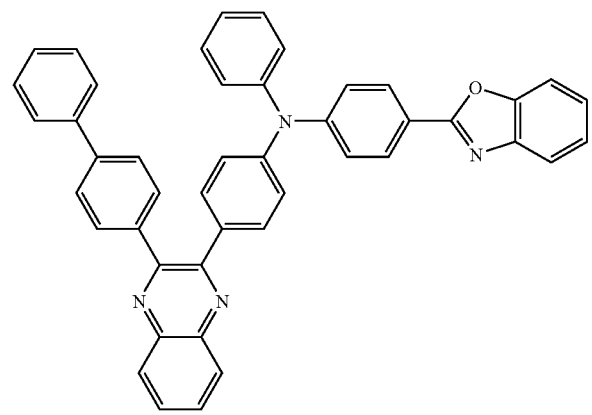
(244)
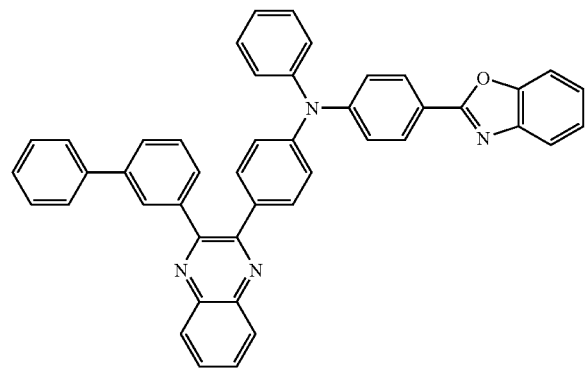
(245)
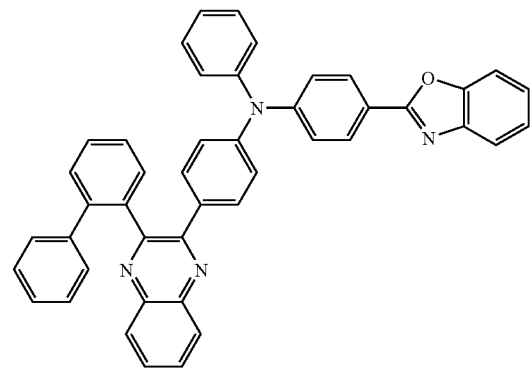

(246)
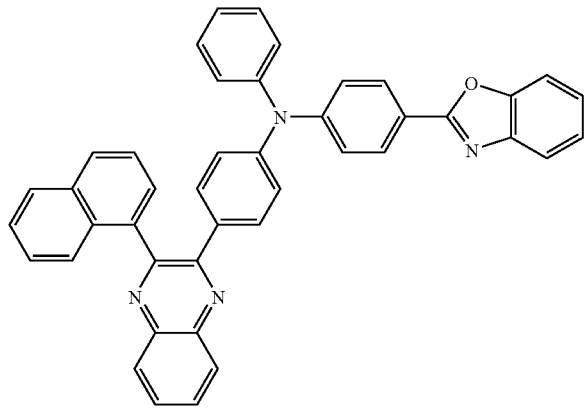
(247)
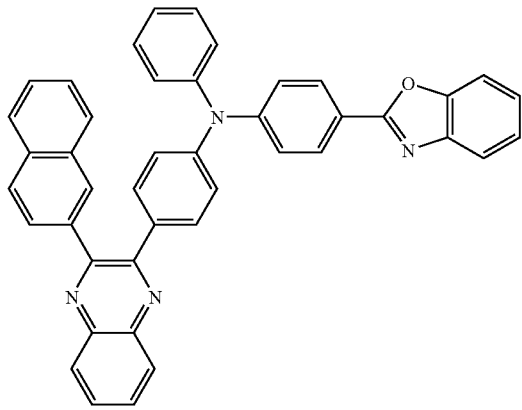
(248)
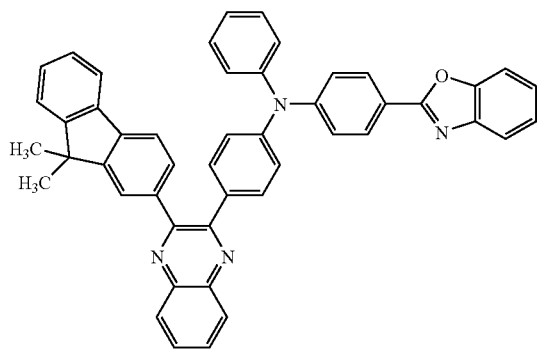
(249)
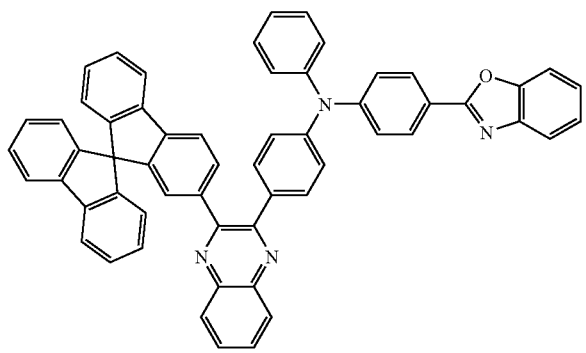
(250)
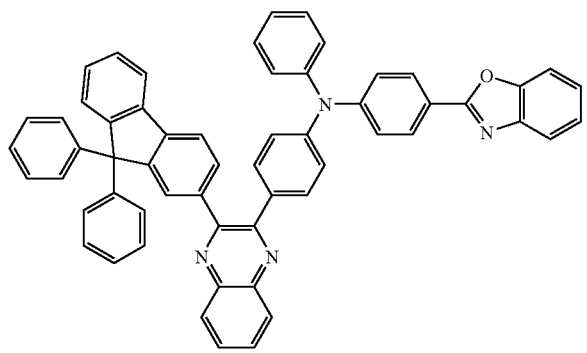
(251)
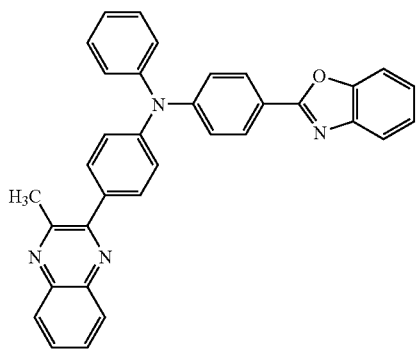

-continued
(252)
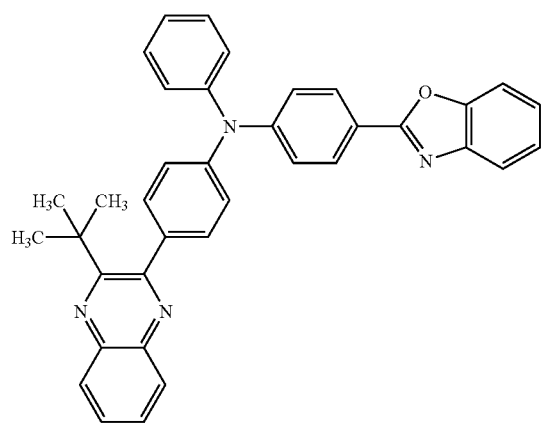
(253)
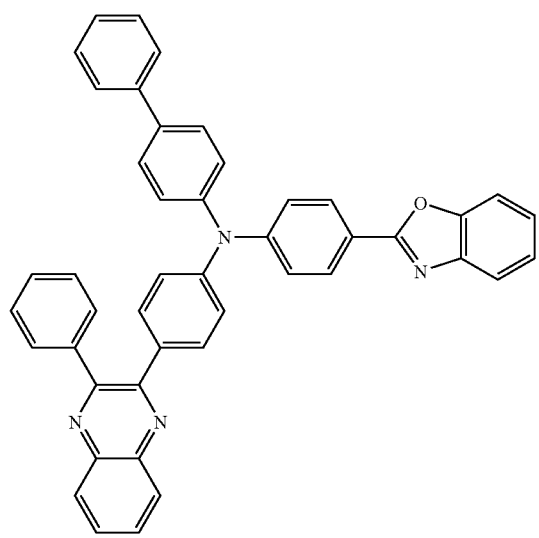
(254)
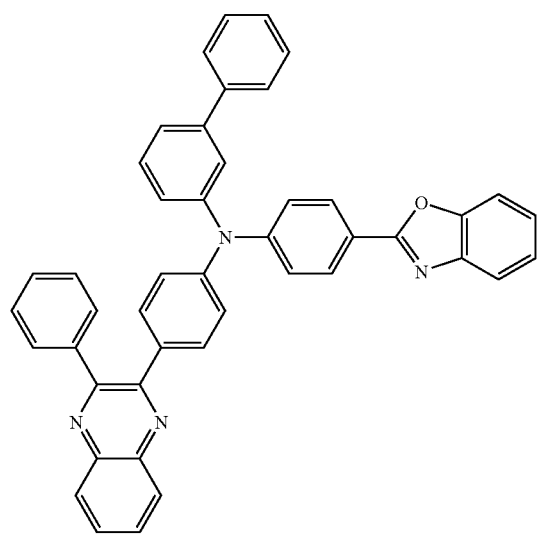
(255)
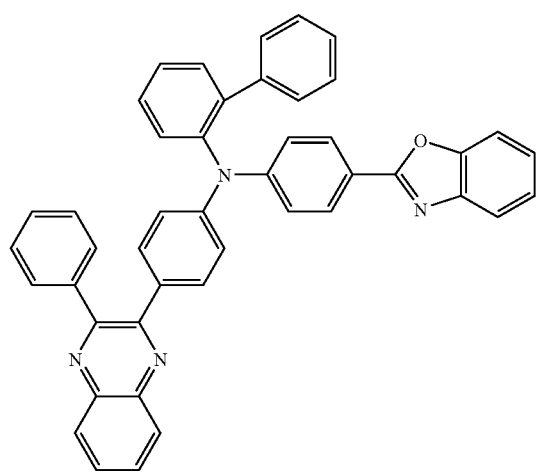
(256)
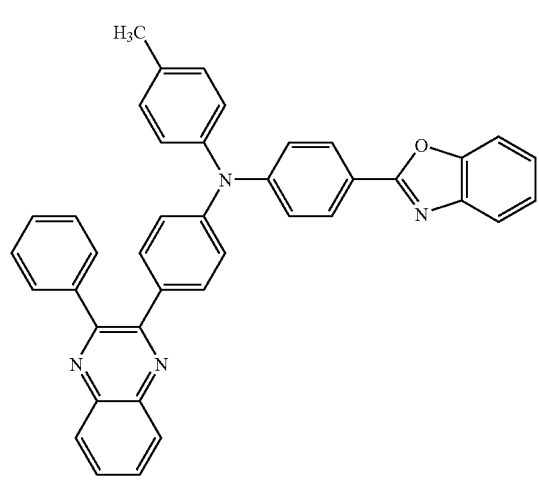
(257)
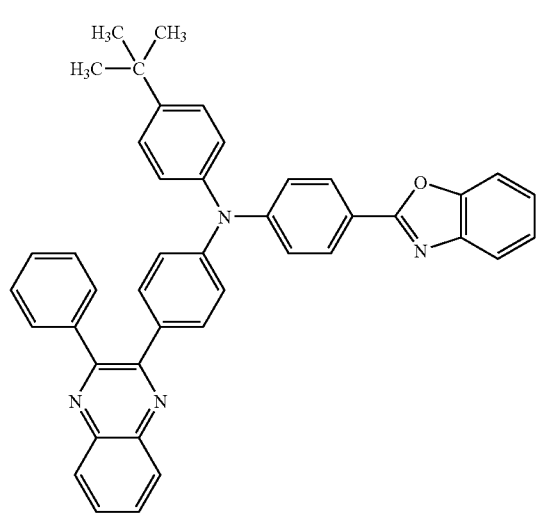

-continued
(258)
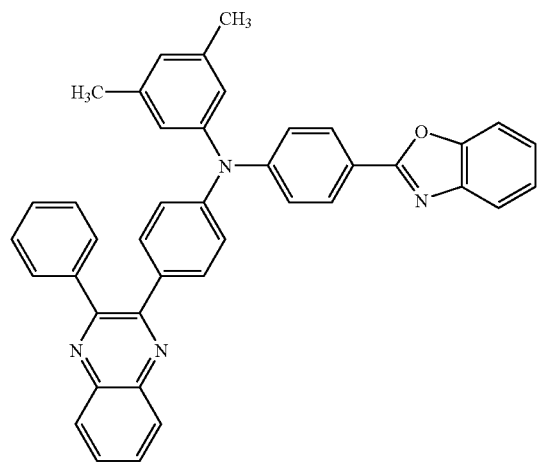
(259)
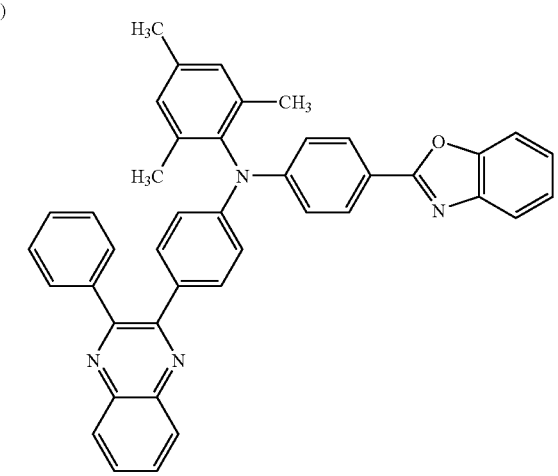
(260)
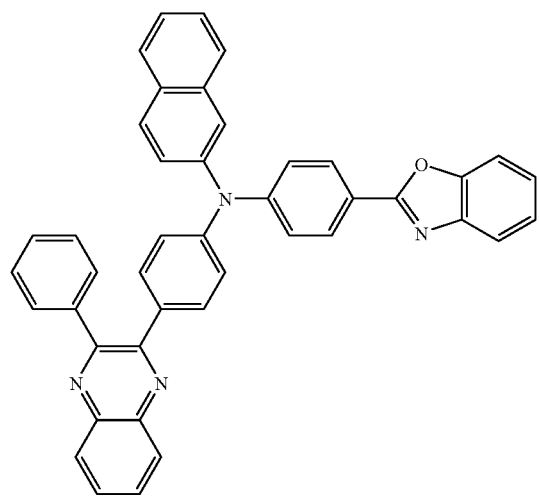
(261)
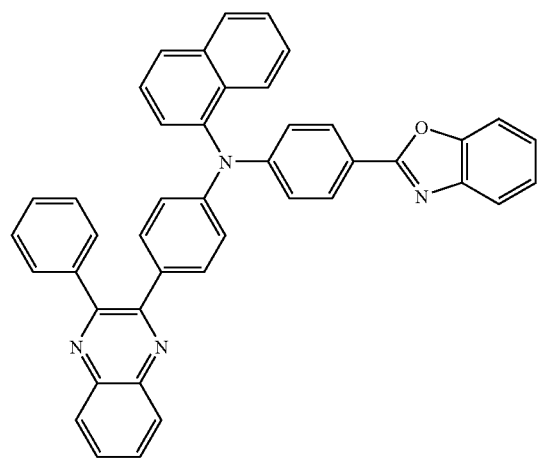
(262)
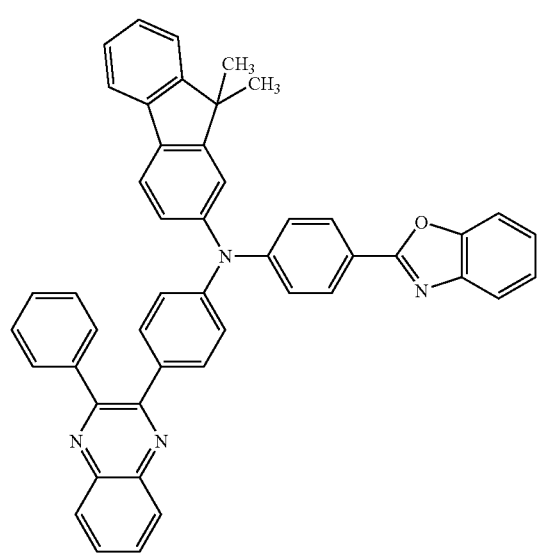
(263)
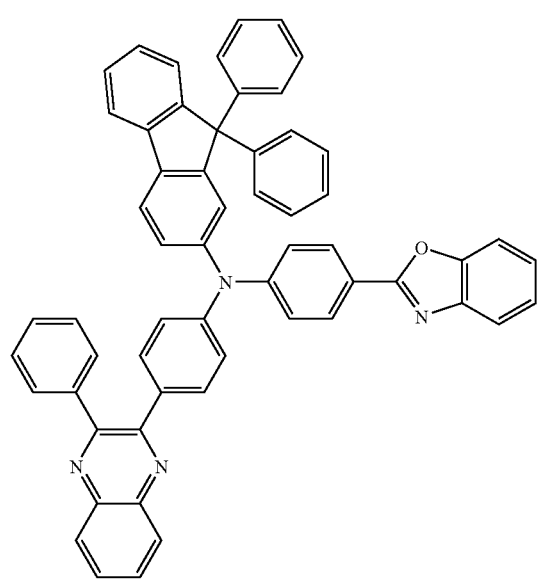

-continued
(264)
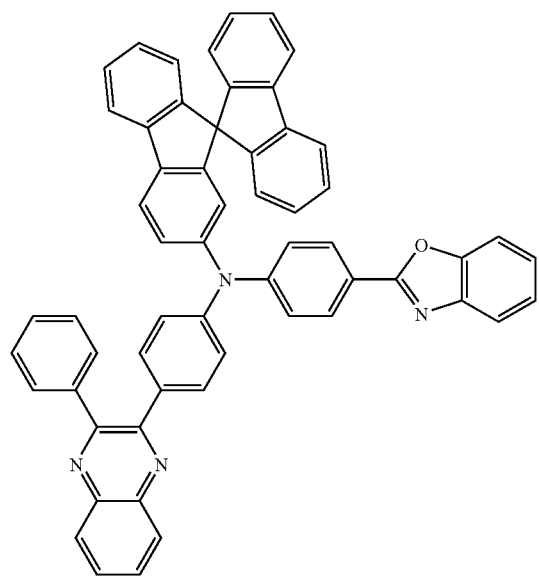
(265)
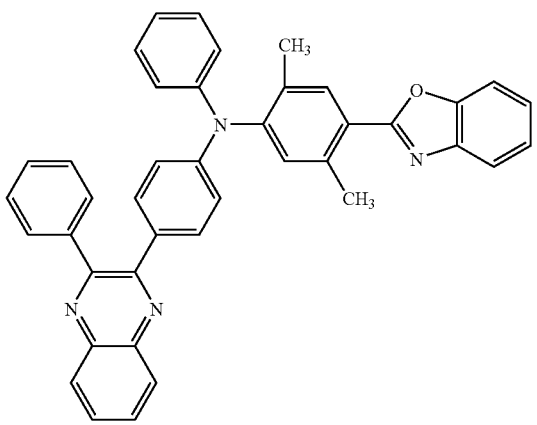
(266)
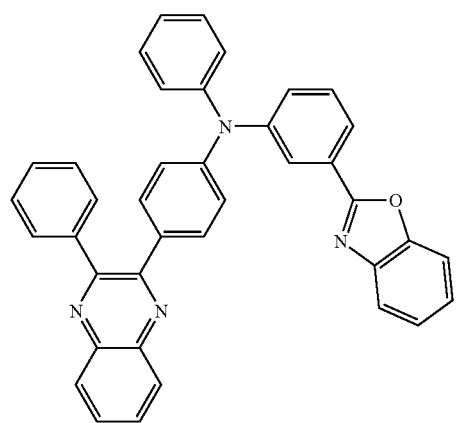
(267)
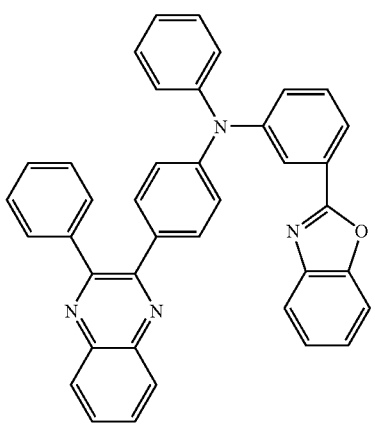
(268)
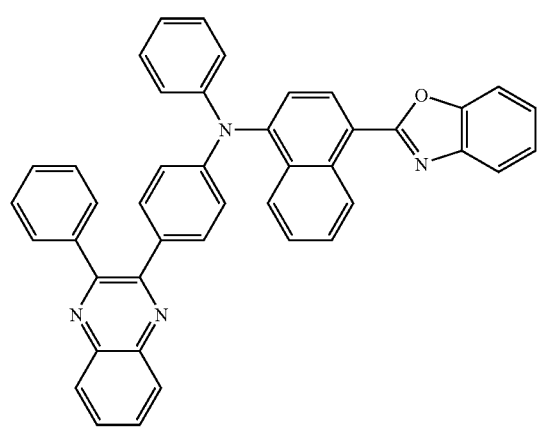
(269)
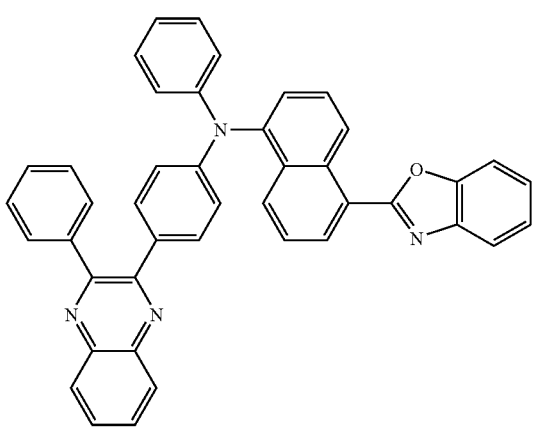

(270)
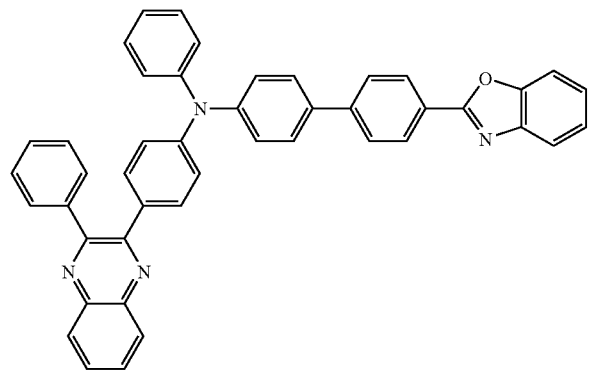
(271)
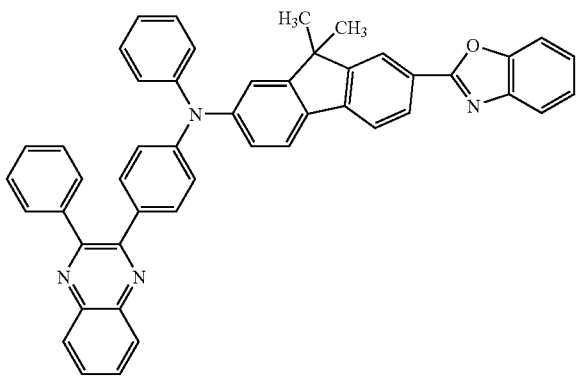
(272)
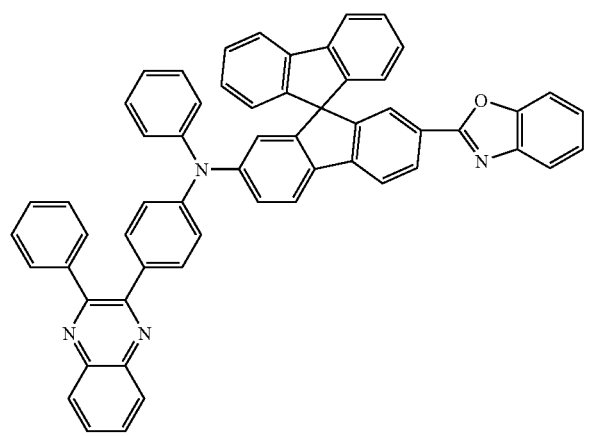
(273)
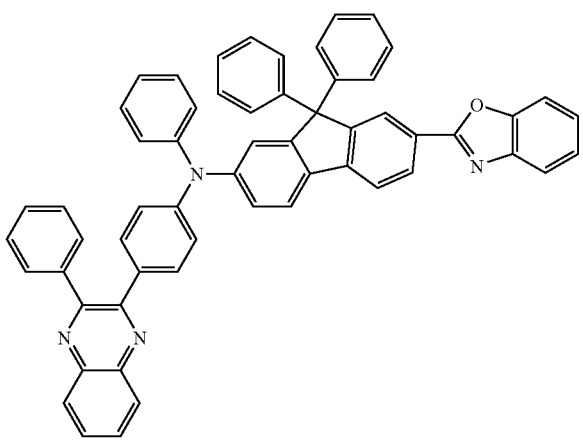
(274)
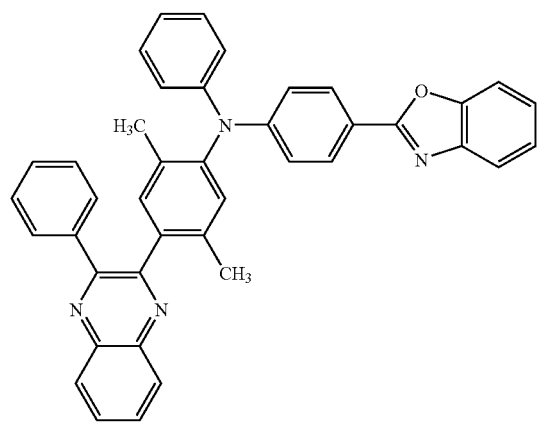
(275)
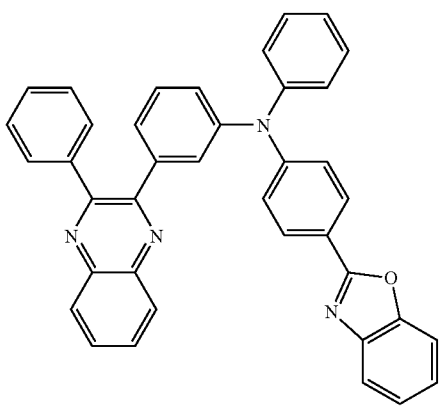

-continued
(276)
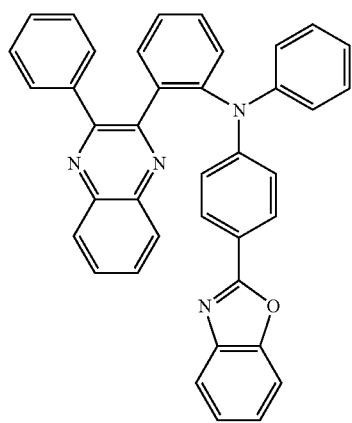
(277)
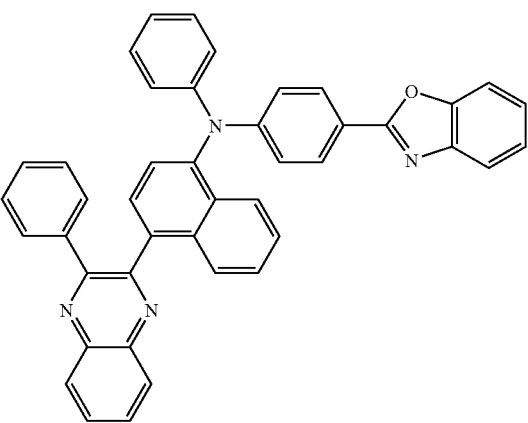
(278)
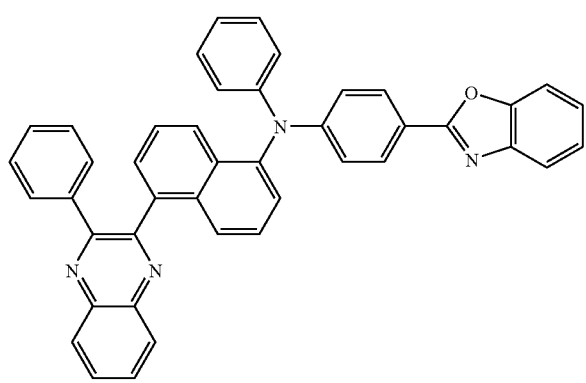
(279)
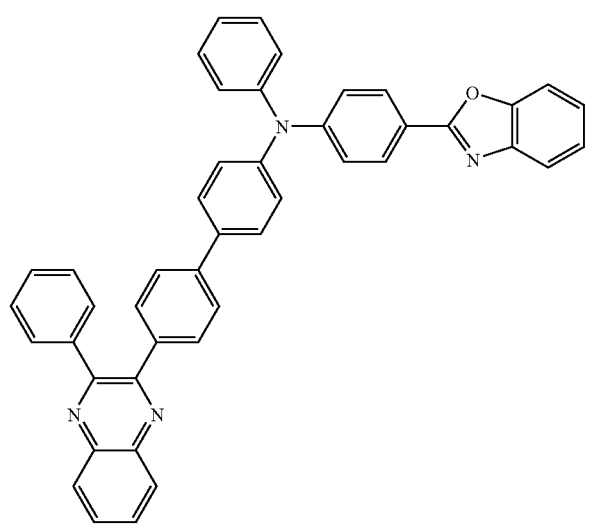
(280)
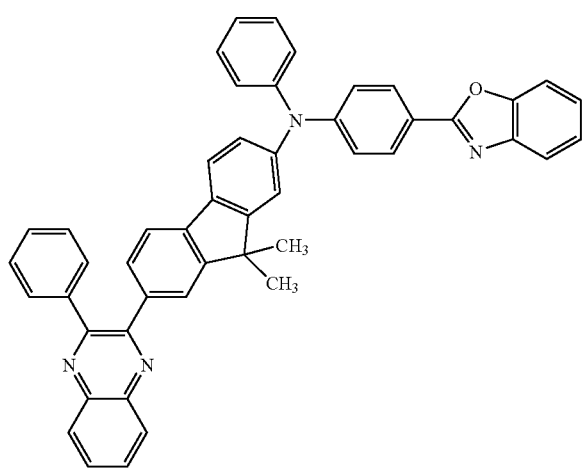
(281)
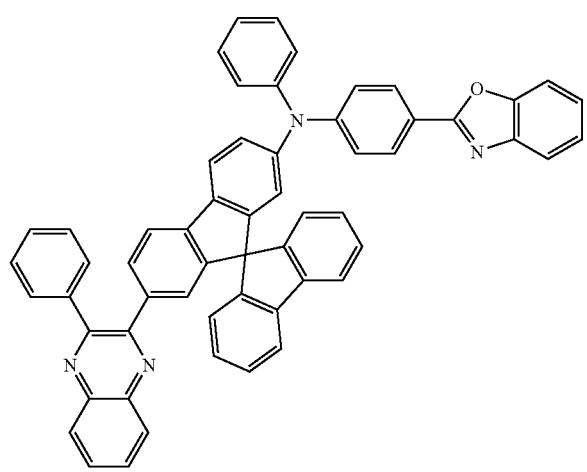

-continued
(282)
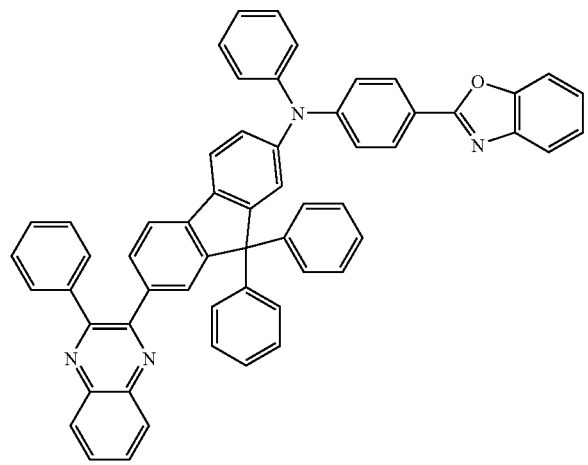
(301)
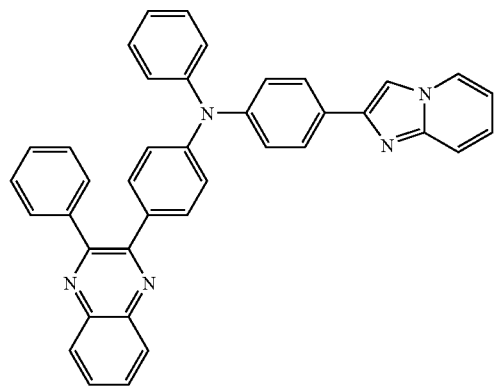
(302)
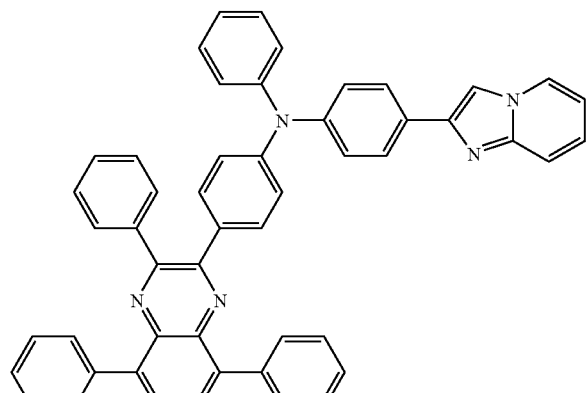
(303)
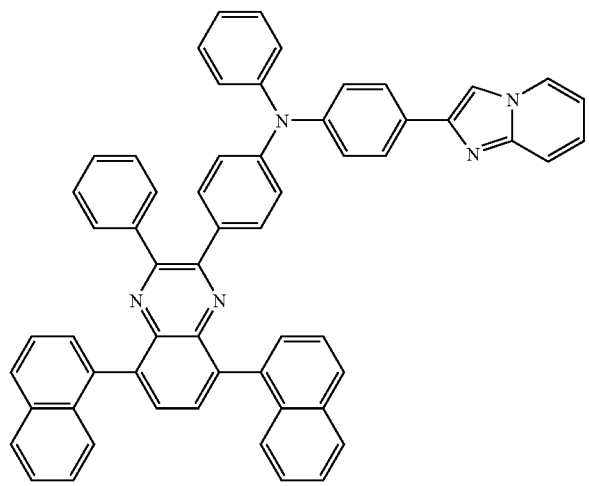
(304)
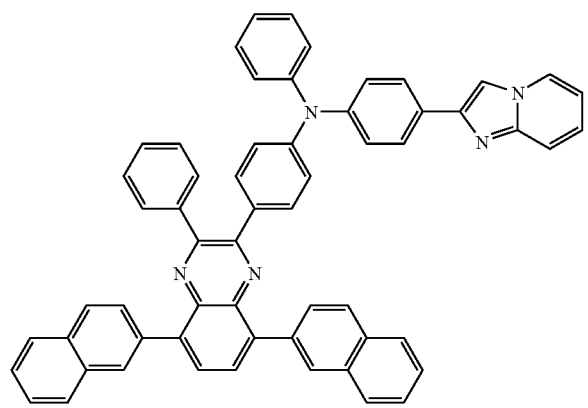
(305)
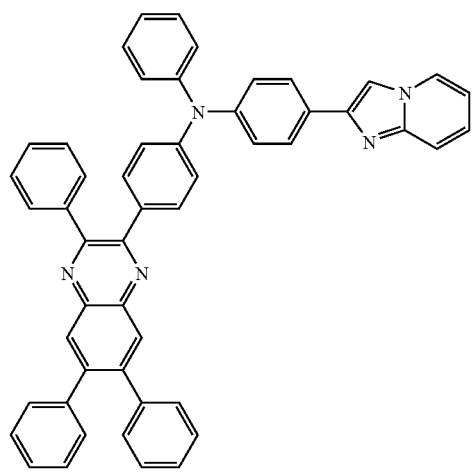

-continued
(306)
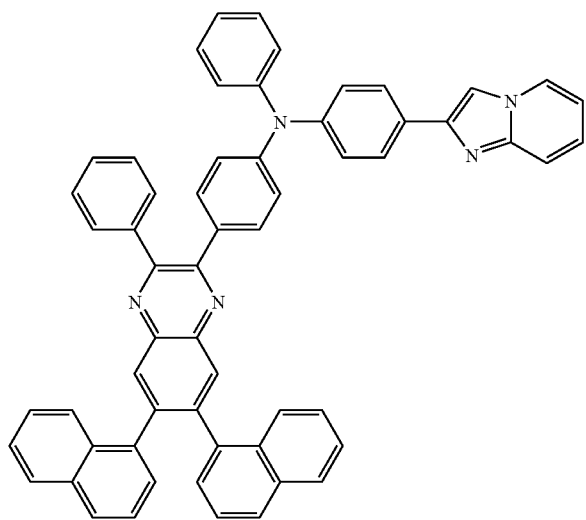
(307)
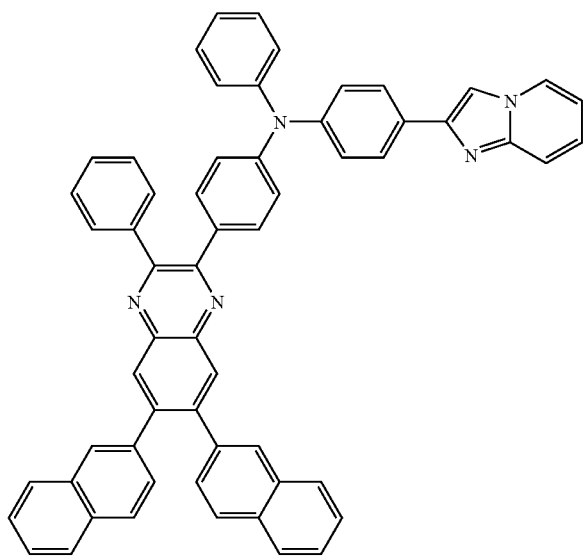
(308)
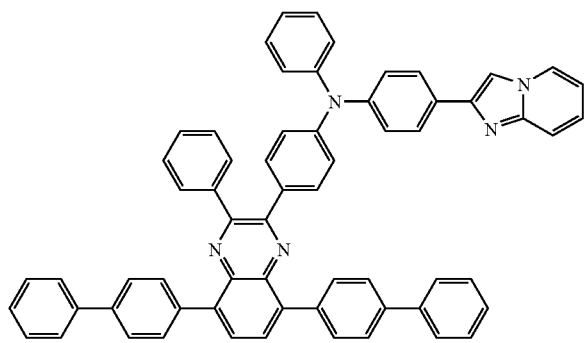
(309)
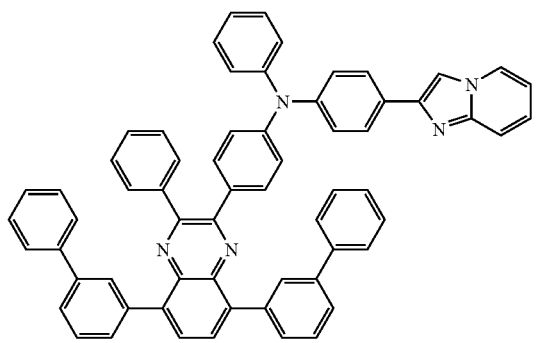
(310)
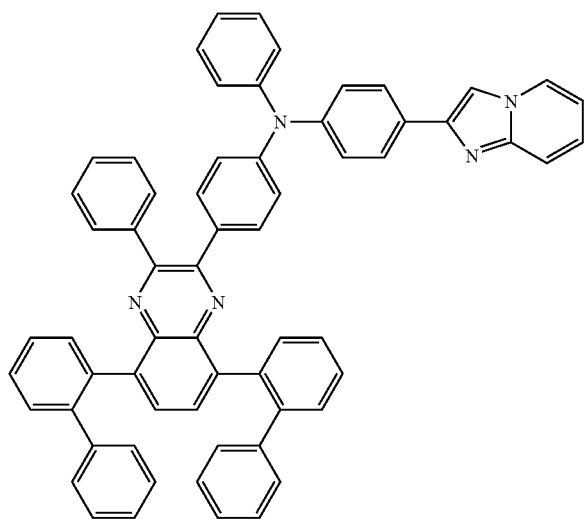
(311)
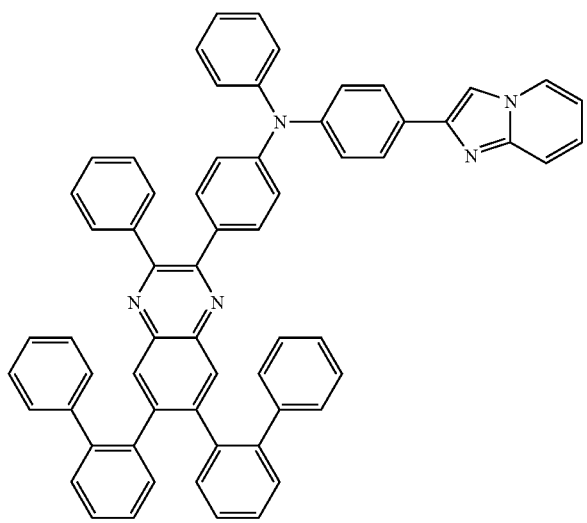

-continued
(312)
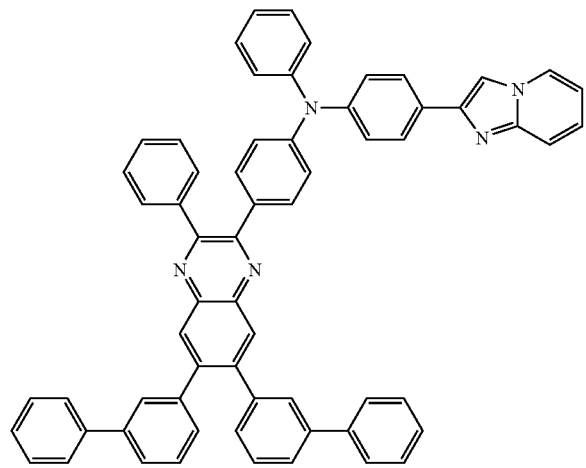
(313)
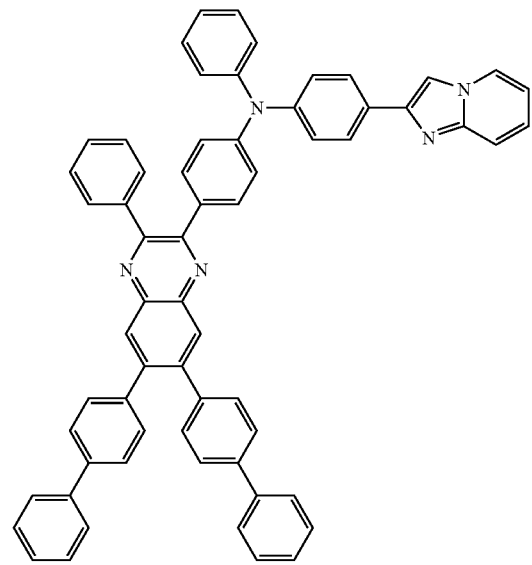
(314)
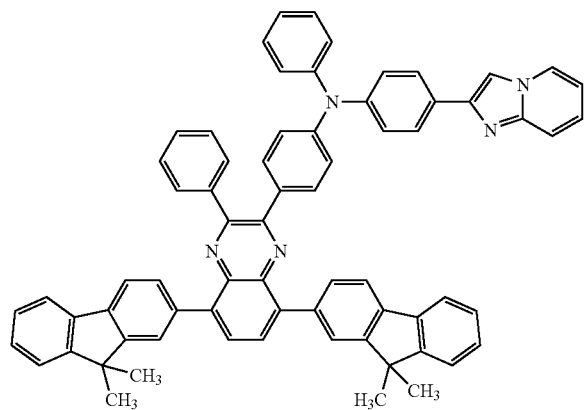
(315)
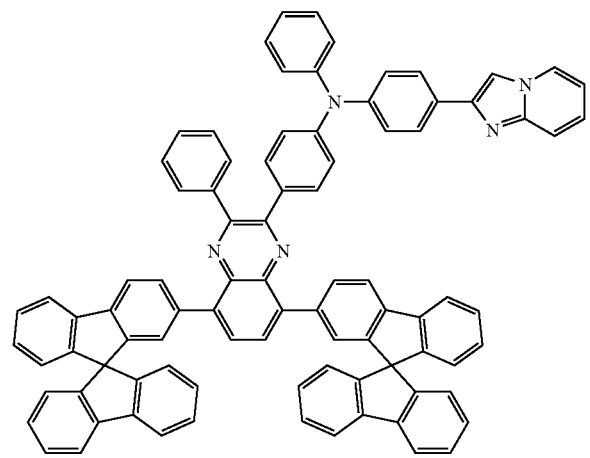
(316)
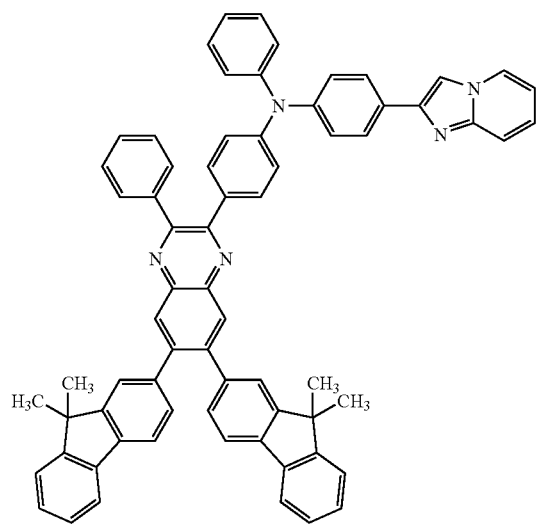
(317)
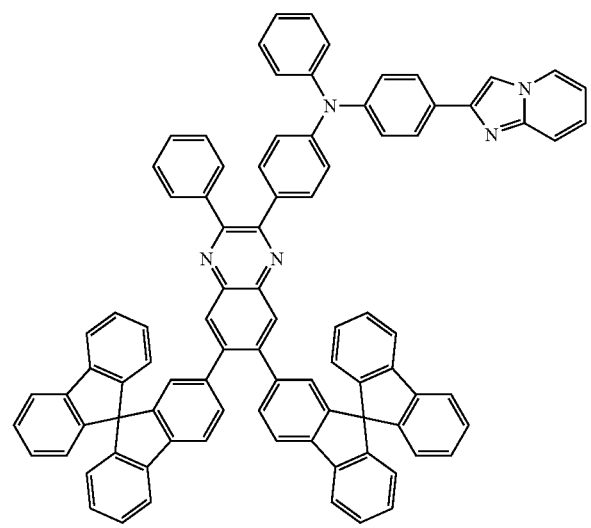

-continued
(318)
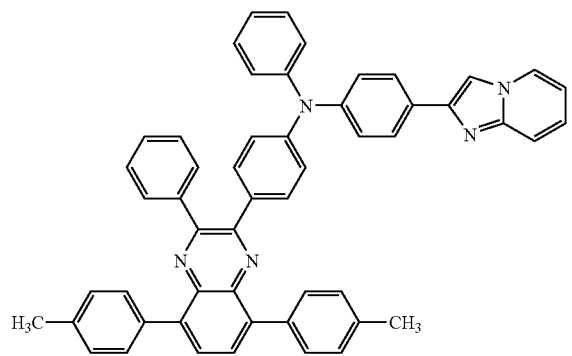
(319)
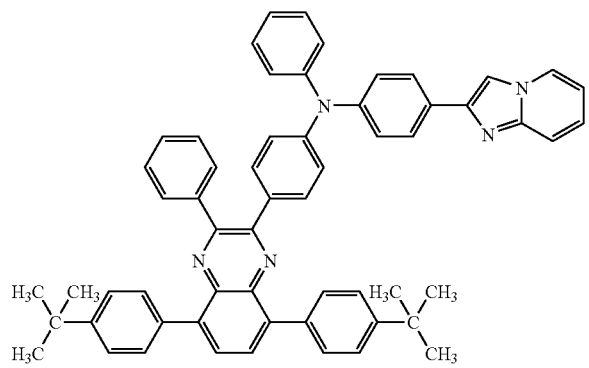
(320)
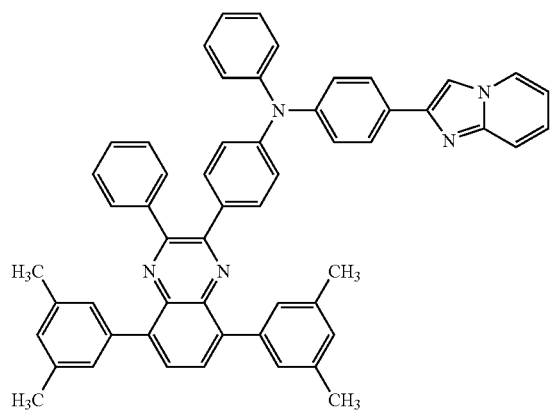
(321)
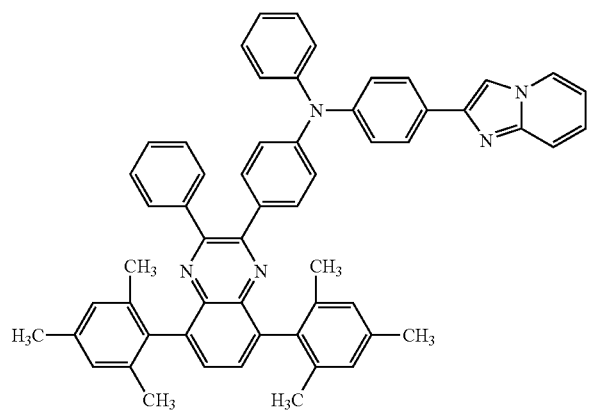
(322)
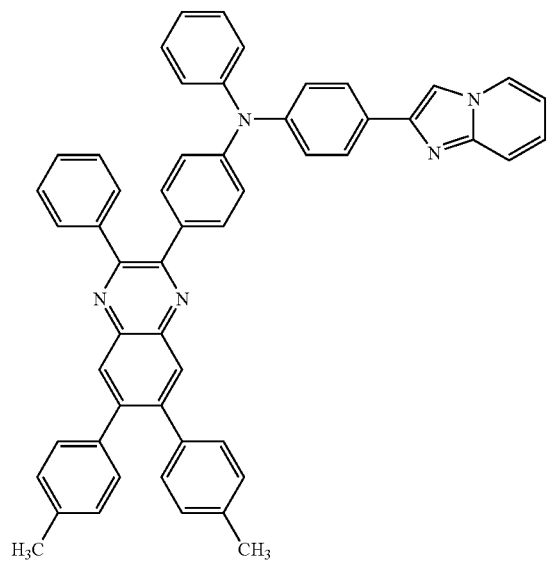
(323)
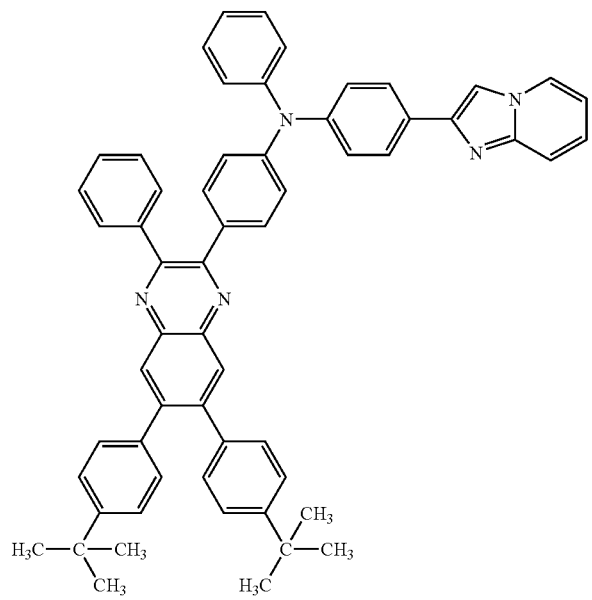

-continued
(324)
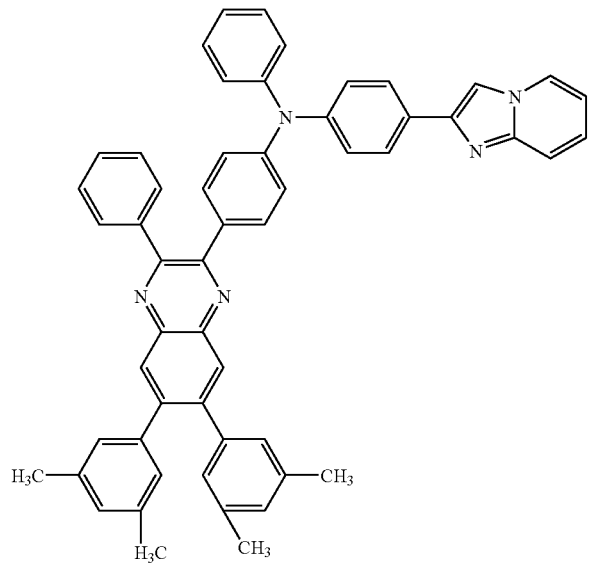
(325)
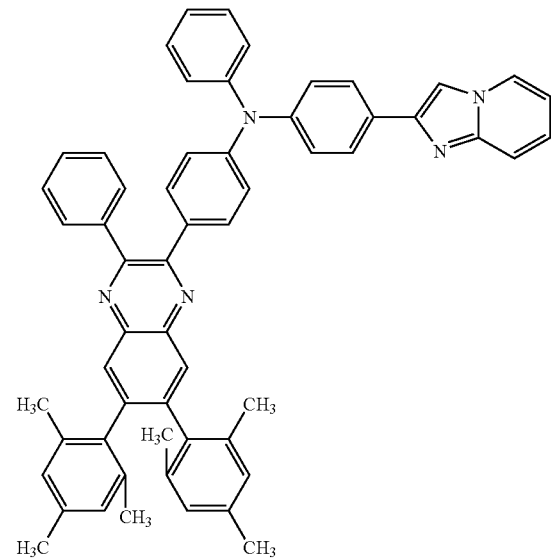
(326)
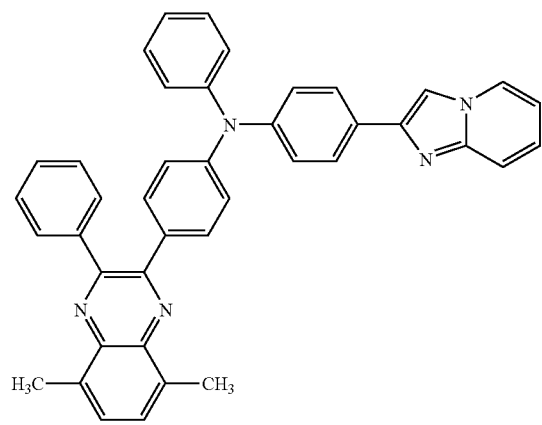
(327)
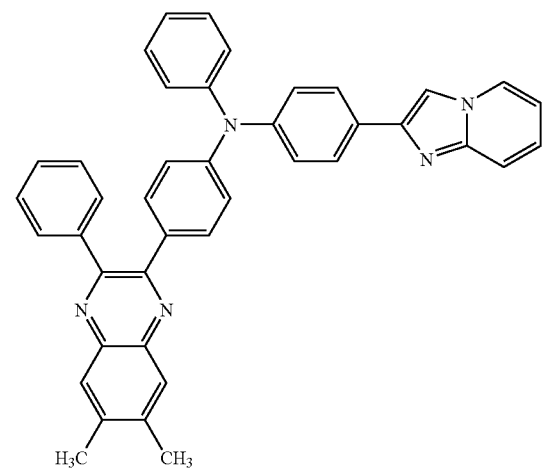
(328)
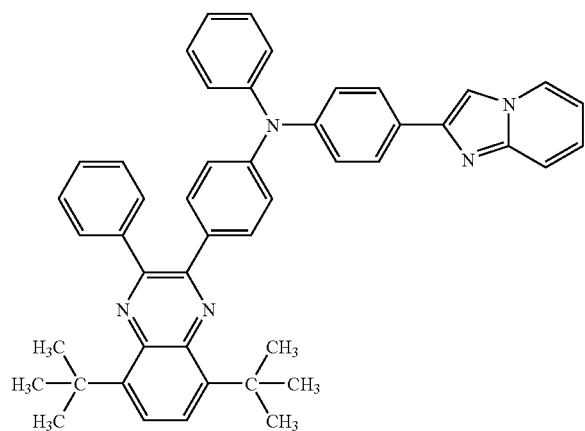
(329)
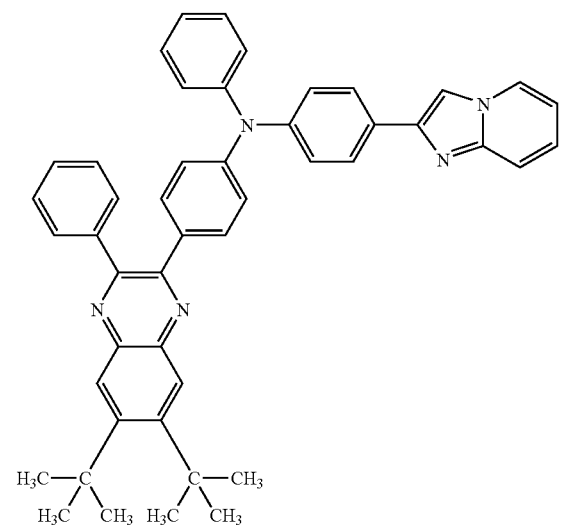

-continued
(330)
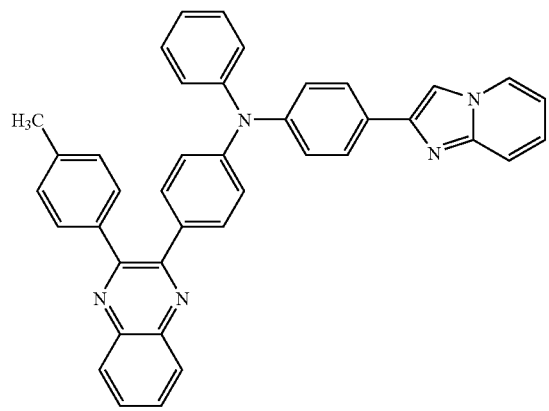
(331)
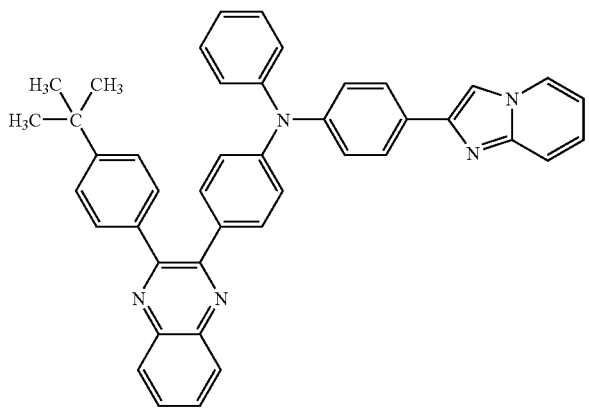
(332)
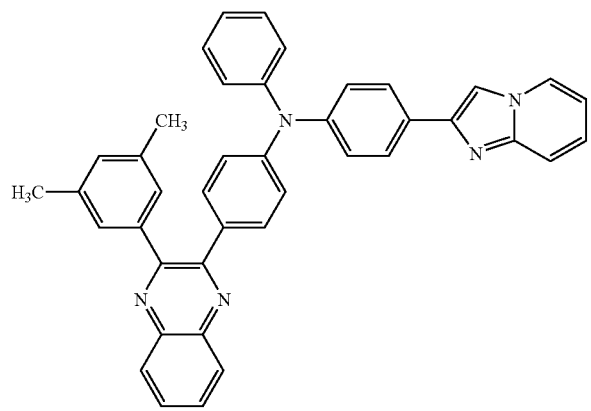
(333)
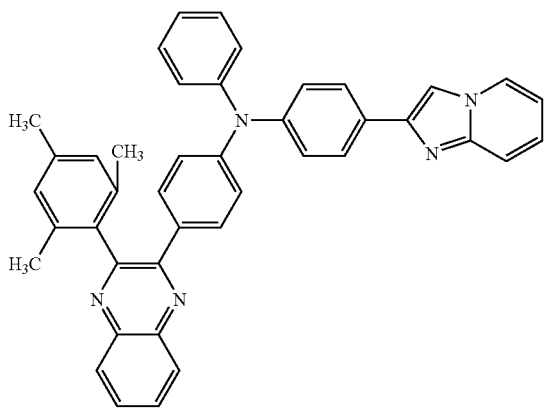
(334)
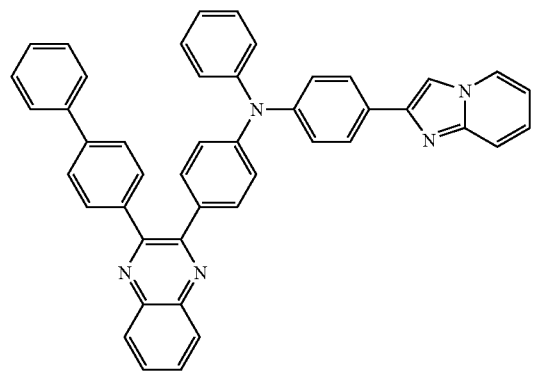
(335)
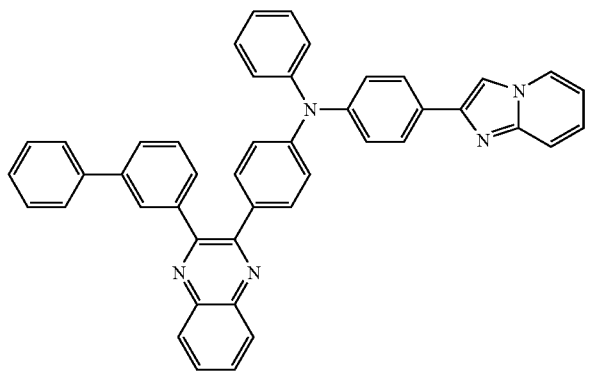
(336)
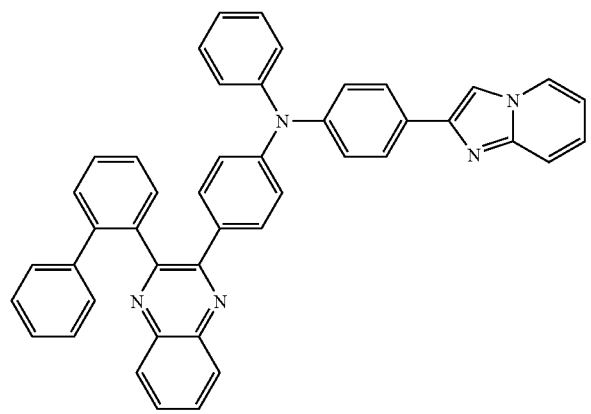
(337)
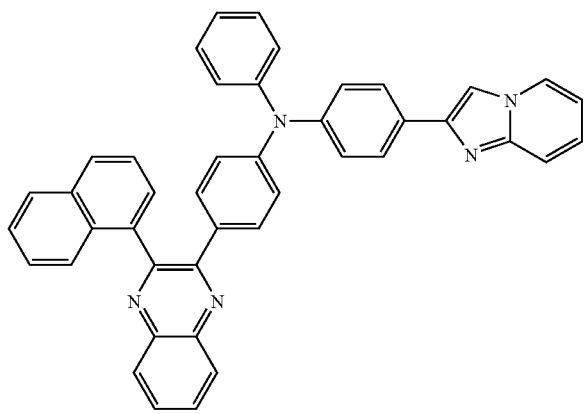

-continued
(338)
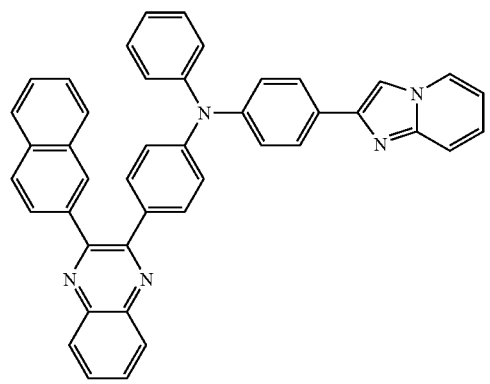
(339)
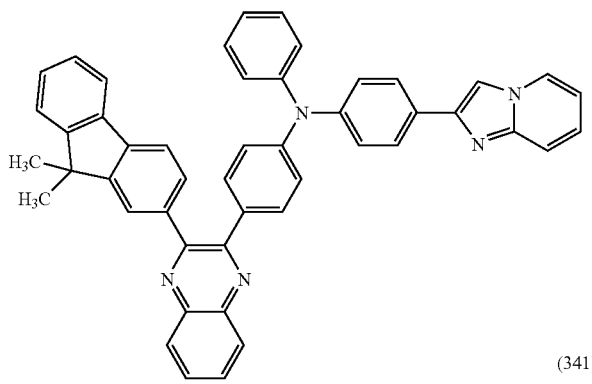
(340)
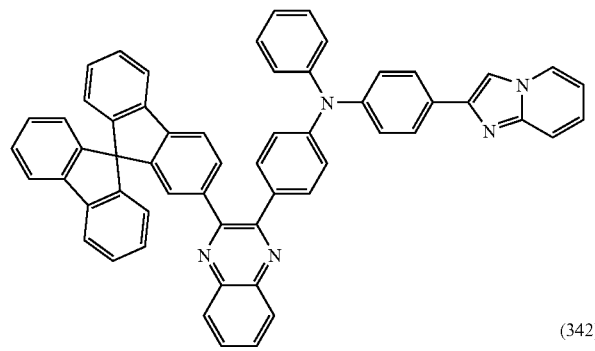
(341)
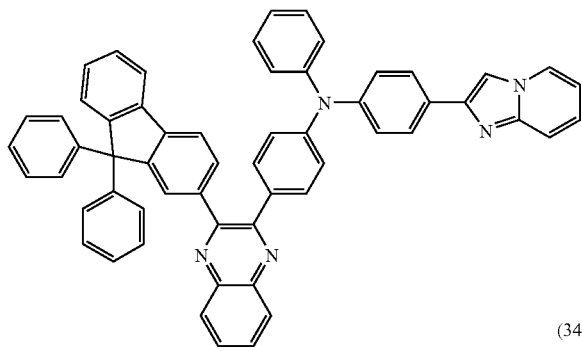
(342)
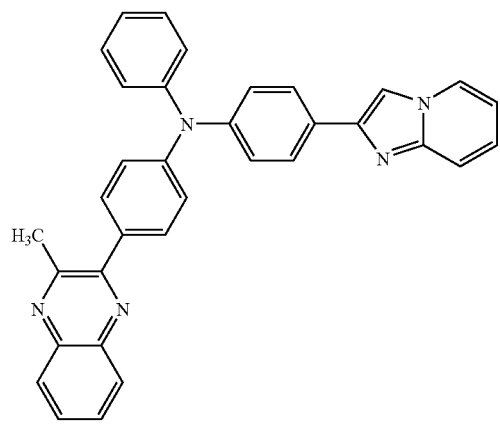
(343)
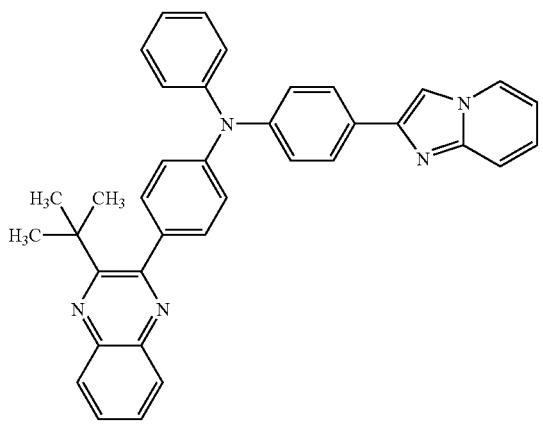
(344)
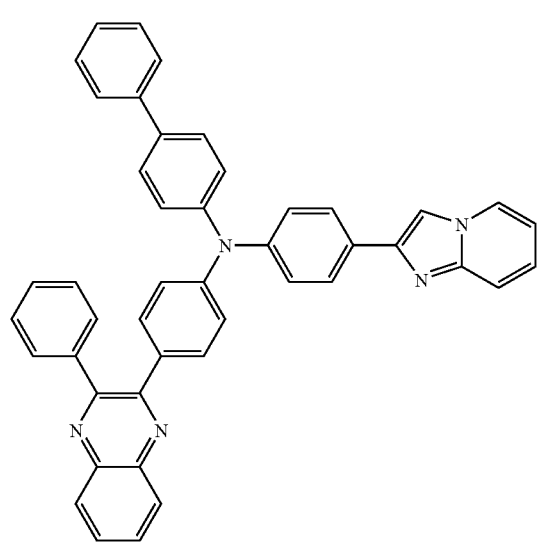
(345)
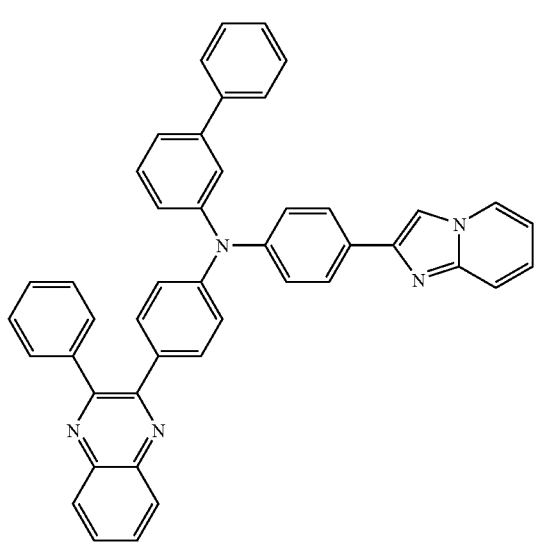

-continued
(346)
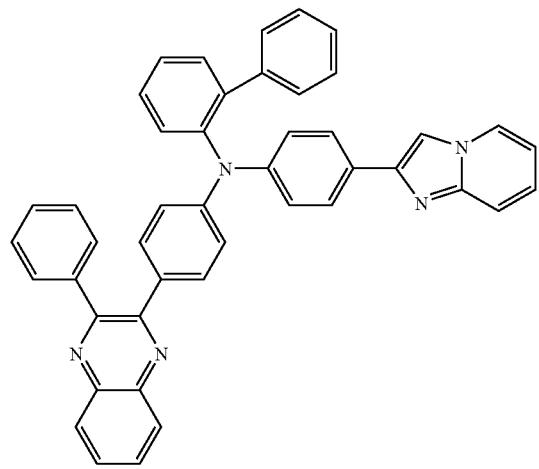
(347)
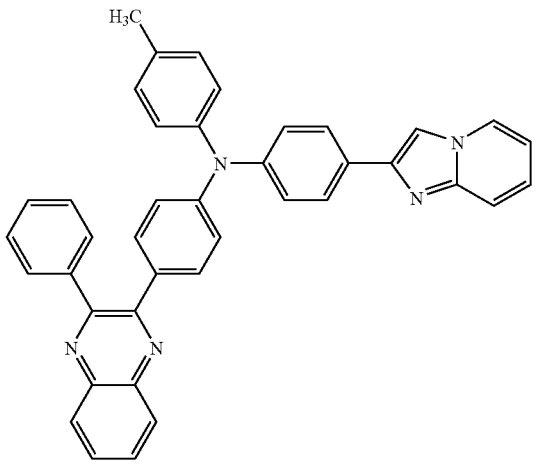
(348)
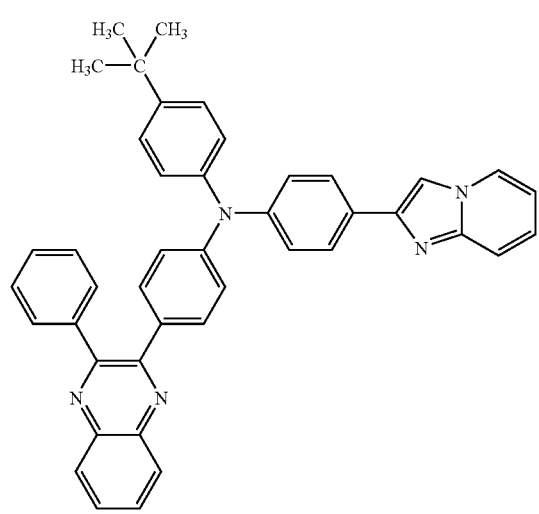
(349)
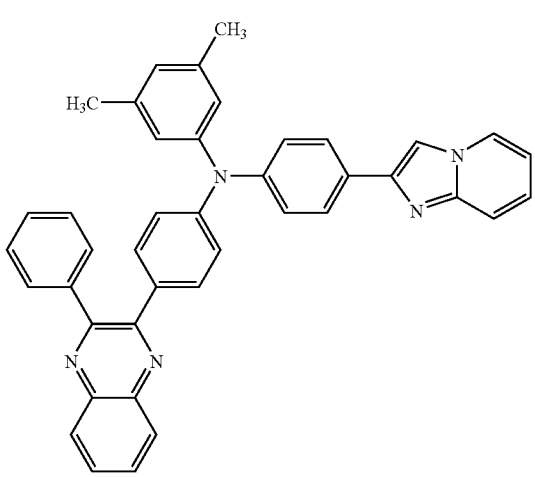
(350)
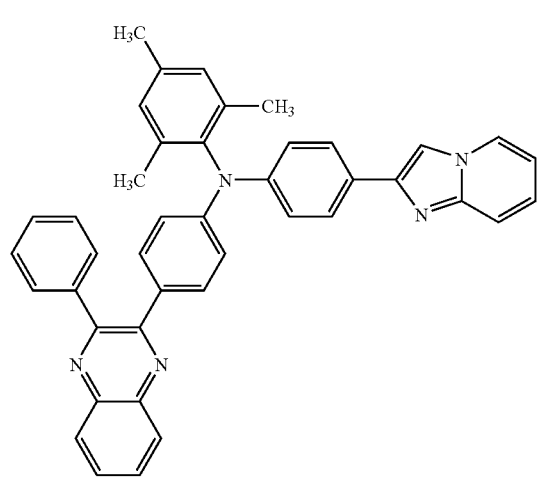
(351)
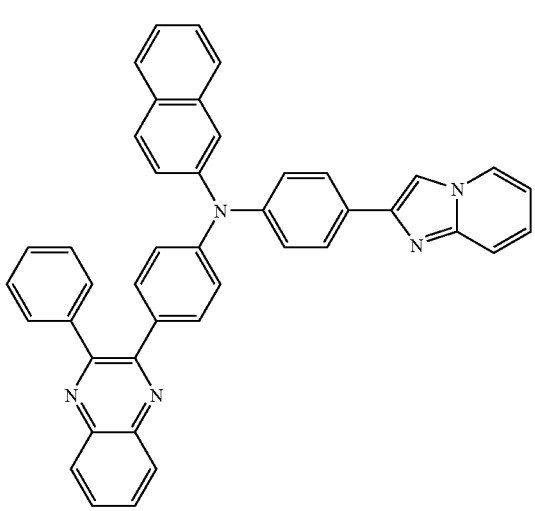

-continued
(352)
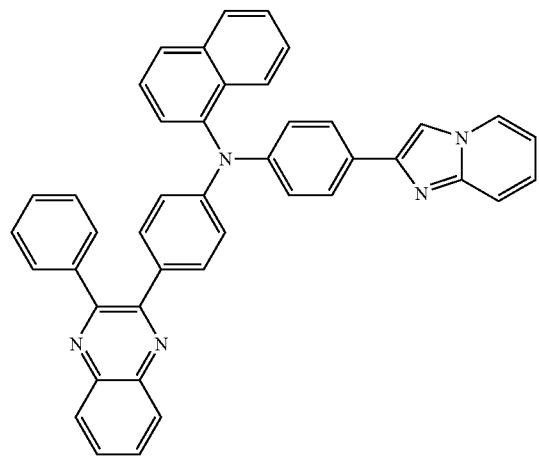
(353)
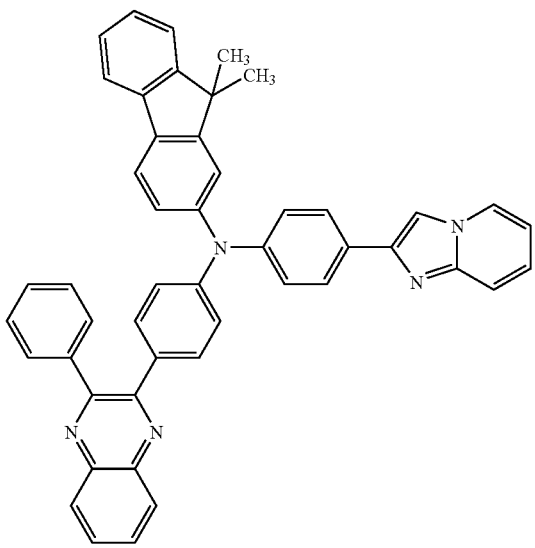
(354)
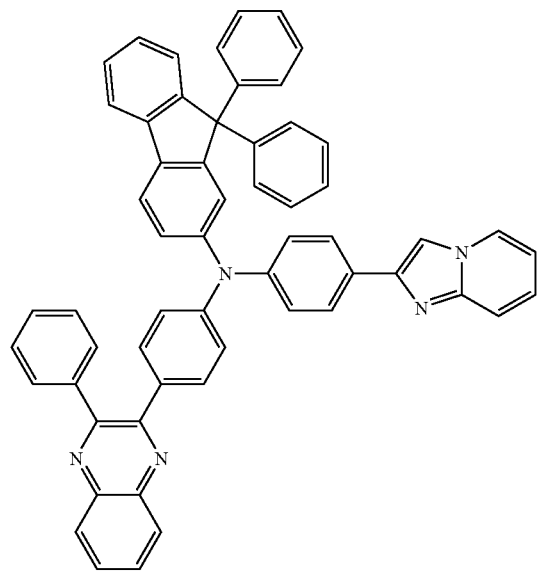
(355)
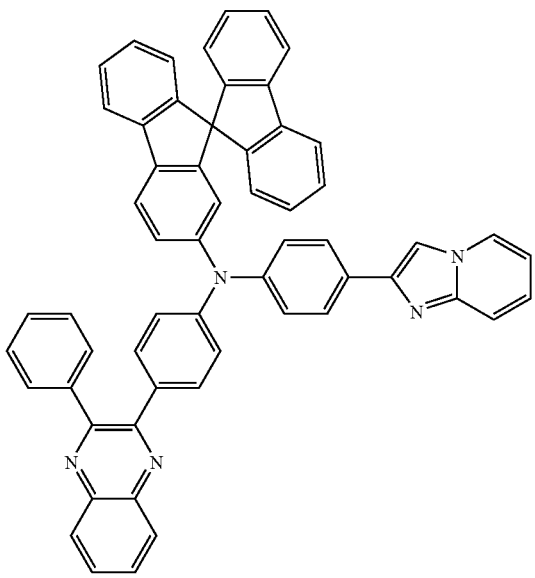
(356)
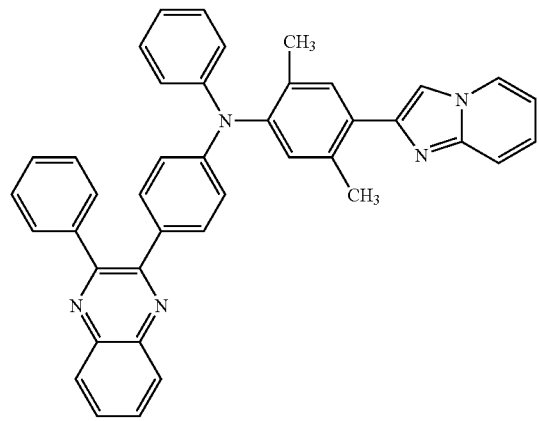
(357)
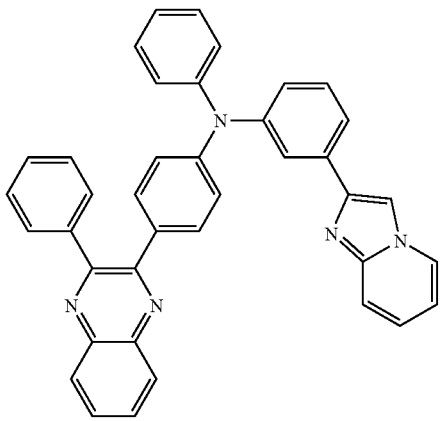

(358)
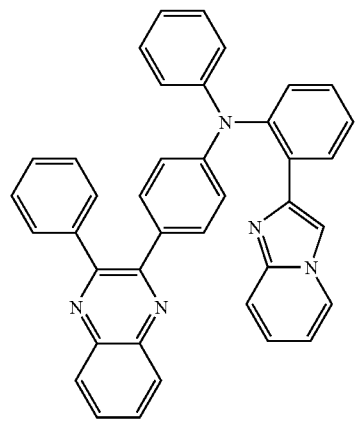
(359)
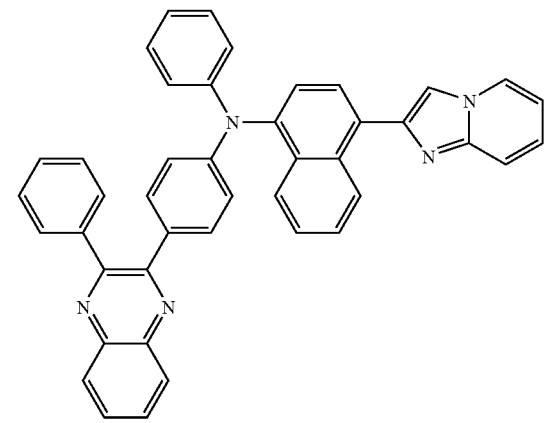
(360)
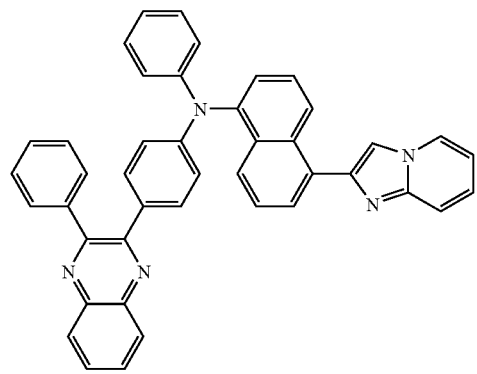
(361)
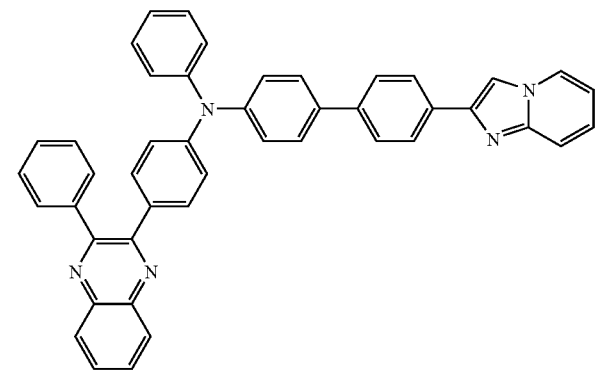
(362)
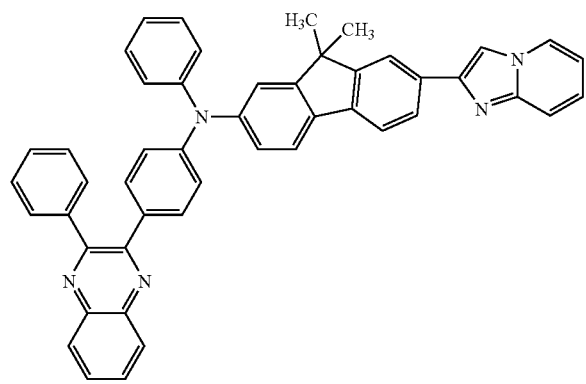
(363)
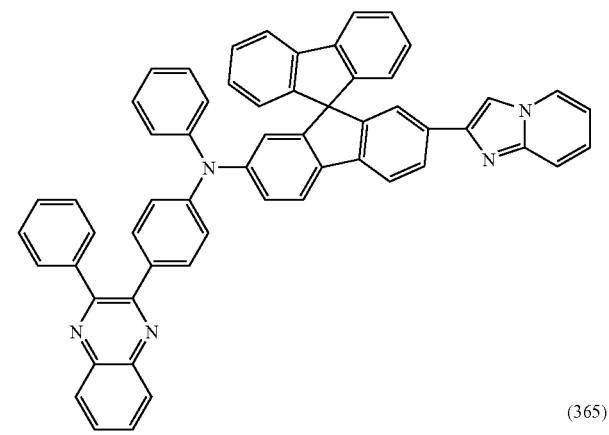
(364)
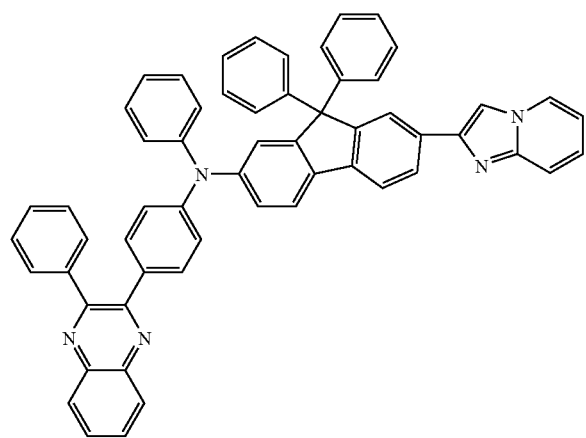
(365)
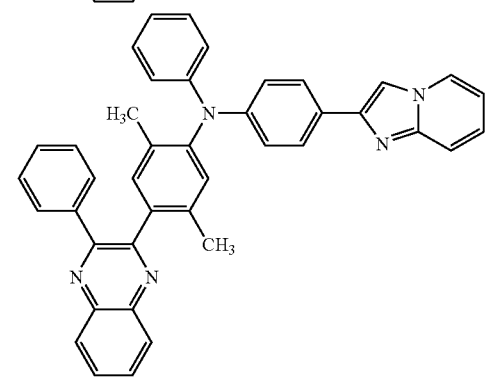

(366)
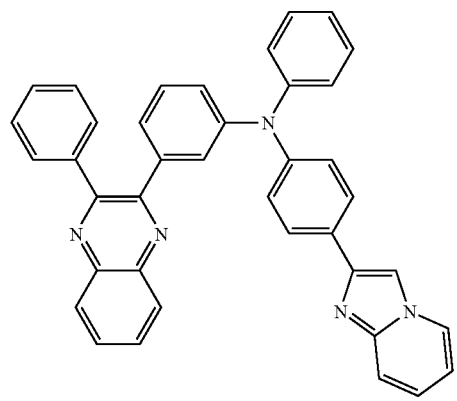
(367)
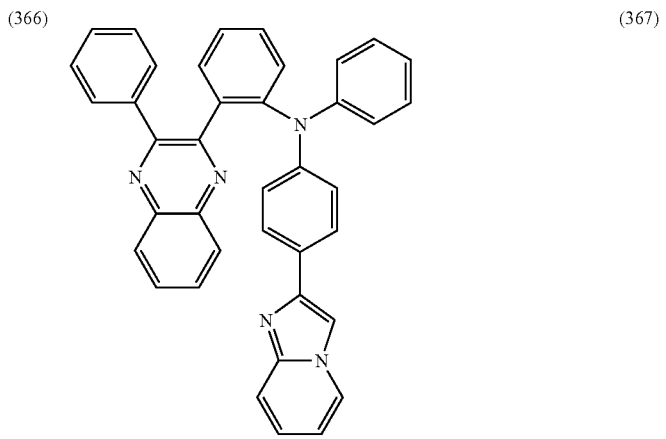
(368)
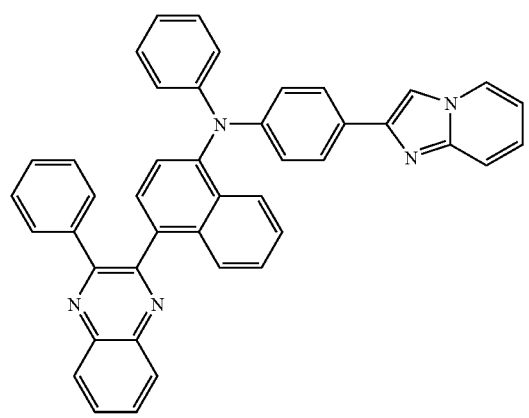
(369)
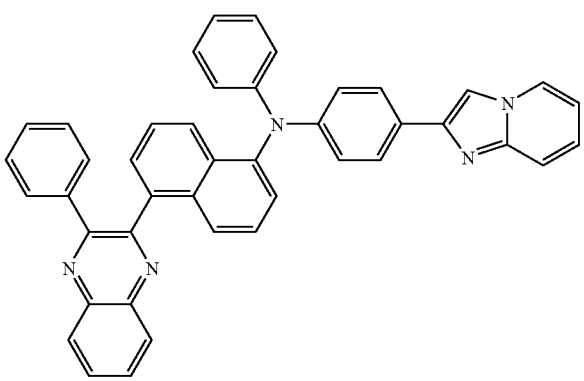
(370)
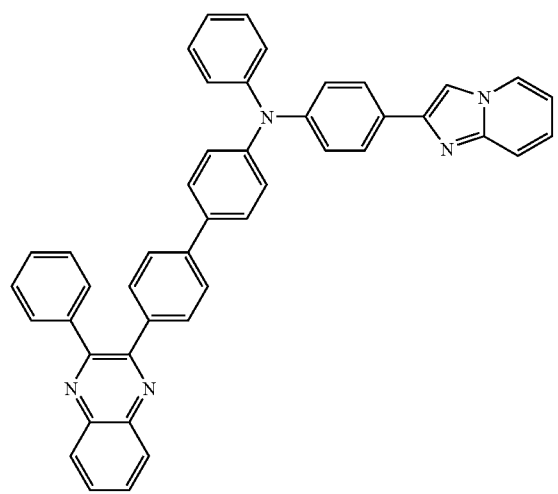
(371)
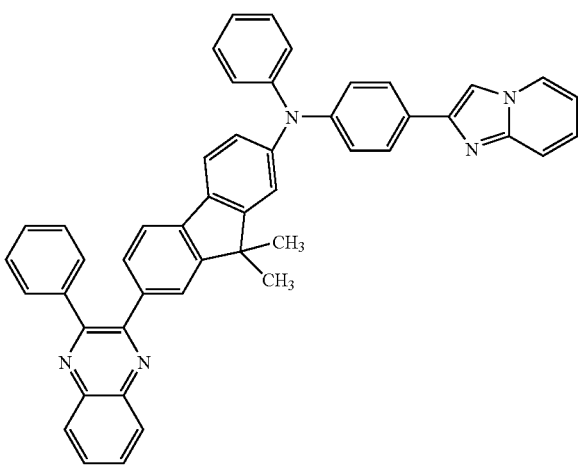

(372)
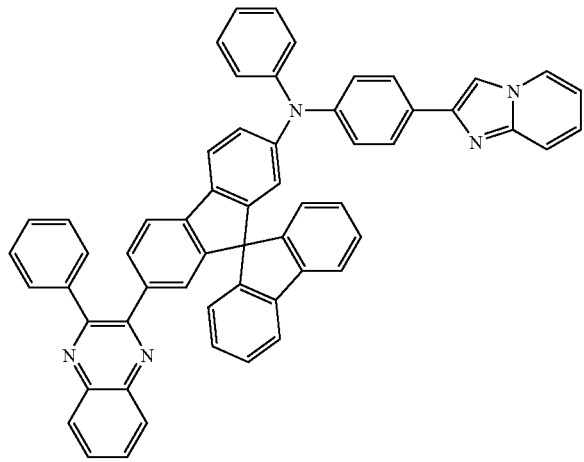
(373)
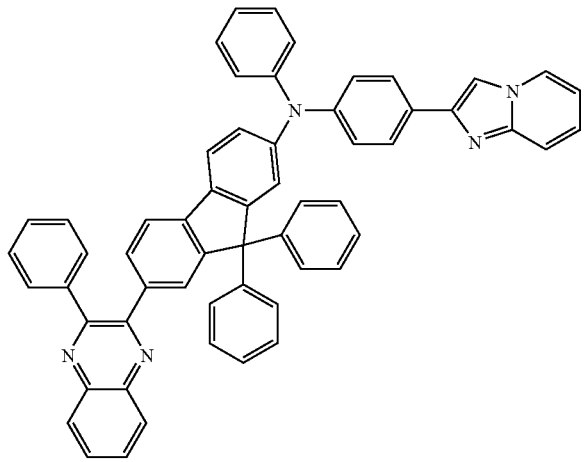
(401)
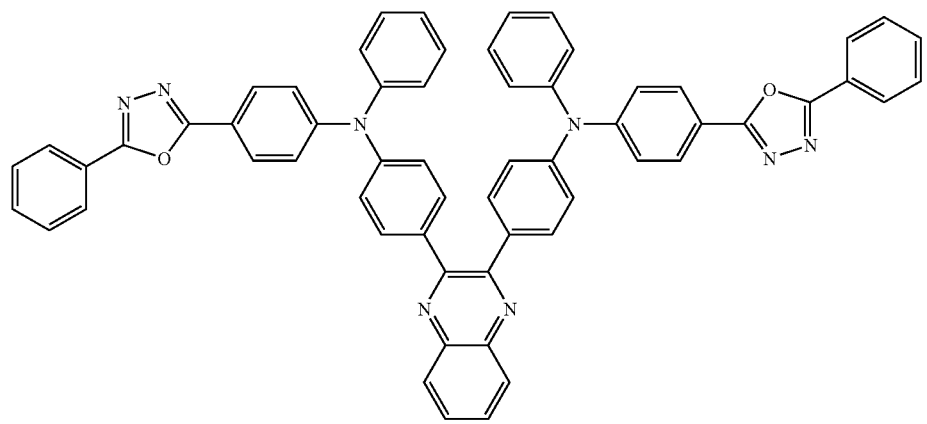
(402)
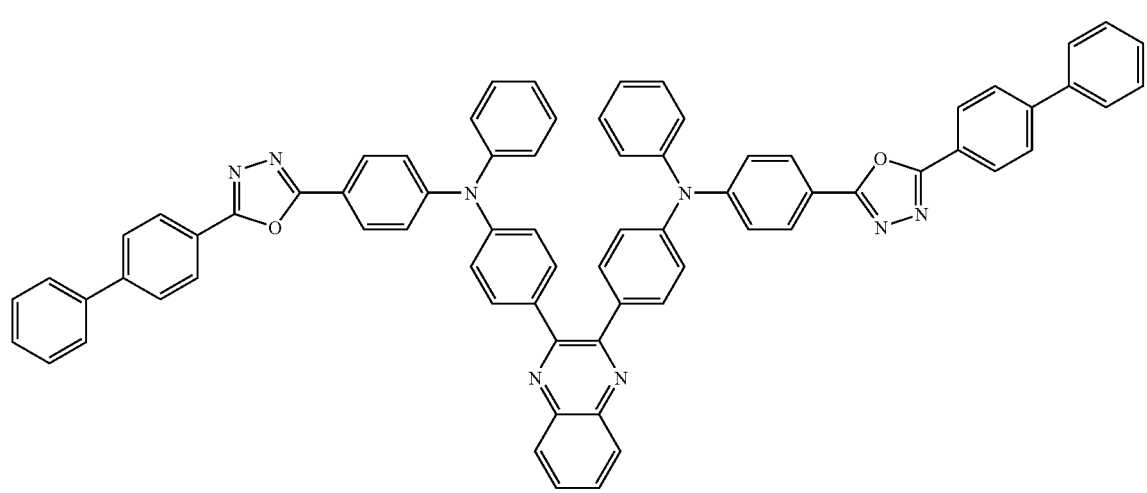

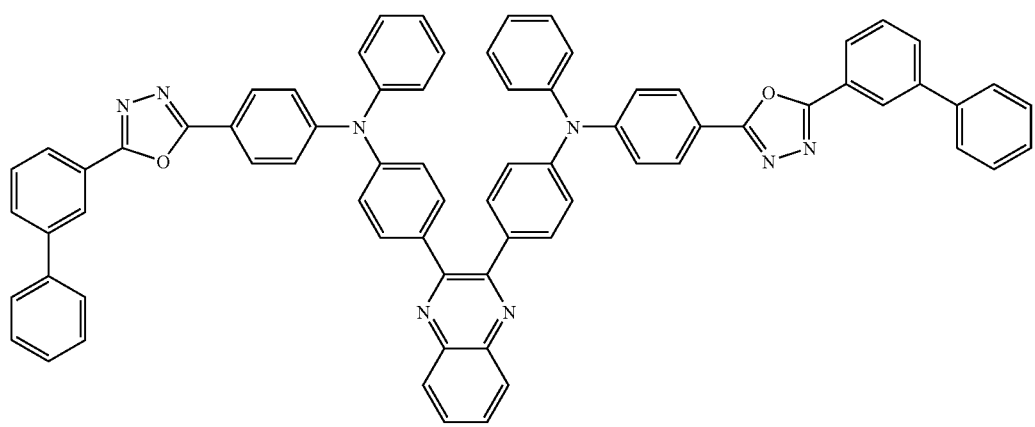
(403)
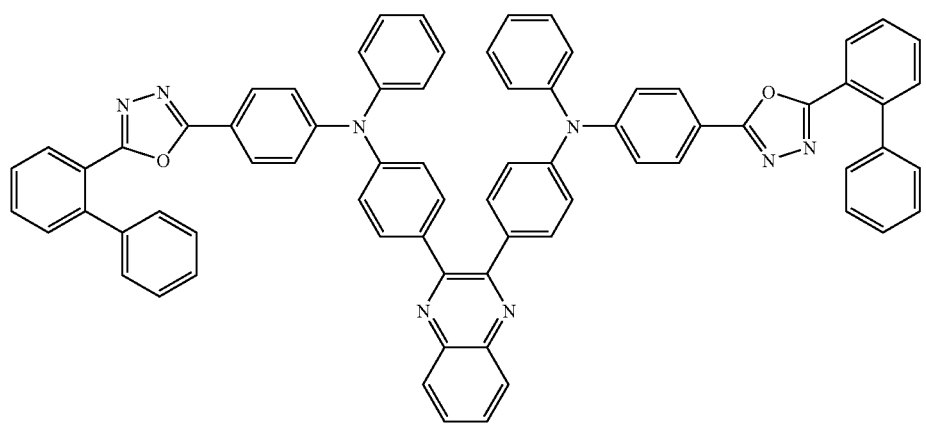
(404)
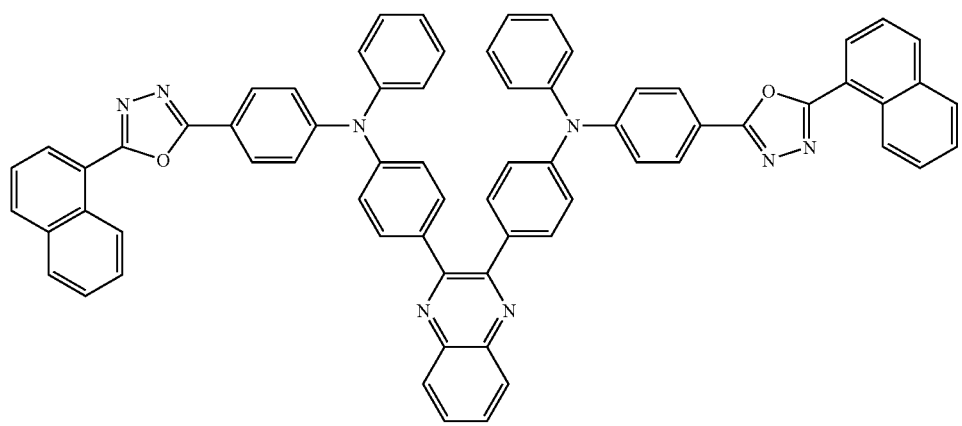
(405)

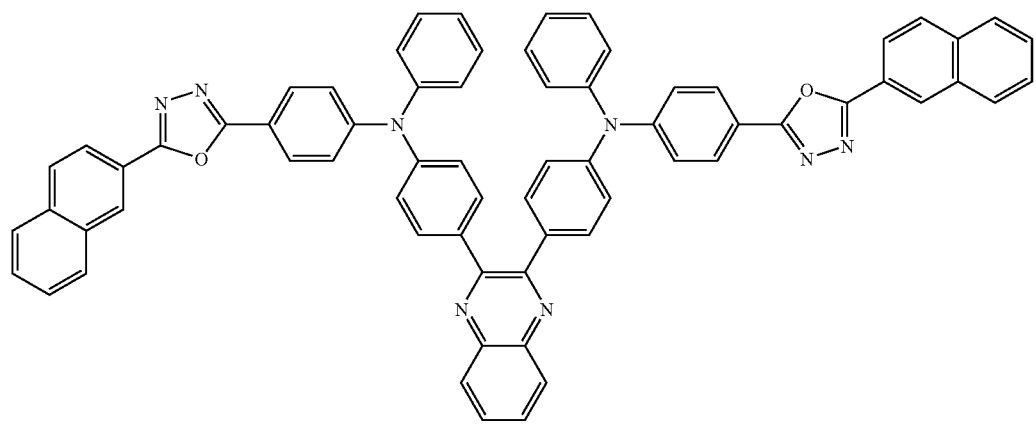
(406)
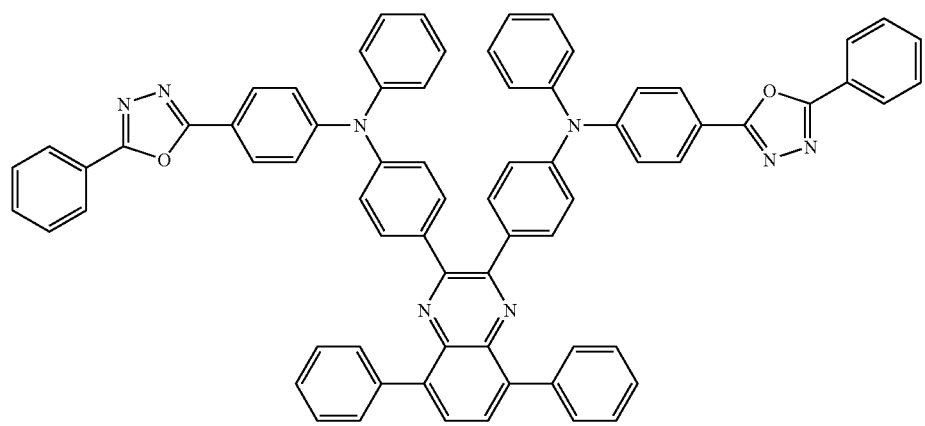
(407)
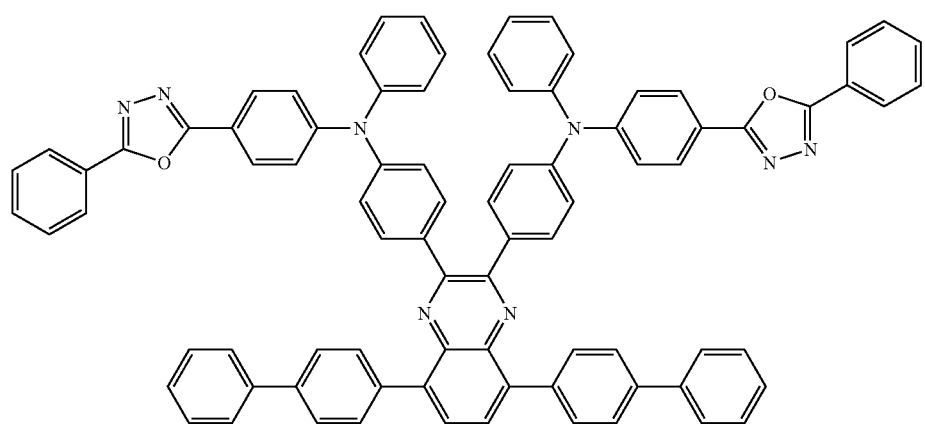
(408)

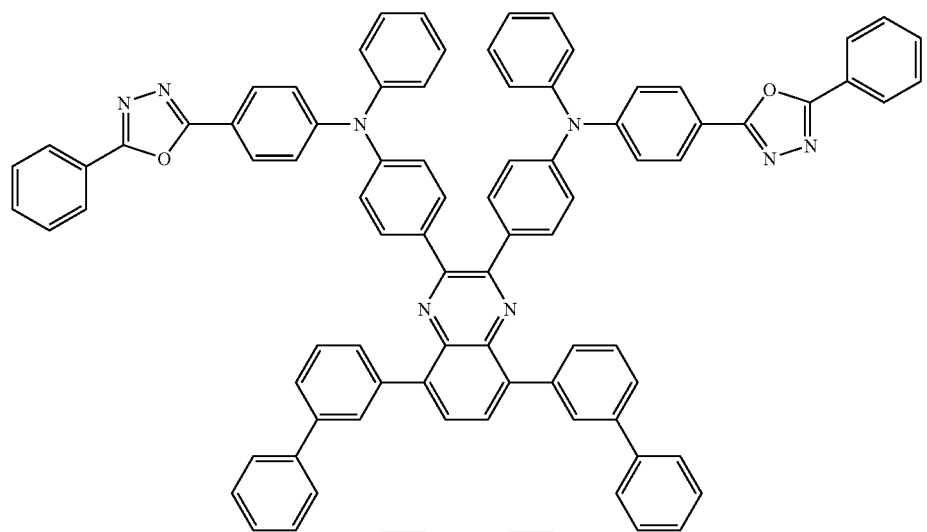
(409)
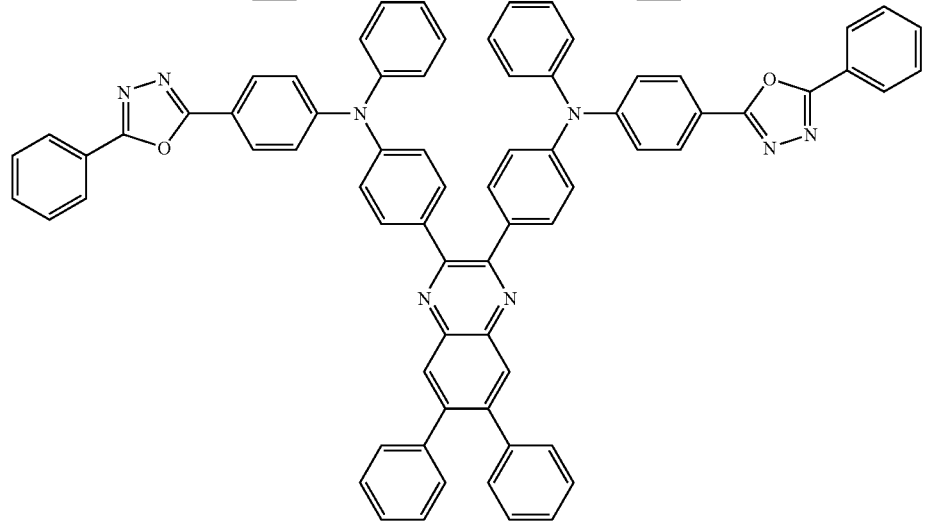
(410)
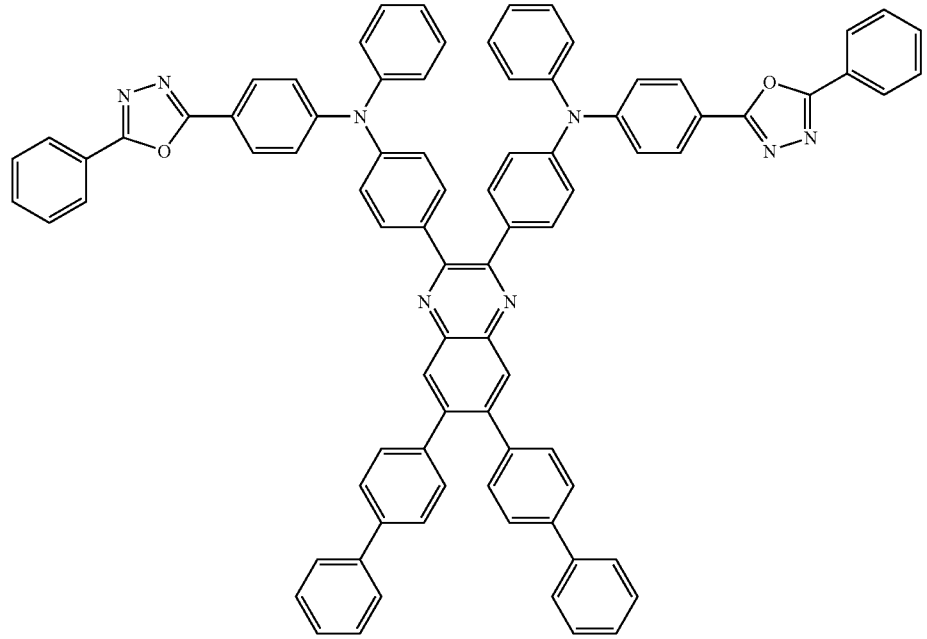
(411)

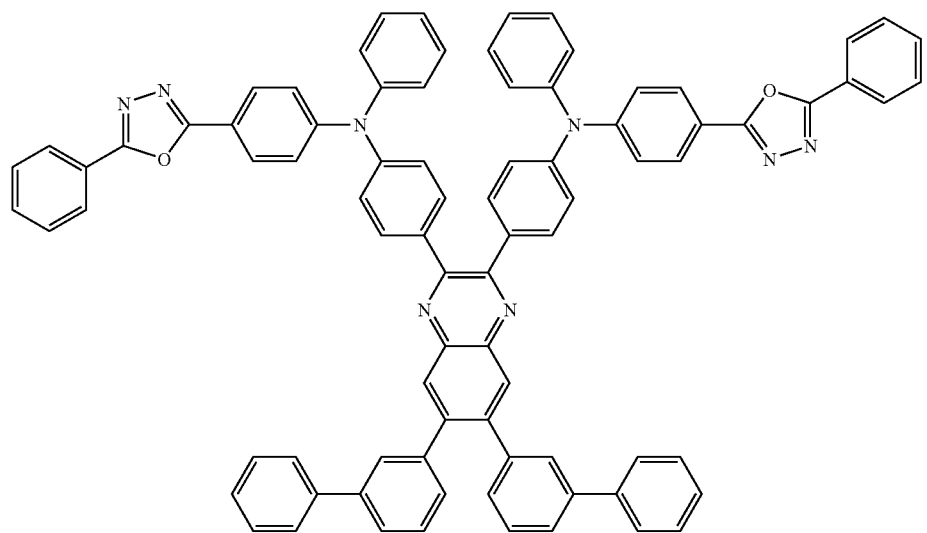
(412)
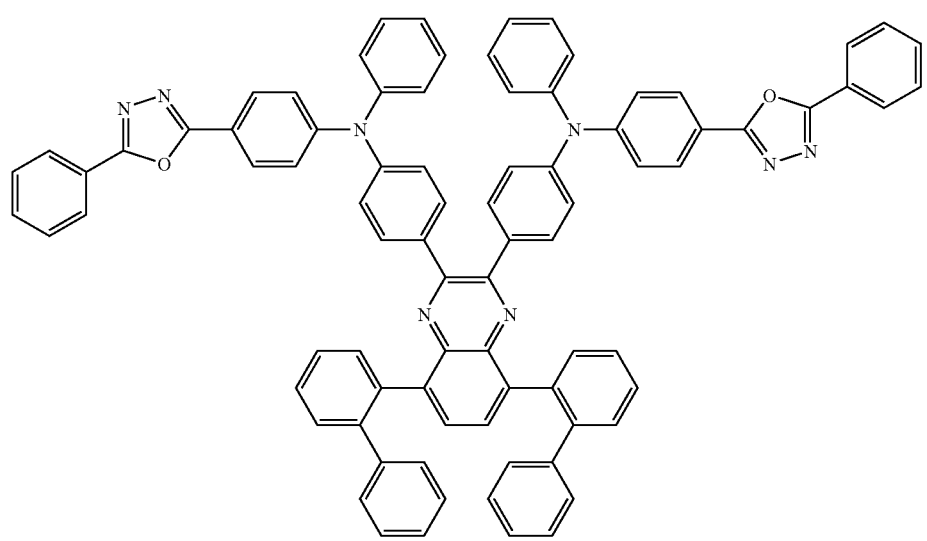
(413)
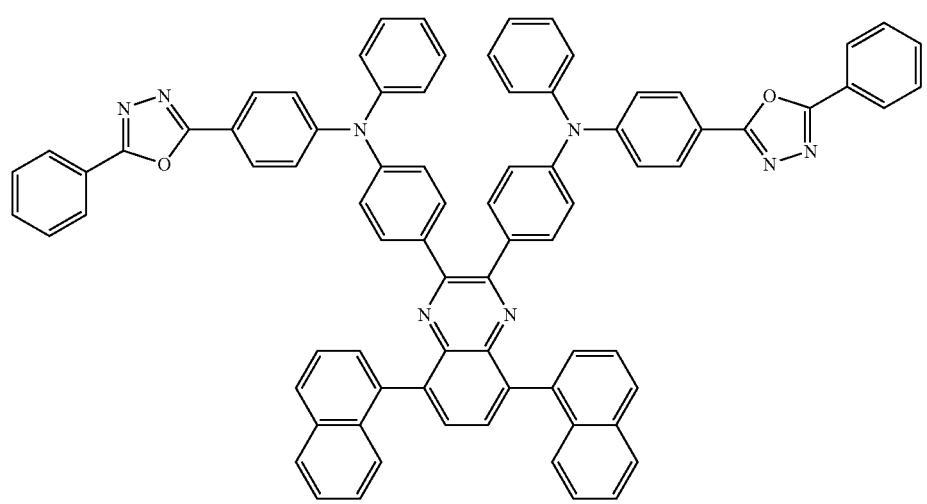
(414)

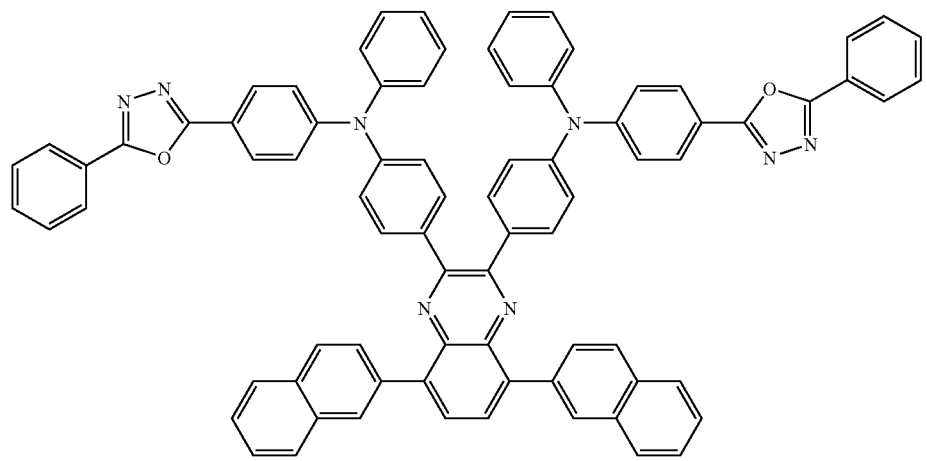
(415)
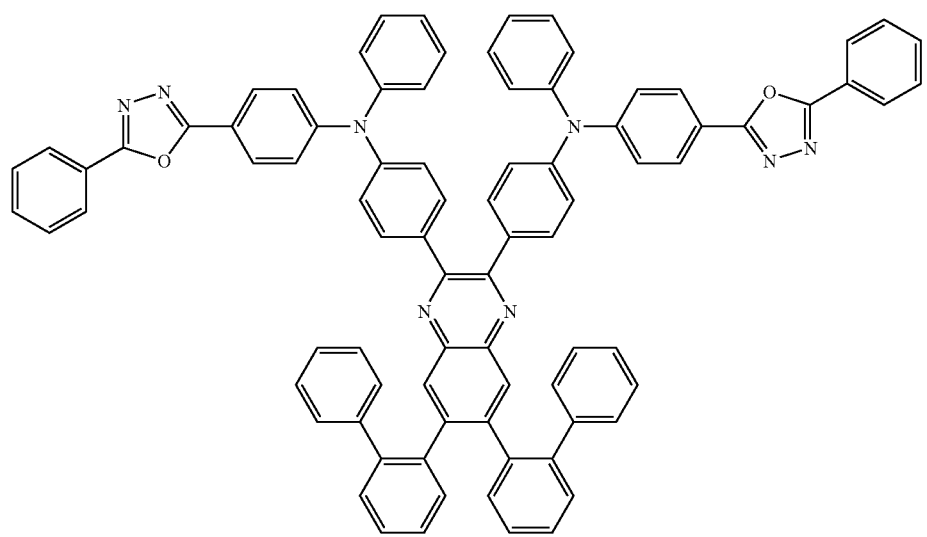
(416)
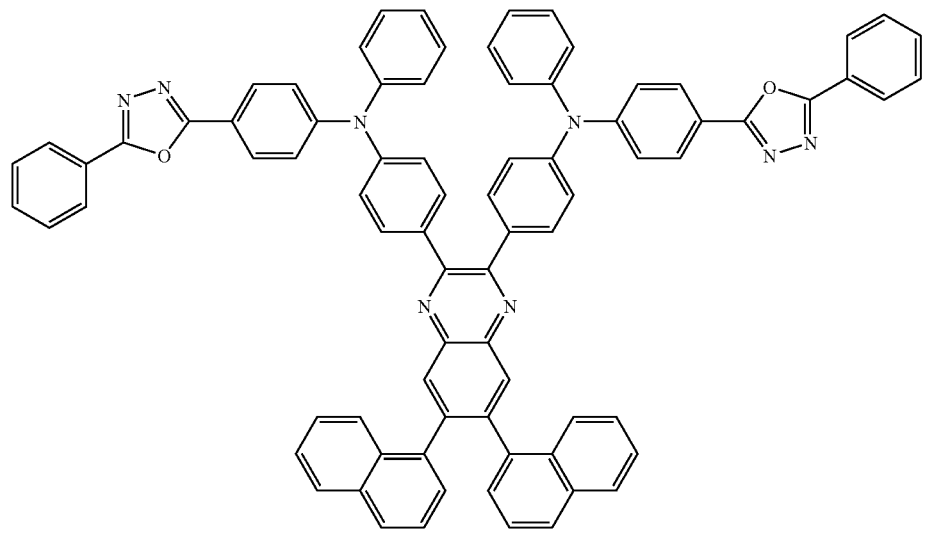
(417)

-continued
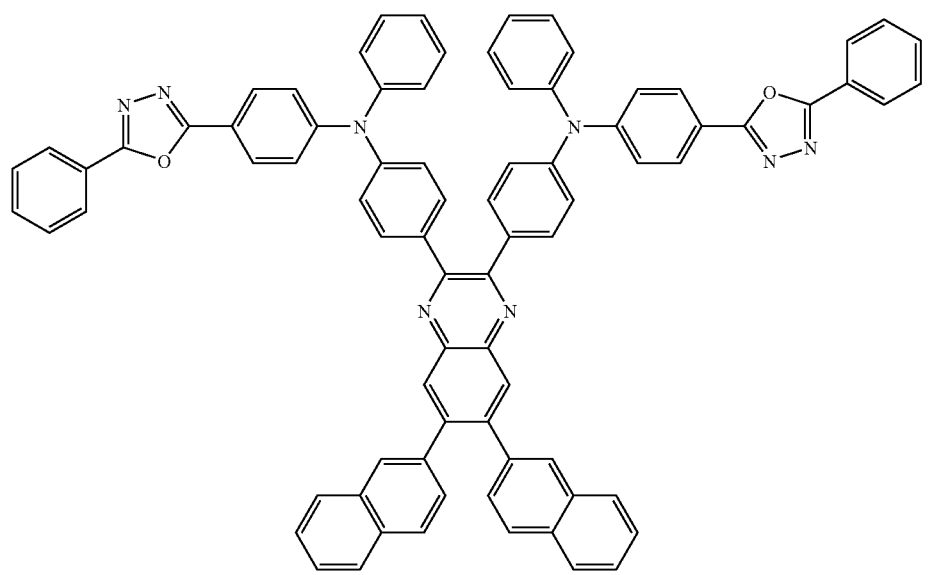
(418)
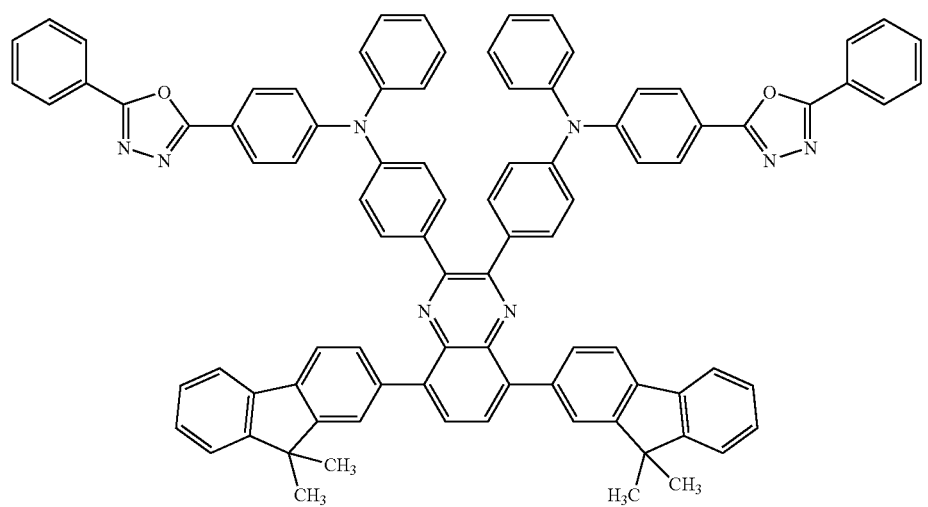
(419)
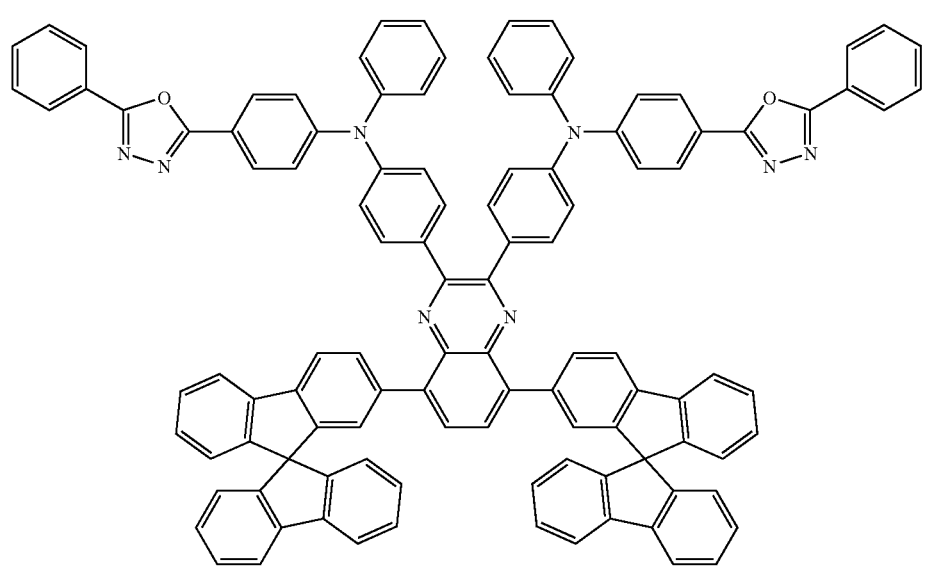
(420)

-continued
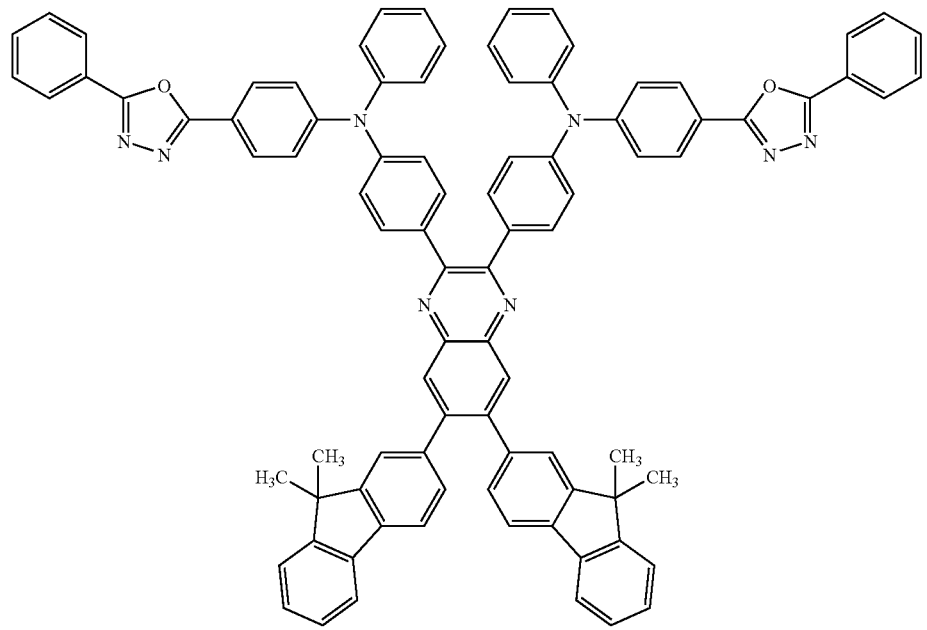
(421)
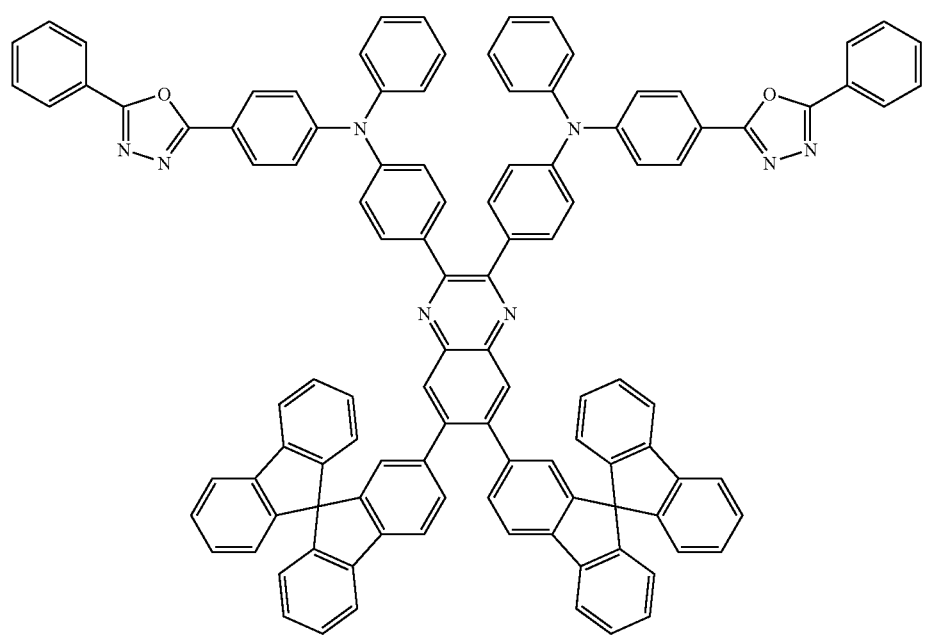
(422)
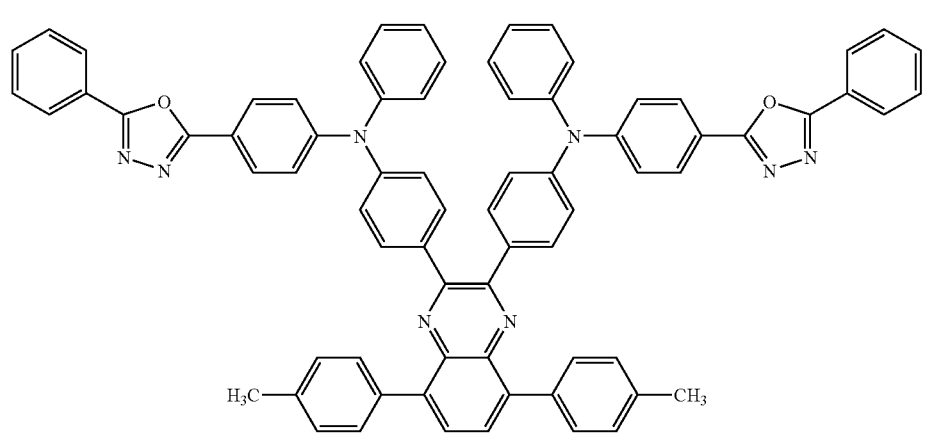
(423)

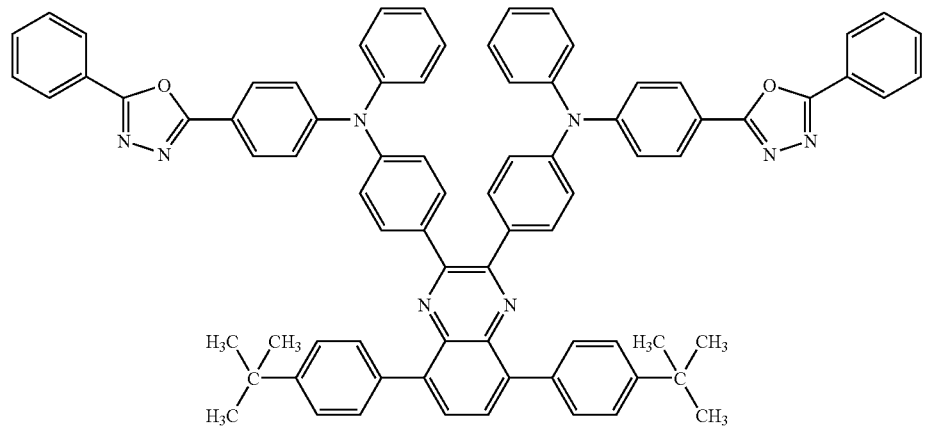
(424)
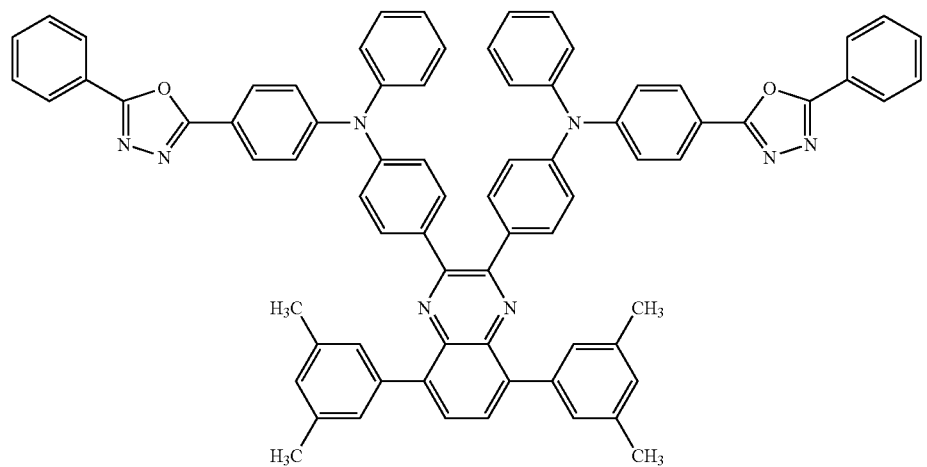
(425)
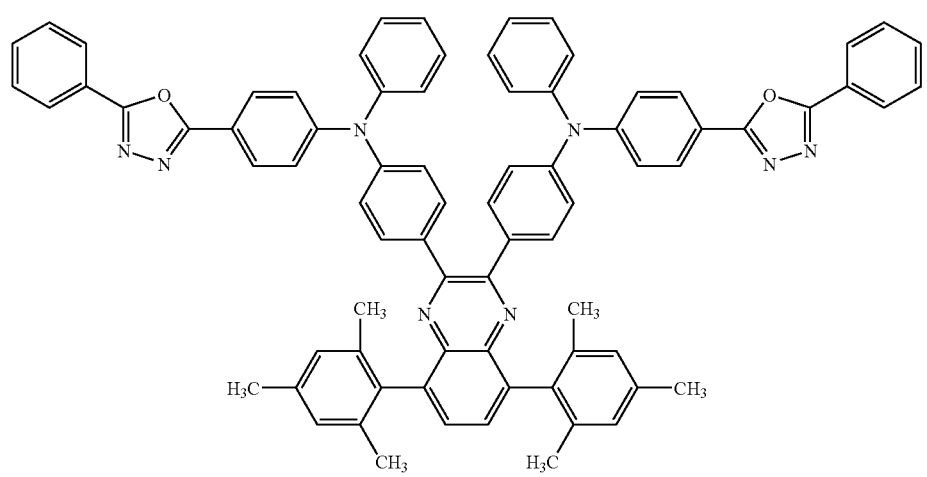
(426)

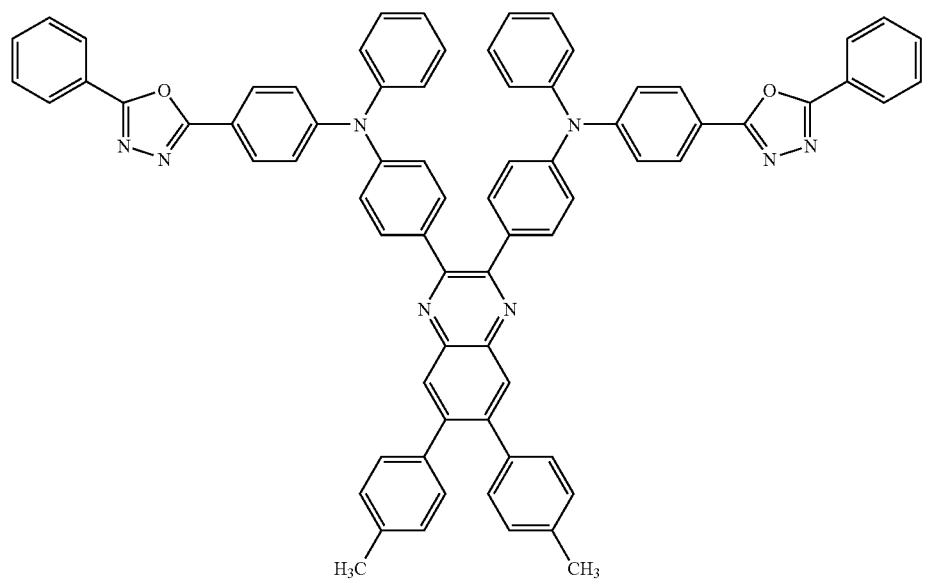
(427)
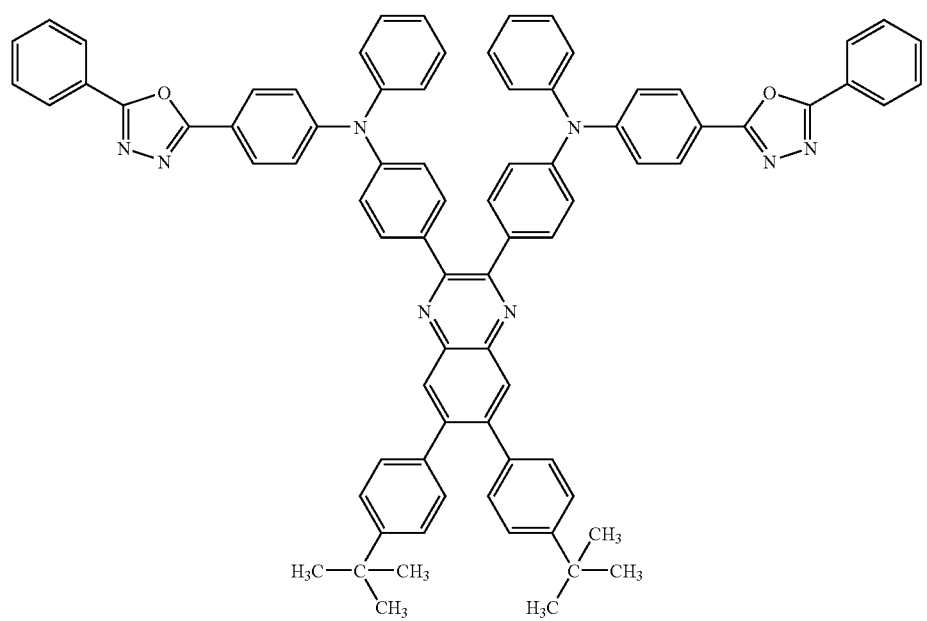
(428)

-continued
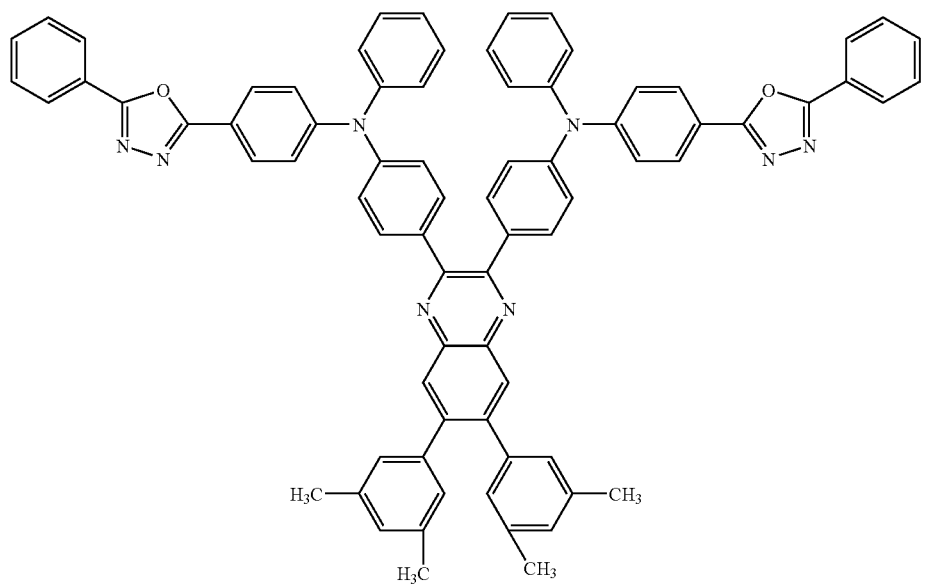
(429)
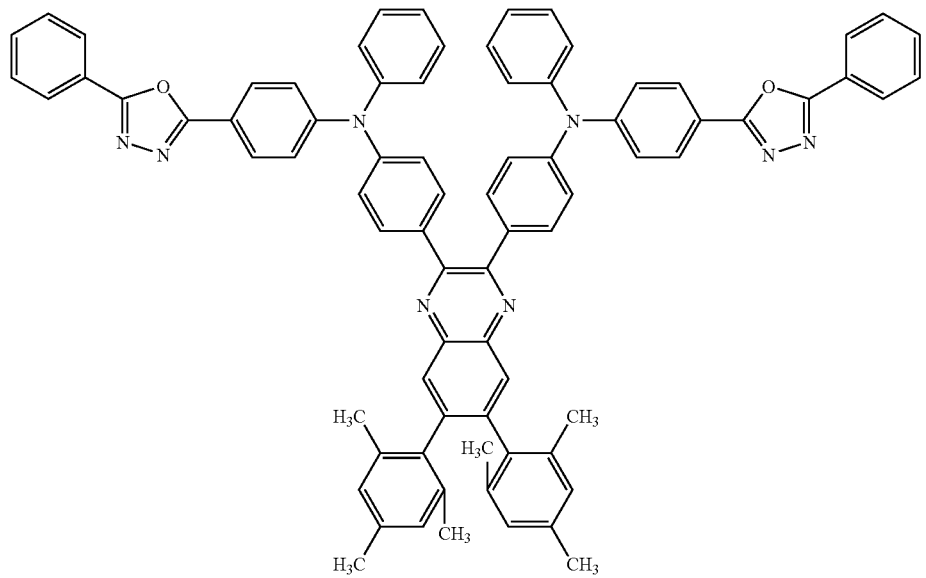
(430)
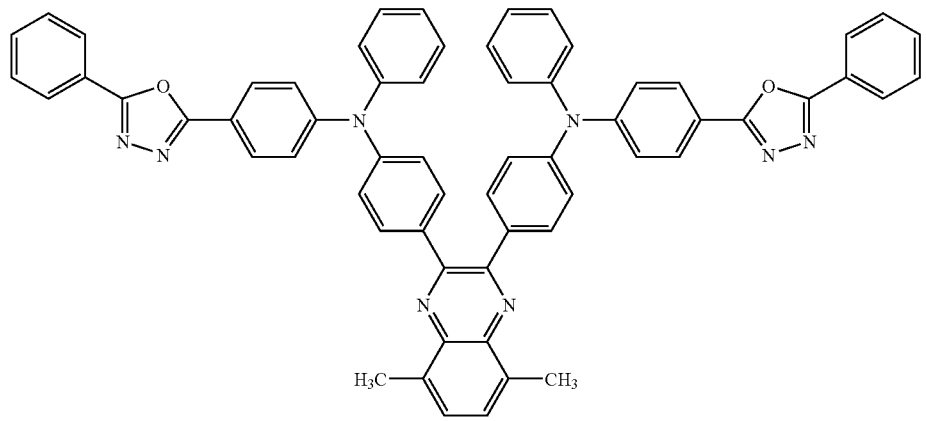
(431)

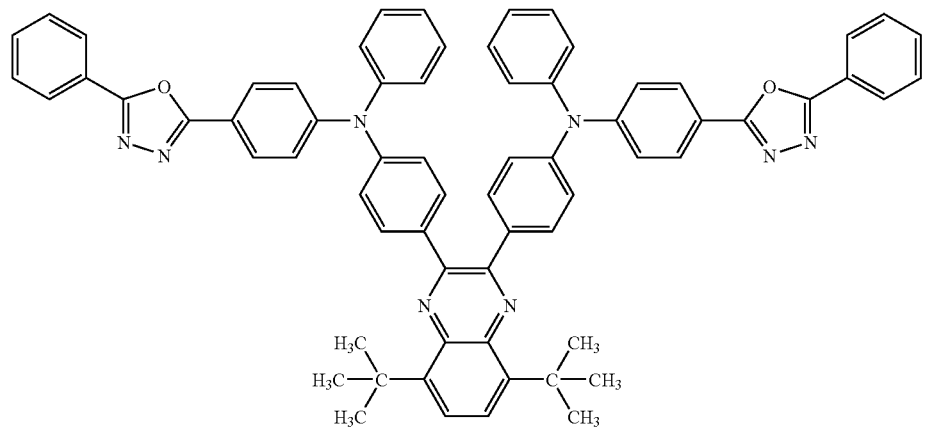
(432)
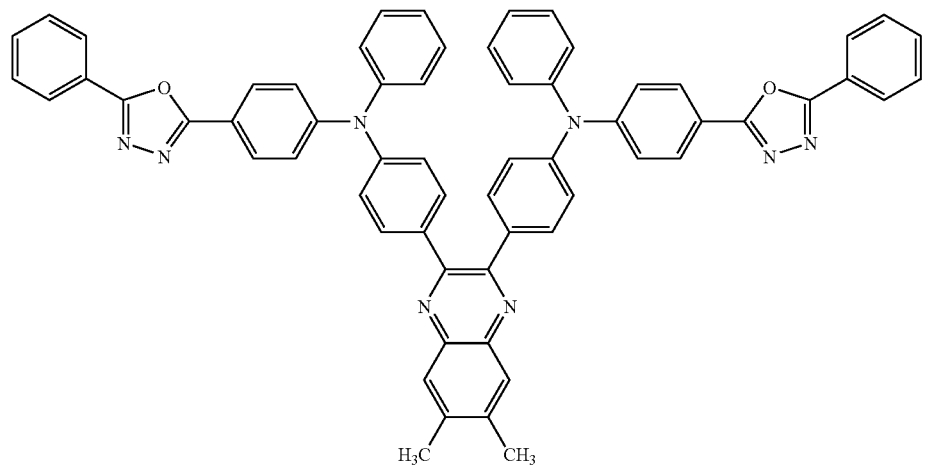
(433)
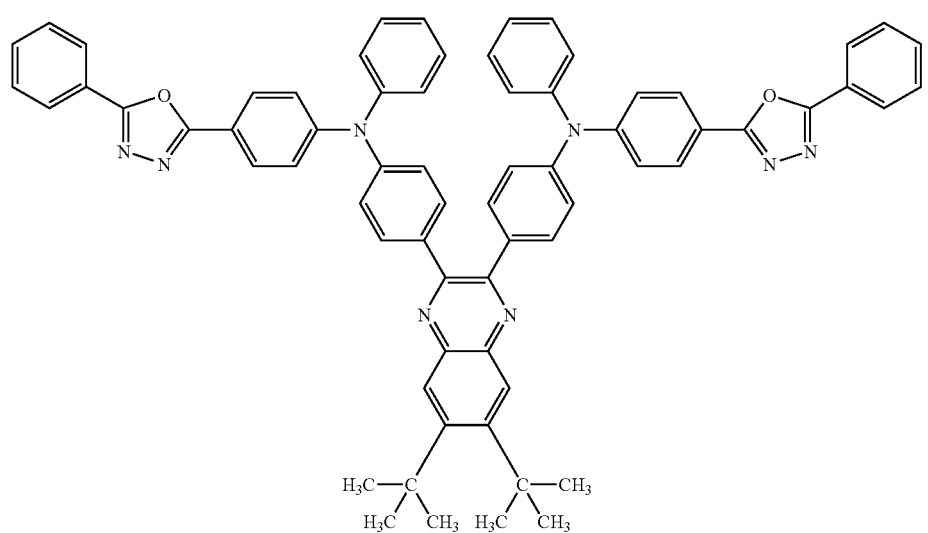
(434)

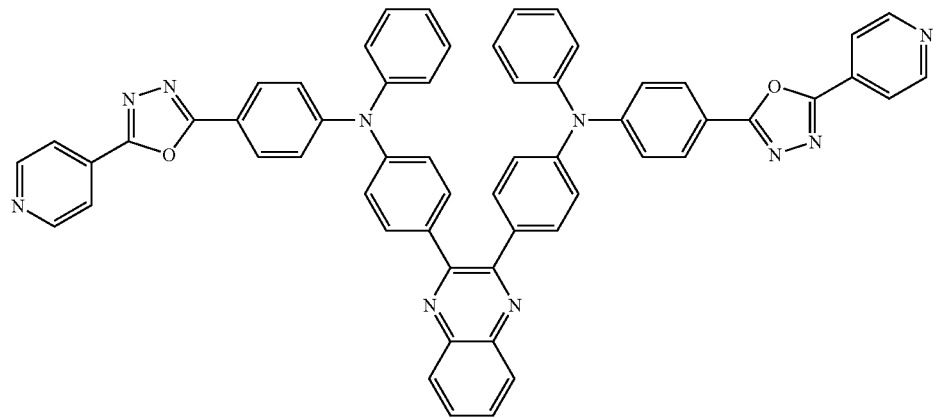
(435)
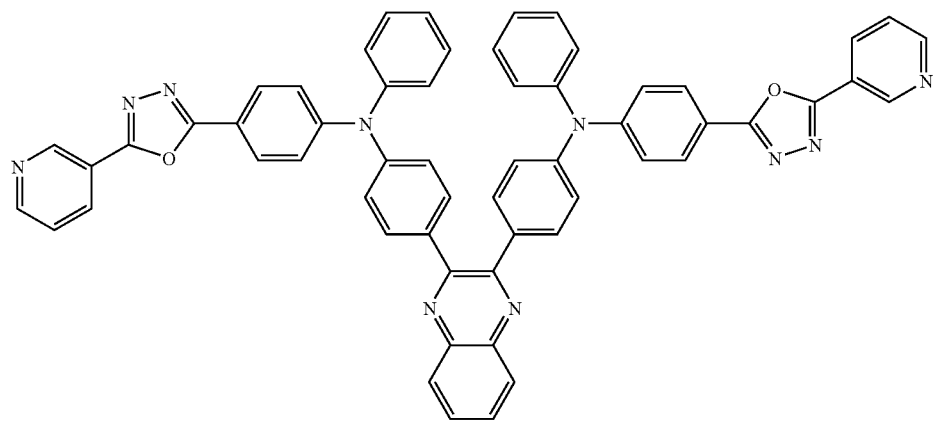
(436)
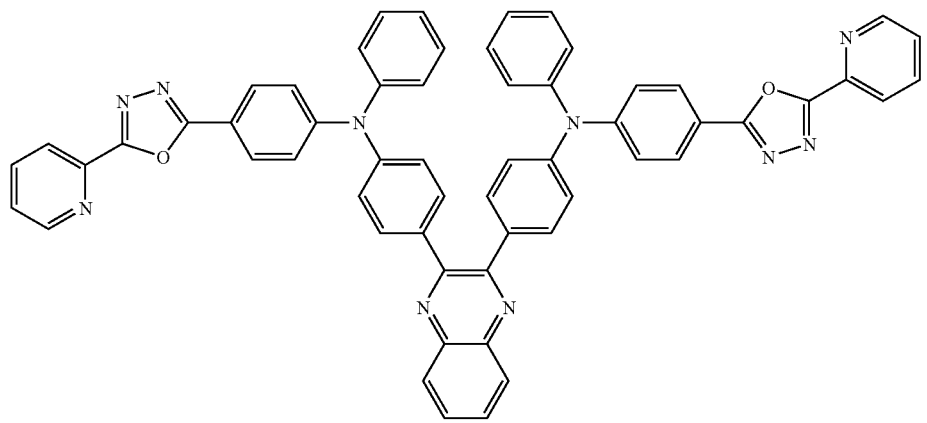
(437)

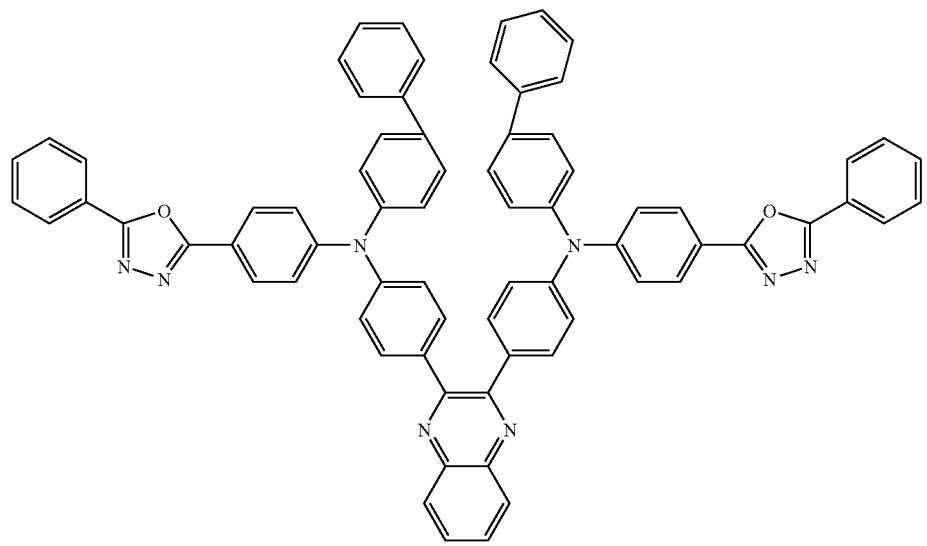
(438)
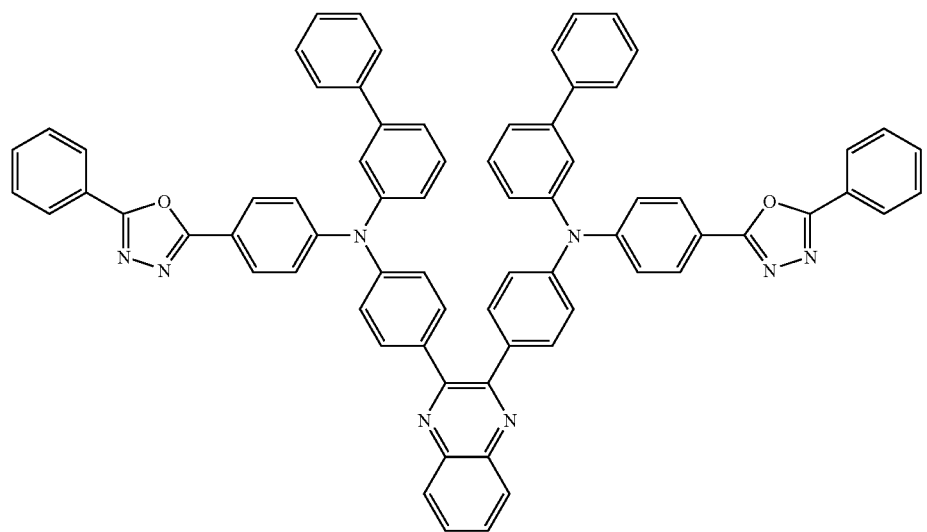
(439)
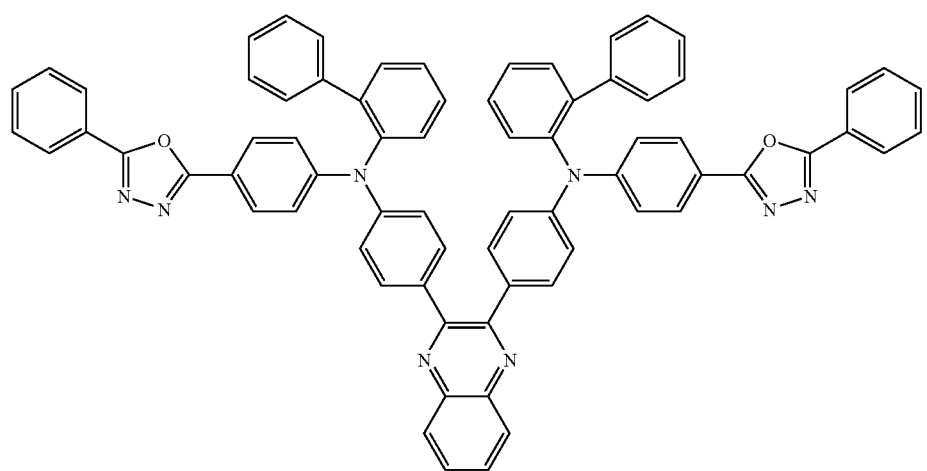
(440)

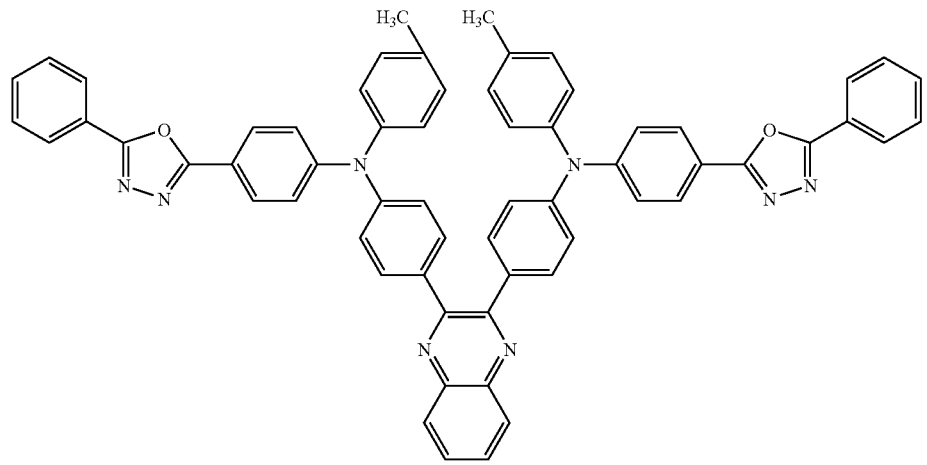
(441)
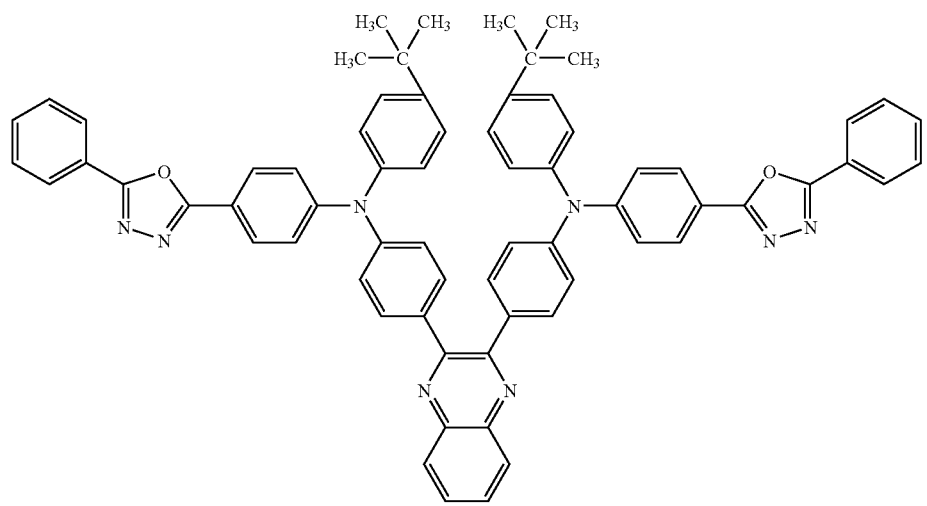
(442)
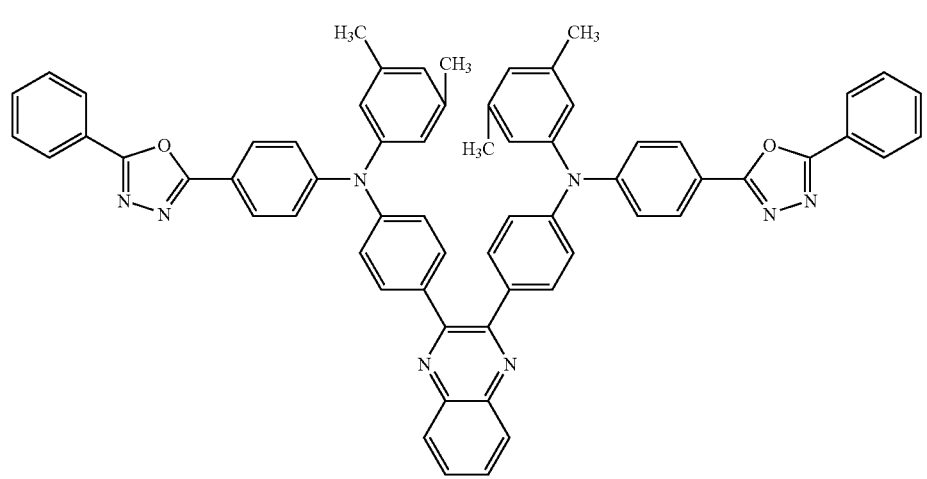
(443)

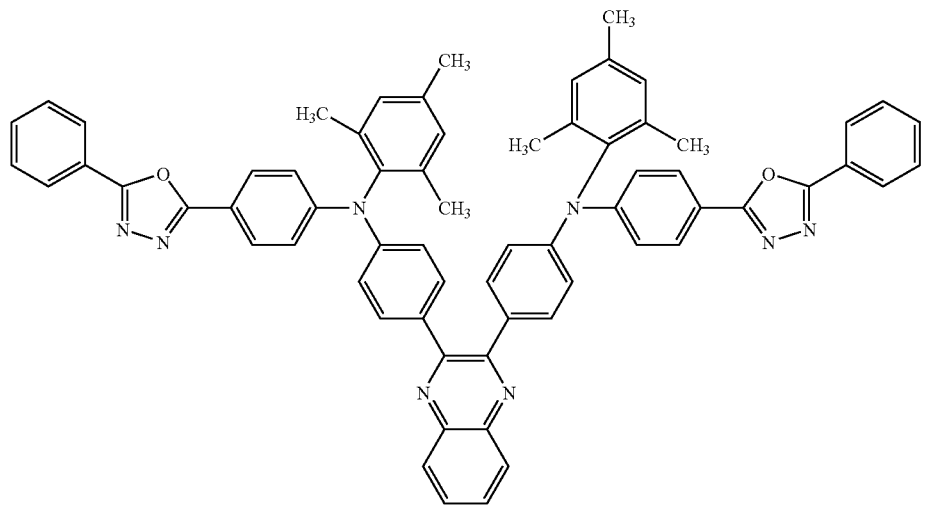
(444)
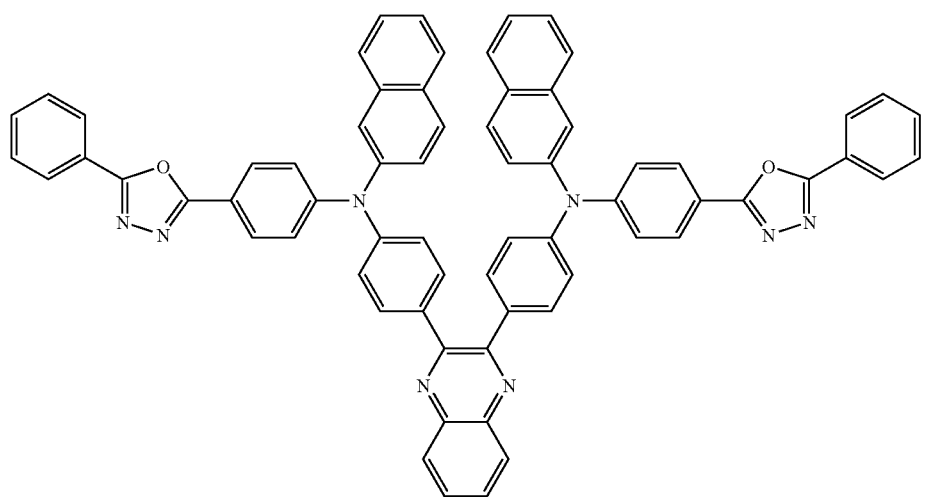
(445)
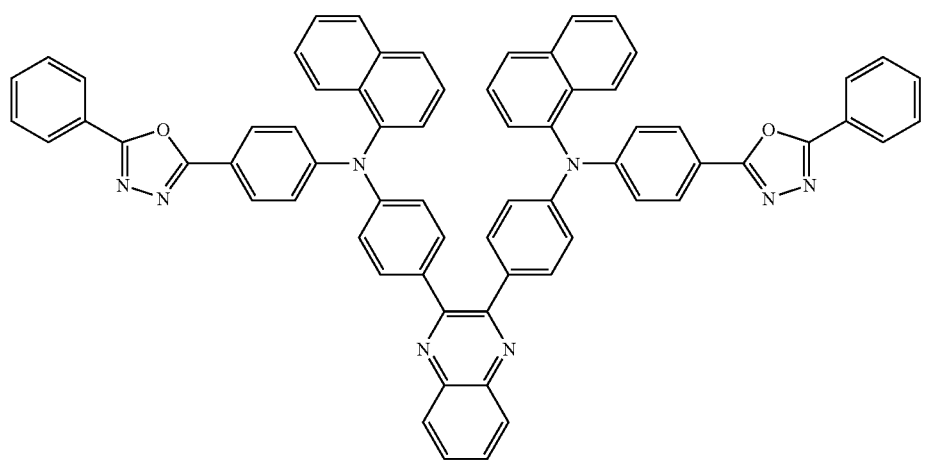
(446)

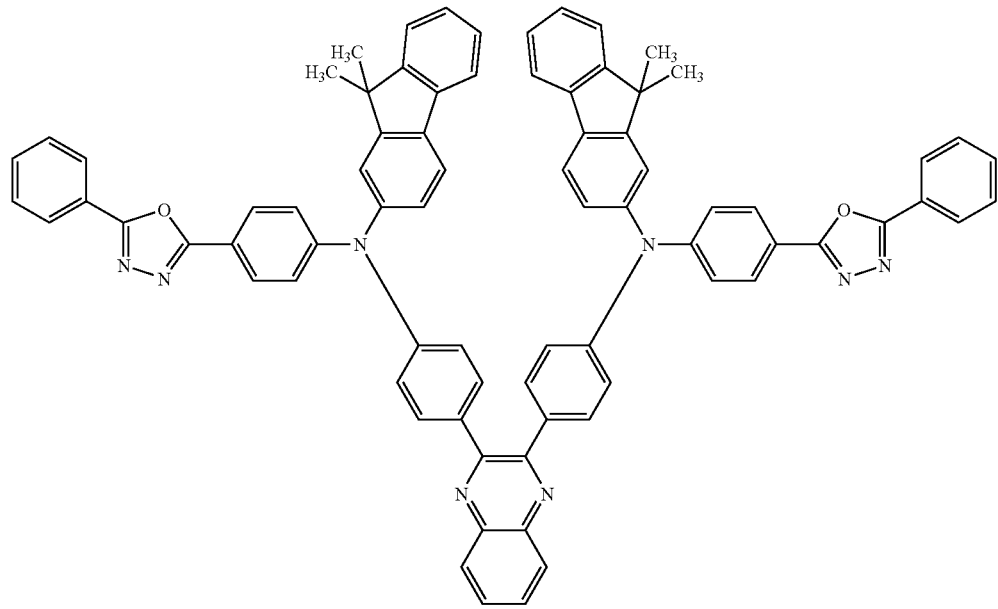
(447)
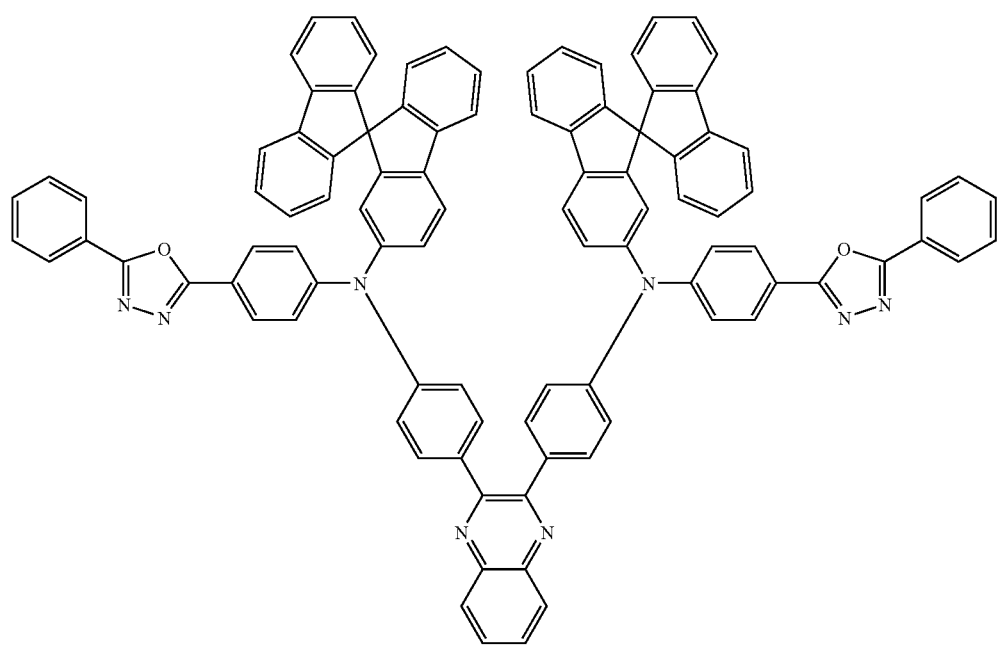
(448)

-continued
(449)
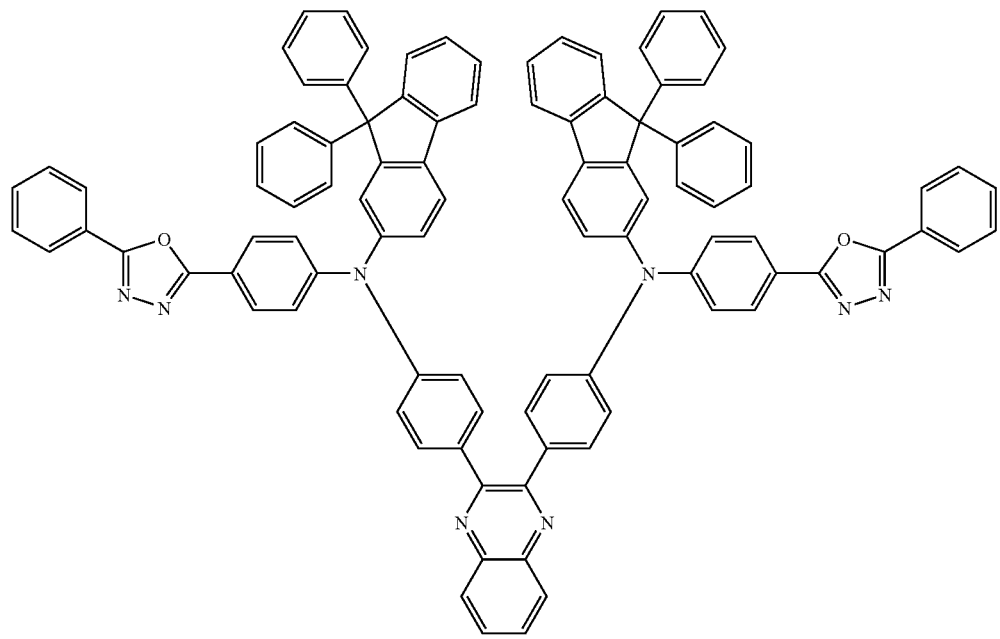
(450)
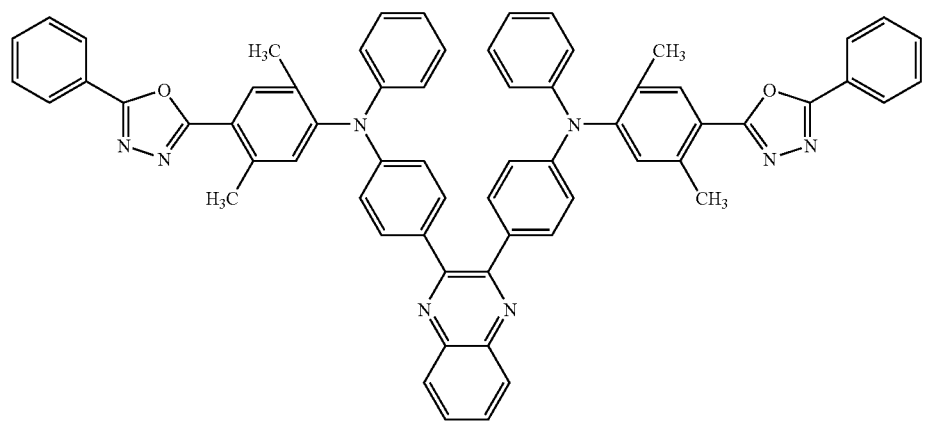
(451)
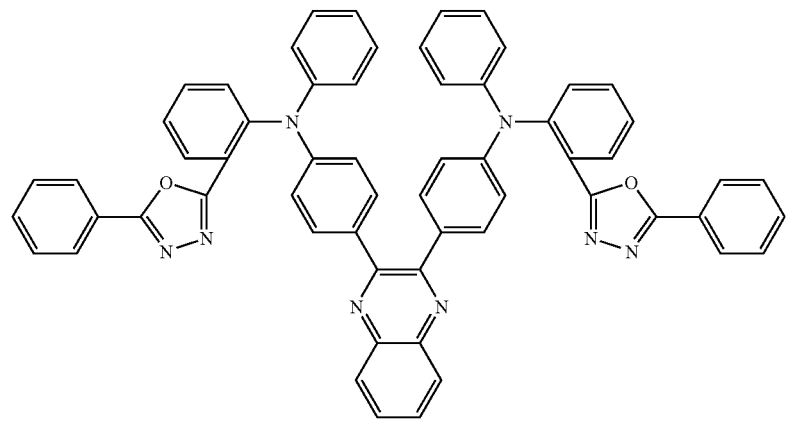

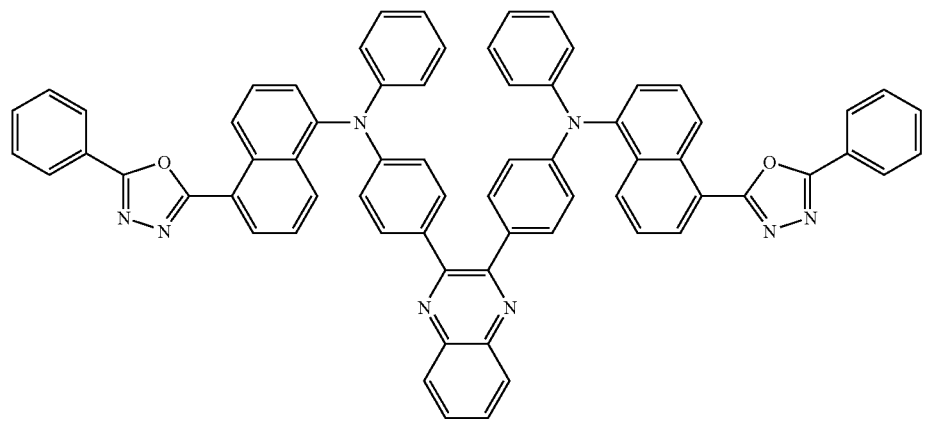
(452)
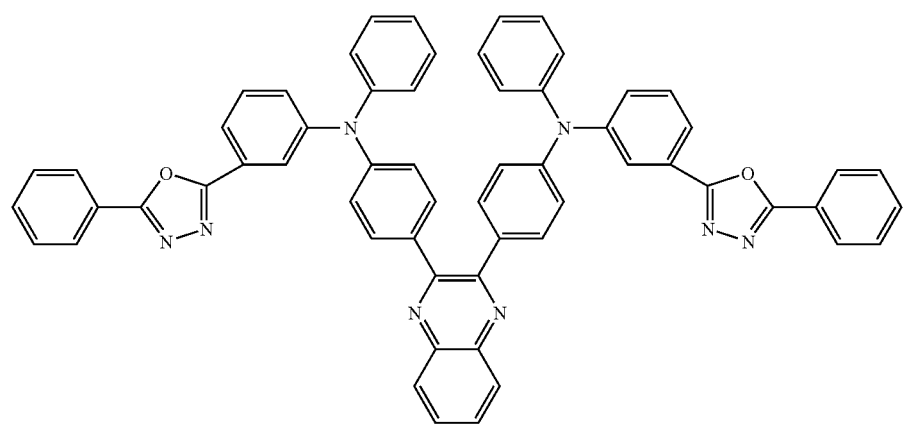
(453)
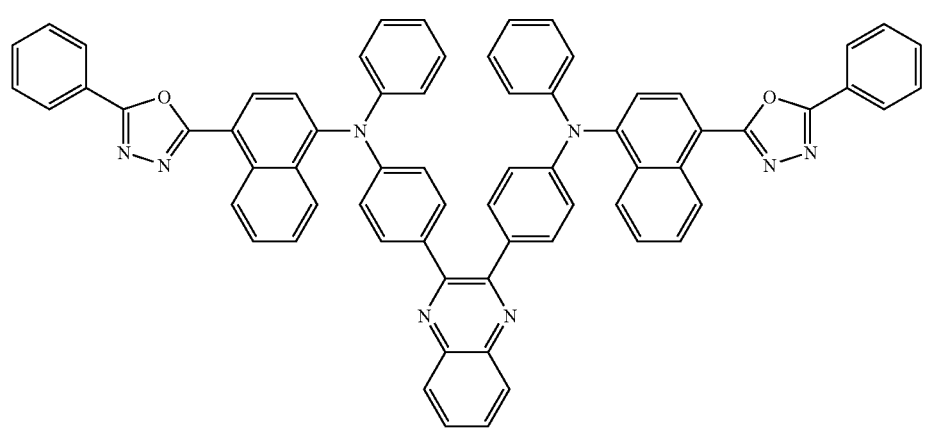
(454)

(455)
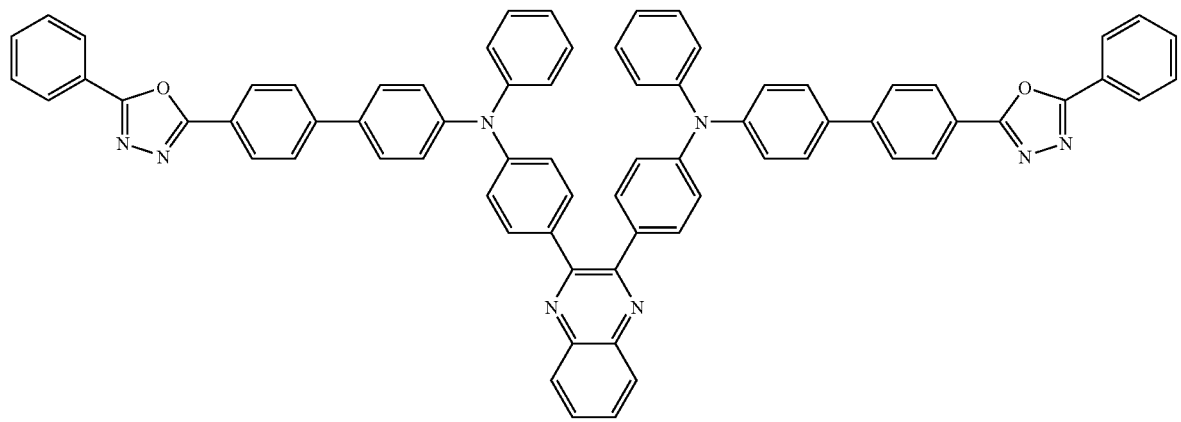
(456)
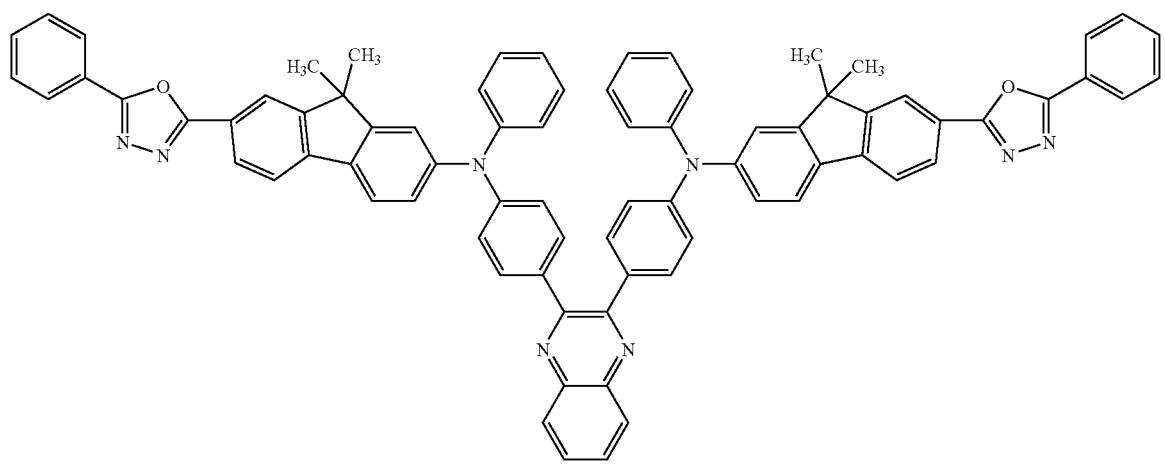
(457)
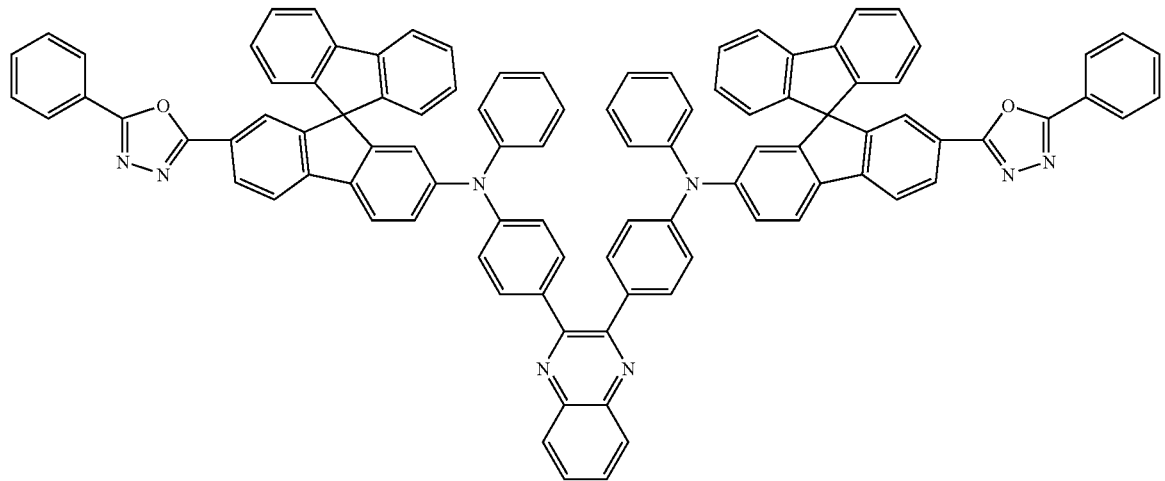

(458)
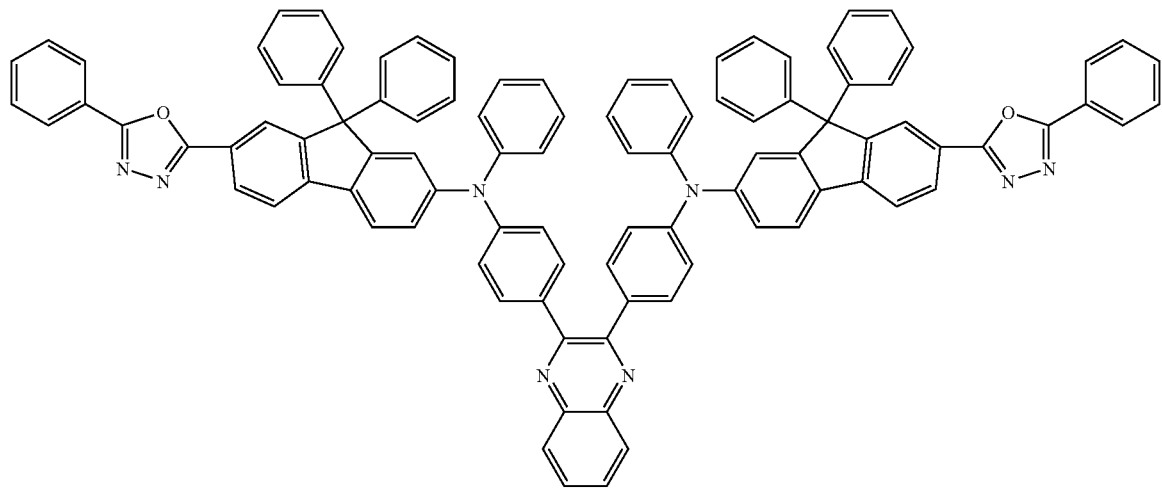
(459)
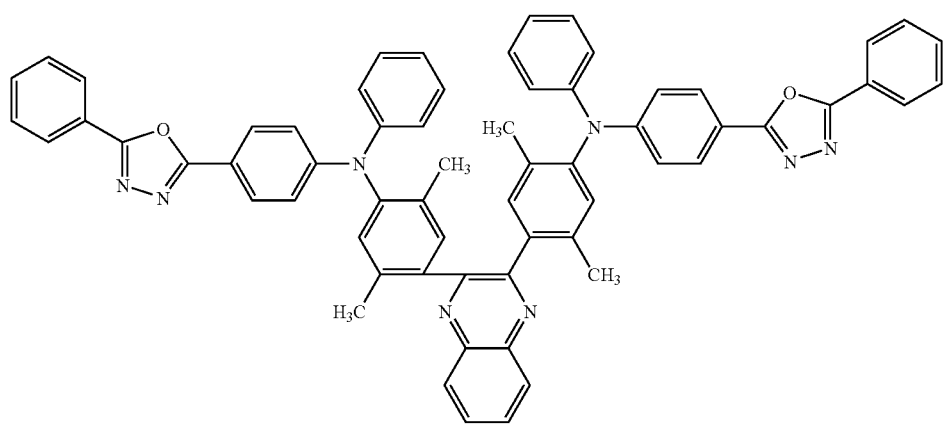
(460)
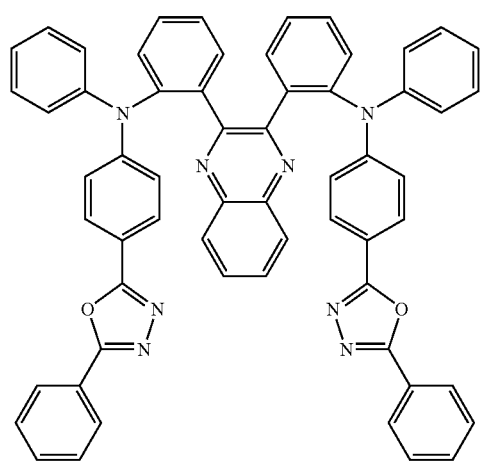

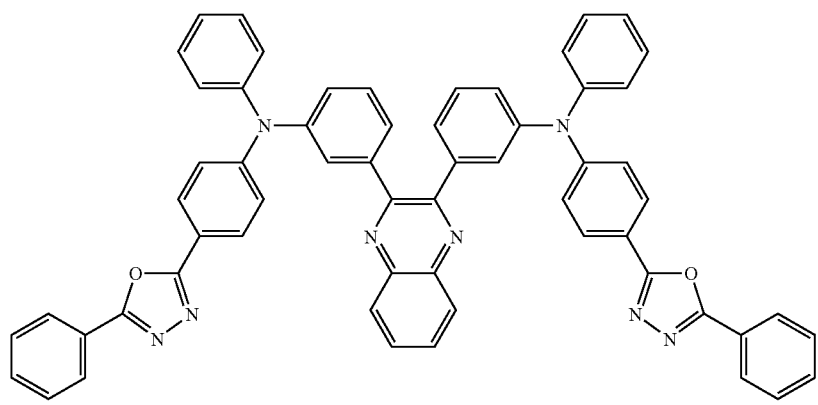
(461)
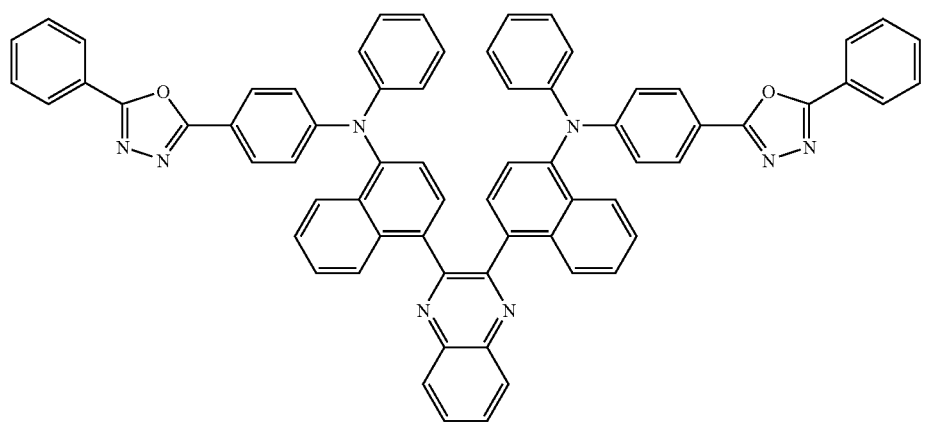
(462)
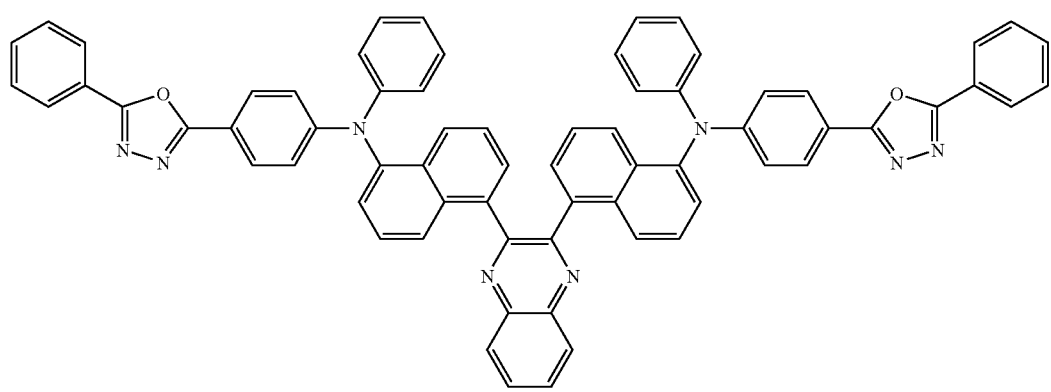
(463)

(464)
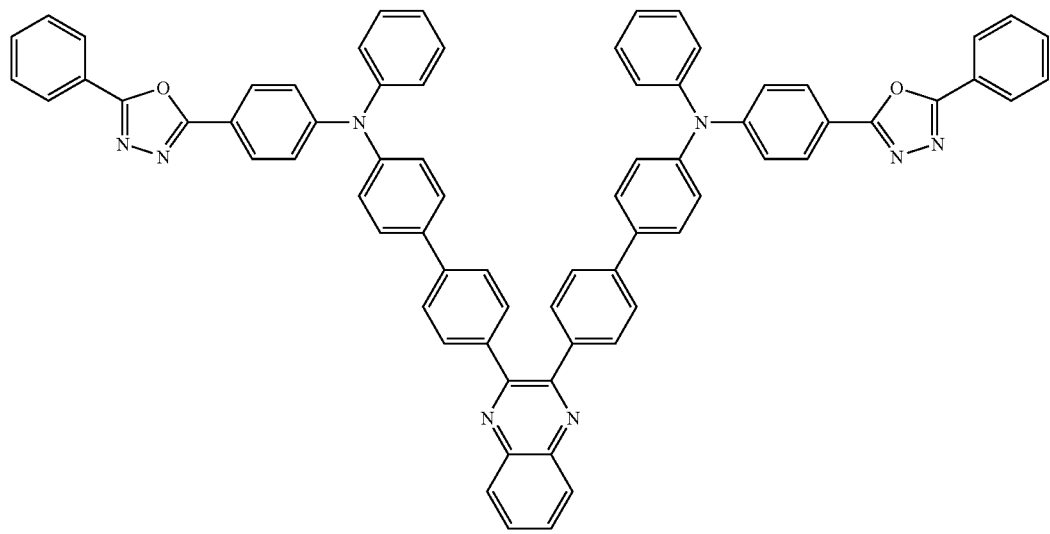
(465)
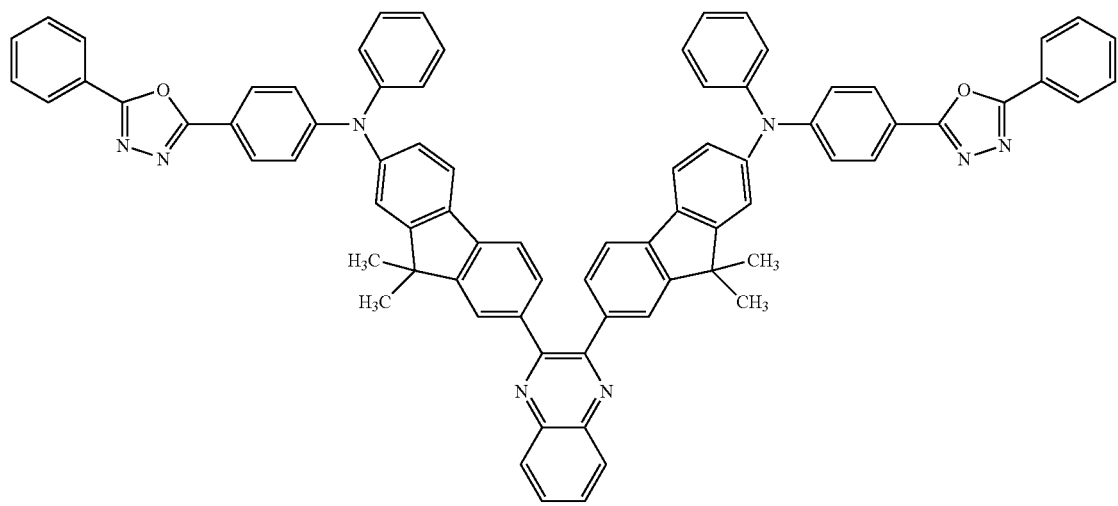
(466)
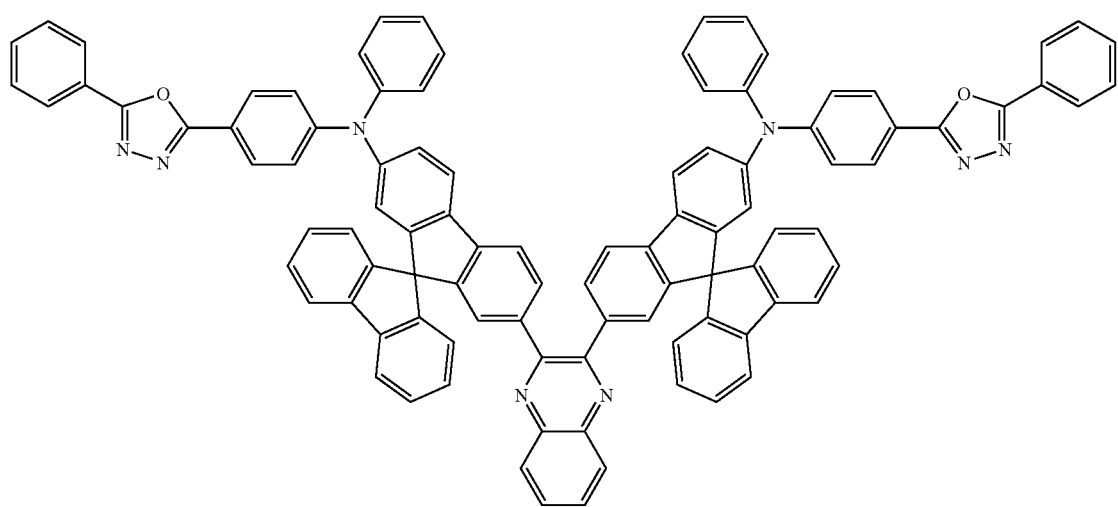

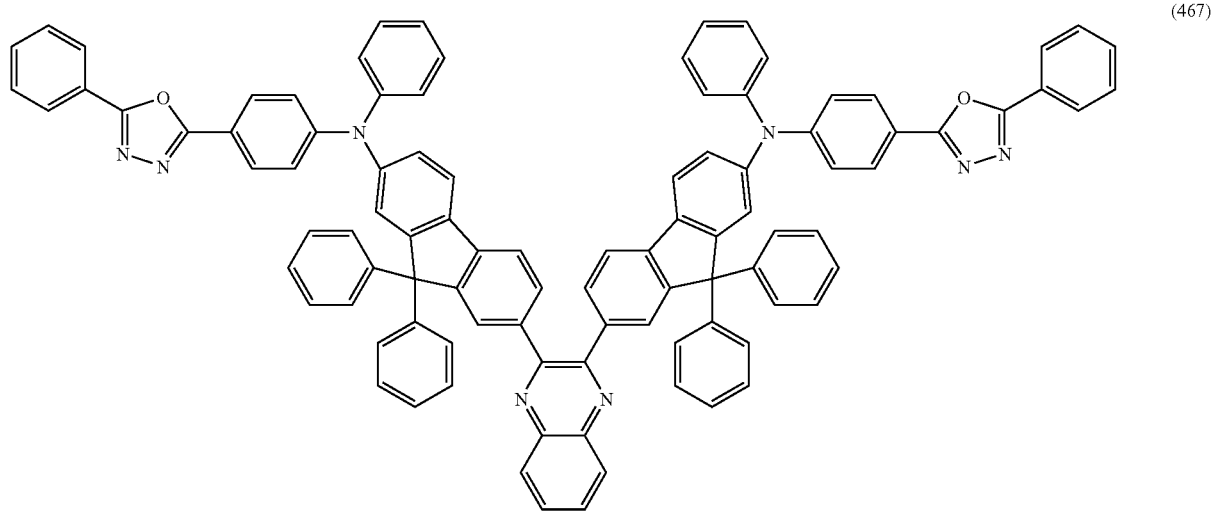
(467)
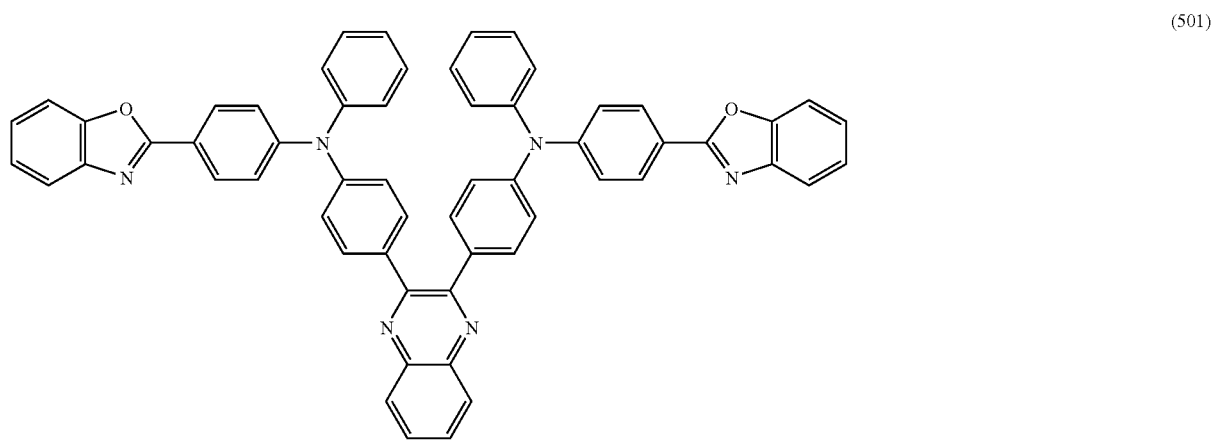
(501)
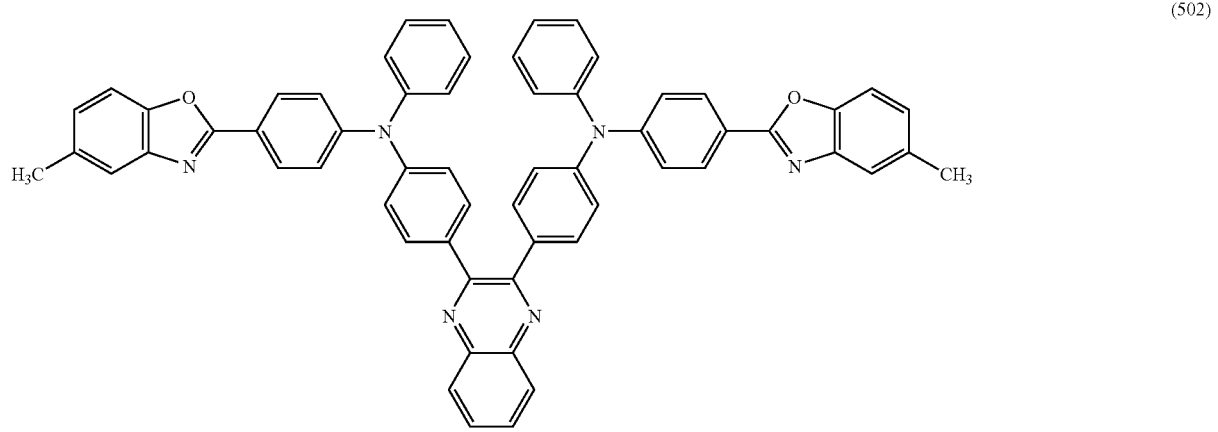
(502)

(503)
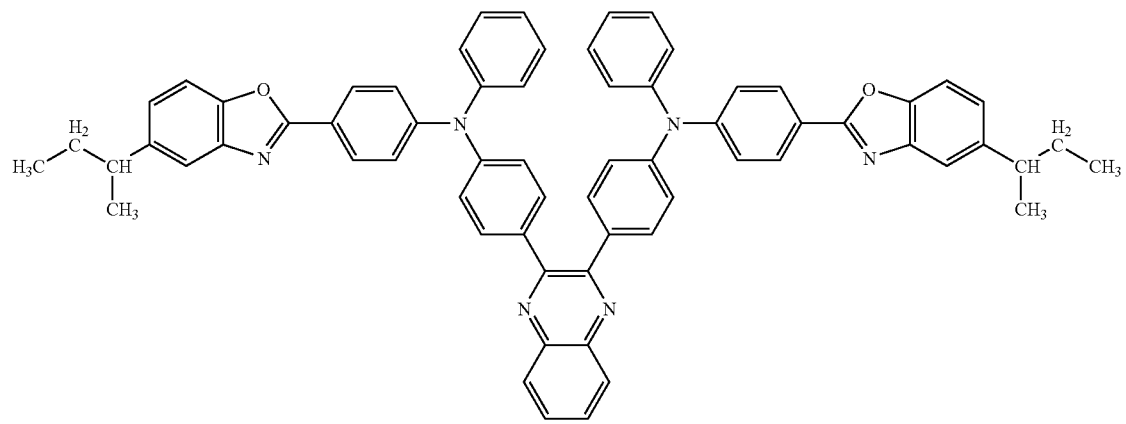
(504)
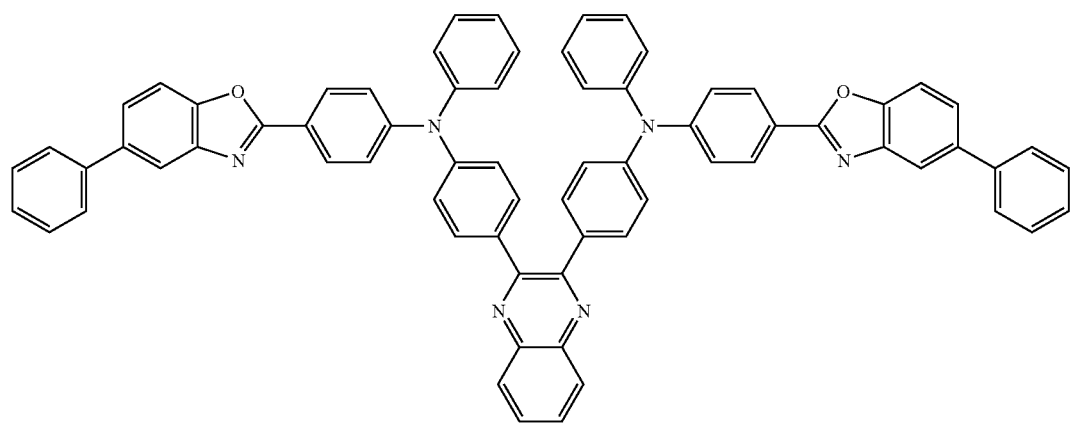
(505)
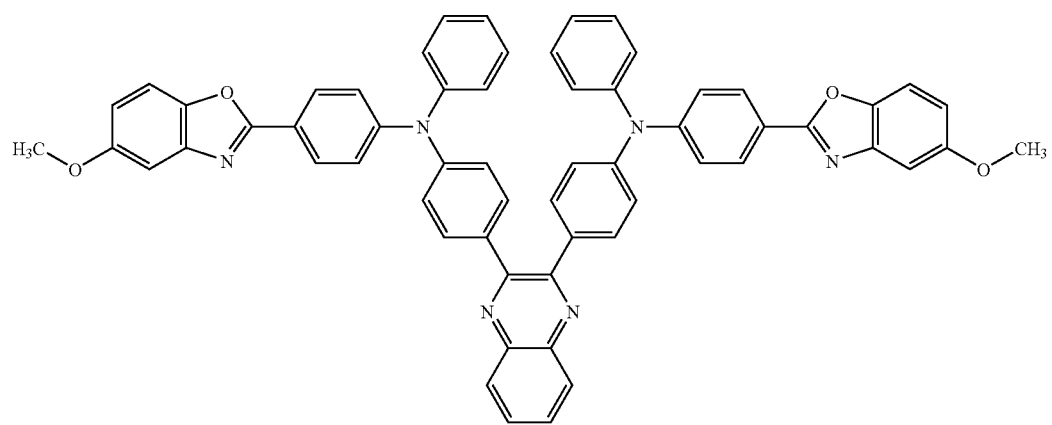

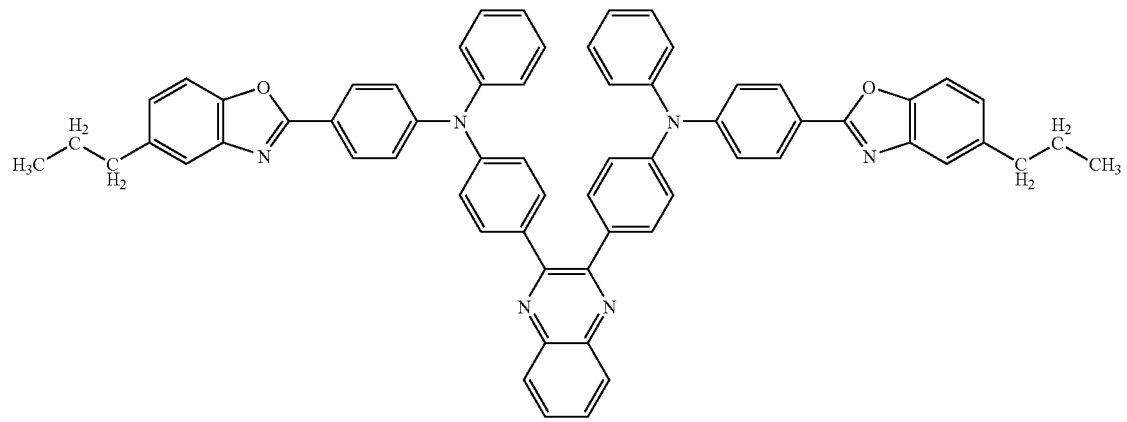
(506)
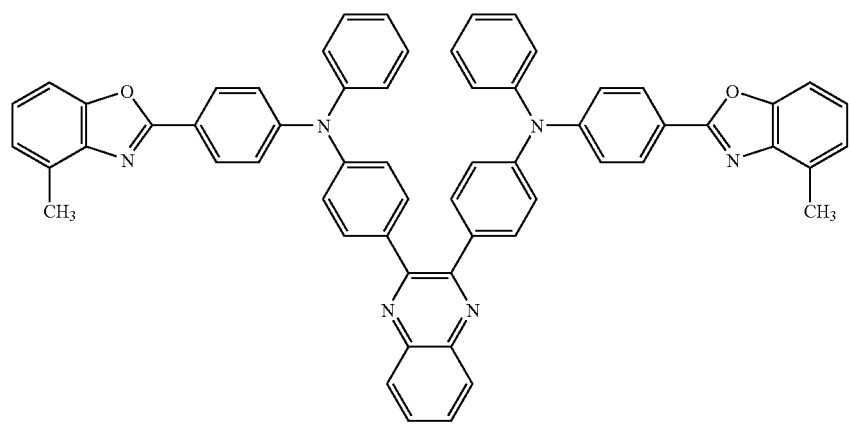
(507)
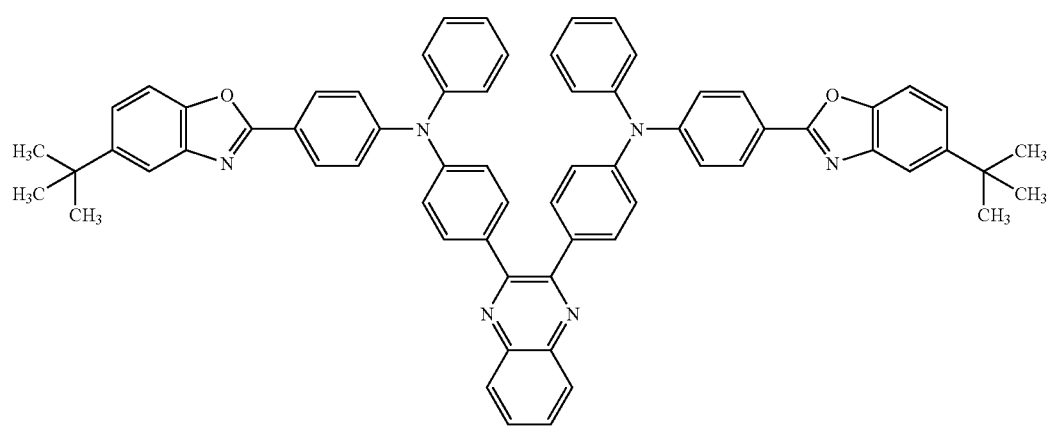
(508)

(509)
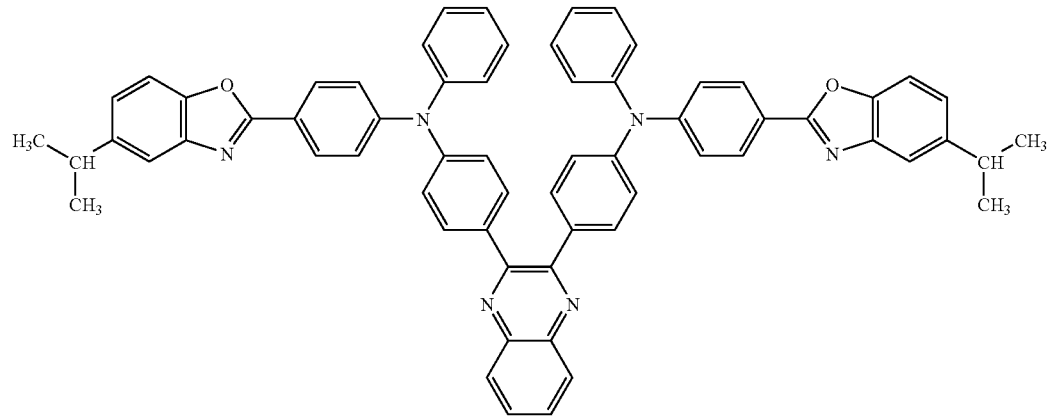
(510)
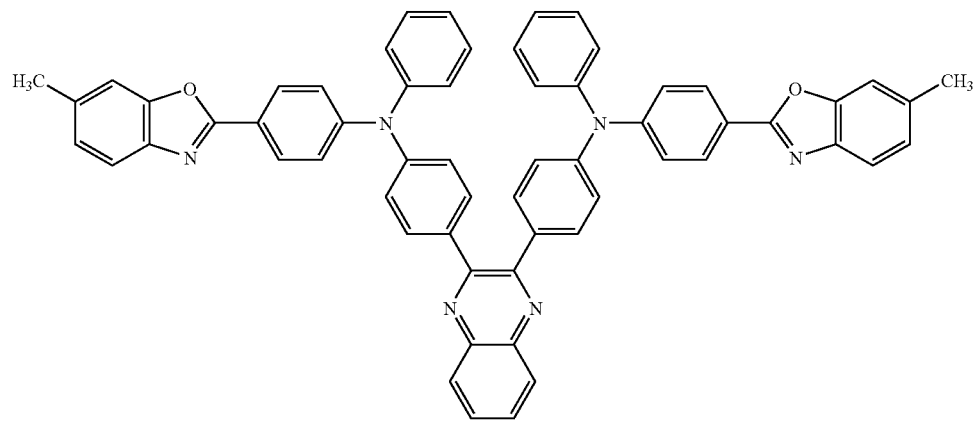
(511)
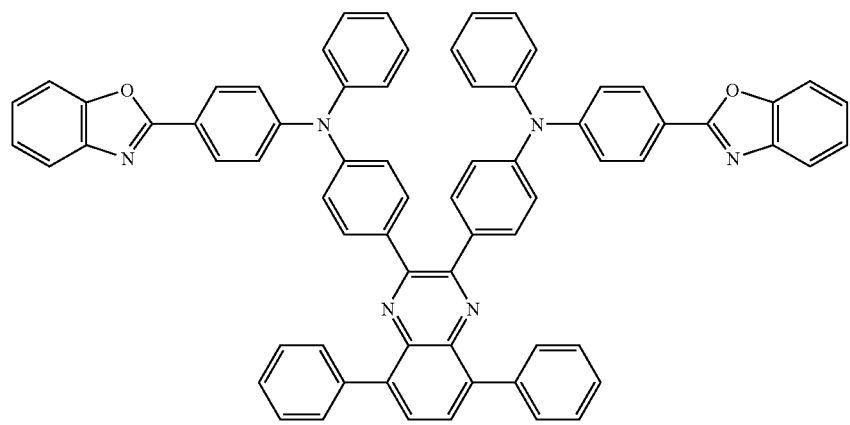

(512)
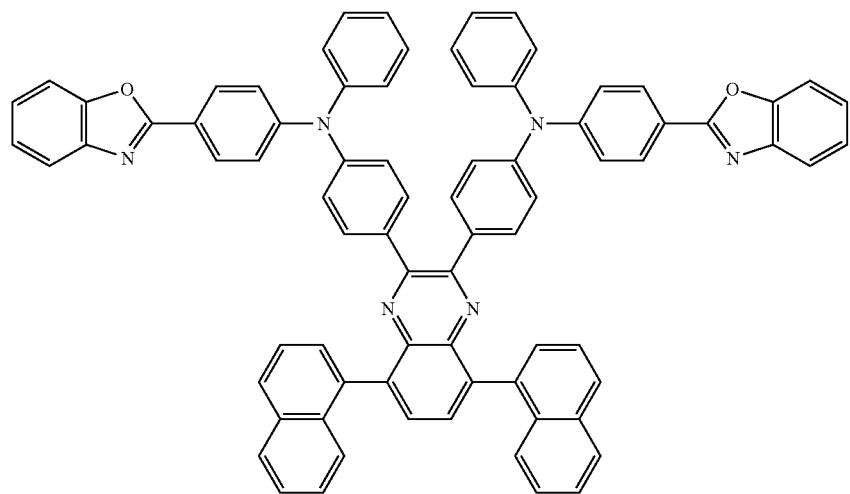
(513)
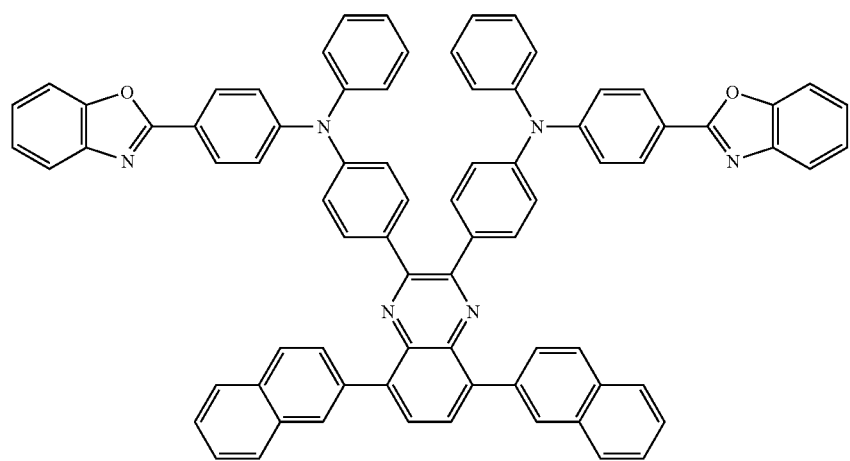
(514)
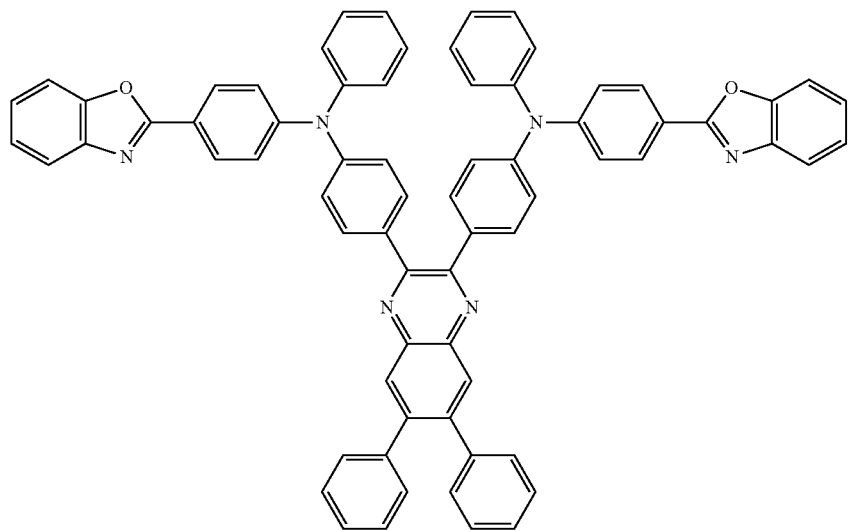

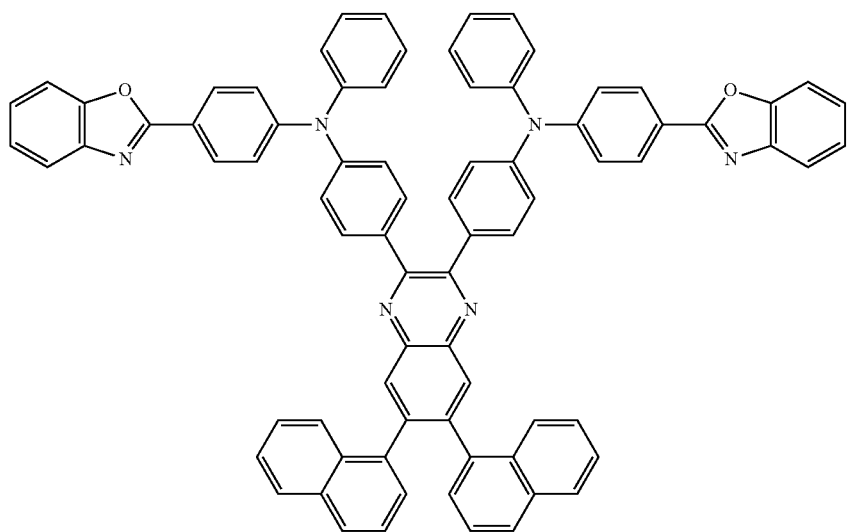
(515)
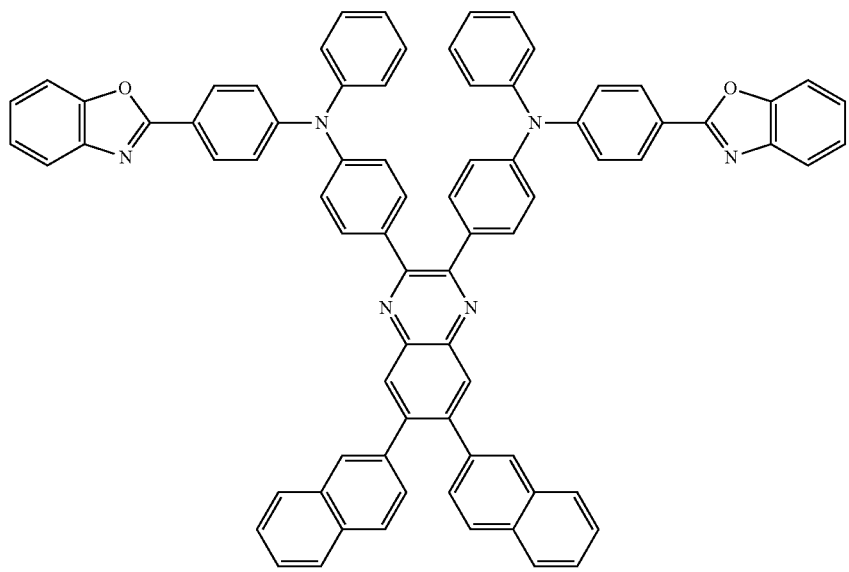
(516)
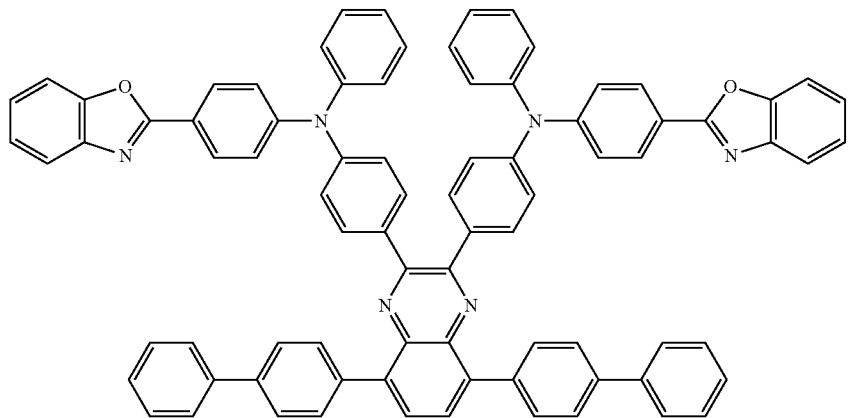
(157)

-continued
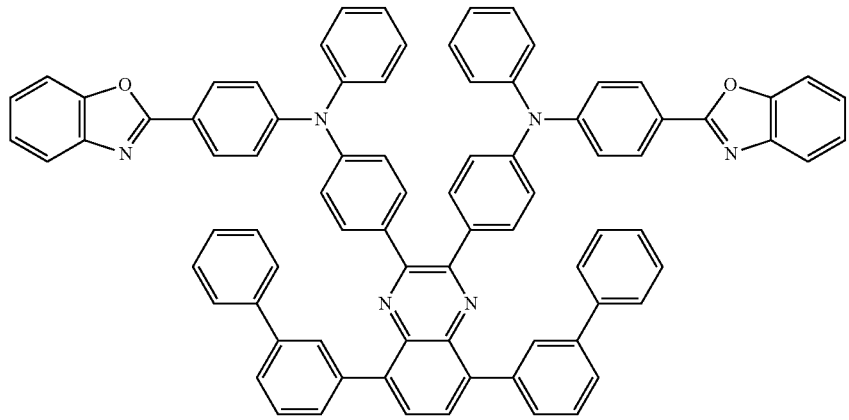
(518)
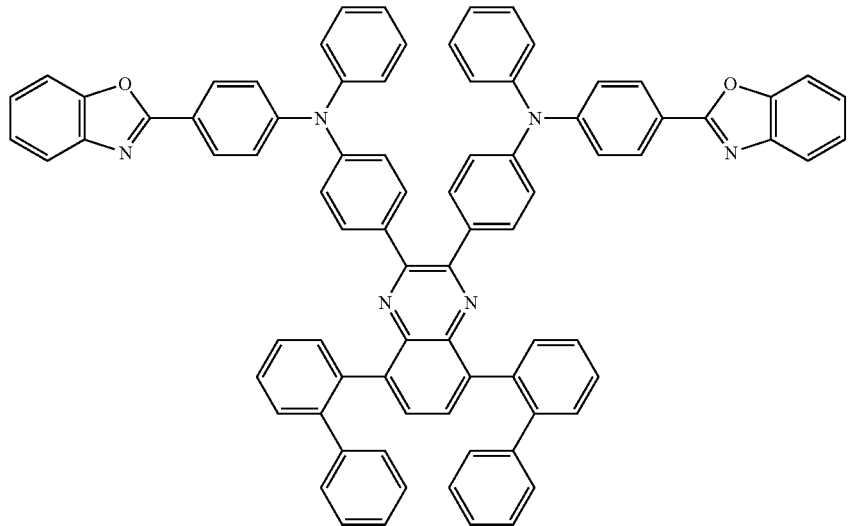
(519)
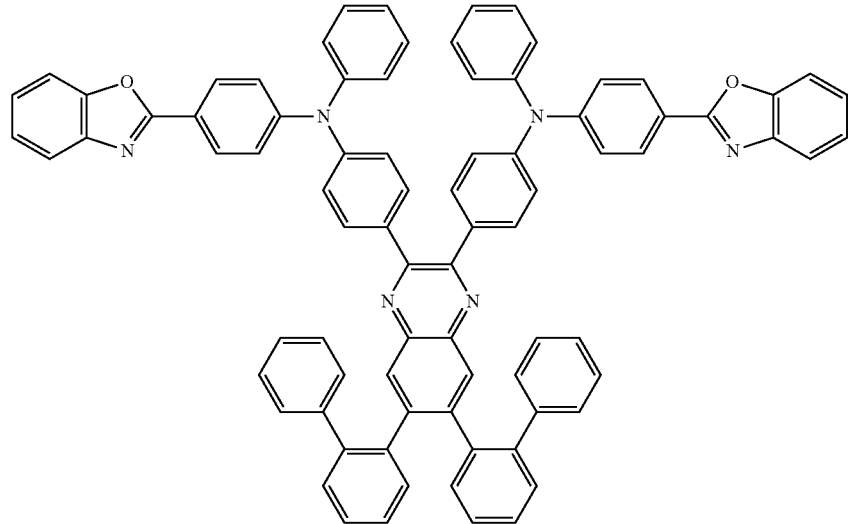
(520)

-continued
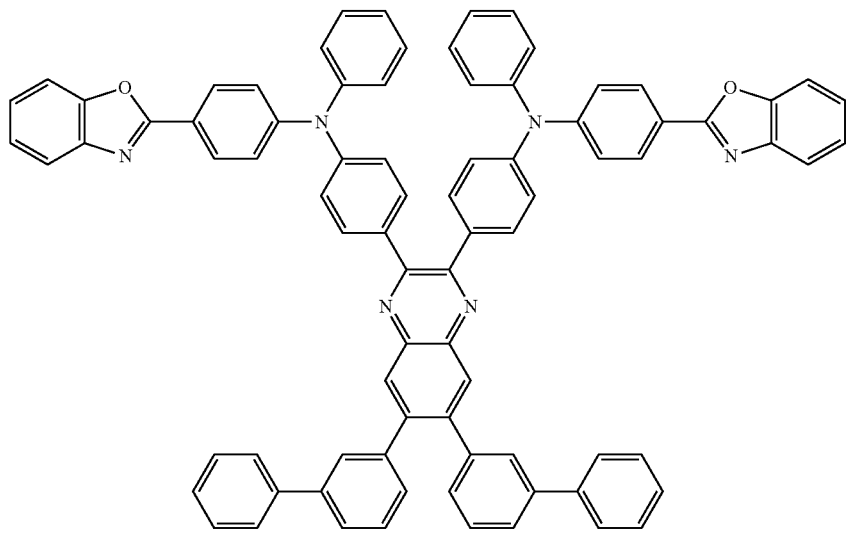
(521)
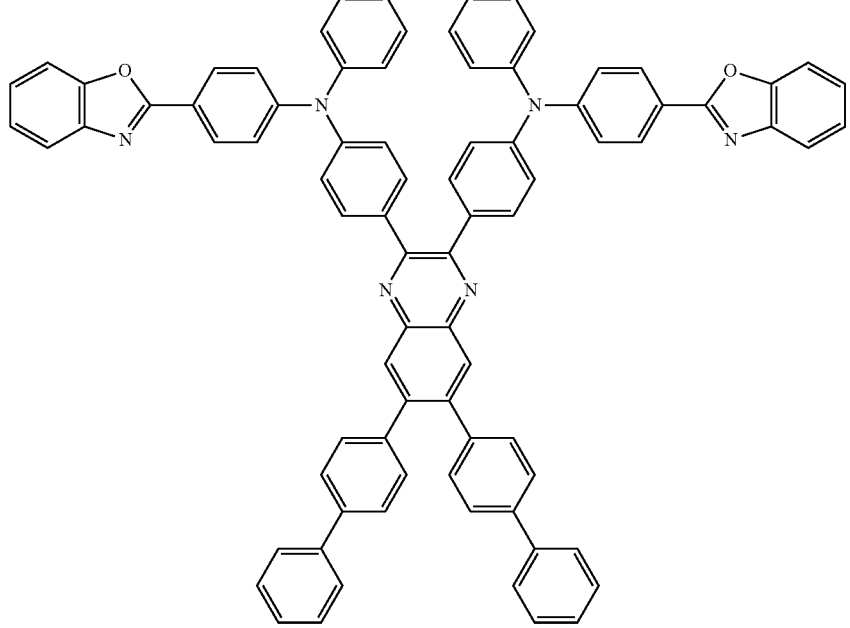
(522)
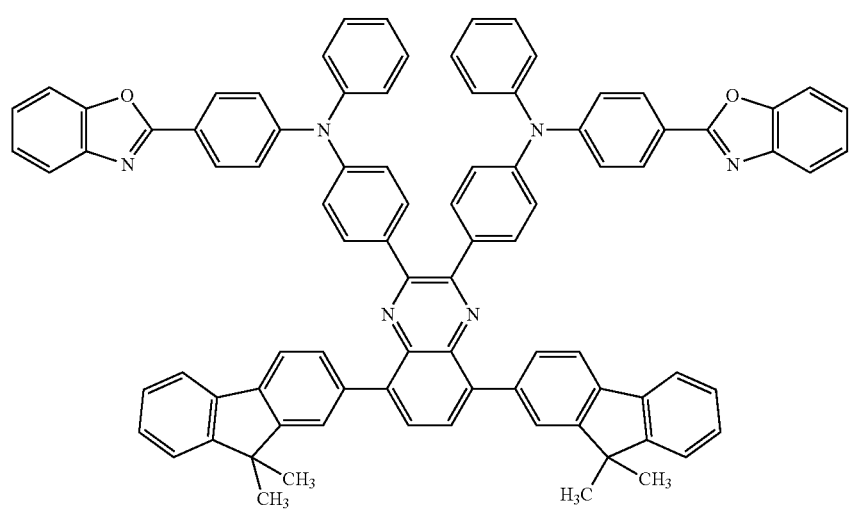
(523)

(524)
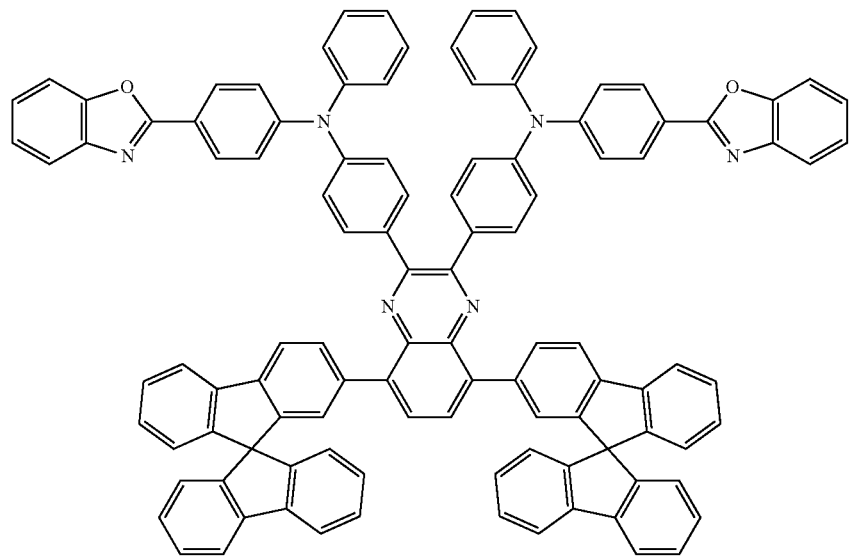
(525)
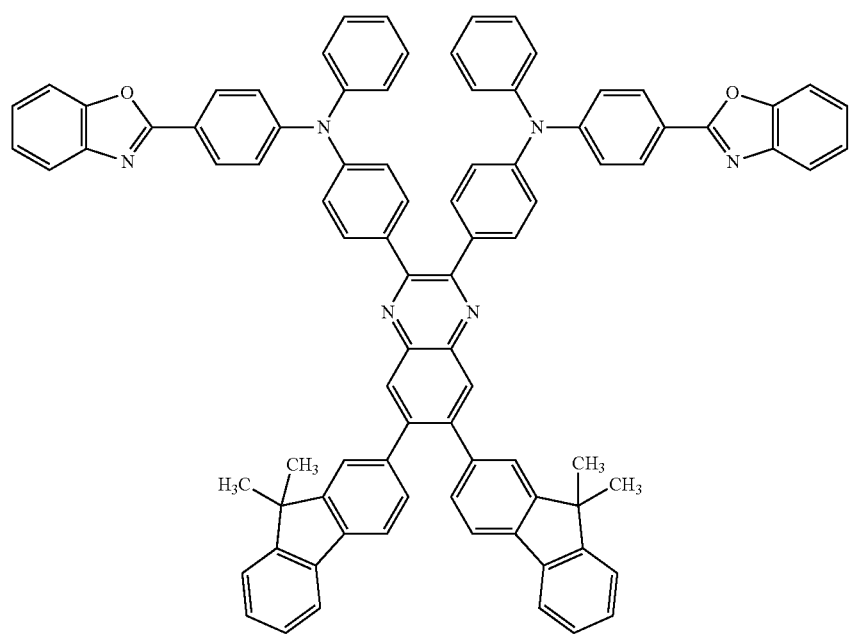

(526)
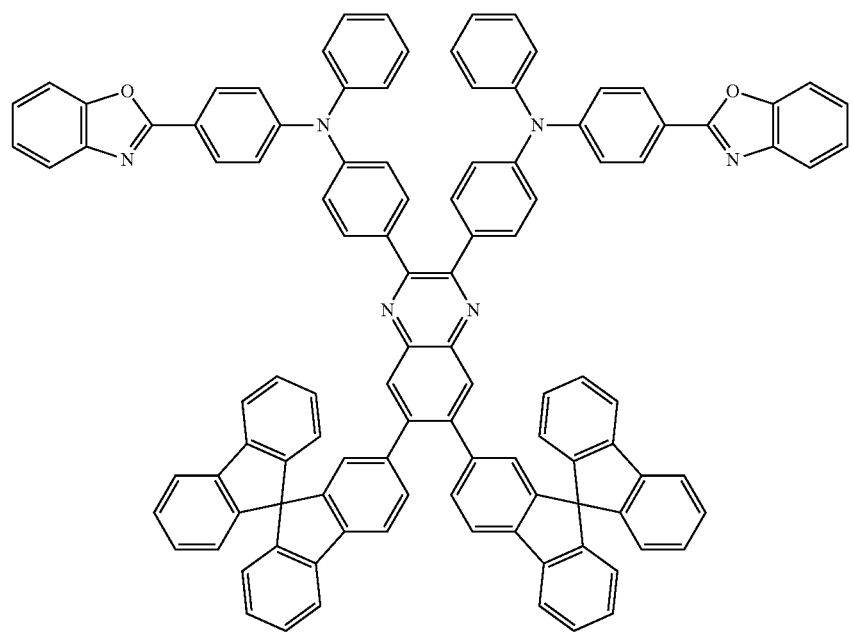
(527)
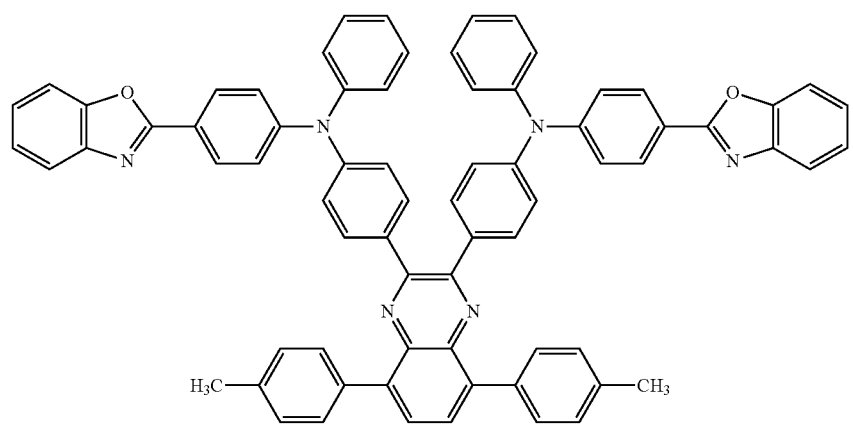
(528)
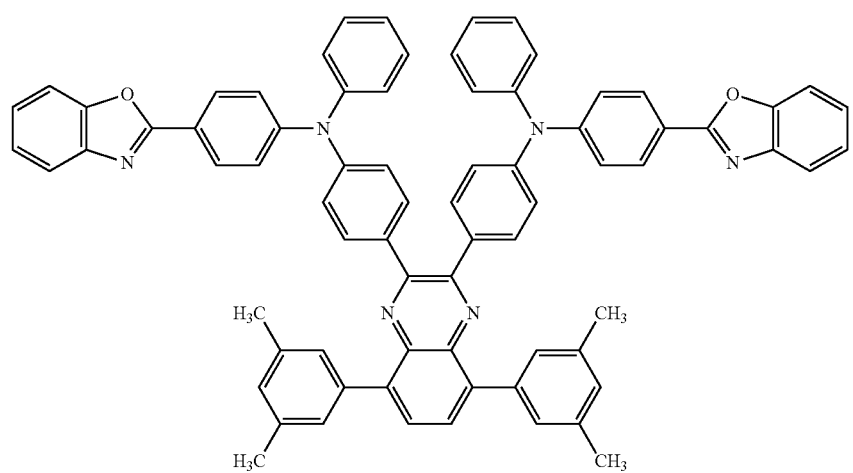

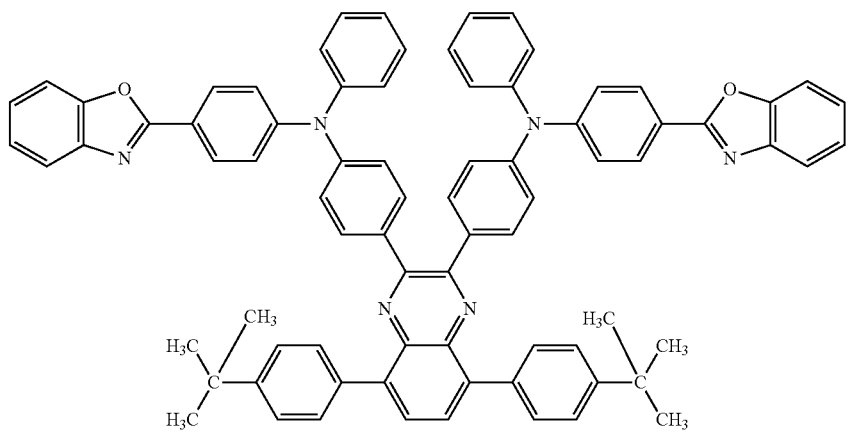
(529)
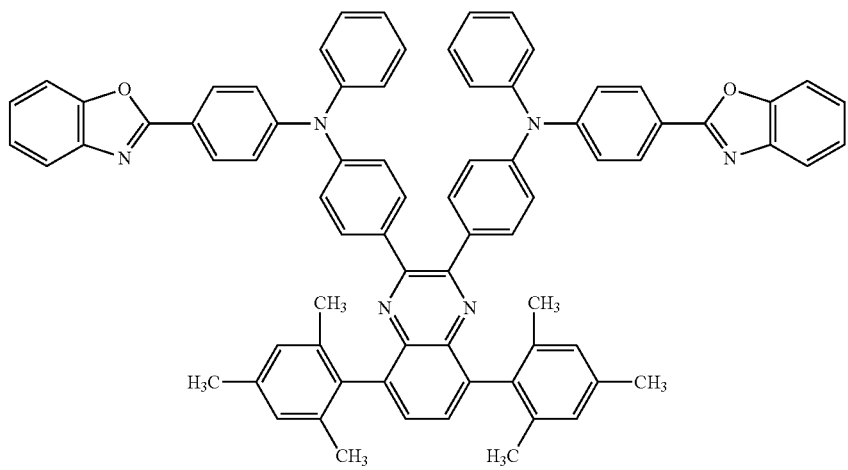
(530)
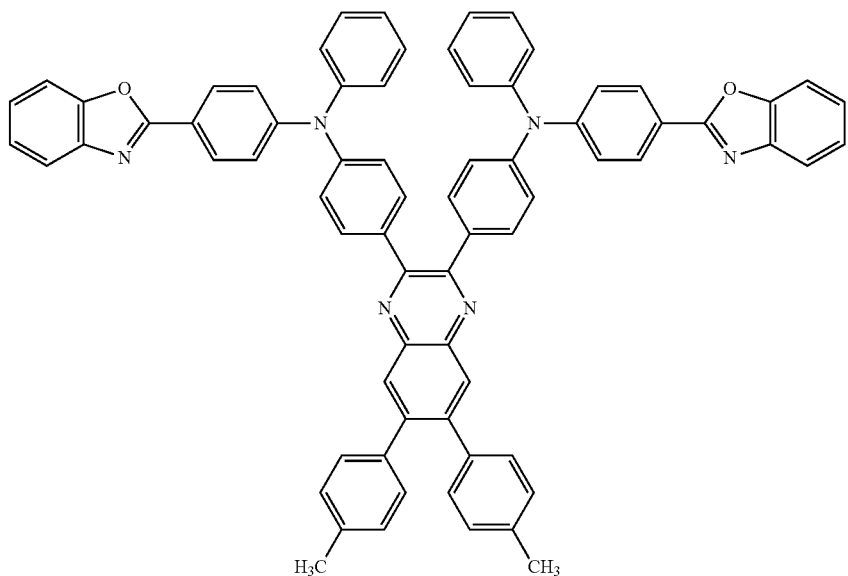
(531)

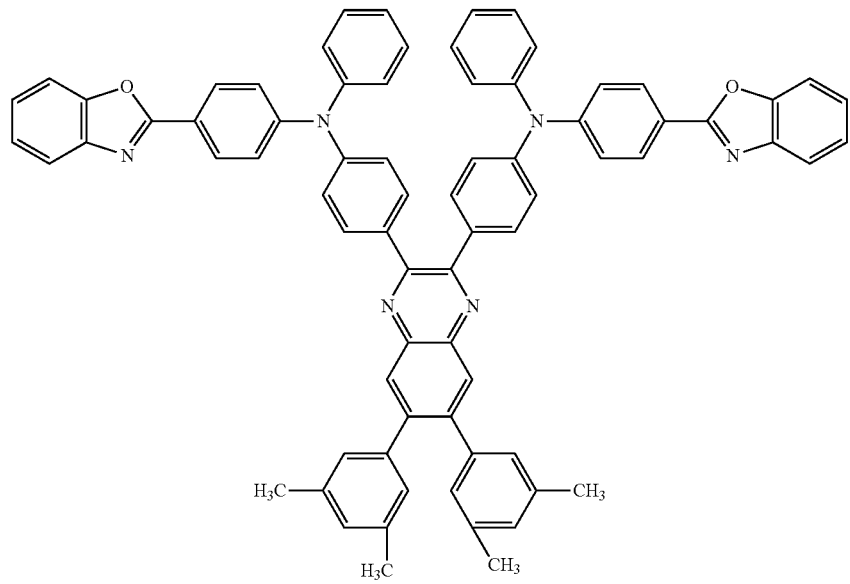
(532)
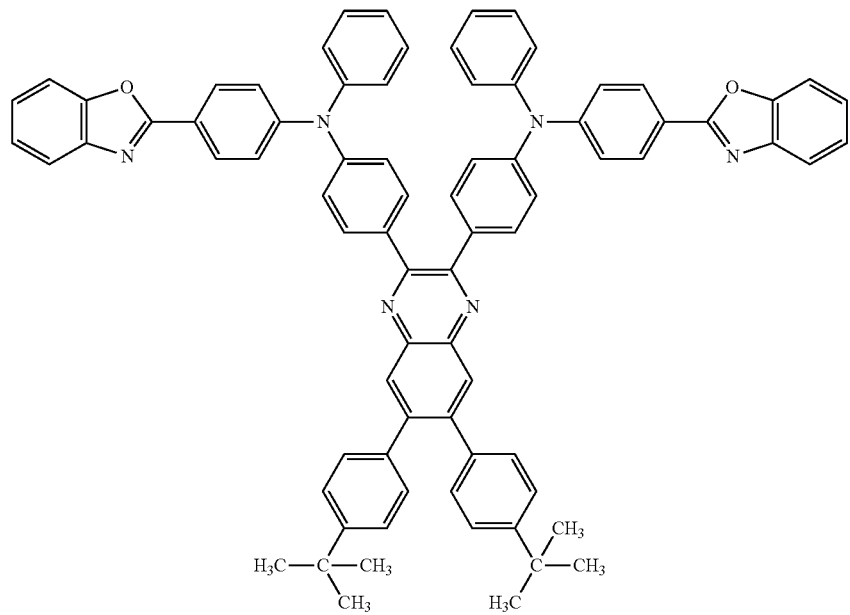
(533)

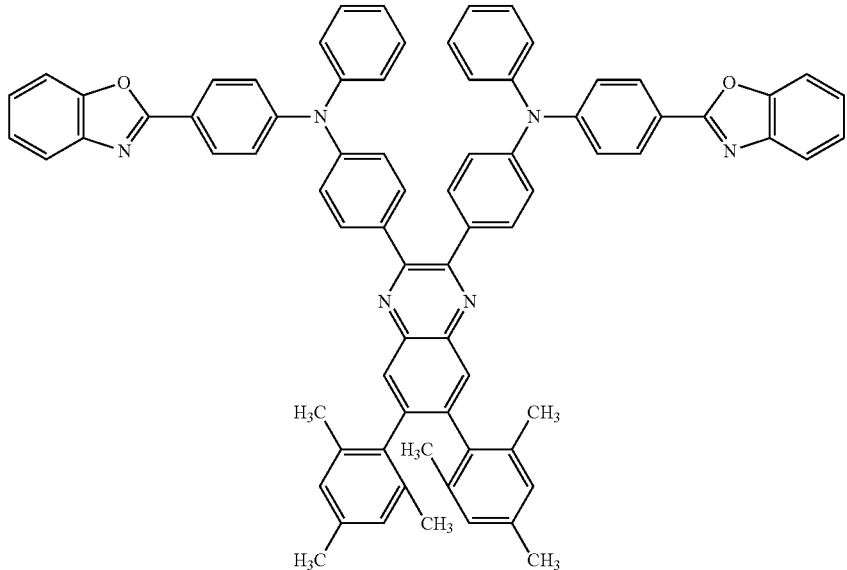
(534)
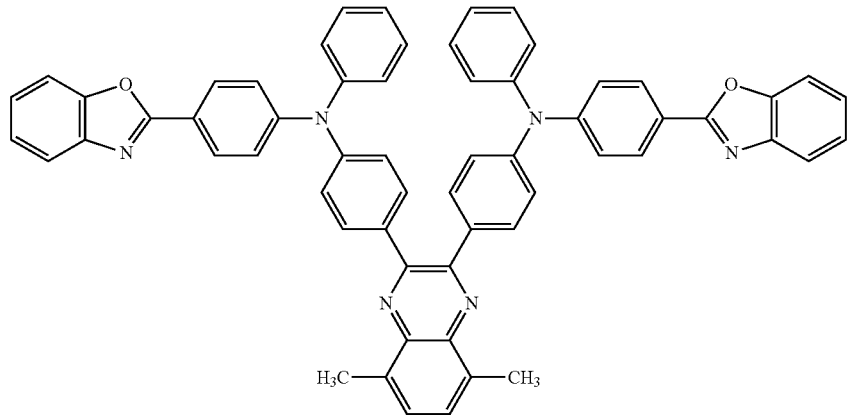
(535)
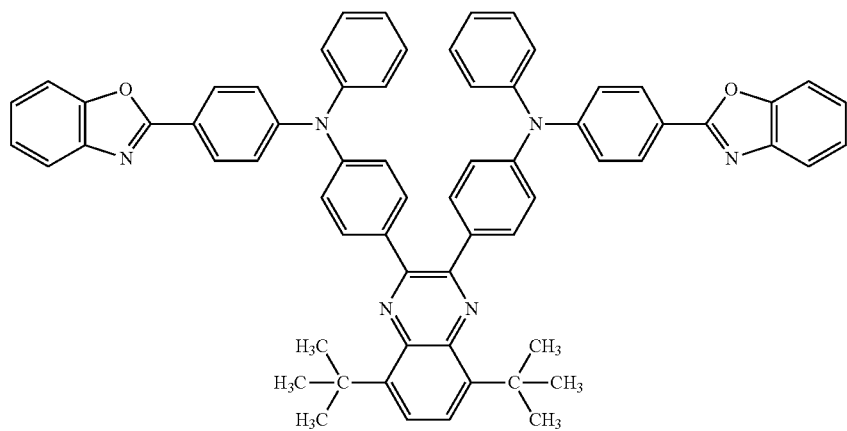
(536)

(537)
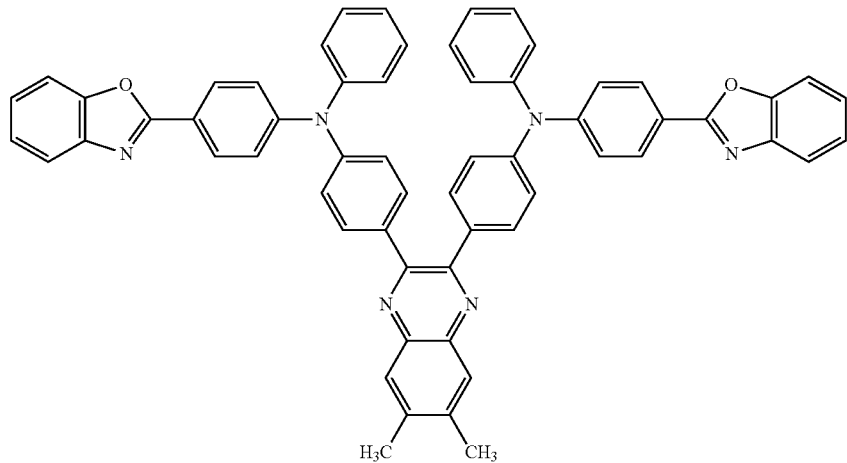
(538)
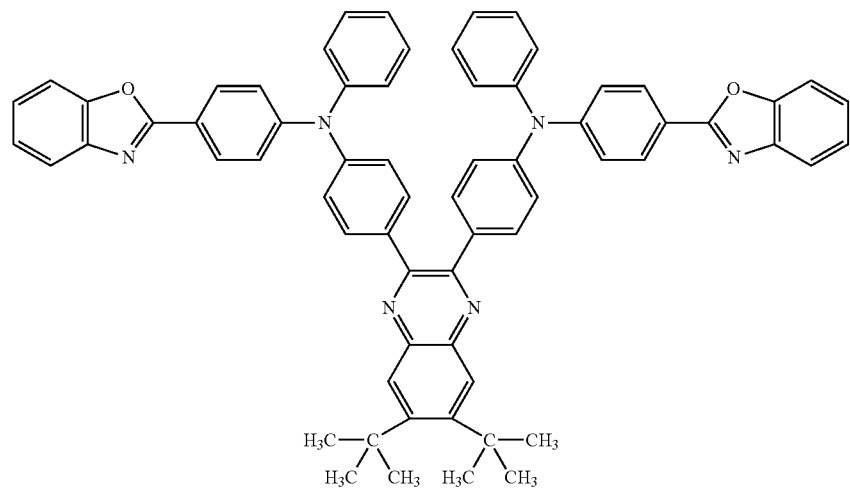
(539)
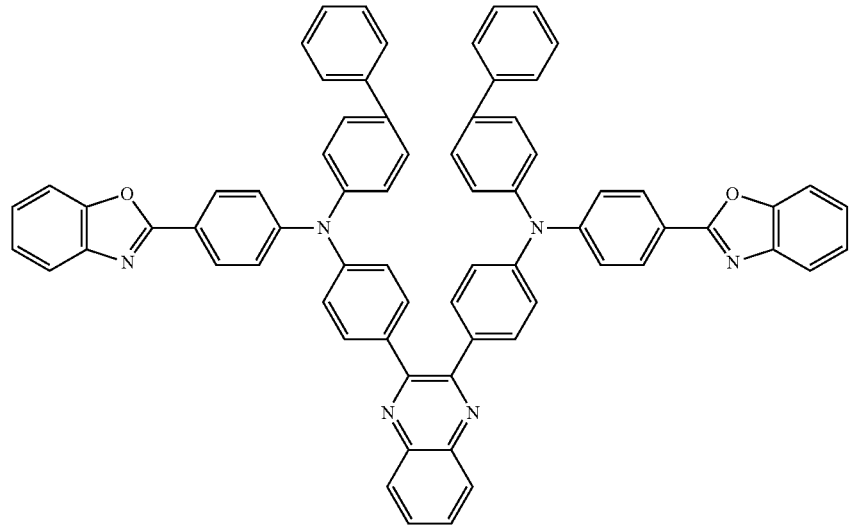

(540)
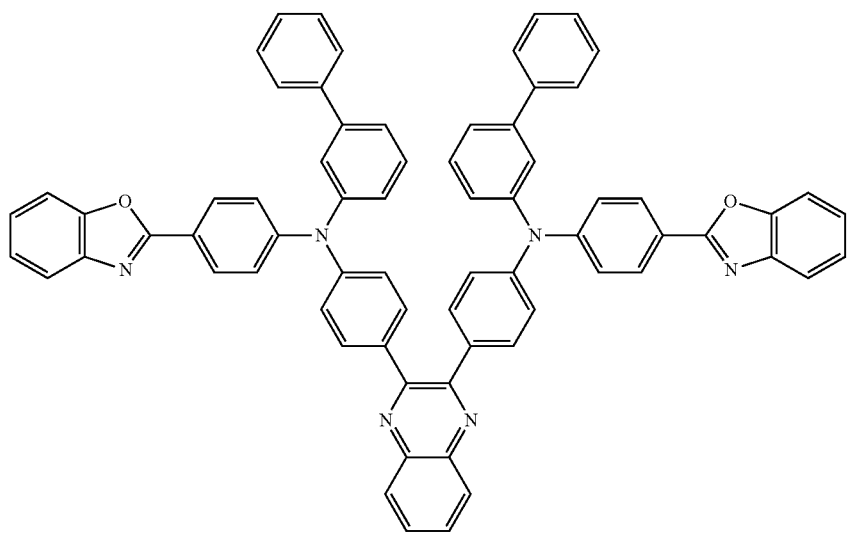
(541)
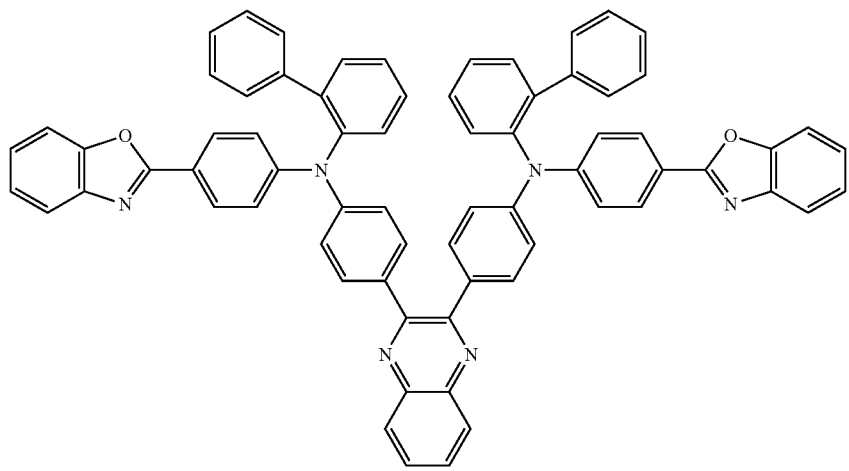
(542)
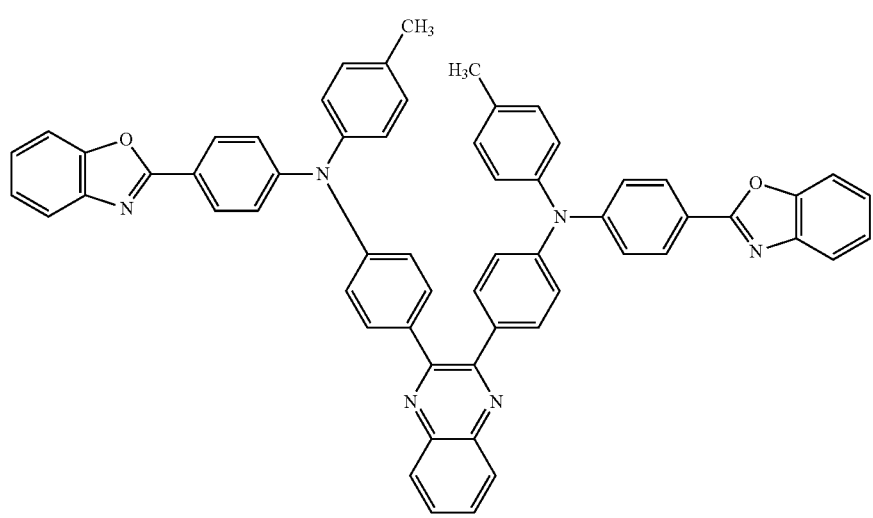

-continued
(543)
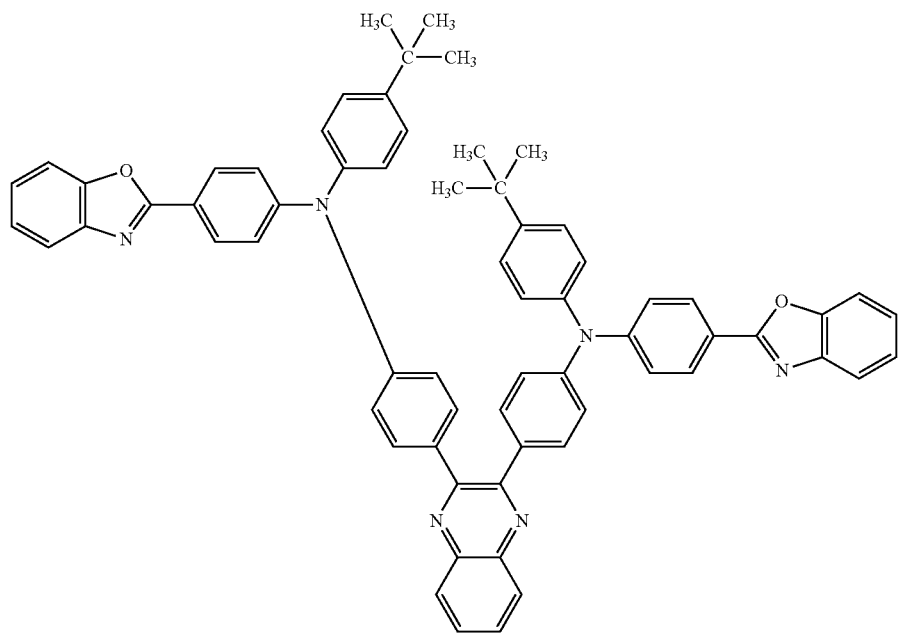
(544)
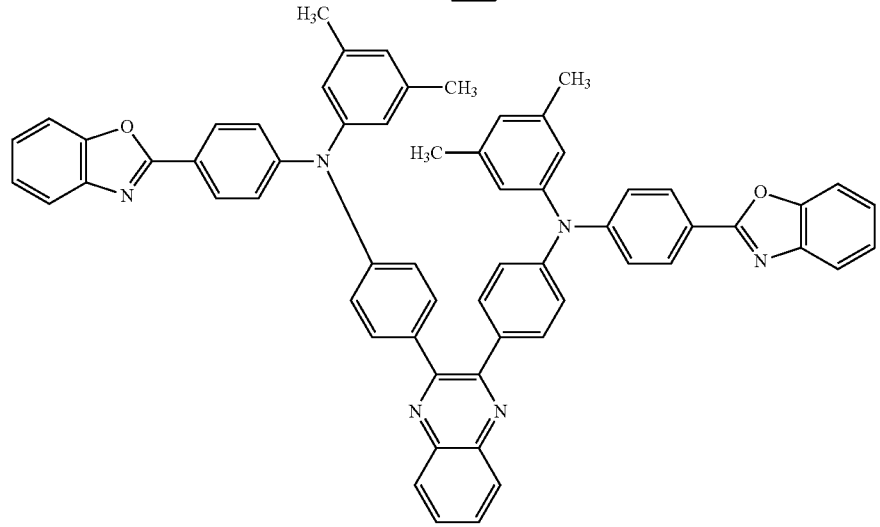
(545)
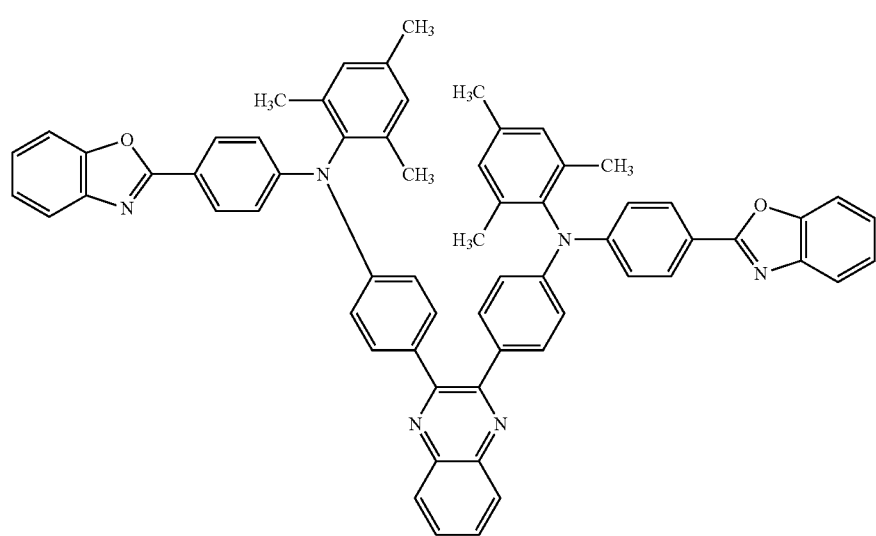

(546)
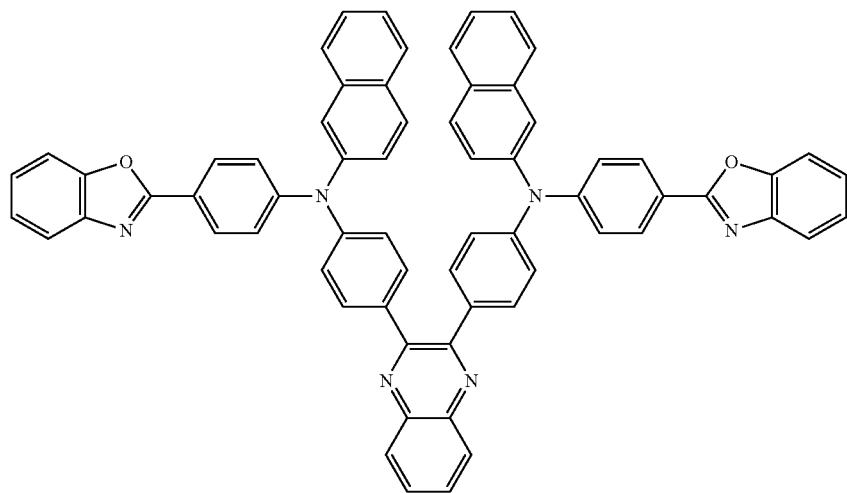
(547)
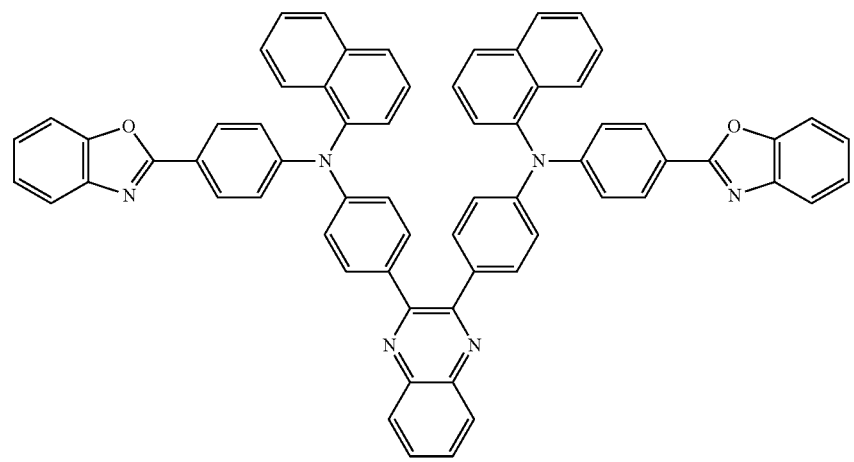
(548)
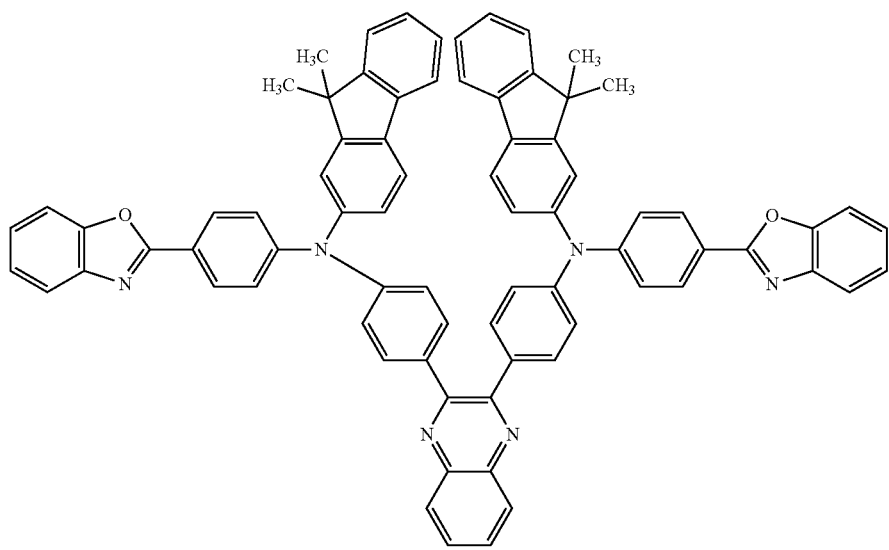

(549)
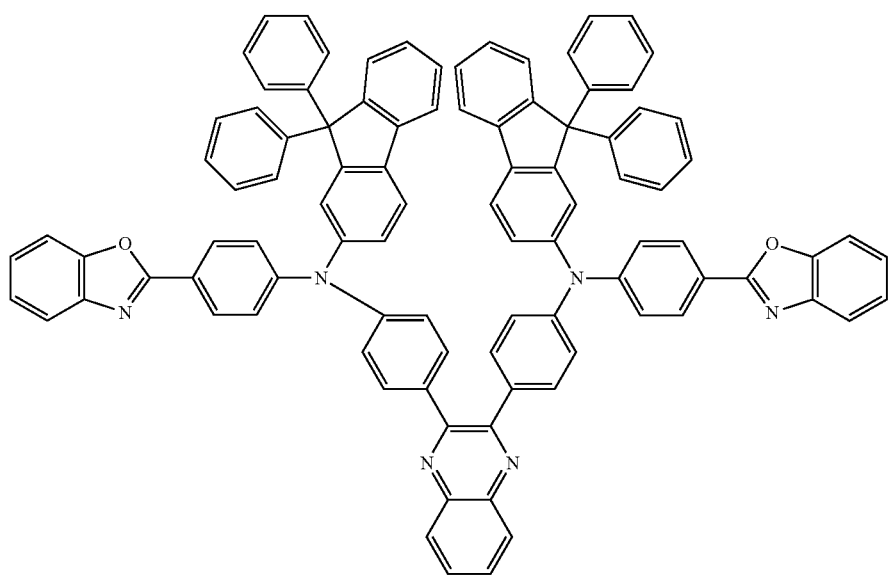
(550)
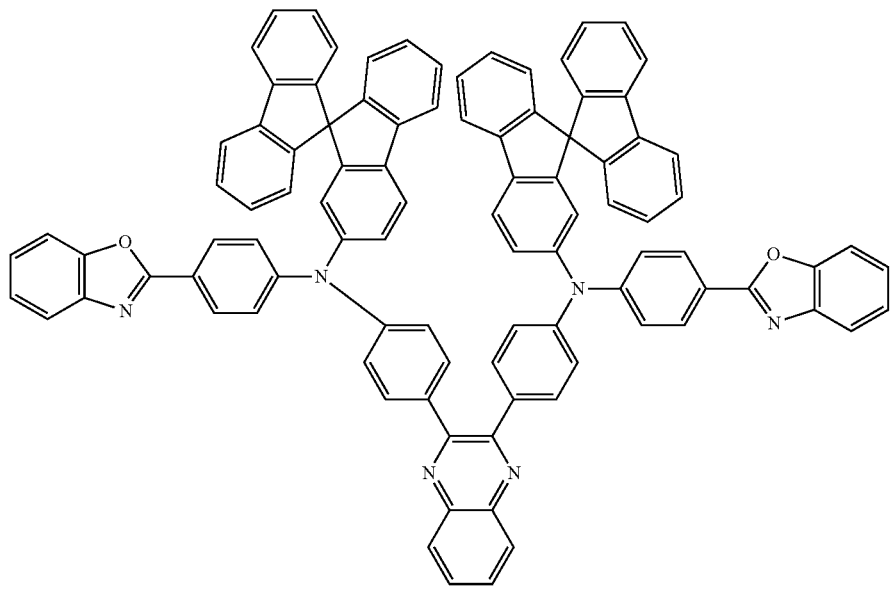
(551)
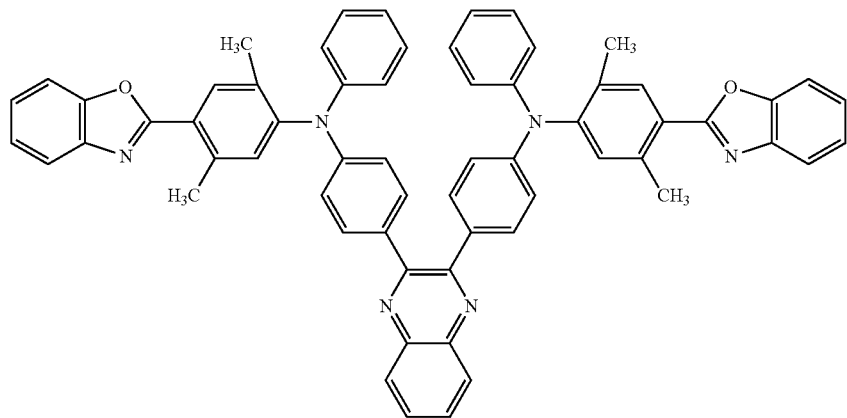

(552)
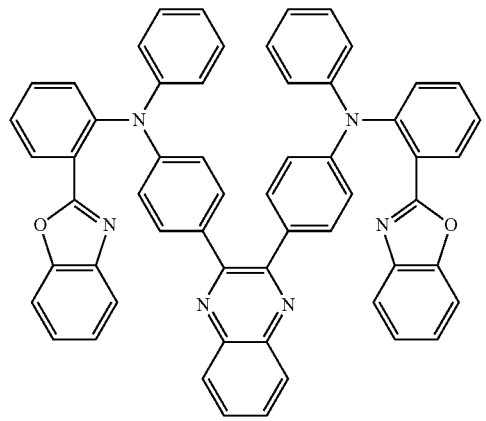
(553)
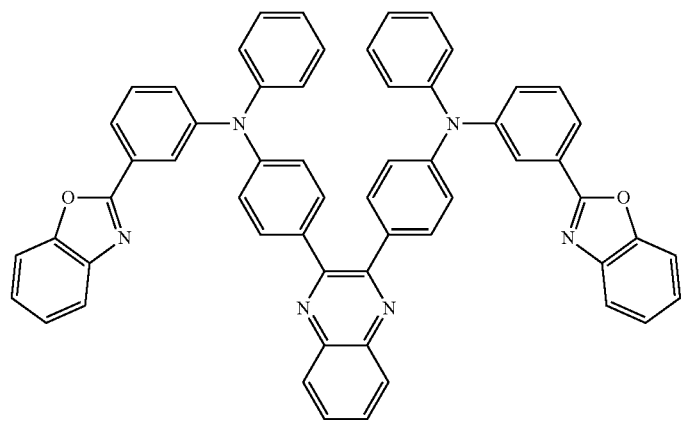
(554)
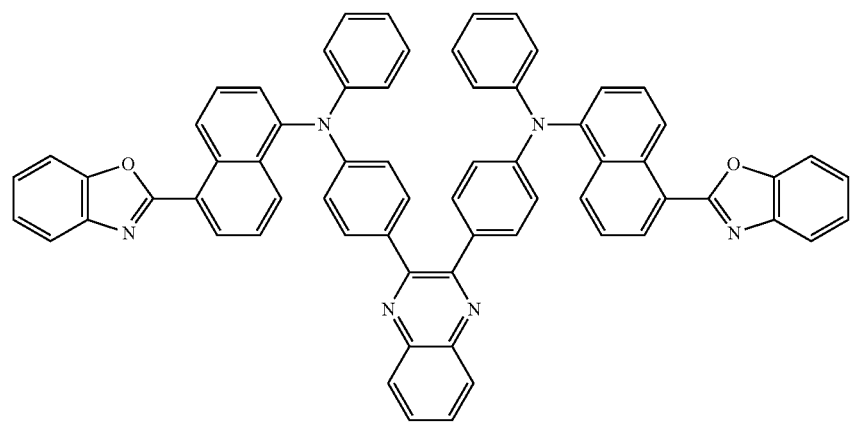

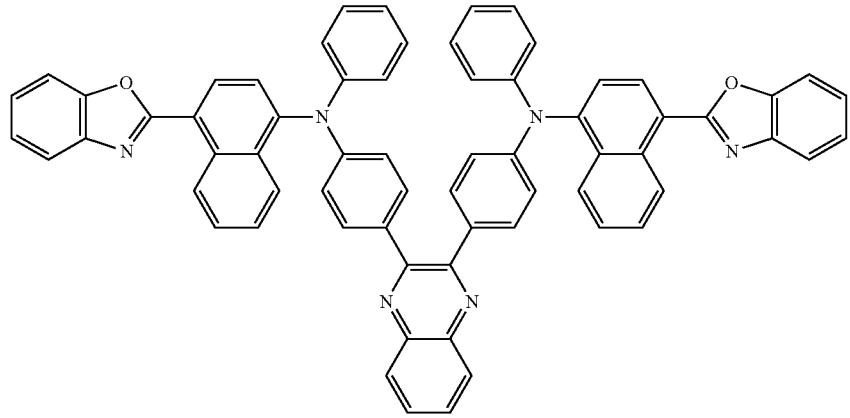
(555)
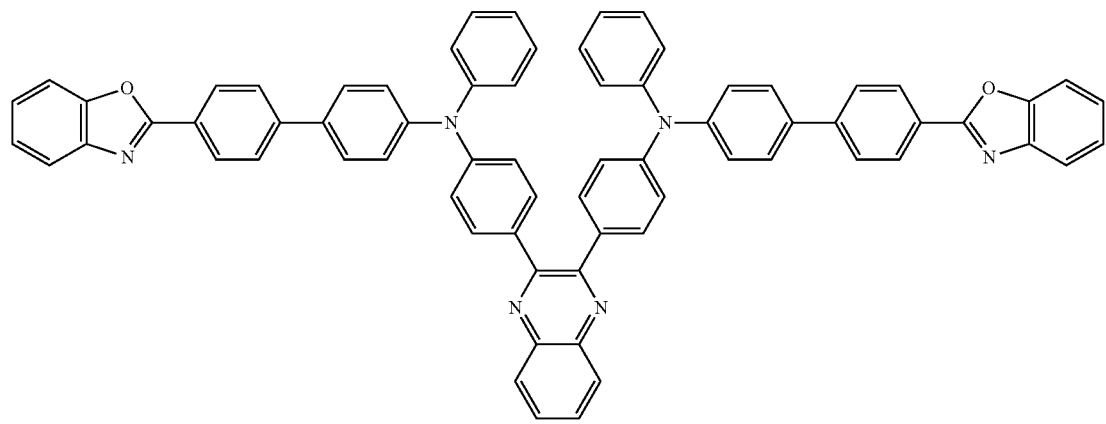
(556)
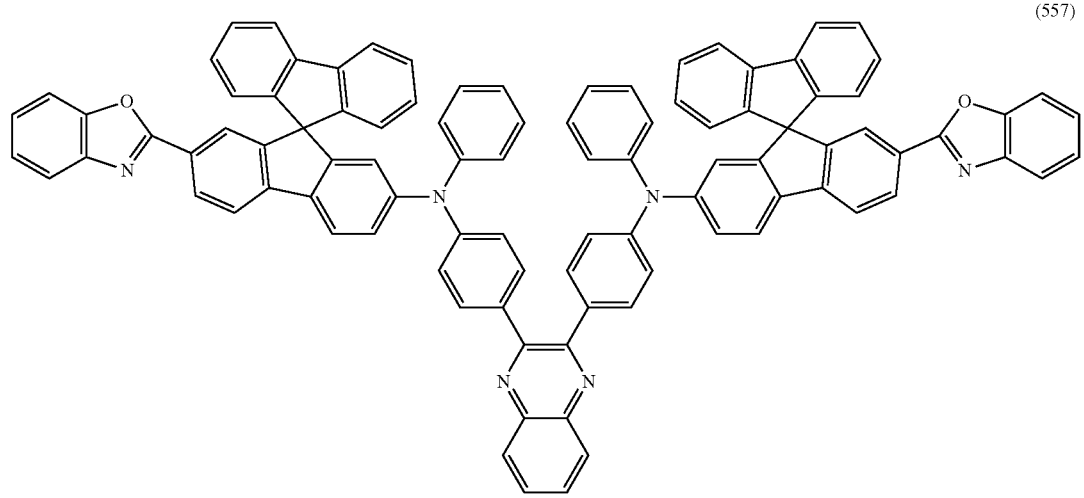
(557)

-continued
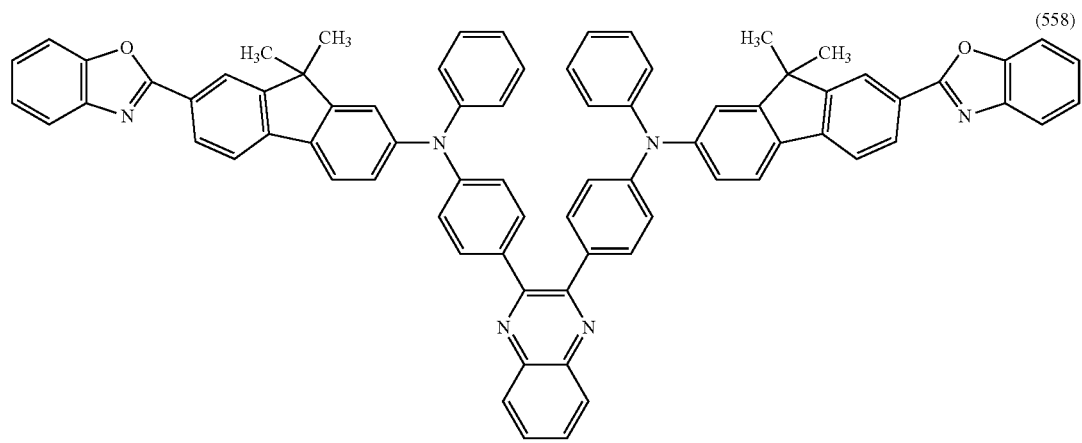
(558)
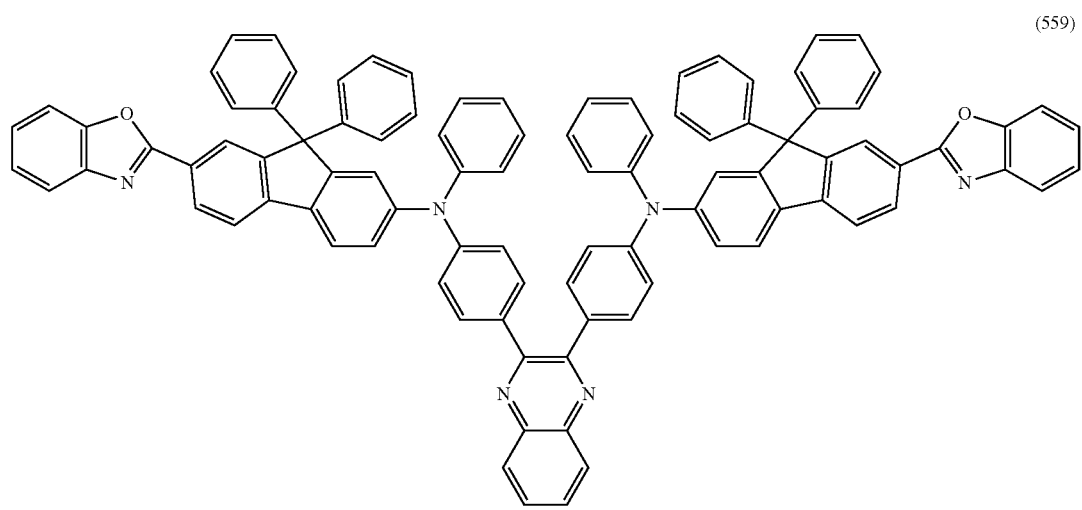
(559)
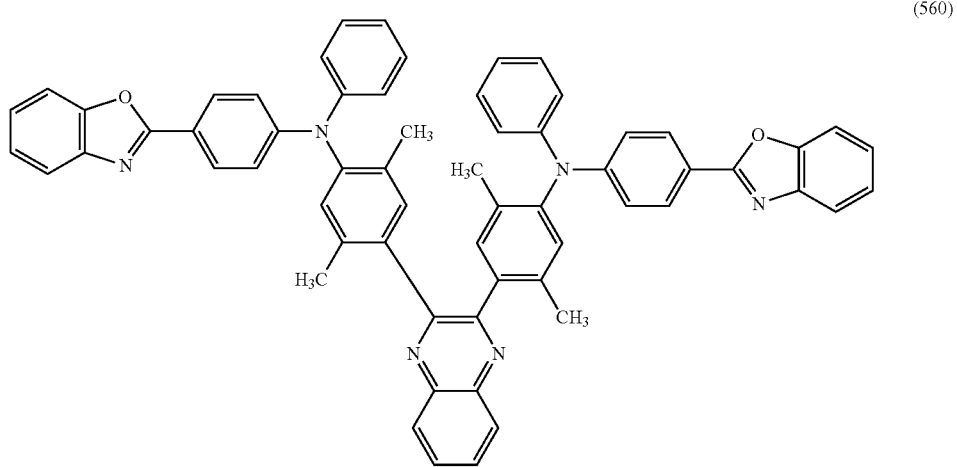
(560)

-continued
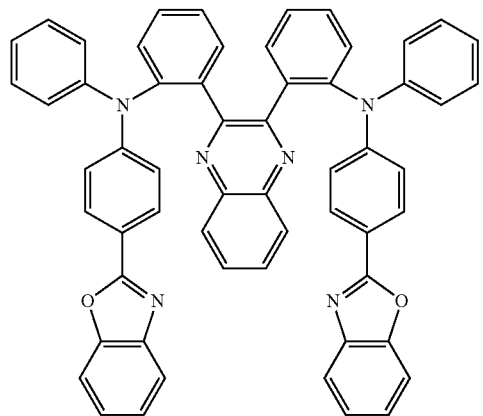
(561)
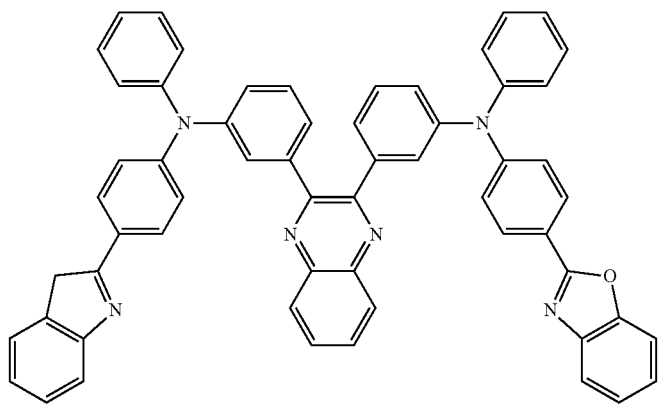
(562)
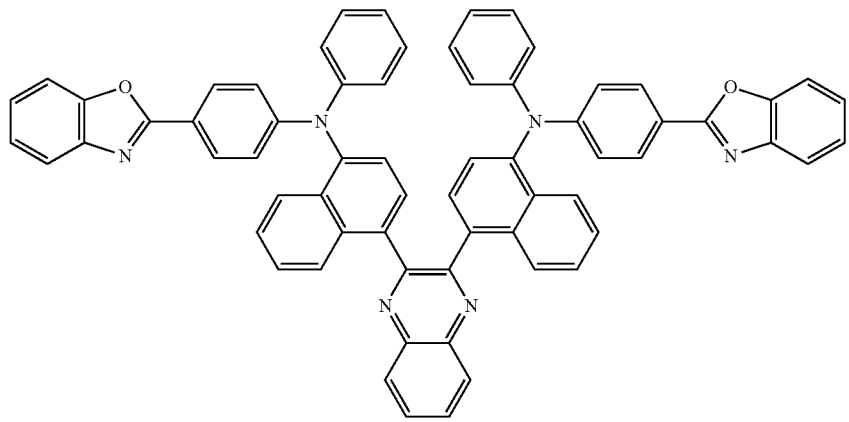
(563)
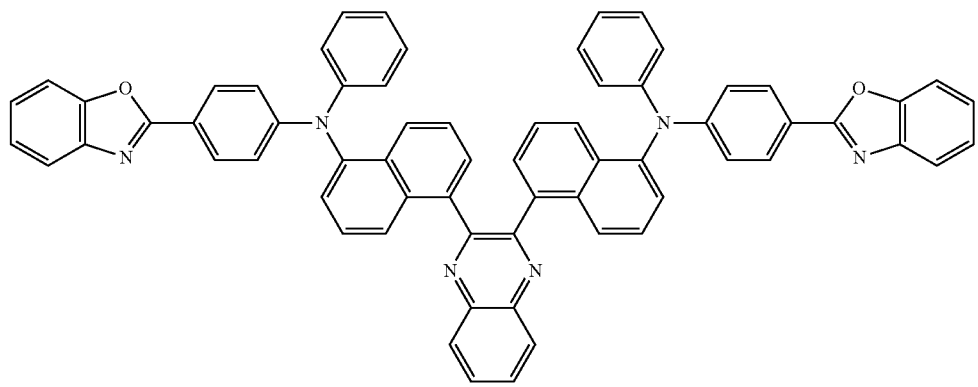
(564)

-continued
(565)
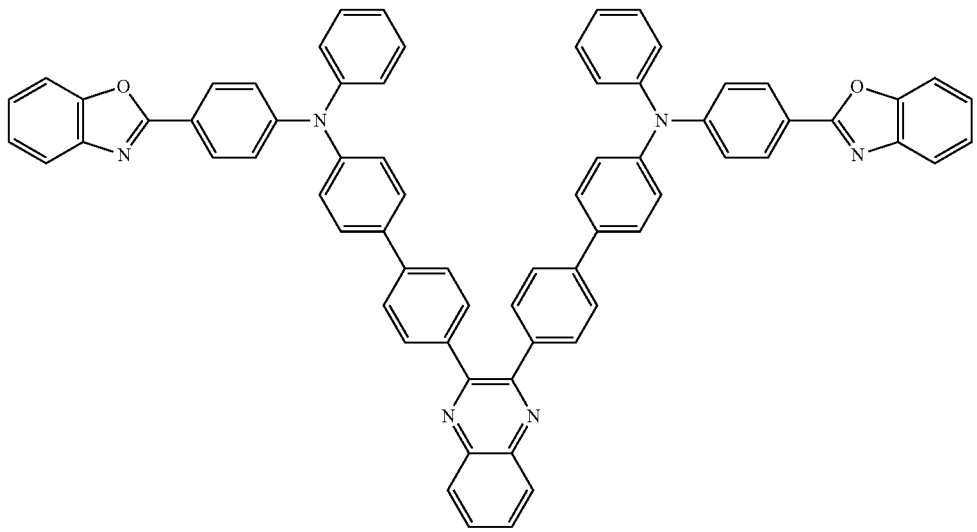
(566)
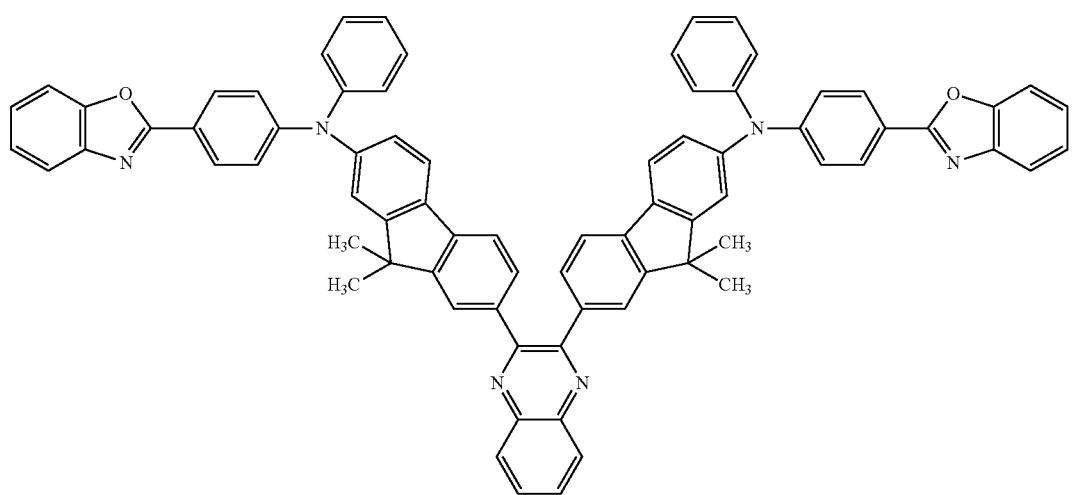
(567)
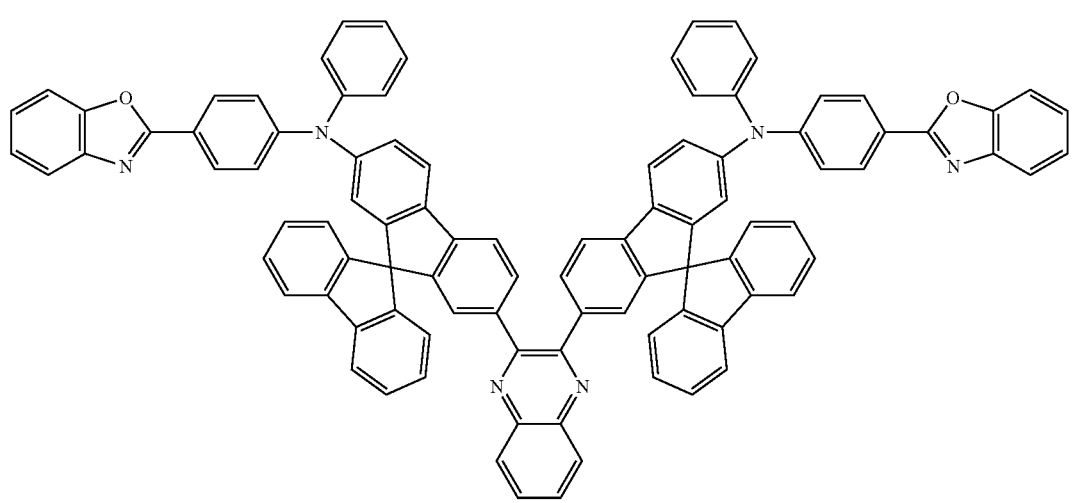

(568)
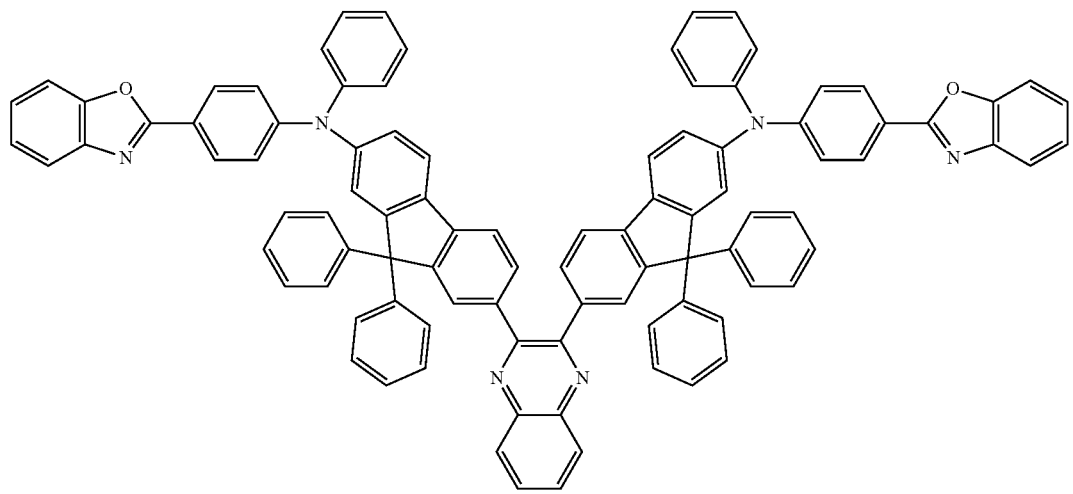
(601)
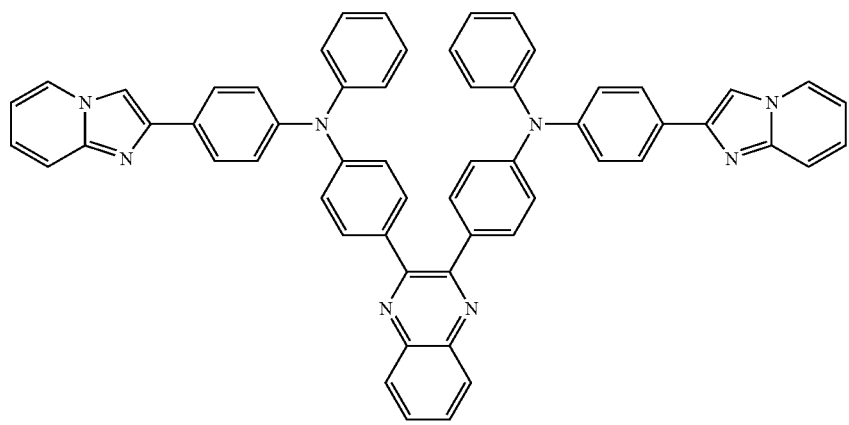
(602)
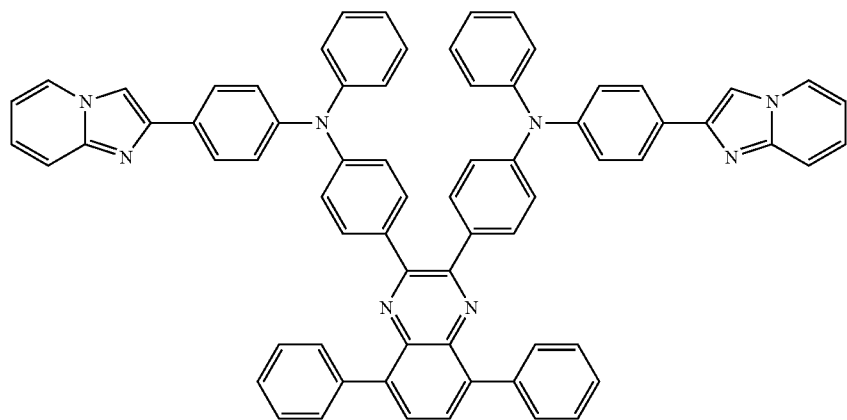

-continued
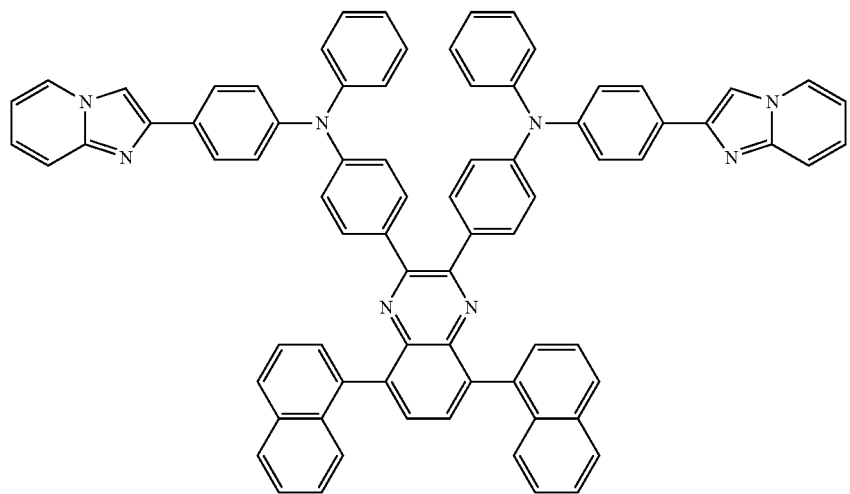
(603)
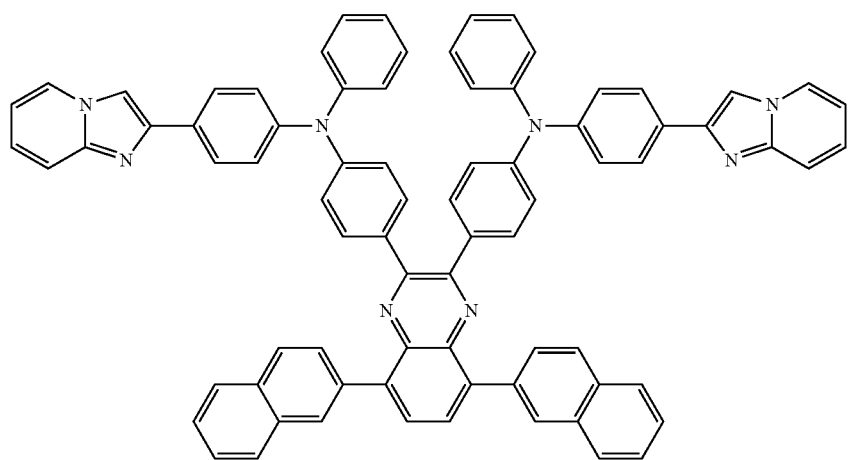
(604)
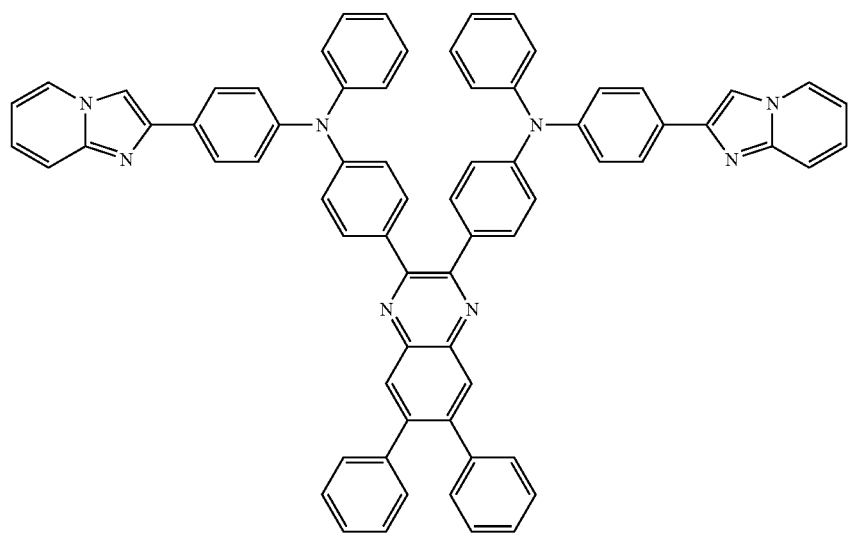
(605)

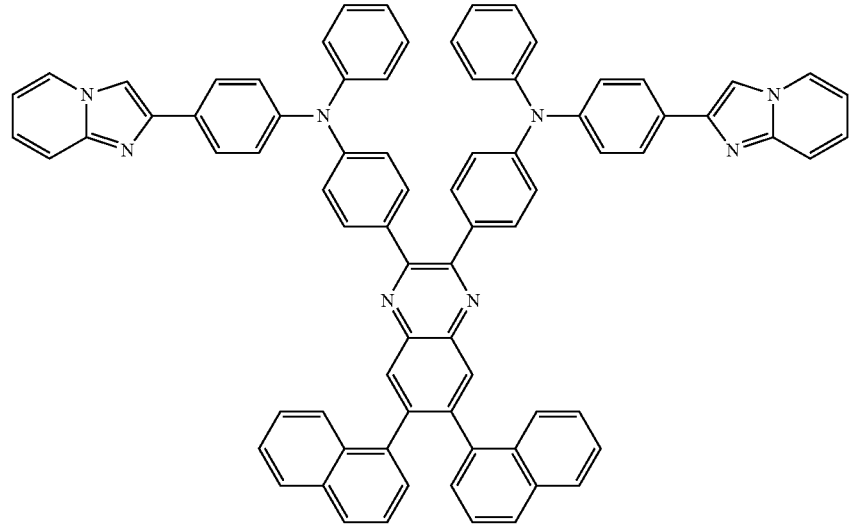
(606)
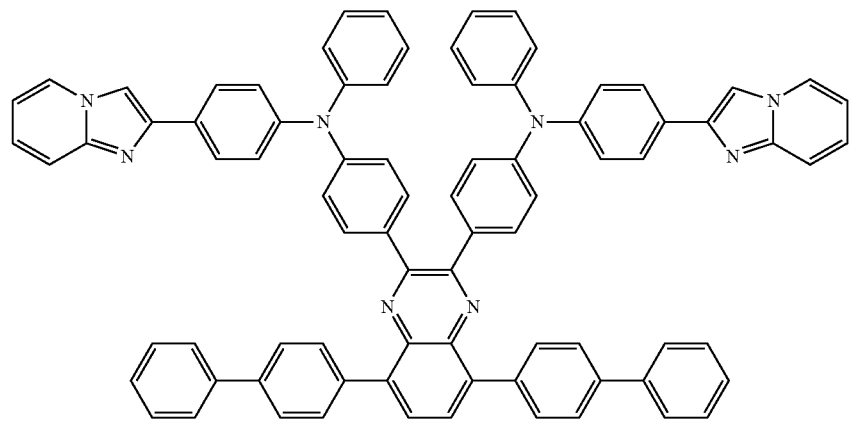
(607)
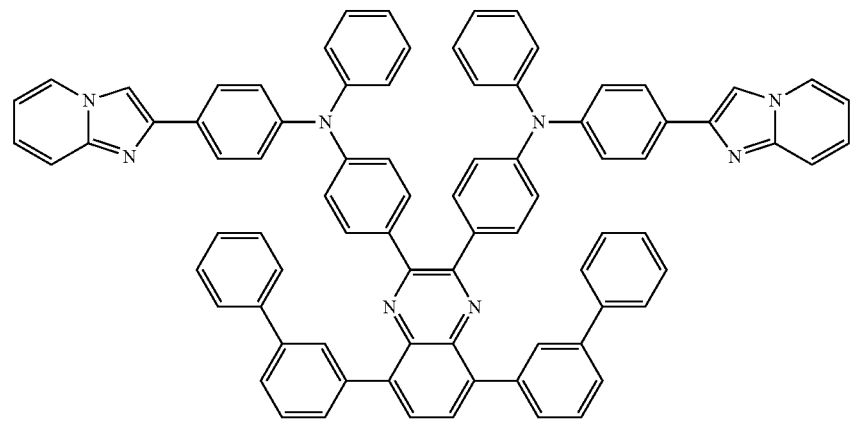
(608)

-continued
(609)
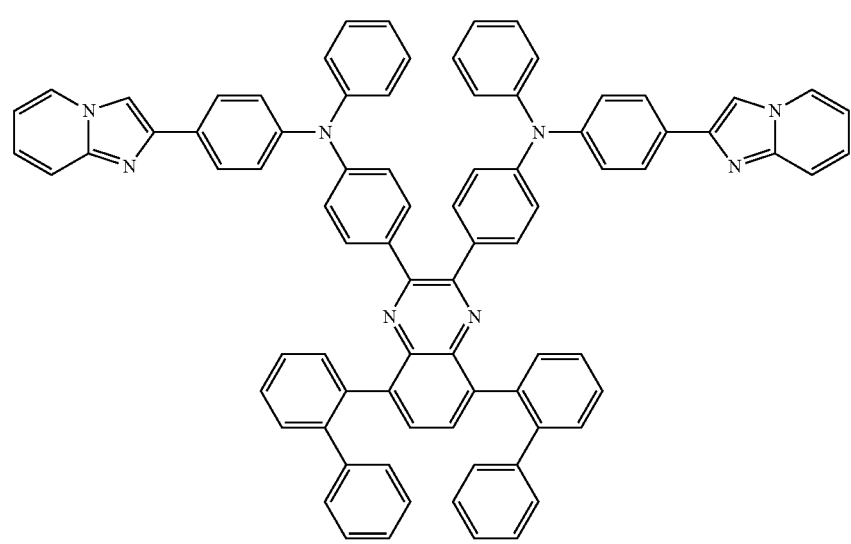
(610)
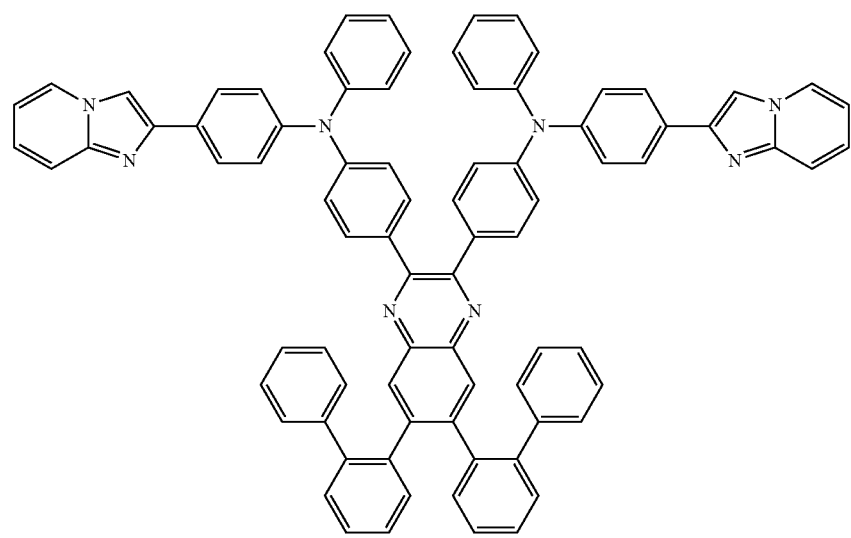
(611)
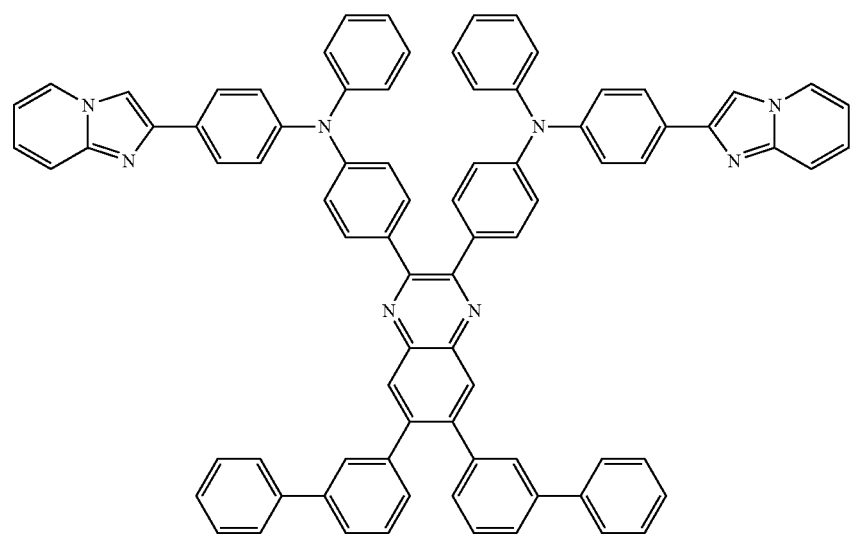

-continued
(612)
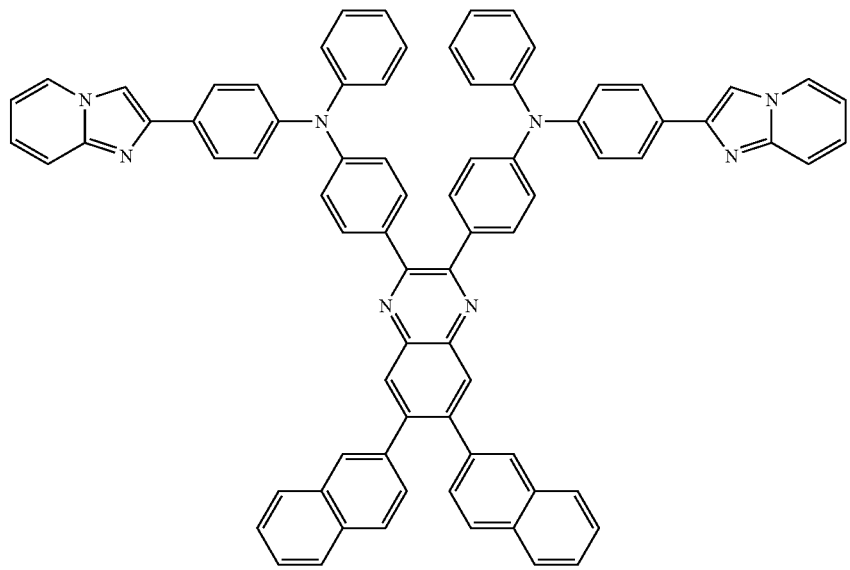
(613)
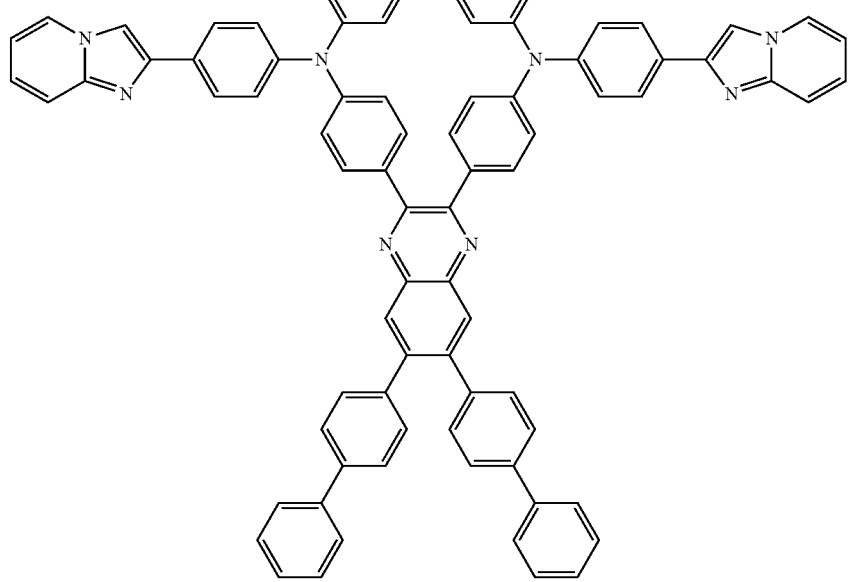
(614)
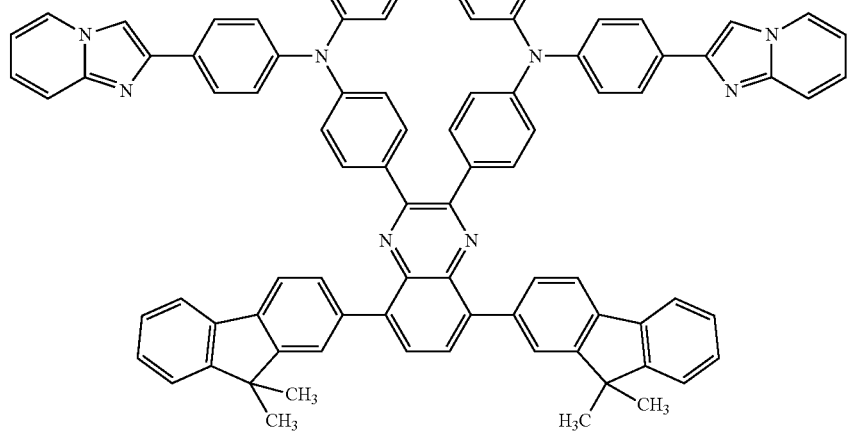

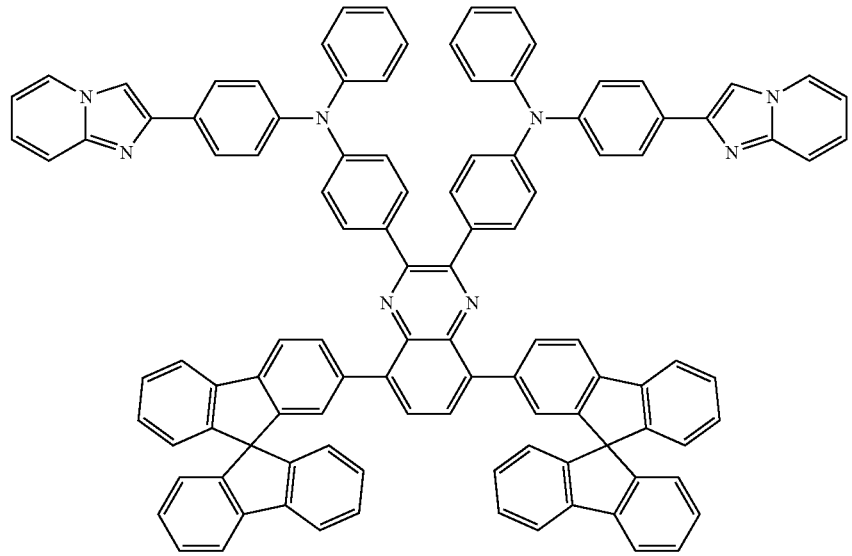
(615)
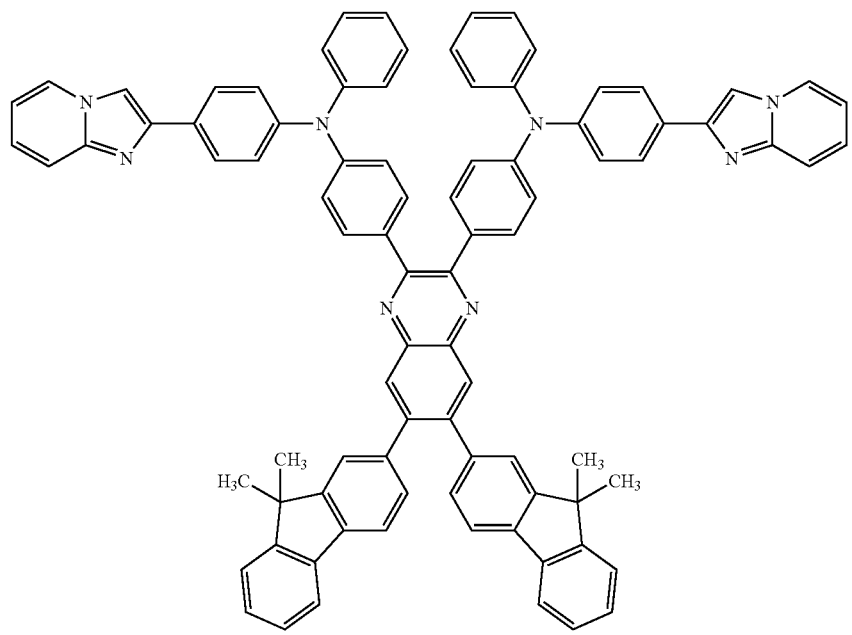
(616)

(617)
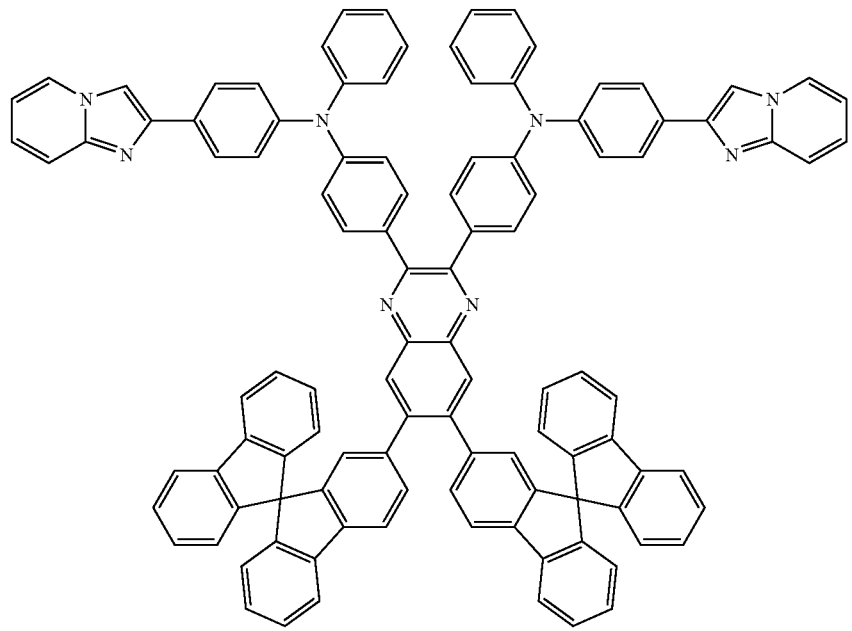
(618)
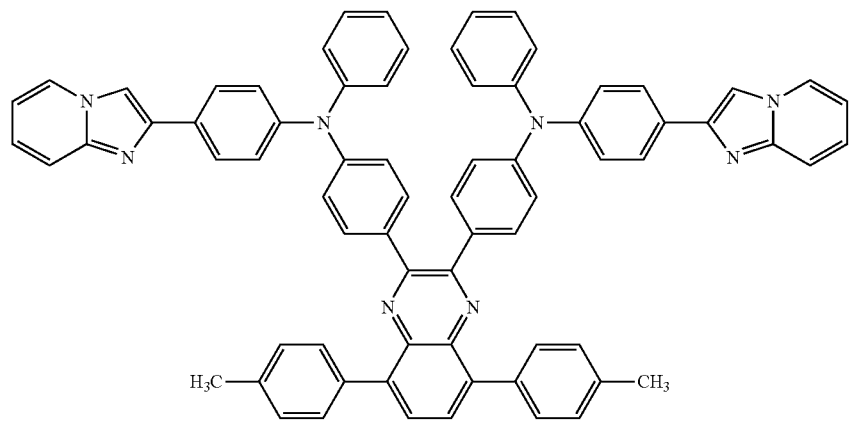
(619)
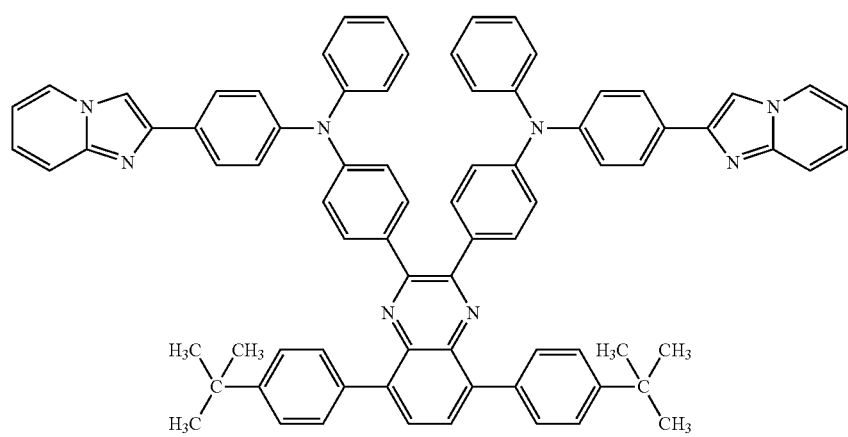

(620)
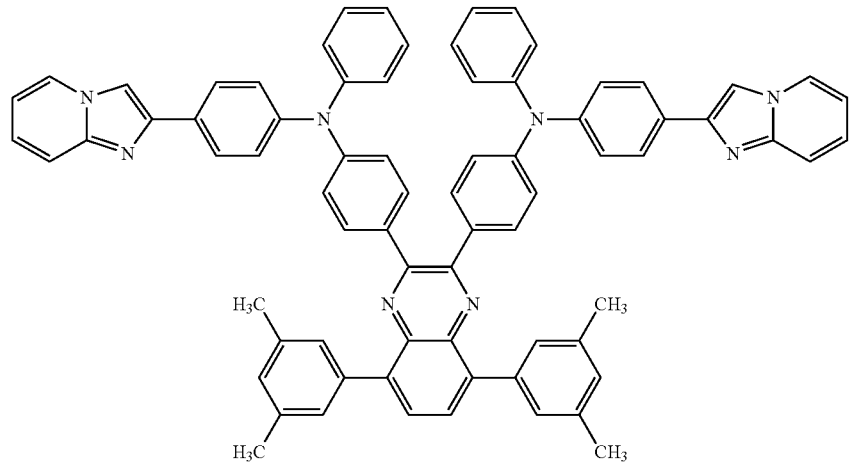
(621)
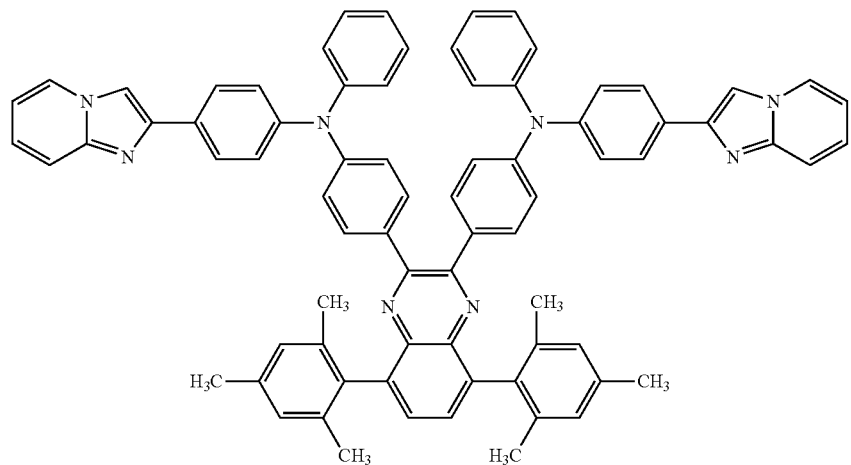
(622)
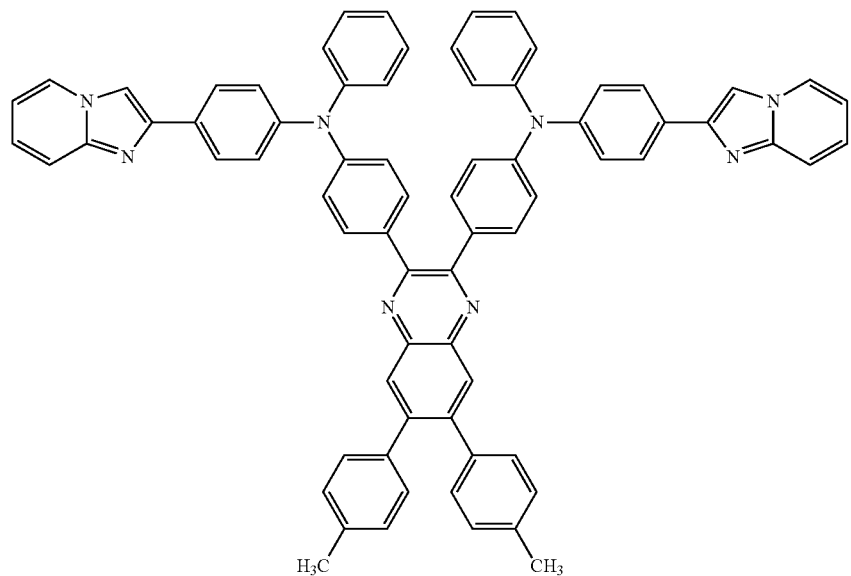

(623)
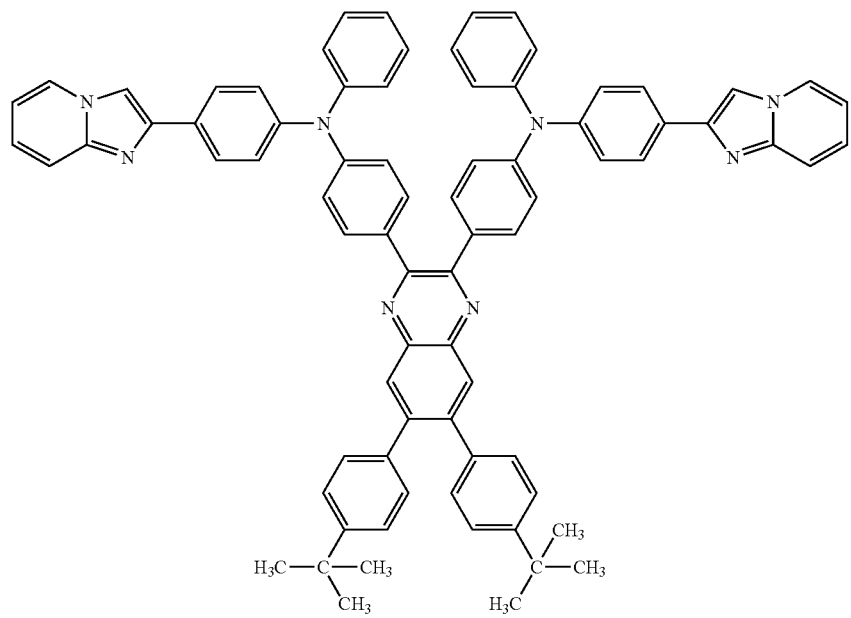
(624)
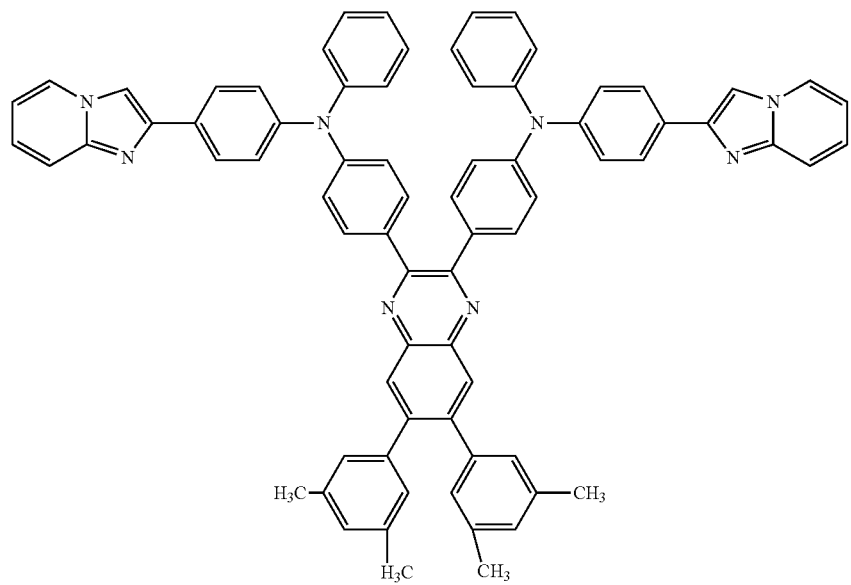

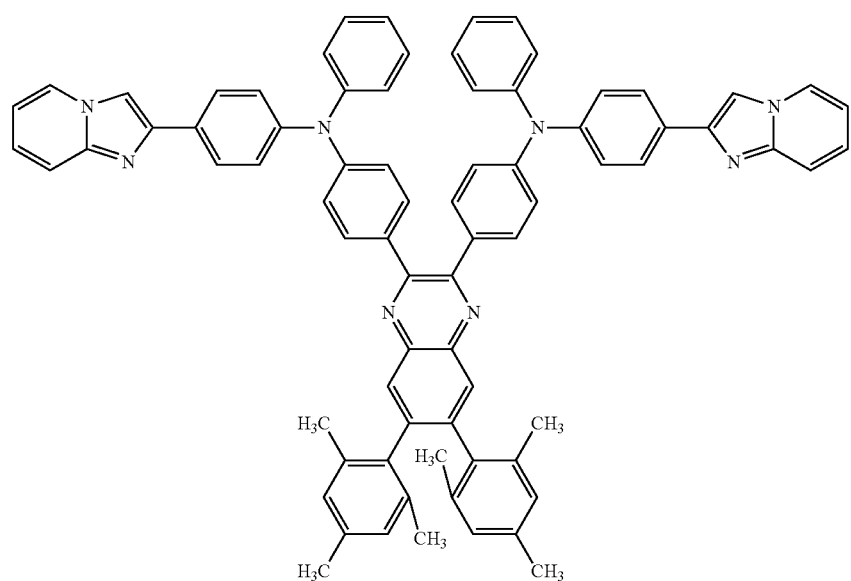
(625)
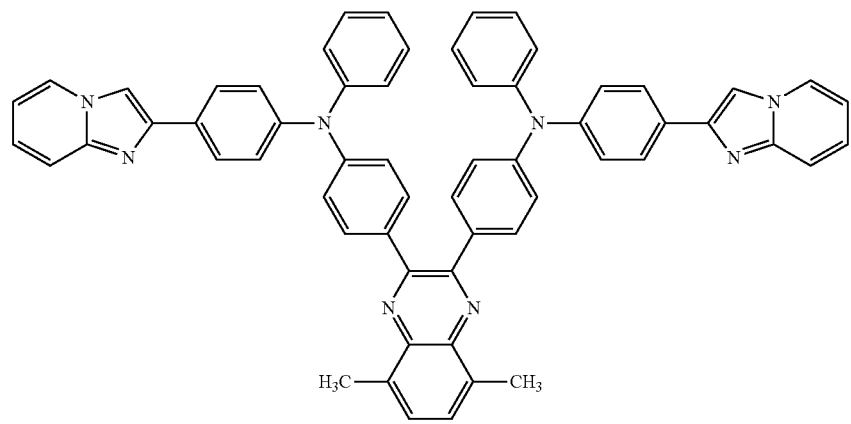
(626)
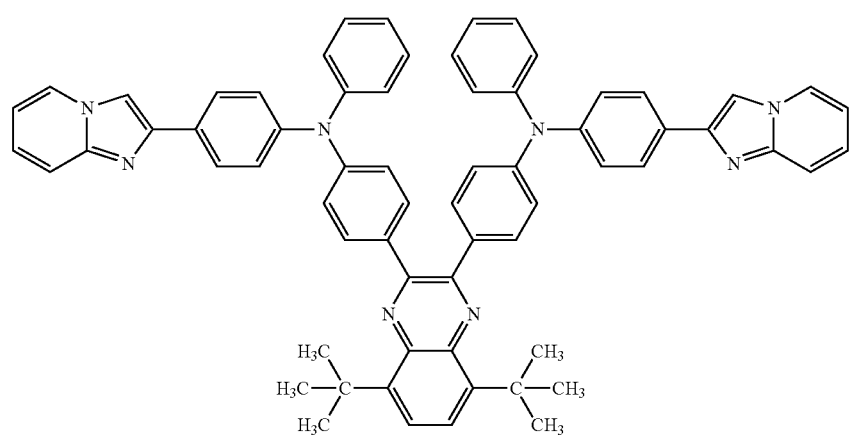
(627)

(628)
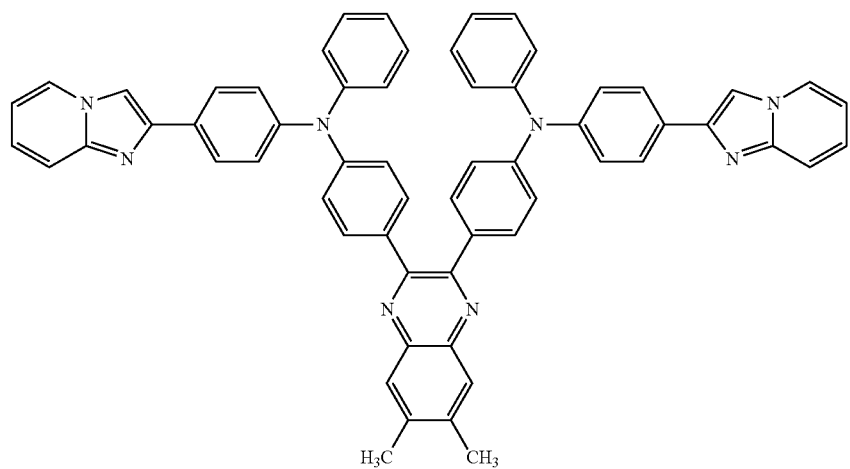
(629)
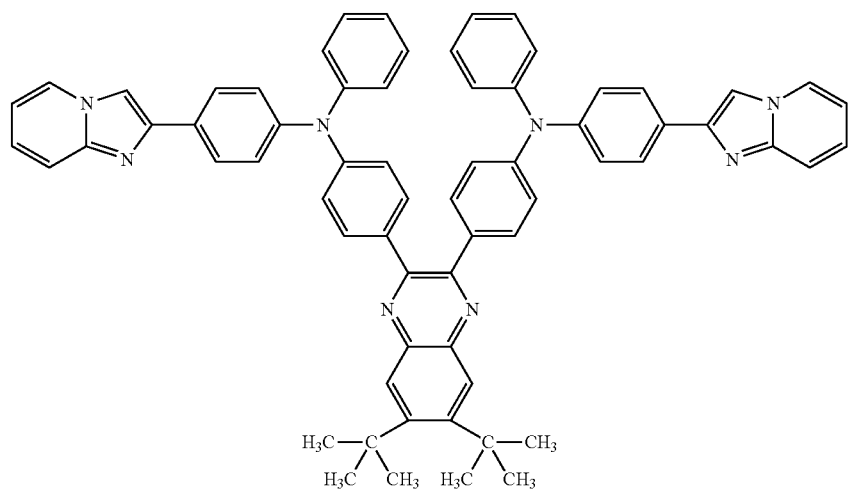
(630)
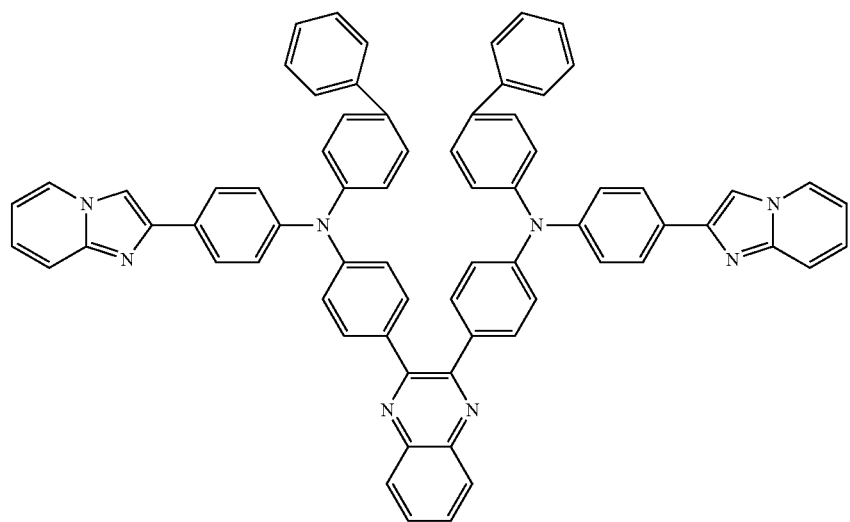

(631)
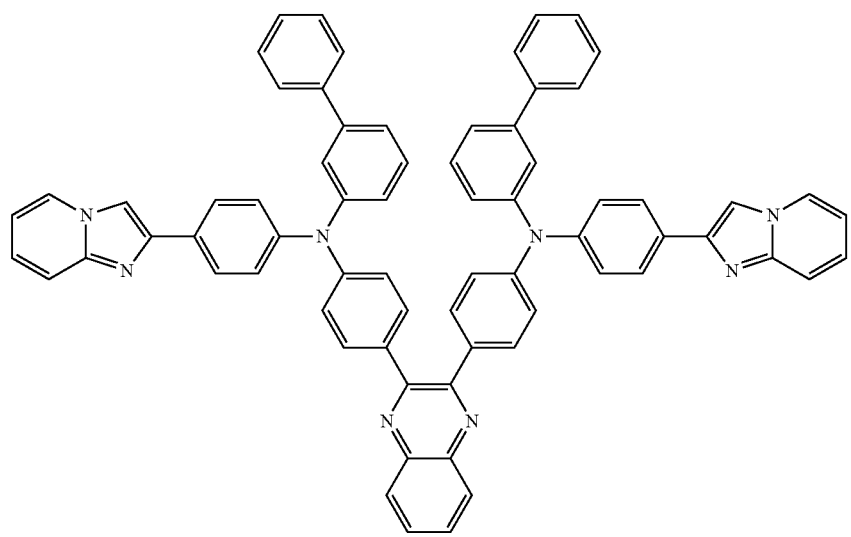
(632)
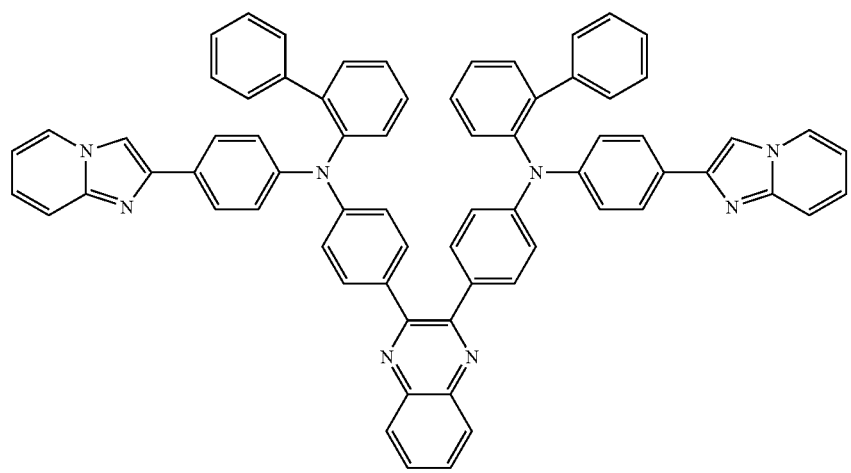
(633)
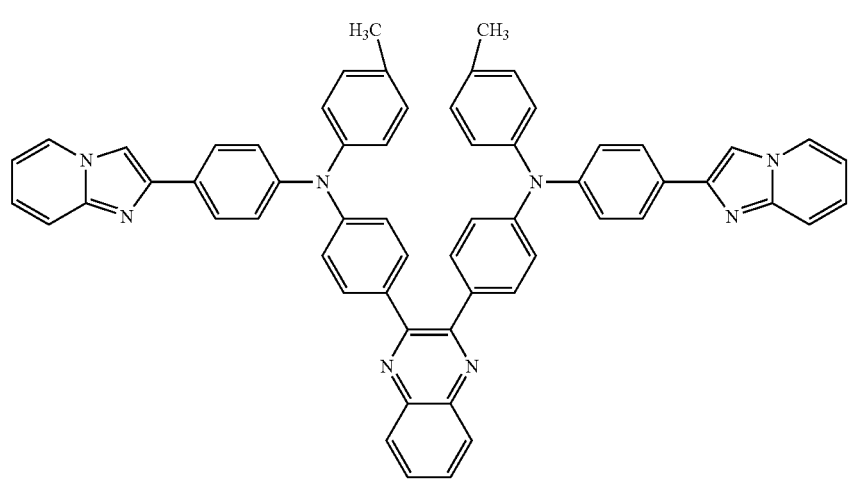

(634)
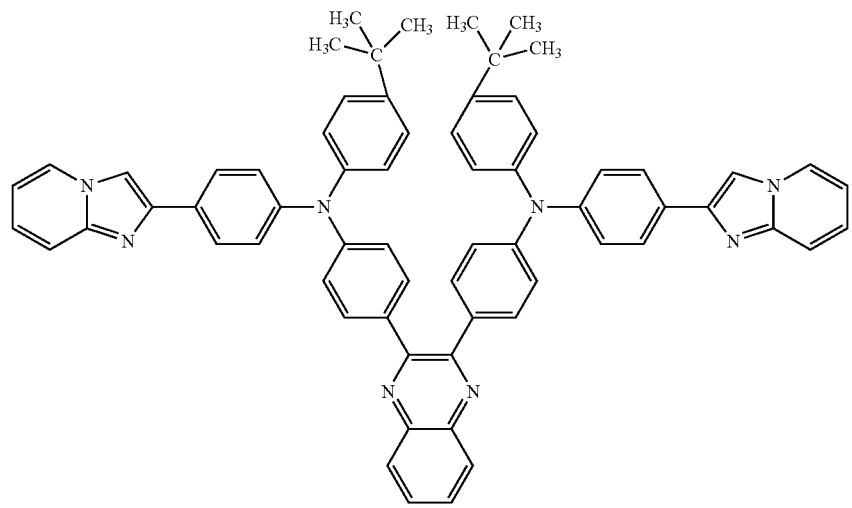
(635)
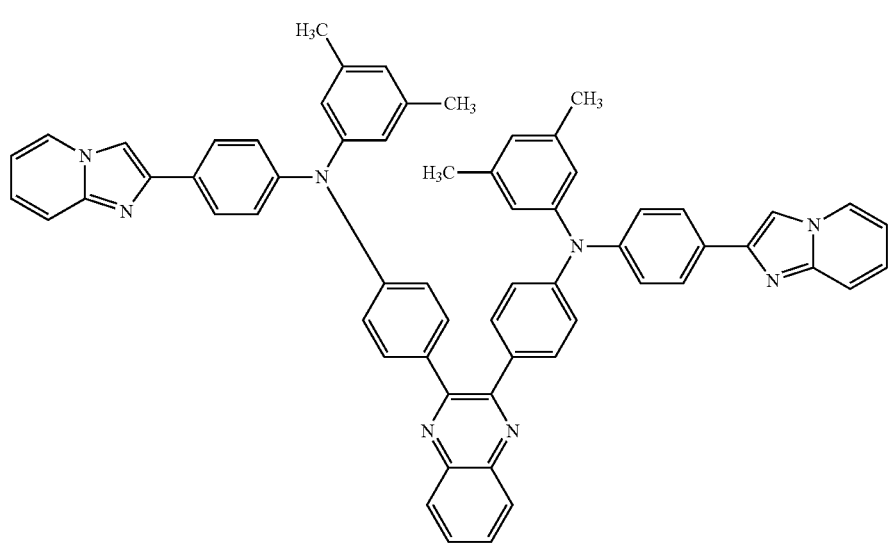
(636)
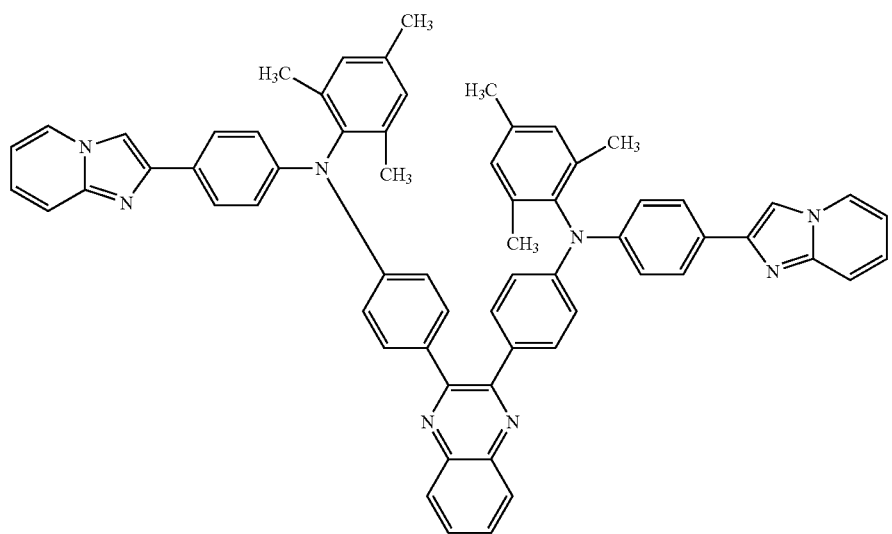

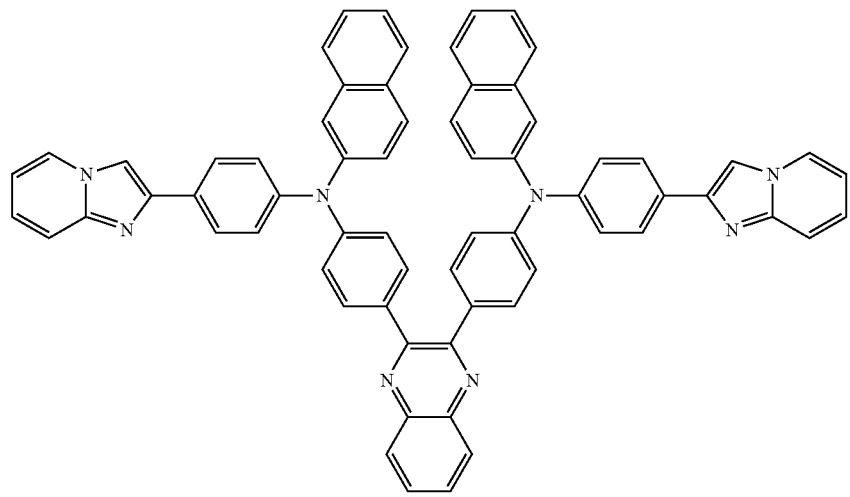
(637)
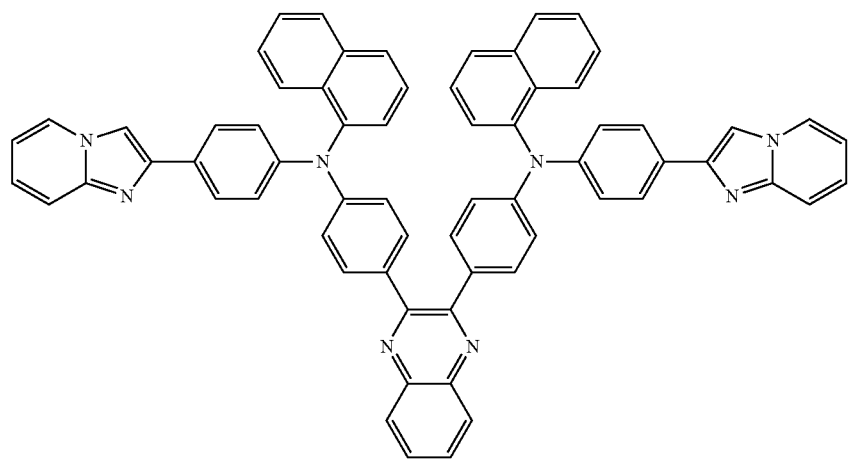
(638)
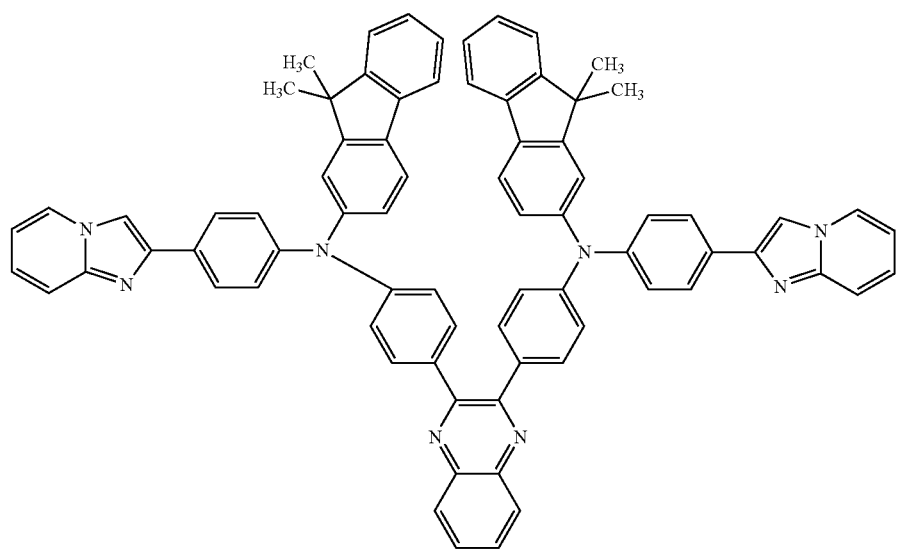
(639)

-continued
(640)
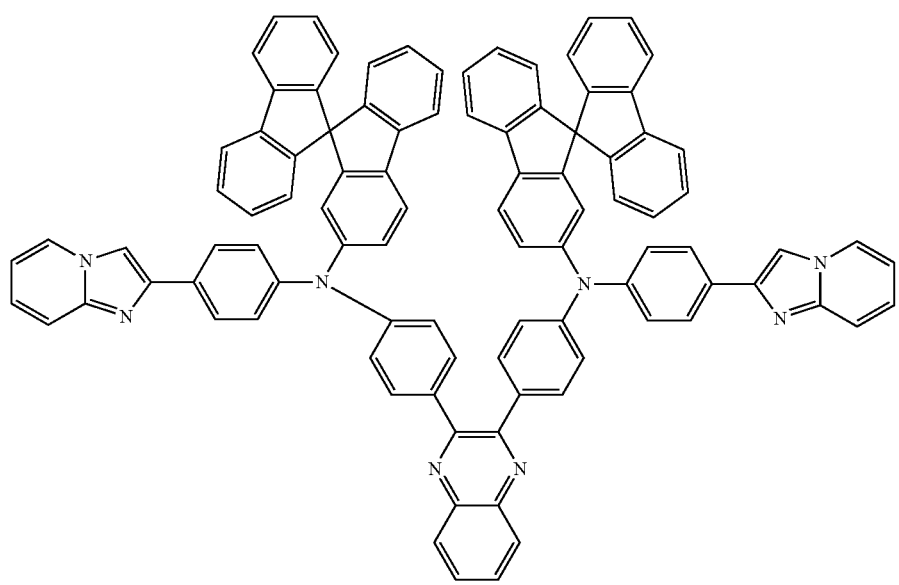
(641)
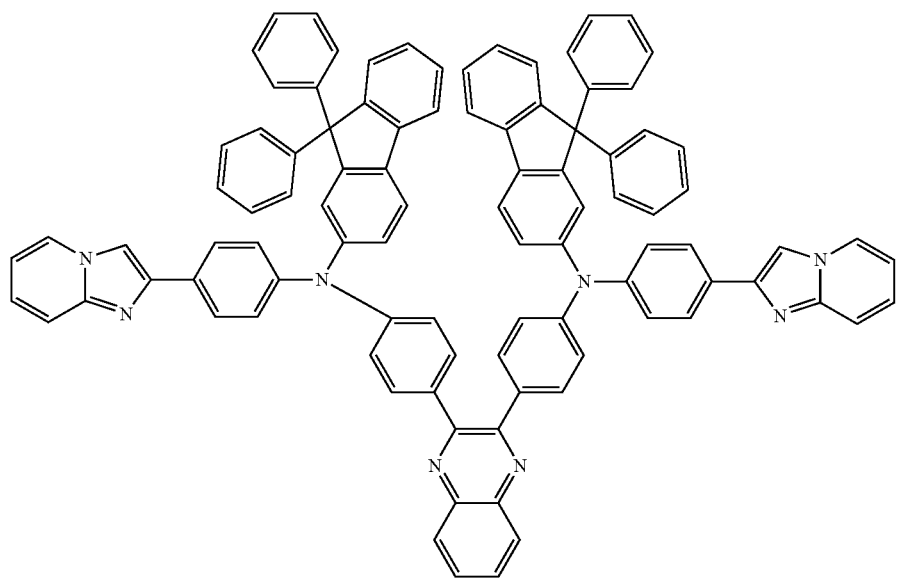
(642)
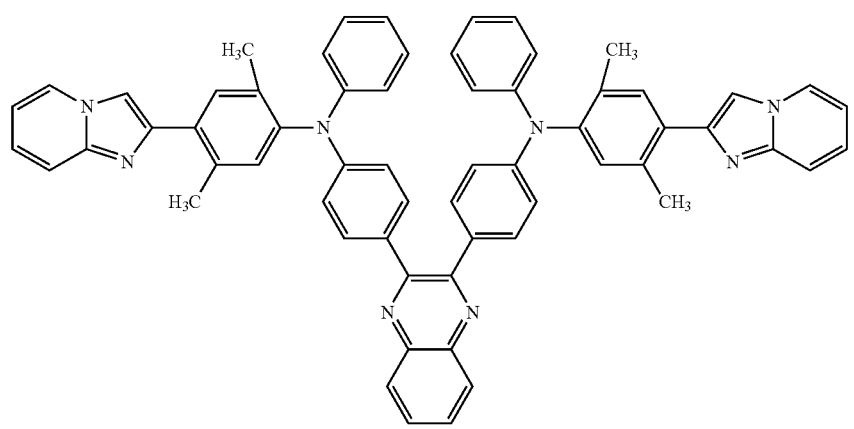

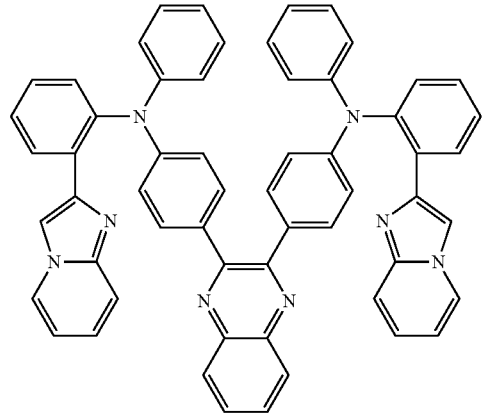
(643)
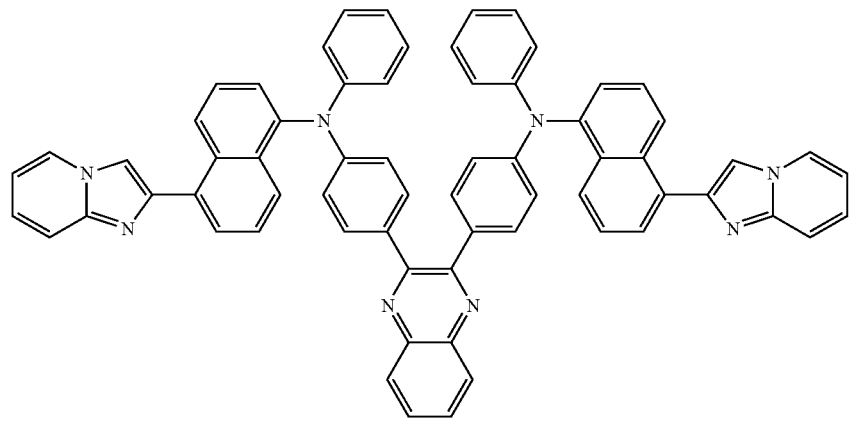
(644)
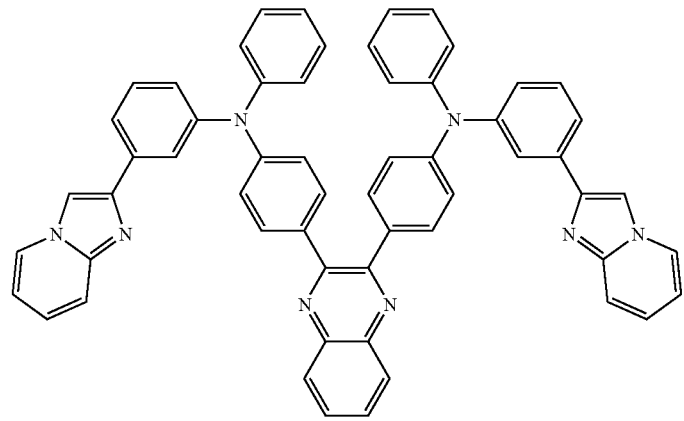
(645)

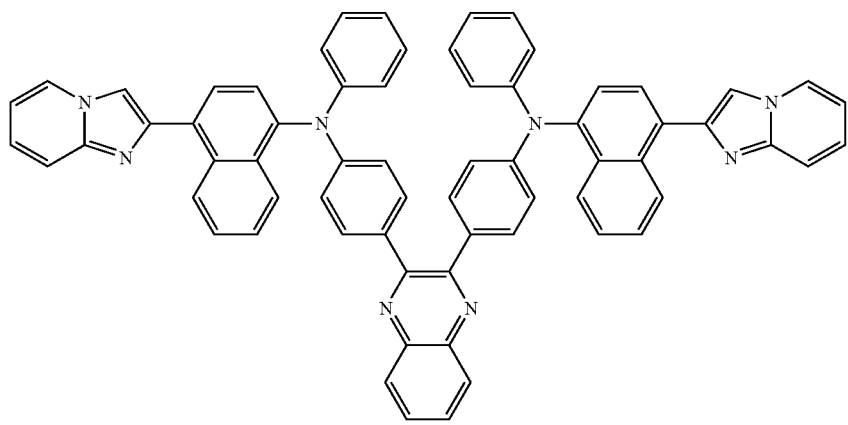
(646)
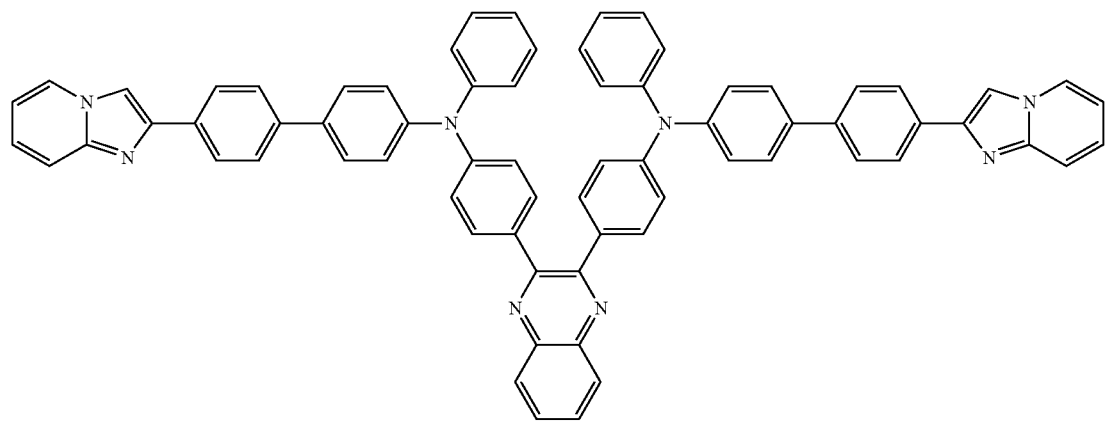
(647)
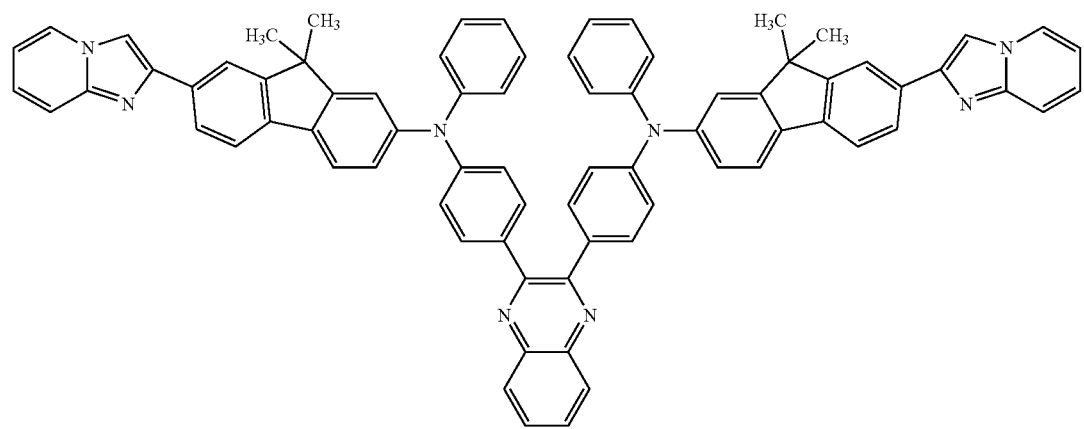
(648)

-continued
(651)
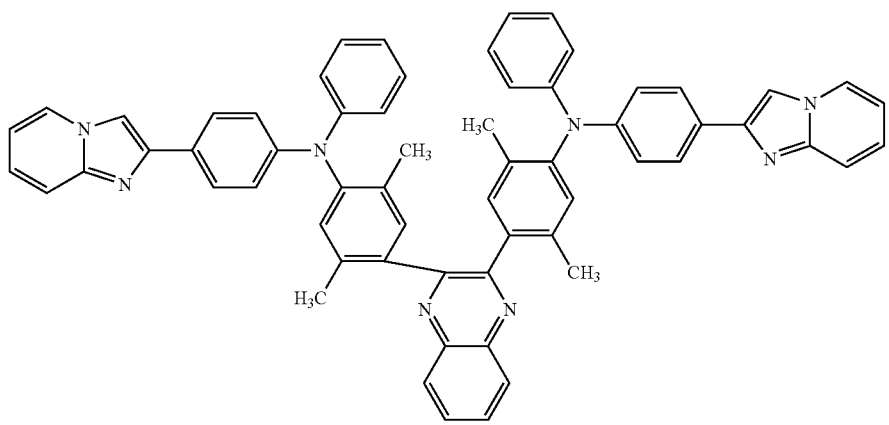
(652)
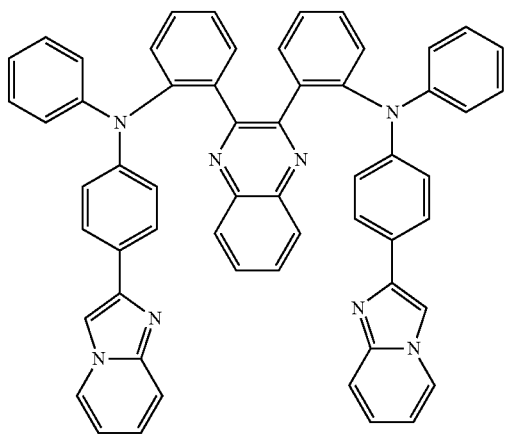
(653)
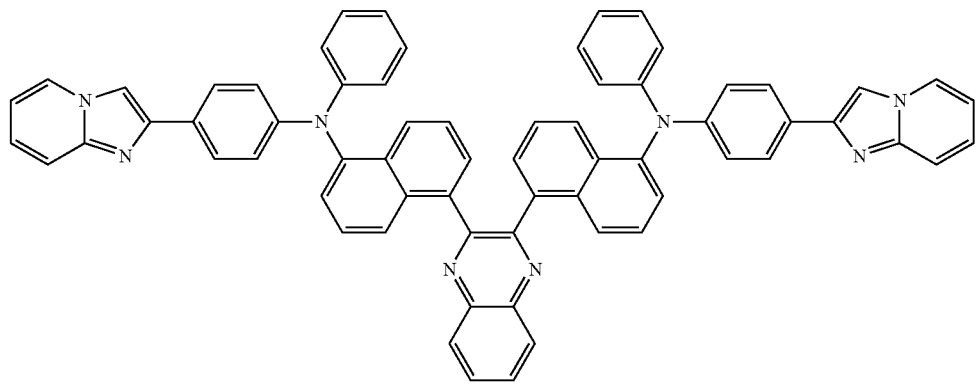
(654)
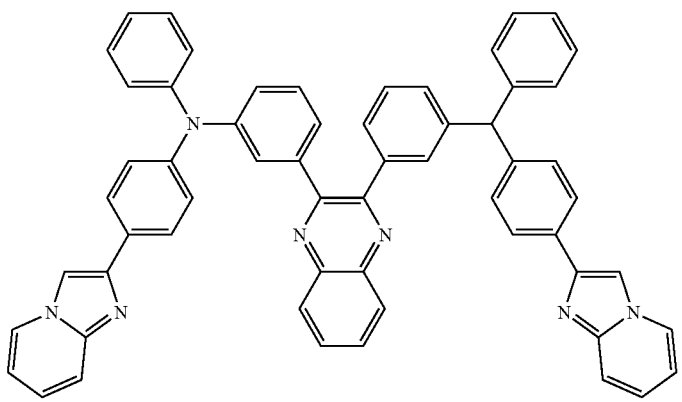

(655)
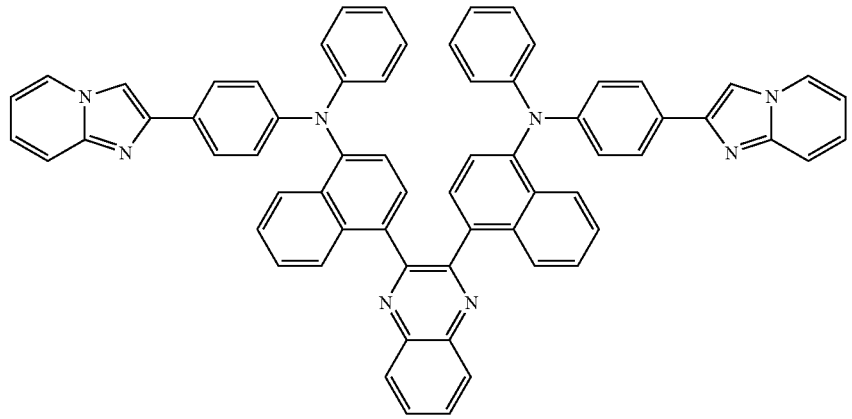
(656)
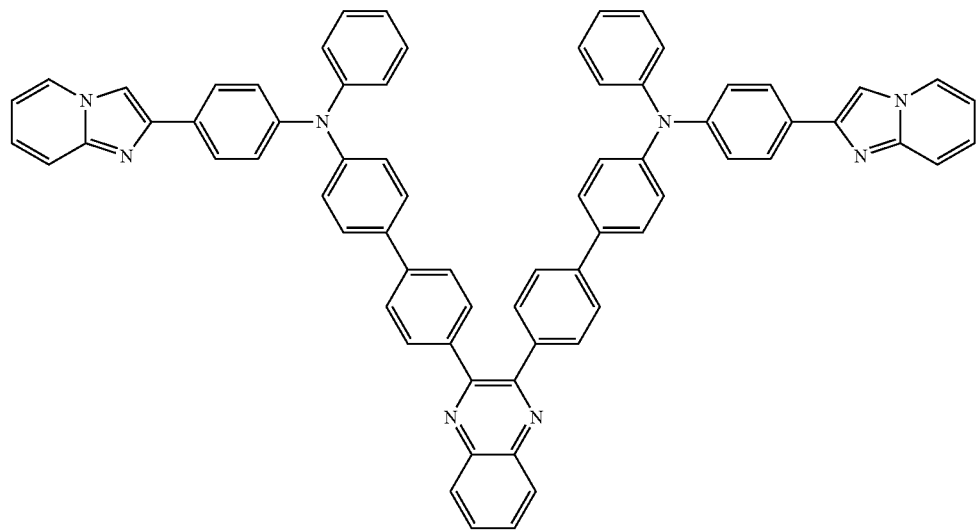
(657)
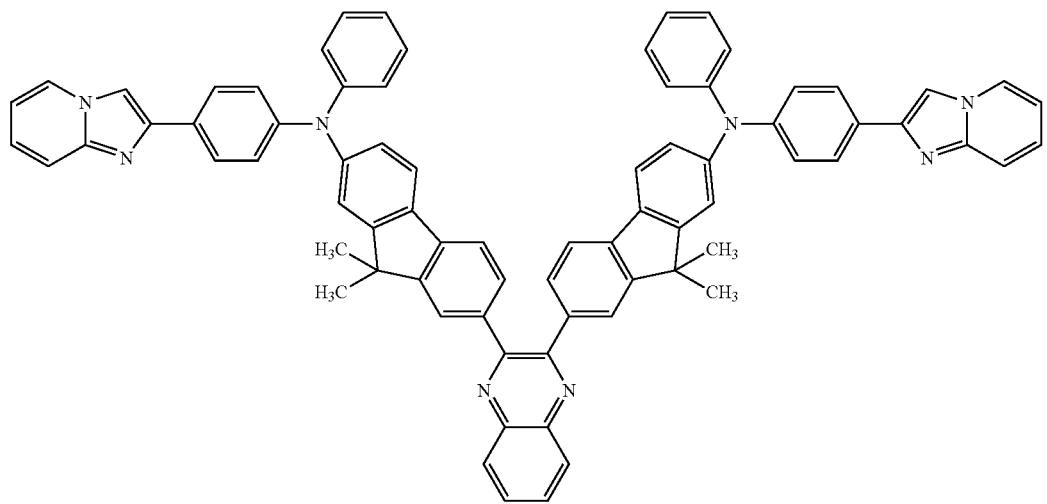

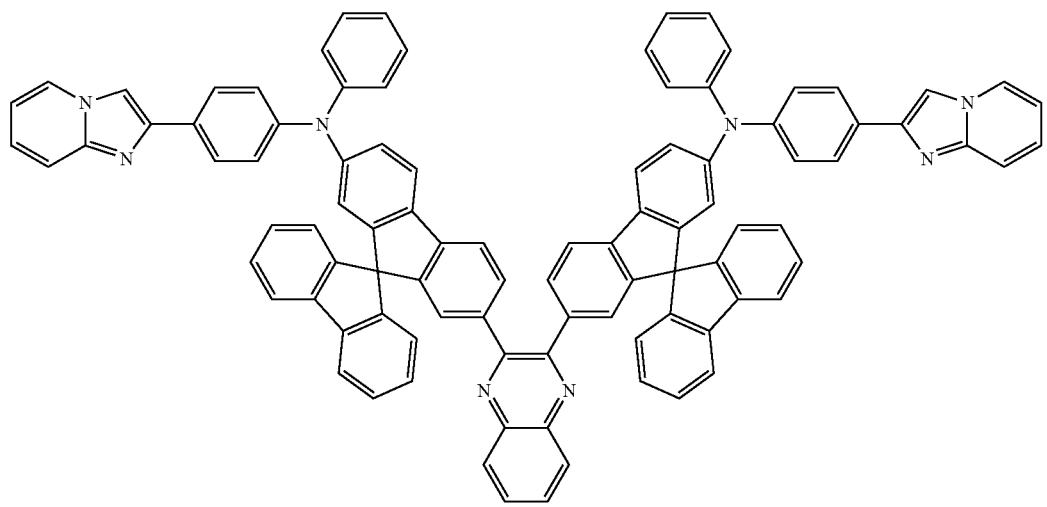

(658)

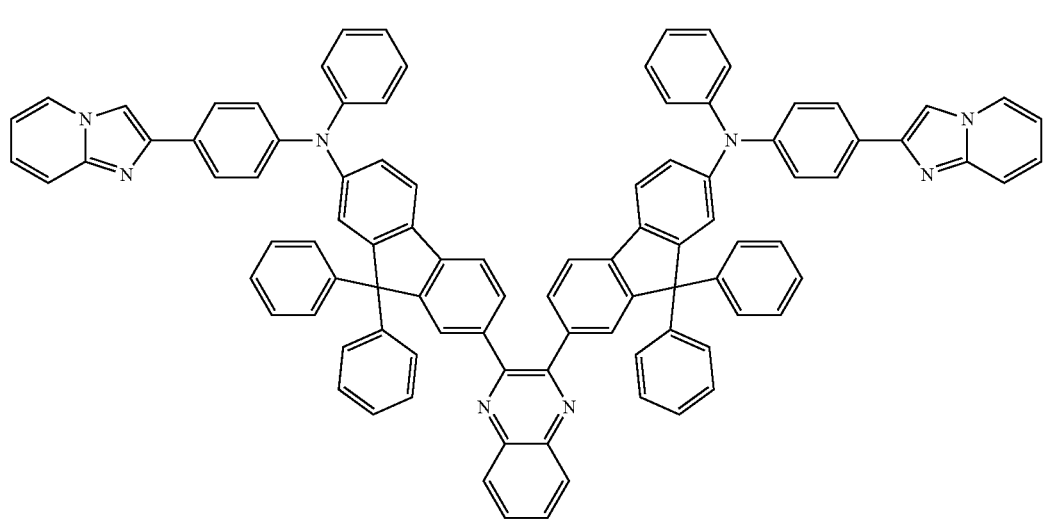

(659)

As a synthetic method of the quinoxaline derivative of the present invention, various reactions can be applied. For example, the quinoxaline derivative of the present invention can be synthesized by the following synthetic reactions. Note that the synthetic method of the quinoxaline derivative of the present invention is not limited to the methods described below.

[Synthetic Method (1) of the Quinoxaline Derivative Represented by the General Formula (G11)]

<Synthetic Method of a Secondary Heteroarylamine (Compound A)>

The secondary heteroarylamine, which is represented by the general formula (Compound A), can be synthesized following the synthetic scheme (Scheme A1-1). That is, a halogenated heteroaryl (Compound A1) is coupled with arylamine (Compound A2) in the presence of a base by using a metal or a metal compound, whereby the secondary heteroarylamine (Compound A) can be obtained.

In the synthetic scheme (Scheme A1-1), Het is a substituted or unsubstituted aromatic heterocycle containing a five-membered ring structure, $Ar^2$ is a substituted or unsubstituted arylene group having 6 to 13 carbon atoms, and $Ar^3$ is a substituted or unsubstituted aryl group having 6 to 13 carbon atoms. Furthermore, $X^1$ represents halogen, which is preferably chlorine, bromine, or iodine.

In the case where the Buchwald-Hartwig reaction is performed in the synthetic scheme (Scheme A1-1), a palladium catalyst that can be used may be, although not limited to, bis(dibenzylideneacetone)palladium(0), palladium(II) acetate, and the like. A ligand for the palladium catalyst that can be used may be, although not limited to, tri(tert-butyl)phosphine, tri(n-hexyl)phosphine, tricyclohexylphosphine, and the like. A base that can be used in the synthetic scheme (Scheme A1-1) may be, although not limited to, an organic base such as sodium tert-butoxide, an inorganic base such as potassium carbonate, and the like. A solvent that can be used may be, although not limited to, toluene, xylene, benzene, tetrahydrofuran, and the like.

Description is made on the case where the Ullmann reaction is performed in the synthetic scheme (Scheme A1-1). In the case of performing the Ullmann reaction, a copper compound can be used. In the synthetic scheme (Scheme A1-1), $R^{104}$ and $R^{105}$ each represent halogen, an acetyl group, or the like, and as halogen, chlorine, bromine, or iodine can be used. It is preferable to use copper(I) iodide where $R^{104}$ is iodine or copper(II) acetate where $R^{105}$ is an acetyl group. The copper compound used for the reaction is not limited to these compounds, and copper can be used instead of the copper compound. A base that can be used in the reaction may be, although not limited to, an inorganic base such as potassium carbonate. A solvent that can be used may be, although not limited to, 1,3-dimethyl-3,4,5,6-tetrahydro-2(1H)-pyrimidinone (abbreviation: DMPU), toluene, xylene, benzene, and the like. In the Ullmann reaction, the target product can be obtained in a shorter time and in a higher yield when the reaction temperature is 100° C. or higher; therefore, it is preferable to use DMPU or xylene that has a high boiling point. Furthermore, since the reaction temperature is more preferably 150° C. or higher, it is more preferable to use DMPU.

<Synthetic Method of a Halogenated Quinoxaline Derivative (Compound B)>

The halogenated quinoxaline derivative, which is represented by the general formula (Compound B), can be synthesized following the synthetic scheme (Scheme A1-2). That is, the halogenated quinoxaline derivative (Compound B) can be obtained by cyclodehydration reaction of a 1,2-phenylenediamine derivative (Compound B1) and a halogenated diketone derivative (Compound B2).

In the synthetic scheme (Scheme A1-2), $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms, $R^1$ is any of an alkyl group having 1 to 4 carbon atoms and a substituted or unsubstituted aryl group having 6 to 13 carbon atoms, and $Ar^1$ is a substituted or unsubstituted arylene group having 6 to 13 carbon atoms. Furthermore, $X^2$ represents halogen or a trifluoromethanesulfonic ester (triflate) group, and if $X^2$ is halogen, halogen is preferably chlorine, bromine, or iodine. A solvent that can be used in Scheme A1-2 may be, although not limited to, a halogen-based solvent such as dichloromethane, chloroform, or carbon tetrachloride, alcohol such as ethanol, methanol, or isopropanol, acetic acid, an aqueous solution of sodium carbonate, an aqueous solution of sodium hydrogen sulfate, an aqueous solution of sodium acetate, a mixed solvent of an aqueous solution of sodium acetate and acetic acid, and the like. In the case where the halogen-based solvent is used, chloroform or carbon tetrachloride that has a higher boiling point is preferably used.

<Synthesis of a Quinoxaline Derivative (G11)>

The quinoxaline derivative represented by the general formula (G11) can be synthesized following the synthetic scheme (Scheme B1). That is, the secondary heteroarylamine (Compound A) is coupled with the halogenated quinoxaline derivative (Compound B) in the presence of a base by using a metal or a metal compound, whereby the quinoxaline derivative (G11) can be obtained.

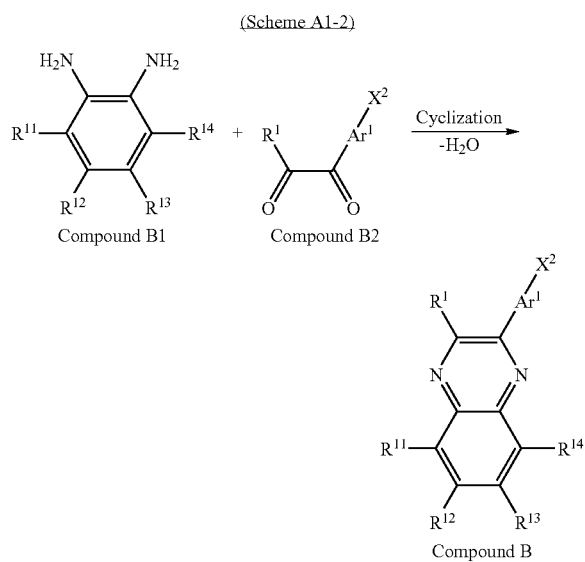

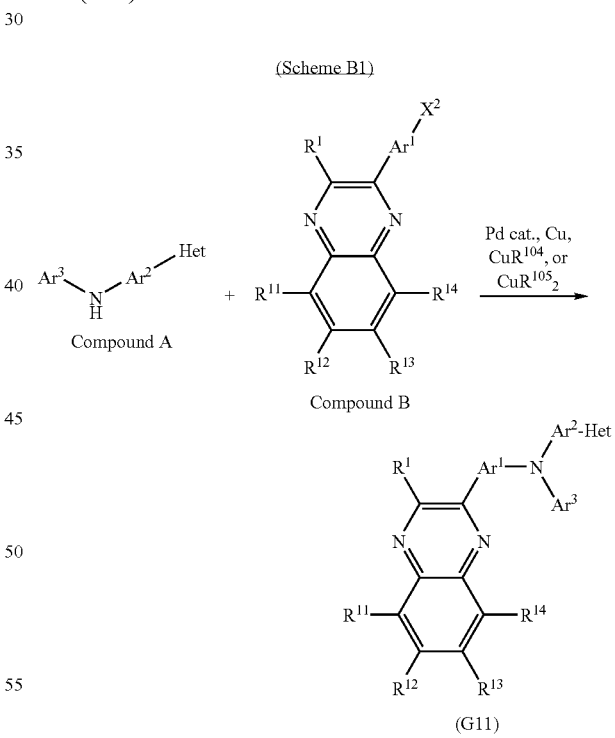

In the synthetic scheme (Scheme B1), Het is a substituted or unsubstituted aromatic heterocycle containing a five-membered ring structure, $Ar^1$ and $Ar^2$ each are a substituted or unsubstituted arylene group having 6 to 13 carbon atoms, $Ar^3$ is a substituted or unsubstituted aryl group having 6 to 13 carbon atoms, $R^1$ is any of an alkyl group having 1 to 4 carbon atoms and a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms. Furthermore, $X^2$ represents halogen or a triflate group, and if $X^2$ is halogen, halogen is preferably chlorine, bromine, or iodine.

In the case where the Buchwald-Hartwig reaction is performed in the synthetic scheme (Scheme B1), a palladium catalyst that can be used may be, although not limited to, bis(dibenzylideneacetone)palladium(0), palladium(II) acetate, and the like. A ligand for the palladium catalyst that can be used may be, although not limited to, tri(tert-butyl)phosphine, tri(n-hexyl)phosphine, tricyclohexylphosphine, and the like. A base that can be used may be, although not limited to, an organic base such as sodium tert-butoxide, an inorganic base such as potassium carbonate, and the like. A solvent that can be used may be, although not limited to, toluene, xylene, benzene, tetrahydrofuran, and the like.

Description is made on the case where the Ullmann reaction is performed in the synthetic scheme (Scheme B1). In the case of performing the Ullmann reaction, a copper compound can be used. In the synthetic scheme (Scheme B1), $R^{104}$ and $R^{105}$ each represent halogen, an acetyl group, or the like, and as halogen, chlorine, bromine, or iodine can be used. It is preferable to use copper(I) iodide where $R^{104}$ is iodine or copper(II) acetate where $R^{105}$ is an acetyl group. The copper compound used for the reaction is not limited to these compounds, and copper can be used instead of the copper compound. A base that can be used in the reaction may be, although not limited to, an inorganic base such as potassium carbonate. A solvent that can be used may be, although not limited to, DMPU, toluene, xylene, benzene, and the like. In the Ullmann reaction, the target product can be obtained in a shorter time and in a higher yield when the reaction temperature is 100° C. or higher; therefore, it is preferable to use DMPU or xylene that has a high boiling point. Furthermore, since the reaction temperature is more preferably 150° C. or higher, it is more preferable to use DMPU.

[Synthetic Method (2) of the Quinoxaline Derivative Represented by the General Formula (G11)]
<Synthesis of a Secondary Amine Having a Quinoxaline Structure (Compound C)>

The secondary amine having a quinoxaline structure, which is represented by the general formula (Compound C), can be synthesized following the synthetic scheme (Scheme A2-2). That is, the halogenated quinoxaline derivative (Compound B) is coupled with arylamine (Compound A2) in the presence of a base by using a metal or a metal compound, whereby the secondary amine having a quinoxaline structure (Compound C) can be obtained.

(Scheme A2-2)

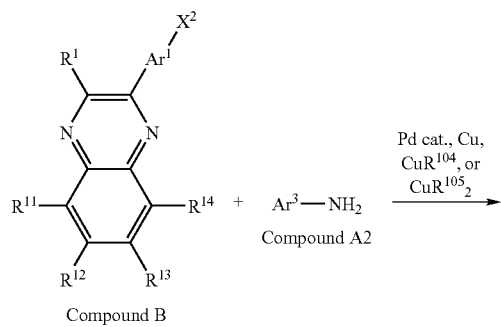

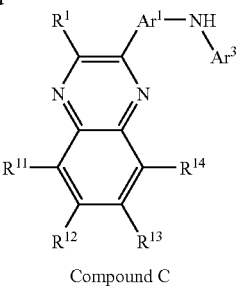

Compound C

In the synthetic scheme (Scheme A2-2), $Ar^1$ is a substituted or unsubstituted arylene group having 6 to 13 carbon atoms, $Ar^3$ is a substituted or unsubstituted aryl group having 6 to 13 carbon atoms, $R^1$ is any of an alkyl group having 1 to 4 carbon atoms and a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms. Furthermore, $X^2$ represents halogen or a triflate group, and if $X^2$ is halogen, halogen is preferably chlorine, bromine, or iodine.

In the case where the Buchwald-Hartwig reaction is performed in the synthetic scheme (Scheme A2-2), a palladium catalyst that can be used may be, although not limited to, bis(dibenzylideneacetone)palladium(0), palladium(II) acetate, and the like. A ligand for the palladium catalyst that can be used may be, although not limited to, tri(tert-butyl)phosphine, tri(n-hexyl)phosphine, tricyclohexylphosphine, and the like. A base that can be used may be, although not limited to, an organic base such as sodium tert-butoxide, an inorganic base such as potassium carbonate, and the like. A solvent that can be used may be, although not limited to, toluene, xylene, benzene, tetrahydrofuran, and the like.

Description is made on the case where the Ullmann reaction is performed in the synthetic scheme (Scheme A2-2). In the case of performing the Ullmann reaction, a copper compound can be used. In the synthetic scheme (Scheme A2-2), $R^{104}$ and $R^{105}$ each represent halogen, an acetyl group, or the like, and as halogen, chlorine, bromine, or iodine can be used. It is preferable to use copper(I) iodide where $R^{104}$ is iodine or copper(II) acetate where $R^{105}$ is an acetyl group. The copper compound used for the reaction is not limited to these compounds, and copper can be used instead of the copper compound. A base that can be used in the reaction may be, although not limited to, an inorganic base such as potassium carbonate. A solvent that can be used may be, although not limited to, DMPU, toluene, xylene, benzene, and the like. In the Ullmann reaction, the target product can be obtained in a shorter time and in a higher yield when the reaction temperature is 100° C. or higher; therefore, it is preferable to use DMPU or xylene that has a high boiling point. Furthermore, since the reaction temperature is more preferably 150° C. or higher, it is more preferable to use DMPU.

<Synthesis of the Quinoxaline Derivative (G11)>

The quinoxaline derivative represented by the general formula (G11) can be synthesized following the synthetic scheme (Scheme B2). That is, the secondary amine having a quinoxaline structure (Compound C) is coupled with the halogenated heteroaryl (Compound A1) in the presence of a base by using a metal or a metal compound, whereby the quinoxaline derivative (G11) can be obtained.

(Scheme B2)

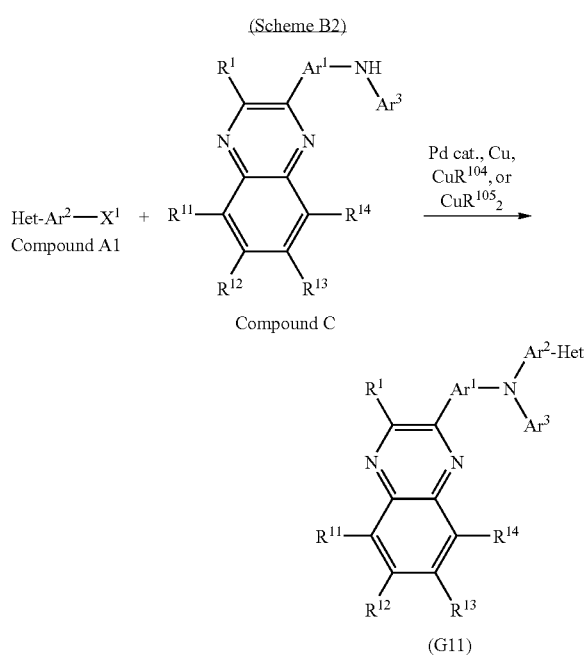

In the synthetic scheme (Scheme B2), Het is a substituted or unsubstituted aromatic heterocycle containing a five-membered ring structure, $Ar^1$ and $Ar^2$ each are a substituted or unsubstituted arylene group having 6 to 13 carbon atoms, $Ar^3$ is a substituted or unsubstituted aryl group having 6 to 13 carbon atoms, $R^1$ is any of an alkyl group having 1 to 4 carbon atoms and a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms. Furthermore, $X^1$ represents halogen and is preferably chlorine, bromine, or iodine.

In the case where the Buchwald-Hartwig reaction is performed in the synthetic scheme (Scheme B2), a palladium catalyst that can be used may be, although not limited to, bis(dibenzylideneacetone)palladium(0), palladium(II) acetate, and the like. A ligand for the palladium catalyst that can be used may be, although not limited to, tri(tert-butyl)phosphine, tri(n-hexyl)phosphine, tricyclohexylphosphine, and the like. A base that can be used may be, although not limited to, an organic base such as sodium tert-butoxide, an inorganic base such as potassium carbonate, and the like. A solvent that can be used may be, although not limited to, toluene, xylene, benzene, tetrahydrofuran, and the like.

Description is made on the case where the Ullmann reaction is performed in the synthetic scheme (Scheme B2). In the case of performing the Ullmann reaction, a copper compound can be used. In the synthetic scheme (Scheme B2), $R^{104}$ and $R^{105}$ each represent halogen, an acetyl group, or the like, and as halogen, chlorine, bromine, or iodine can be used. It is preferable to use copper(I) iodide where $R^{104}$ is iodine or copper(II) acetate where $R^{105}$ is an acetyl group. The copper compound used for the reaction is not limited to these compounds, and copper can be used instead of the copper compound. A base that can be used in the reaction may be, although not limited to, an inorganic base such as potassium carbonate. A solvent that can be used may be, although not limited to, DMPU, toluene, xylene, benzene, and the like. In the Ullmann reaction, the target product can be obtained in a shorter time and in a higher yield when the reaction temperature is 100° C. or higher; therefore, it is preferable to use DMPU or xylene that has a high boiling point. Furthermore, since the reaction temperature is more preferably 150° C. or higher, it is more preferable to use DMPU.

[Synthetic Method (1) of the Quinoxaline Derivative Represented by the General Formula (G21)]

<Synthetic Method of a Halogenated Quinoxaline Derivative (Compound D)>

The halogenated quinoxaline derivative represented by the general formula (Compound D) can be synthesized following the synthetic scheme (Scheme A3-2). That is, the halogenated quinoxaline derivative (Compound D) can be obtained by cyclodehydration reaction of a 1,2-phenylenediamine derivative (Compound B1) and a halogenated diketone derivative (Compound B3).

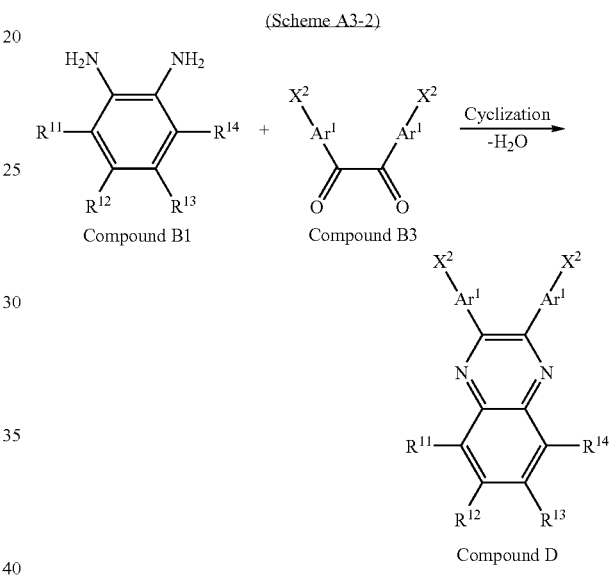

In the synthetic scheme (Scheme A3-2), $Ar^1$ is a substituted or unsubstituted arylene group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms. Furthermore, $X^2$ represents halogen or a triflate group, and if $X^2$ is halogen, halogen is preferably chlorine, bromine, or iodine. A solvent that can be used in Scheme A3-2 may be, although not limited to, a halogen-based solvent such as dichloromethane, chloroform, or carbon tetrachloride, alcohol such as ethanol, methanol, or isopropanol, acetic acid, an aqueous solution of sodium carbonate, an aqueous solution of sodium hydrogen sulfate, an aqueous solution of sodium acetate, a mixed solvent of an aqueous solution of sodium acetate and acetic acid, and the like. In the case where the halogen-based solvent is used, chloroform or carbon tetrachloride that has a higher boiling point is preferably used.

<Synthesis of a Quinoxaline Derivative (G21)>

The quinoxaline derivative represented by the general formula (G21) can be synthesized following the synthetic scheme (Scheme B3). That is, the secondary heteroarylamine (Compound A) is coupled with the halogenated quinoxaline derivative (Compound D) in the presence of a base by using a metal or a metal compound, whereby the quinoxaline derivative (G21) can be obtained.

(Scheme B3)

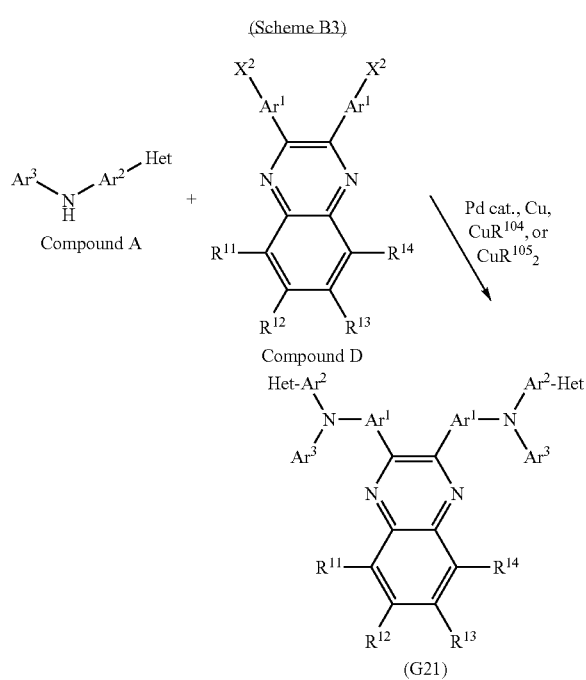

Compound A

Compound D (G21)

In the synthetic scheme (Scheme B3), Het is a substituted or unsubstituted aromatic heterocycle containing a five-membered ring structure, $Ar^1$ and $Ar^2$ each are a substituted or unsubstituted arylene group having 6 to 13 carbon atoms, $Ar^3$ is a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms. Furthermore, $X^2$ represents halogen or a triflate group, and if $X^2$ is halogen, halogen is preferably chlorine, bromine, or iodine.

In the case where the Buchwald-Hartwig reaction is performed in the synthetic scheme (Scheme B3), a palladium catalyst that can be used may be, although not limited to, bis(dibenzylideneacetone)palladium(0), palladium(II) acetate, and the like. A ligand for the palladium catalyst that can be used may be, although not limited to, tri(tert-butyl) phosphine, tri(n-hexyl)phosphine, tricyclohexylphosphine, and the like. A base that can be used may be, although not limited to, an organic base such as sodium tert-butoxide, an inorganic base such as potassium carbonate, and the like. A solvent that can be used may be, although not limited to, toluene, xylene, benzene, tetrahydrofuran, and the like.

Description is made on the case where the Ullmann reaction is performed in the synthetic scheme (Scheme B3). In the case of performing the Ullmann reaction, a copper compound can be used. In the synthetic scheme (Scheme B3), $R^{104}$ and $R^{105}$ each represent halogen, an acetyl group, or the like, and as halogen, chlorine, bromine, or iodine can be used. It is preferable to use copper(I) iodide where $R^{104}$ is iodine or copper(II) acetate where $R^{105}$ is an acetyl group. The copper compound used for the reaction is not limited to these compounds, and copper can be used instead of the copper compound. A base that can be used in the reaction may be, although not limited to, an inorganic base such as potassium carbonate. A solvent that can be used may be, although not limited to, DMPU, toluene, xylene, benzene, and the like. In the Ullmann reaction, the target product can be obtained in a shorter time and in a higher yield when the reaction temperature is 100° C. or higher; therefore, it is preferable to use DMPU or xylene that has a high boiling point. Furthermore, since the reaction temperature is more preferably 150° C. or higher, it is more preferable to use DMPU.

[Synthetic Method (2) of the Quinoxaline Derivative Represented by the General Formula (G21)]

<Synthesis of a Secondary Amine Having a Quinoxaline Structure (Compound E)>

The secondary amine having a quinoxaline structure, which is represented by the general formula (Compound E), can be synthesized following the synthetic scheme (Scheme A4-2). That is, the halogenated quinoxaline derivative (Compound D) is coupled with arylamine (Compound A2) in the presence of a base by using a metal or a metal compound, whereby the secondary amine having a quinoxaline structure (Compound E) can be obtained.

(Scheme A4-2)

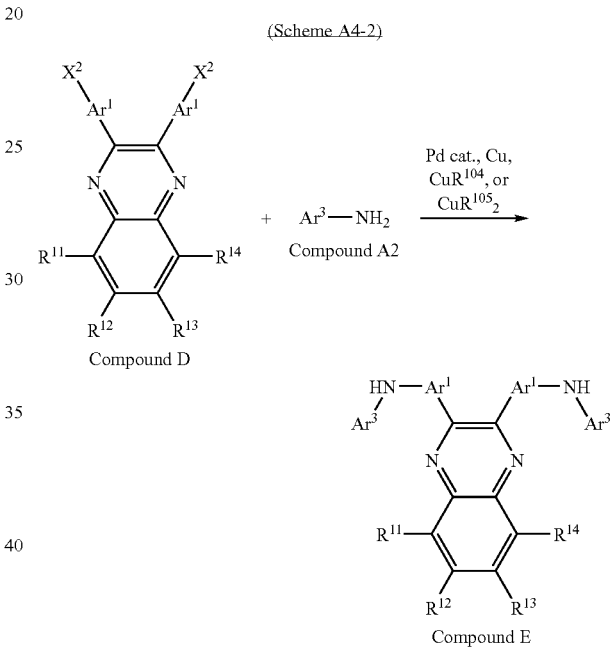

Compound D

Compound A2

Compound E

In the synthetic scheme (Scheme A4-2), Het is a substituted or unsubstituted aromatic heterocycle containing a five-membered ring structure, $Ar^1$ is a substituted or unsubstituted arylene group having 6 to 13 carbon atoms, $Ar^3$ is a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms. Furthermore, $X^2$ represents halogen or a triflate group, and if $X^2$ is halogen, halogen is preferably chlorine, bromine, or iodine.

In the case where the Buchwald-Hartwig reaction is performed in the synthetic scheme (Scheme A4-2), a palladium catalyst that can be used may be, although not limited to, bis(dibenzylideneacetone)palladium(0), palladium(II) acetate, and the like. A ligand for the palladium catalyst that can be used may be, although not limited to, tri(tert-butyl) phosphine, tri(n-hexyl)phosphine, tricyclohexylphosphine, and the like. A base that can be used may be, although not limited to, an organic base such as sodium tert-butoxide, an inorganic base such as potassium carbonate, and the like. A solvent that can be used may be, although not limited to, toluene, xylene, benzene, tetrahydrofuran, and the like.

Description is made on the case where the Ullmann reaction is performed in the synthetic scheme (Scheme A4-2). In the case of performing the Ullmann reaction, a copper compound can be used. In the synthetic scheme (Scheme A4-2), $R^{104}$ and $R^{105}$ each represent halogen, an acetyl group, or the like, and as halogen, chlorine, bromine, or iodine can be used. It is preferable to use copper(I) iodide where $R^{104}$ is iodine or copper(II) acetate where $R^{105}$ is an acetyl group. The copper compound used for the reaction is not limited to these compounds, and copper can be used instead of the copper compound. A base that can be used in the reaction may be, although not limited to, an inorganic base such as potassium carbonate. A solvent that can be used may be, although not limited to, DMPU, toluene, xylene, benzene, and the like. In the Ullmann reaction, the target product can be obtained in a shorter time and in a higher yield when the reaction temperature is 100° C. or higher; therefore, it is preferable to use DMPU or xylene that has a high boiling point. Furthermore, since the reaction temperature is more preferably 150° C. or higher, it is more preferable to use DMPU.

<Synthesis of the Quinoxaline Derivative (G21)>

The quinoxaline derivative represented by the general formula (G21) can be synthesized following the synthetic scheme (Scheme B4). That is, the secondary amine having a quinoxaline structure (Compound E) is coupled with the halogenated heteroaryl (Compound A1) in the presence of a base by using a metal or a metal compound, whereby the quinoxaline derivative (G21) can be obtained

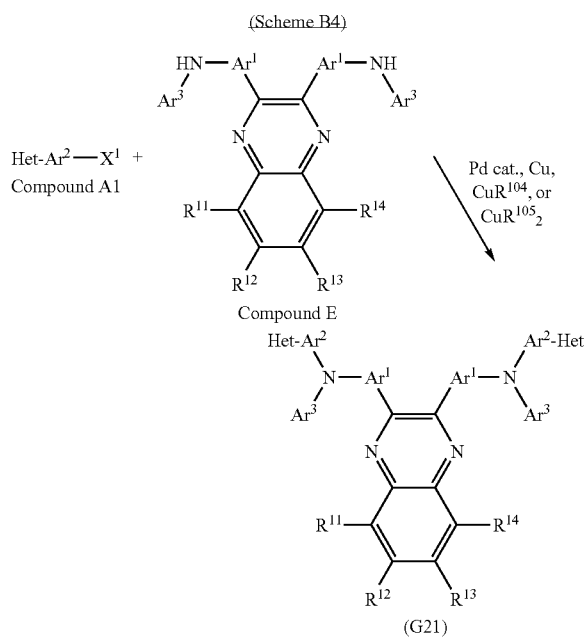

In the synthetic scheme (Scheme B4), Het is a substituted or unsubstituted aromatic heterocycle containing a five-membered ring structure, $Ar^1$ and $Ar^2$ each are a substituted or unsubstituted arylene group having 6 to 13 carbon atoms, $Ar^3$ is a substituted or unsubstituted aryl group having 6 to 13 carbon atoms, and $R^{11}$ to $R^{14}$ may be the same or different from one another, each of which represents any of hydrogen, an alkyl group having 1 to 4 carbon atoms, and a substituted or unsubstituted aryl group having 6 to 13 carbon atoms. Furthermore, $X^1$ represents halogen and is preferably chlorine, bromine, or iodine.

In the case where the Buchwald-Hartwig reaction is performed in the synthetic scheme (Scheme B4), a palladium catalyst that can be used may be, although not limited to, bis(dibenzylideneacetone)palladium(0), palladium(II) acetate, and the like. A ligand for the palladium catalyst that can be used may be, although not limited to, tri(tert-butyl)phosphine, tri(n-hexyl)phosphine, tricyclohexylphosphine, and the like. A base that can be used may be, although not limited to, an organic base such as sodium tert-butoxide, an inorganic base such as potassium carbonate, and the like. A solvent that can be used may be, although not limited to, toluene, xylene, benzene, tetrahydrofuran, and the like.

Description is made on the case where the Ullmann reaction is performed in the synthetic scheme (Scheme B4). In the case of performing the Ullmann reaction, a copper compound can be used. In the synthetic scheme (Scheme B4), $R^{104}$ and $R^{105}$ each represent halogen, an acetyl group, or the like, and as halogen, chlorine, bromine, or iodine can be used. It is preferable to use copper(I) iodide where $R^{104}$ is iodine or copper(II) acetate where $R^{105}$ is an acetyl group. The copper compound used for the reaction is not limited to these compounds, and copper can be used instead of the copper compound. A base that can be used in the reaction may be, although not limited to, an inorganic base such as potassium carbonate. A solvent that can be used may be, although not limited to, DMPU, toluene, xylene, benzene, and the like. In the Ullmann reaction, the target product can be obtained in a shorter time and in a higher yield when the reaction temperature is 100° C. or higher; therefore, it is preferable to use DMPU or xylene that has a high boiling point. Furthermore, since the reaction temperature is more preferably 150° C. or higher, it is more preferable to use DMPU.

The quinoxaline derivative of the present invention is bipolar and excellent in both electron transporting properties and hole transporting properties. Accordingly, by applying the quinoxaline derivative of the present invention to electronic devices, excellent electrical properties can be obtained.

In addition, since the quinoxaline derivative of the present invention emits visible light, it can be favorably used for a light emitting element. Furthermore, due to its large band gap, the quinoxaline derivative of the present invention can be favorably used as a host material for dispersing a light emitting material in a light emitting layer of a light emitting element. Still furthermore, since the quinoxaline derivative of the present invention has high triplet excitation energy, it can be favorably used as a host material of a phosphorescent substance.

Embodiment Mode 2

In this embodiment mode, one mode of a light emitting element using the quinoxaline derivative shown in Embodiment Mode 1 is described with reference to FIG. 1 and FIG. 2.

A light emitting element of the present invention has a plurality of layers between a pair of electrodes. The plurality of layers are stacked layers obtained by combining a layer formed of a substance with a high carrier injecting property and a layer formed of a substance with a high carrier transporting property so that a light emitting region is formed in a region away from the electrodes, that is, recombination of carriers is performed in an area away from the electrodes.

In this embodiment mode, the light emitting element has a first electrode 102, a second electrode 104, and an EL layer 103 formed between the first electrode 102 and the second electrode 104. Note that description in this embodiment mode is made below supposing that the first electrode 102 functions as an anode and the second electrode 104 functions as a cathode. That is, description is made below supposing that light emission is obtained when a voltage is applied between the first electrode 102 and the second electrode 104 so that the first electrode 102 has a higher potential than the second electrode 104.

A substrate 101 is used as a support of the light emitting element. As the substrate 101, for example, glass, plastic, or metal can be used. Note that other materials may also be used as long as the substrate 101 can function as a support of the light emitting element. In the case where light emitted from the light emitting element is extracted to the outside through the substrate, the substrate 101 preferably has light transmitting properties.

As the first electrode 102, it is preferable to use a metal, an alloy, a conductive compound, a mixture thereof, or the like that has a high work function (specifically, a work function of 4.0 eV or higher). For example, there are indium oxide-tin oxide (ITO: indium tin oxide), indium oxide-tin oxide containing silicon or silicon oxide, indium oxide-zinc oxide (IZO: indium zinc oxide), and indium oxide containing tungsten oxide and zinc oxide (IWZO). These conductive metal oxide films are generally deposited by sputtering, but may also be formed by ink jet, spin coating, or the like by application of a sol-gel method or the like. For example, a film of indium oxide-zinc oxide (IZO) can be formed by sputtering using a target in which 1 wt % to 20 wt % of zinc oxide is added to indium oxide. Besides, a film of indium oxide containing tungsten oxide and zinc oxide (IWZO) can be formed by sputtering using a target in which 0.5 wt % to 5 wt % of tungsten oxide and 0.1 wt % to 1 wt % of zinc oxide are added to indium oxide. Alternatively, it is possible to use gold (Au), platinum (Pt), nickel (Ni), tungsten (W), chromium (Cr), molybdenum (Mo), iron (Fe), cobalt (Co), copper (Cu), palladium (Pd), titanium (Ti), nitrides of the metal materials (such as titanium nitride), or the like.

If a layer containing a composite material described below is used as a layer in contact with the first electrode 102, a wide variety of metals, alloys, electrically conductive compounds, a mixture of them, or the like can be used as the first electrode 102 regardless of their work functions. For example, aluminum (Al), silver (Ag), or an aluminum alloy (AlSi) can be used. Besides, it is also possible to use an element belonging to Group 1 or Group 2 of the periodic table, which has a low work function, that is, an alkali metal such as lithium (Li) or cesium (Cs), an alkaline earth metal such as magnesium (Mg), calcium (Ca), or strontium (Sr), or an alloy containing these elements (e.g., MgAg or AlLi); or a rare earth metal such as europium (Eu) or ytterbium (Yb), or an alloy thereof. A film of an alkali metal, an alkaline earth metal, or an alloy containing such a metal can be formed by vacuum evaporation. An alloy film containing an alkali metal or an alkaline earth metal can also be formed by sputtering. Alternatively, silver paste or the like can be deposited by ink jet or the like.

The EL layer 103 shown in this embodiment mode has a hole injecting layer 111, a hole transporting layer 112, a light emitting layer 113, an electron transporting layer 114, and an electron injecting layer 115. Note that the EL layer 103 is acceptable as long as it has the quinoxaline derivative shown in Embodiment Mode 1, and a stacked structure of the other layers is not particularly limited. That is, there is no particular limitation on the stacked structure of the EL layer 103. The quinoxaline derivative shown in Embodiment Mode 1 may be combined as appropriate with layers containing a substance with a high electron transporting property, a substance with a high hole transporting property, a substance with a high electron injecting property, a substance with a high hole injecting property, a bipolar substance (substance with a high electron and hole transporting property), a substance with a high light emitting property, or the like. For example, the EL layer 103 can be formed by an appropriate combination of a hole injecting layer, a hole transporting layer, a light emitting layer, an electron transporting layer, an electron injecting layer, and the like. Materials of each layer are specifically described below.

The hole injecting layer 111 is a layer containing a substance with a high hole injecting property. As the substance with a high hole injecting property, molybdenum oxide, vanadium oxide, ruthenium oxide, tungsten oxide, manganese oxide, or the like can be used. In addition, as a low molecular organic compound, there are a phthalocyanine-based compound such as phthalocyanine (abbreviation: $H_2Pc$), copper (II) phthalocyanine (abbreviation: CuPc), or vanadyl phthalocyanine (abbreviation: VOPc); an aromatic amine compound such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphtyl)-N-(9-phenylcarbazol-3-yl)amino]-9-phenylcarbazole (abbreviation: PCzPCN1); and the like.

Alternatively, as the hole injecting layer 111, it is possible to use a composite material in which a substance with a high hole transporting property is mixed with an acceptor substance. Note that by using the material in which a substance with a high hole transporting property is mixed with an acceptor substance, the material of an electrode can be selected regardless of the work function. That is, the first electrode 102 can be formed of not only a material with a high work function but also a material with a low work function. Such a composite material can be obtained by co-evaporation of a substance with a high hole transporting property and an acceptor substance.

Note that in this specification, 'composition' refers to not only a state in which two kinds of materials are simply mixed, but also a state in which a plurality of materials are mixed so that electric charges are donated and accepted between the materials.

As the organic compound used for the composite material, various compounds can be used such as an aromatic amine compound, a carbazole derivative, an aromatic hydrocarbon, and a high molecular-compound (oligomer, dendrimer, polymer, or the like). Note that the organic compound used for the composite material is preferably an organic compound with a high hole transporting property. Specifically, it is preferable to use a substance with a hole mobility of $10^{-6}$ cm$^2$/Vs or higher, although other substances may also be used as long as the hole transporting property thereof is higher than the electron transporting property thereof. The organic compounds that can be used for the composite material are specifically described below.

As the organic compounds that can be used for the composite material, for example, there are aromatic amine compounds such as MTDATA, TDATA, DPAB, DNTPD, DPA3B, PCzPCA1, PCzPCA2, PCzPCN1, 4,4'-bis[N-(1-napthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl]-2,3,5,6-tetraphenylbenzene; and aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

As the acceptor substance, there are organic compounds such as 7,7,8,8-tetracyano-2,3,5,6-tetrafluoroquinodimethane (abbreviation: $F_4$-TCNQ) and chloranil, and a transition metal oxide. In addition, an oxide of a metal belonging to Group 4 to Group 8 of the periodic table can also be used. Specifically, it is preferable to use vanadium oxide, niobium oxide, tantalum oxide, chromium oxide, molybdenum oxide, tungsten oxide, manganese oxide, or rhenium oxide because of their high electron accepting property. Among them, molybdenum oxide is more preferably used since it is stable in the air and has a low hygroscopic property, and thus is easily treated.

Alternatively, as the hole injecting layer 111, it is possible to use a high molecular compound (oligomer, dendrimer, polymer, or the like). For example, there are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'phenylamino}phenyl)methacrylamide] (abbreviation: PTPDMA), or poly[N,N'-bis(4-butylphenyl)-N,N'-bis(phenyl)benzidine] (abbreviation: Poly-TPD). Further alternatively, high molecular compounds doped with acid such as poly(3,4-ethylenedioxythiophene)/poly(styrenesufonic acid) (PEDOT/PSS), or polyaniline/poly(styrenesufonic acid) (PAni/PSS) can be used.

In addition, a composite material may be formed using the aforementioned high molecular compound such as PVK, PVTPA, PTPDMA, or Poly-TPD, and the aforementioned acceptor substance, as the hole injecting layer 111.

The hole transporting layer 112 is a layer containing a substance with a high hole transporting property. As a low molecular organic compound of the substance with a high hole transporting property, there are aromatic amine compounds such as NPB (or α-NPD), TPD, 4,4'-bis[N-(9,9-dimethylfluoren-2-yl)-N-phenylamino]biphenyl (abbreviation; DFLDPBi), and 4,4'-bis[N-(spiro-9,9'-bifluoren-2-yl)-N-phenylamino]biphenyl (abbreviation: BSPB). These substances are mainly substances each having a hole mobility of $10^{-6}$ $cm^2/Vs$ or higher, although other substances may also be used as long as the hole transporting property thereof is higher than the electron transporting property thereof. Note that the layer containing a substance with a high hole transporting property is not limited to a single layer, but two or more layers containing the aforementioned substances may be stacked.

Alternatively, the hole transporting layer 112 may be formed of a composite material in which a substance with a high hole transporting property is mixed with an acceptor substance.

Further alternatively, the hole transporting layer 1112 may be formed of a high molecular compound such as PVK, PVTPA, PTPDMA, or Poly-TPD.

The light emitting layer 113 is a layer containing a substance with a high light emitting property, and can be formed of various materials. The quinoxaline derivative shown in Embodiment Mode 1, which exhibits blue to green emission, can be favorably used as a light emitting substance for a light emitting element.

The electron transporting layer 114 is a layer containing a substance with a high electron transporting property. As a low molecular organic compound of the substance with a high electron transporting property, there are metal complexes such as tris(8-quinolinolato)aluminum(III) (abbreviation: Alq), tris(4-methyl-8-quinolinolato)aluminum(III) (abbreviation: $Almq_3$), bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ). In addition to the metal complexes, heterocyclic compounds can also be used such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ01), 2,2',2"-(1,3,5-benzenetriyl)tris(1-phenyl-1H-benzimidazole) (abbreviation: TPBI), bathophenanthroline (abbreviation: BPhen), and bathocuproine (abbreviation: BCP). These substances are mainly substances each having an electron mobility of $10^{-6}$ $cm^2/Vs$ or higher, though other substances may also be used as long as the electron transporting property thereof is higher than the hole transporting property thereof. Note that the electron transporting layer is not limited to a single layer, but two or more layers containing the aforementioned substances may be stacked.

Alternatively, a high molecular compound can be used as the electron transporting layer 114. For example, it is possible to use poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy).

The electron injecting layer 115 is a layer containing a substance with a high electron injecting property. As the substance with a high electron injecting property, it is possible to use an alkali metal, an alkaline earth metal, or a compound thereof such as lithium fluoride (LiF), cesium fluoride (CsF), or calcium fluoride ($CaF_2$). For example, as a layer made of a substance with electron transporting properties, which is mixed with an alkali metal, an alkaline earth metal, or a compound thereof, for example, a layer made of Alq mixed with magnesium (Mg), may be used. Note that a layer made of a substance with electron transporting properties, which is mixed with an alkali metal or an alkaline earth metal, is more preferably used as the electron injecting layer, since electrons are efficiently injected from the second electrode 104.

As a substance forming the second electrode 104, it is preferable to use a metal, an alloy, an electrically conductive compound, a mixture thereof, or the like that has a low work function (specifically, a work function of 3.8 eV or lower). As specific examples of such a cathode material, there are elements belonging to Group 1 or Group 2 of the periodic table, that is, an alkali metal such as lithium (Li) or cesium (Cs), an alkaline earth metal such as magnesium (Mg), calcium (Ca), or strontium (Sr), and an alloy containing these elements (MgAg, AlLi); a rare earth metal such as europium (Eu) or ytterbium (Yb), and an alloy thereof; and the like. A film of an alkali metal, an alkaline earth metal, or an alloy thereof can be formed by vacuum evaporation. An alloy film containing an alkali metal or an alkaline earth metal can also be formed by sputtering. Alternatively, silver paste or the like can be deposited by ink jet or the like.

When the electron injecting layer 115 that has a function of promoting electron injection is provided between the second electrode 104 and the electron transporting layer 114, the second electrode 104 can be formed of various conductive materials such as Al, Ag, ITO, or indium oxide-tin oxide containing silicon or silicon oxide, regardless of their work functions. These conductive materials can be deposited by sputtering, ink jet, spin coating, or the like.

The EL layer can be formed by various methods including a dry process and a wet process. For example, vacuum evaporation, ink jet, spin coating, or the like can be used. Furthermore, each electrode or each layer may be formed by a different deposition method.

For example, the EL layer may be formed by a wet process using a high molecular compound selected from the aforementioned materials. Alternatively, the EL layer may be formed by a wet process using a low molecular organic compound. Further alternatively, the EL layer may be formed by a dry process such as vacuum evaporation using a low molecular organic compound.

Similarly, the electrodes can be formed by a wet process using a sol-gel method, or formed by a wet process using a paste of a metal material. Furthermore, the electrodes may also be formed by a dry process such as sputtering or vacuum evaporation.

For example, in the case where the light emitting element of the present invention is applied to a display device that is manufactured using a large-sized substrate, the light emitting layer is preferably formed by a wet process. Formation of the light emitting layer by ink jet facilitates independent formation of the light emitting layer having different emission color even when a large-sized substrate is used.

In the light emitting element of the present invention having the aforementioned structure, current flows due to a potential difference provided between the first electrode 102 and the second electrode 104, whereby holes and electrons are recombined in the EL layer 103 and light is emitted.

Light emission is extracted to the outside through one or both of the first electrode 102 and the second electrode 104. Accordingly, one or both of the first electrode 102 and the second electrode 104 are electrodes with light transmitting properties. For example, when only the first electrode 102 has light transmitting properties, light emission is extracted from the substrate side through the first electrode 102. When only the second electrode 104 has light transmitting properties, light emission is extracted from the opposite side to the substrate through the second electrode 104. When both the first electrode 102 and the second electrode 104 have light transmitting properties, light emission is extracted from both the substrate side and the opposite side to the substrate through the first electrode 102 and the second electrode 104.

Note that the structure of the layers provided between the first electrode 102 and the second electrode 104 is not limited to the aforementioned structure. Any structure other than the aforementioned structure can be employed as long as the quinoxaline derivative shown in Embodiment Mode 1 is provided and a light emitting region where holes and electrons are recombined is positioned away from the first electrode 102 and the second electrode 104 so as to prevent quenching caused by proximity of the light emitting region to a metal.

That is, there is no particular limitation on the stacked structure of the layers, and the quinoxaline derivative shown in Embodiment Mode 1 may be combined as appropriate with layers containing a substance with a high electron transporting property, a substance with a high hole transporting property, a substance with a high electron injecting property, a substance with a high hole injecting property, a bipolar substance (a substance with a high electron and hole transporting property), or the like.

Figure 2:
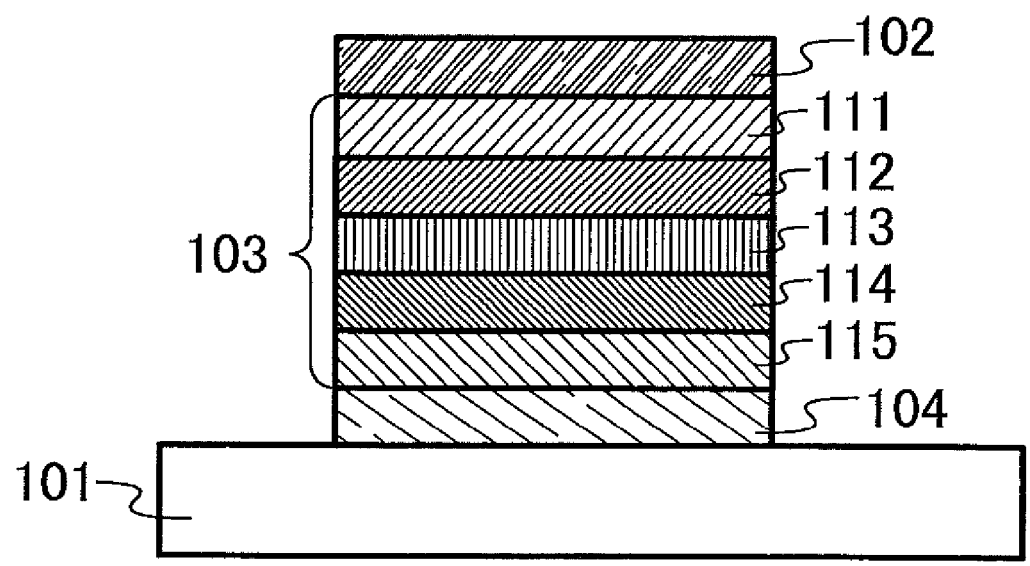
FIG. 2 is a diagram illustrating a light emitting element of the present invention.

Furthermore, as illustrated in FIG. 2, it is possible to adopt such a structure that the second electrode 104 functioning as a cathode, the EL layer 103, and the first electrode 102 functioning as an anode are stacked in this order over the substrate 101. FIG. 2 illustrates a structure in which the electron injecting layer 115, the electron transporting layer 114, the light emitting layer 113, the hole transporting layer 112, and the hole injecting layer 111 are stacked in this order over the second electrode 104.

Note that in this embodiment mode, the light emitting element is manufactured over a substrate made of glass, plastic, or the like. By forming a plurality of such light emitting elements over a substrate, a passive matrix light emitting device can be manufactured. In addition, for example, a thin film transistor (TFT) is formed over a substrate made of glass, plastic, or the like, and the light emitting element may be formed over an electrode electrically connected to the TFT. Accordingly, an active matrix light emitting device in which the driving of a light emitting element is controlled by a TFT can be manufactured. Note that there is no particular limitation on the structure of a TFT, which may be a staggered TFT or an inverted staggered TFT. Besides, a driver circuit formed over a TFT substrate may include one or both of an N-type TFT and a P-type TFT. There is also no particular limitation on the crystallinity of a semiconductor film used for a TFT, which may be an amorphous semiconductor film, a crystalline semiconductor film, or a single crystal semiconductor film. The single crystal semiconductor film can be formed by Smart Cut (registered trademark) or the like.

The quinoxaline derivative of the present invention is bipolar and is a substance having light emitting properties. Thus, as described in this embodiment mode, the quinoxaline derivative of the present invention can be used for a light emitting layer without containing other light emitting substances.

Furthermore, since the quinoxaline derivative of the present invention is bipolar, a light emitting region is hardly localized at the interface of the stacked layers. Thus, it is possible to manufacture a light emitting element having excellent characteristics, in which a change in emission spectrum or a decrease in emission efficiency due to exciplex formation or the like hardly occurs during driving. In addition, a light emitting element with high emission efficiency can be obtained.

Furthermore, the quinoxaline derivative of the present invention is bipolar and excellent in carrier transporting properties (electron transporting properties and hole transporting properties). Accordingly, by applying the quinoxaline derivative of the present invention to a light emitting element, the driving voltage of the light emitting element can be reduced, resulting in lower power consumption.

Embodiment Mode 3

In this embodiment mode, a light emitting element having a structure different from that shown in Embodiment Mode 2 is described.

When the light emitting layer 113 shown in Embodiment Mode 2 has such a structure that the quinoxaline derivative shown in Embodiment Mode 1 is dispersed in another substance, light emission can be obtained from the quinoxaline derivative shown in Embodiment Mode 1. The quinoxaline derivative shown in Embodiment Mode 1 exhibits blue to green emission; thus, a light emitting element exhibiting blue to green emission can be obtained.

As the substance in which the quinoxaline derivative shown in Embodiment Mode 1 is dispersed, various materials can be used: 4,4'-bis(N-carbazolyl)-biphenyl (abbreviation: CBP), 2,2',2"-(1,3,5-benzenetri-yl)-tris[1-phenyl-1H-benzimidazole] (abbreviation: TPBI), 9,10-di(2-naphthyl)anthracene (abbreviation: DNA), 2-tert-butyl-9,10-di(2-naphthyl)anthracene (abbreviation: t-BuDNA), and the like as well as the substance with a high hole transporting property and the substance with a high electron transporting property, which are described in Embodiment Mode 2.

The quinoxaline derivative shown in Embodiment Mode 1 is bipolar and excellent in carrier transporting properties (electron transporting properties and hole transporting properties). Accordingly, by applying the quinoxaline derivative to a light emitting element, the driving voltage of the light emitting element can be reduced, resulting in lower power consumption.

Note that the layers other than the light emitting layer 113 may have the structure shown in Embodiment Mode 2, as appropriate.

Embodiment Mode 4

In this embodiment mode, a light emitting element having a structure different from those shown in Embodiment Modes 2 and 3 is described.

When the light emitting layer 113 shown in Embodiment Mode 2 has such a structure that a light emitting substance is dispersed in the quinoxaline derivative shown in Embodiment Mode 1, light emission can be obtained from the light emitting substance.

The quinoxaline derivative shown in Embodiment Mode 1 is bipolar, and has a large band gap and high triplet excitation energy. Accordingly, the quinoxaline derivative shown in Embodiment Mode 1 can be used as a host material in a light emitting layer having such a structure that a light emitting substance (a guest material) is dispersed in another substance (a host material).

When the quinoxaline derivative shown in Embodiment Mode 1 is used as a material in which another light emitting substance is dispersed, emission color originating from the light emitting substance can be obtained. In addition, it is also possible to obtain mixed emission color of the emission color originating from the quinoxaline derivative shown in Embodiment Mode 1 and the emission color originating from the light emitting substance dispersed in the quinoxaline derivative.

In the case where the quinoxaline derivative shown in Embodiment Mode 1 is used as a host material, if a guest material emits fluorescence, it is preferable to use as the guest material a substance that has a LUMO (lowest unoccupied molecular orbital) level lower than the quinoxaline derivative shown in Embodiment Mode 1 and a HOMO (highest occupied molecular orbital) level higher than the quinoxaline derivative shown in Embodiment Mode 1. For example, as a light emitting material for blue emission, there are N,N'-bis[4-(9H-carbazol-9-yl)phenyl]-N,N'-diphenylstylbene-4,4'-diamine (abbreviation: YGA2S), 4-(9H-carbazol-9-yl)-4'-(10-phenyl-9-anthryl)triphenylamine (abbreviation: YGAPA), and the like. As a light emitting material for green emission, there are N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracene-2-amine (abbreviation: 2YGABPhA), N,N,9-triphenylanthracene-9-amine (abbreviation: DPhAPhA), and the like. As a light emitting material for yellow emission, there are rubrene, 5,12-bis(1,1'-biphenyl-4-yl)-6,11-diphenyltetracene (abbreviation: BPT), and the like. As a light emitting material for red emission, there are N,N,N',N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-a]fluoranthene-3,10-diamine (abbreviation: p-mPhAFD), and the like.

In the case where the quinoxaline derivative shown in Embodiment Mode 1 is used as a host material, if a guest material emits phosphorescence, it is preferable to use as the guest material a substance that has triplet excitation energy lower than the quinoxaline derivative shown in Embodiment Mode 1. For example, there are organic metal complexes such as bis[2-(2'-benzo[4,5-α]thienyl)pyridinato-N,C$^{3'}$]iridium(III)acetylacetonate (abbreviation: Ir(btp)$_2$(acac)), bis(1-phenylisoquinolinato-N,C$^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H,23H-porphyrinplatinum(II) (abbreviation: PtOEP).

The quinoxaline derivative shown in Embodiment Mode 1 is bipolar and excellent in carrier transporting properties (electron transporting properties and hole transporting properties). Accordingly, by applying the quinoxaline derivative to a light emitting element, the driving voltage of the light emitting element can be reduced, resulting in lower power consumption.

Furthermore, plural kinds of materials can be used as a substance (a host material) in which a light emitting substance (a guest material) is dispersed. Therefore, the light emitting layer may contain a second host material in addition to the quinoxaline derivative shown in Embodiment Mode 1.

Furthermore, since the quinoxaline derivative of the present invention is bipolar, a light emitting region is hardly localized at the interface of stacked layers. Thus, in the case where a substance emitting phosphorescence is used, the T-T annihilation can be suppressed.

Note that the layers other than the light emitting layer 113 may have the structure shown in Embodiment Mode 2, as appropriate.

Embodiment Mode 5

In this embodiment mode, a mode of a light emitting element of the present invention, which has such a structure that a plurality of light emitting units are stacked (hereinafter referred to as a stacked element), is described with reference to FIG. 3. This light emitting element is a stacked light emitting element in which a plurality of light emitting units are provided between a first electrode and a second electrode. Each of the light emitting units may have a structure similar to those shown in Embodiment Modes 2 to 4. That is, the light emitting element shown in Embodiment Mode 2 is a light emitting element having one light emitting unit. In this embodiment mode, a light emitting element having a plurality of light emitting units is described.

Figure 3:
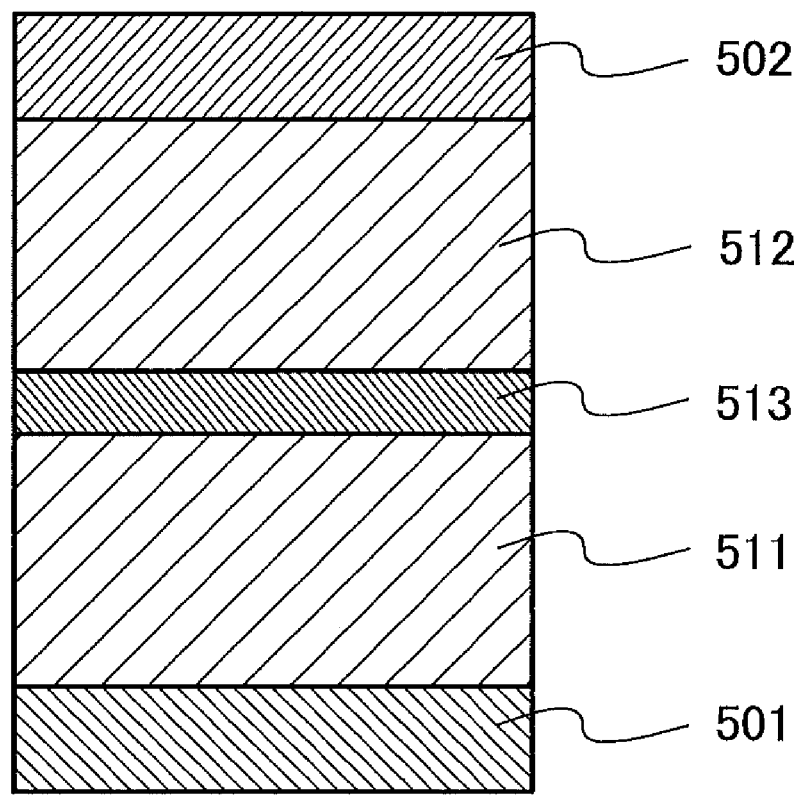
FIG. 3 is a diagram illustrating a light emitting element of the present invention.

In FIG. 3, a first light emitting unit 511 and a second light emitting unit 512 are stacked between a first electrode 501 and a second electrode 502. The first electrode 501 and the second electrode 502 may be similar to those shown in Embodiment Mode 2. In addition, the first light emitting unit 511 and the second light emitting unit 512 may have the same structure or different structures, and the structure thereof can be similar to that described in Embodiment Mode 2.

A charge generating layer 513 is a layer that injects electrons into one of the light emitting units and injects holes into the other light emitting unit when a voltage is applied between the first electrode 501 and the second electrode 502. The charge generating layer 513 may be a single layer or stacked layers. As a stacked structure of a plurality of layers, a layer for injecting holes and a layer for injecting electrons are preferably stacked.

As a layer for injecting holes, a semiconductor such as molybdenum oxide, vanadium oxide, rhenium oxide, or ruthenium oxide, or an insulator can be used. Alternatively, an acceptor substance may be added to a substance with a high hole transporting property. A mixture of a substance with a high hole transporting property and an acceptor substance corresponds to the composite material shown in Embodiment Mode 2. As the acceptor substance, there are 7,7,8,8-tetracyano-2,3,5,6-tetrafluoroquinodimethane (abbreviation: $F_4$-TCNQ), and a metal oxide such as vanadium oxide, molybdenum oxide, or tungsten oxide. As the substance with a high hole transporting property, various compounds can be used such as an aromatic amine compound, a carbazole derivative, aromatic hydrocarbon, and a high molecular compound (oligomer, dendrimer, polymer, or the like). Note that the substance with a high hole transporting property is preferably a substance with a hole mobility of $10^{-6}$ cm$^2$/Vs or higher, although other substances may also be used as long as the hole transporting property thereof is higher than the electron transporting property thereof. The composite material of the substance with a high hole transporting property and the acceptor substance is excellent in carrier injecting properties and carrier transporting properties; thus, low voltage driving and low current driving can be realized.

As a layer for injecting electrons, an insulator such as lithium oxide, lithium fluoride, or cesium carbonate, or a semiconductor can be used. Alternatively, a donor substance may be added to a substance with a high electron transporting property. As the donor substance, it is possible to use an alkali metal, an alkaline earth metal, a rare earth metal, a metal belonging to Group 13 of the periodic table, or an oxide or carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the donor substance. As the substance with a high electron transporting property, the materials shown in Embodiment Mode 2 can be used. Note that the substance with a high electron transporting property is preferably a substance with an electron mobility of $10^{-6}$ cm$^2$/Vs or higher, although other substances may also be used as long as the electron transporting property thereof is higher than the hole transporting property thereof. The composite material of the substance with a high electron transporting property and the donor substance is excellent in carrier injecting properties and carrier transporting properties; thus, low voltage driving and low current driving can be realized.

Besides, the electrode materials shown in Embodiment Mode 2 can also be used for the charge generating layer 513. For example, a layer containing a substance with a high hole transporting property and a metal oxide may be combined with a transparent conductive film to form the charge generating layer 513. Note that in view of light extraction efficiency, the charge generating layer 513 is preferably a layer with a high light transmitting property.

In any case, the charge generating layer 513 interposed between the first light emitting unit 511 and the second light emitting unit 512 may adopt any structure as long as electrons can be injected into one of the first light emitting unit 511 and the second light emitting unit 512 and holes can be injected into the other thereof when a voltage is applied between the first electrode 501 and the second electrode 502. For example, in the case where a voltage is applied so that the first electrode has a higher potential than the second electrode, the charge generating layer 513 may have any structure as long as electrons can be injected into the first light emitting unit 511 and holes can be injected into the second light emitting unit 512.

Although the light emitting element having the two light emitting units is described in this embodiment mode, a light emitting element in which three or more light emitting units are stacked can be applied in a similar way. Like the light emitting element of this embodiment mode, when a plurality of light emitting units are arranged between a pair of electrodes so as to be separated with a charge generating layer, a high luminance can be attained at a low current density, contributing to a long lifetime of the light emitting element. In addition, a lighting device which consumes less power can be realized.

When each light emitting unit is allowed to emit a different color, light emission of a desired color can be obtained from the whole light emitting element. For example, in a light emitting element having two light emitting units, white light can be emitted from the whole light emitting element by allowing a first light emitting unit and a second light emitting unit to emit light of complementary colors. Note that 'complementary color' refers to a relationship between colors from which an achromatic color is obtained when they are mixed. That is, white light emission can be obtained by mixing the lights obtained from substances that emit light of complementary colors. Besides, light emission of a desired color can be similarly obtained from a light emitting element having three light emitting units. For example, when a first light emitting unit emits red light, a second light emitting unit emits green light, and a third light emitting unit emits blue light, white light emission can be obtained from the whole light emitting element.

Note that this embodiment mode can be combined with other embodiment modes as appropriate.

Embodiment Mode 6

In this embodiment mode, a light emitting device having a light emitting element of the present invention is described.

In this embodiment mode, a light emitting device that has a pixel portion provided with a light emitting element of the present invention is described with a reference to FIGS. 4A and 4B. Note that FIG. 4A is a top view illustrating a light emitting device, and FIG. 4B is a cross-sectional view taken along lines A-A' and B-B' of FIG. 4A. This light emitting device includes a driver circuit portion (source driver circuit) 601, a pixel portion 602, and a driver circuit portion (gate driver circuit) 603 in order to control the emission of the light emitting element. Furthermore, reference numeral 604 denotes a sealing substrate; 605, a sealing material; and 607, a space surrounded by the sealing material 605.

A lead wiring 608 is a wiring for transmitting signals to be inputted to the source driver circuit 601 and the gate driver circuit 603, and receives video signals, clock signals, start signals, reset signals, and the like from an FPC (flexible printed circuit) 609 that serves as an external input terminal. Although only the FPC is illustrated here, this FPC may be provided with a printed wiring board (PWB). The light emitting device in this specification refers not only to a light emitting device itself but also to a light emitting device attached with an FPC or a PWB.

Next, the cross-sectional structure of the light emitting device is described with reference to FIG. 4B. The driver circuit portions and the pixel portion are provided over an element substrate 610; however, FIG. 4B illustrates only the source driver circuit 601 included in the driver circuit portions and one pixel in the pixel portion 602.

Note that as the source driver circuit 601, a CMOS circuit combining an N-channel TFT 623 and a P-channel TFT 624 is formed. Alternatively, the driver circuit may include various CMOS circuits, PMOS circuits, or NMOS circuits. Although this embodiment mode shows a driver-integrated type in which the driver circuits and the pixel portion are formed over the same substrate, the driver circuits are not necessarily formed over the same substrate as the pixel portion, but may be formed outside the substrate.

The pixel portion 602 has a plurality of pixels each provided with a switching TFT 611, a current controlling TFT 612, and a first electrode 613 electrically connected to a drain of the current controlling TFT 612. Note that an insulator 614 is formed to cover an end portion of the first electrode 613. Here, the insulator 614 is formed using a positive photosensitive acrylic resin film.

In order to improve the coverage, the insulator 614 is formed so as to have a curved surface with a curvature at either an upper end portion or a lower end portion. For example, in the case of using a positive photosensitive acrylic film for the insulator 614, it is preferable that the insulator 614 have a curved surface with a curvature radius (0.2 μm to 3 μm) only at the upper end portion. Alternatively, the insulator 614 may be formed using either negative photosensitive acrylic that becomes insoluble in an etchant after light irradiation, or positive photosensitive acrylic that becomes dissoluble in an etchant after light irradiation.

An EL layer 616 and a second electrode 617 are formed over the first electrode 613. Here, the first electrode 613 can be formed using various kinds of metals, alloys, electrically conductive compounds, or mixtures thereof. In the case where the first electrode is used as an anode, it is preferable to use, among these materials, a metal, an alloy, an electrically conductive compound, or a mixture thereof, which has a high work function (preferably, a work function of 4.0 eV or higher). For example, it is possible to use a single layer film such as an indium oxide-tin oxide film containing silicon, an indium oxide-zinc oxide film, a titanium nitride film, a chromium film, a tungsten film, a Zn film, a Pt film, or the like, as well as a stacked layer film of a titanium nitride film and a film mainly containing aluminum, a three-layer film of a titanium nitride film, a film mainly containing aluminum, and a titanium nitride film, or the like. Note that the use of the stacked layer structure in the first electrode 613 leads to the reduction in its resistance, which allows the first electrode 613 to function not only as the first electrode 613 but also as a wiring since good ohmic contact with the drain of the current controlling TFT 612 is attainable.

The EL layer 616 is formed by various methods such as evaporation using an evaporation mask, ink jet, or spin coating. The EL layer 616 has the layer for controlling the carrier transport, which is described in Embodiment Modes 2 to 5. Any of low molecular compounds, high molecular compounds, oligomers, and dendrimers may be employed as the material for the EL layer 616. Besides, inorganic compounds as well as organic compounds may be used for the EL layer 616.

The second electrode 617 can be formed using various kinds of metals, alloys, electrically conductive compounds, or mixtures thereof. In the case where the second electrode 617 is used as a cathode, it is preferable to use, among these materials, a metal, an alloy, an electrically conductive compound, or a mixture thereof, which has a low work function (preferably, a work function of 3.8 eV or lower). For example, it is possible to use an element belonging to Group 1 or Group 2 of the periodic table, i.e., an alkali metal such as lithium (Li) or cesium (Cs), an alkaline earth metal such as magnesium (Mg), calcium (Ca), or strontium (Sr), or an alloy containing any of these metals (such as MgAg or AlLi), or the like. In the case where light generated in the EL layer 616 is transmitted through the second electrode 617, the second electrode 617 may also be formed using a stacked layer film of a thin metal film with a reduced thickness and a transparent conductive film (for example, indium oxide-tin oxide (ITO), indium oxide-tin oxide containing silicon or silicon oxide, indium oxide-zinc oxide (IZO), or indium oxide containing tungsten oxide and zinc oxide (IWZO)).

Furthermore, the sealing substrate 604 and the element substrate 610 are attached to each other with the sealing material 605, whereby a light emitting element 618 is provided in the space 607 surrounded by the element substrate 610, the sealing substrate 604, and the sealing material 605. Note that the space 607 is filled with an inert gas (nitrogen, argon, or the like) or a filler such as the sealing material 605.

As the sealing material 605, an epoxy resin is preferably used. In addition, it is preferable to use a material that prevents penetration of moisture or oxygen as much as possible. As the sealing substrate 604, a plastic substrate made of FRP (Fiberglass-Reinforced Plastics), PVF (polyvinyl fluoride), polyester, acrylic, or the like can be used as well as a glass substrate or a quartz substrate.

In such a manner, the light emitting device having the light emitting element of the present invention can be obtained.

The light emitting device of the present invention has the light emitting element shown in Embodiment Modes 2 to 5. Since the light emitting element shown in Embodiment Modes 2 to 5 has a low driving voltage, the light emitting device with low power consumption can be obtained.

Figure 5A:
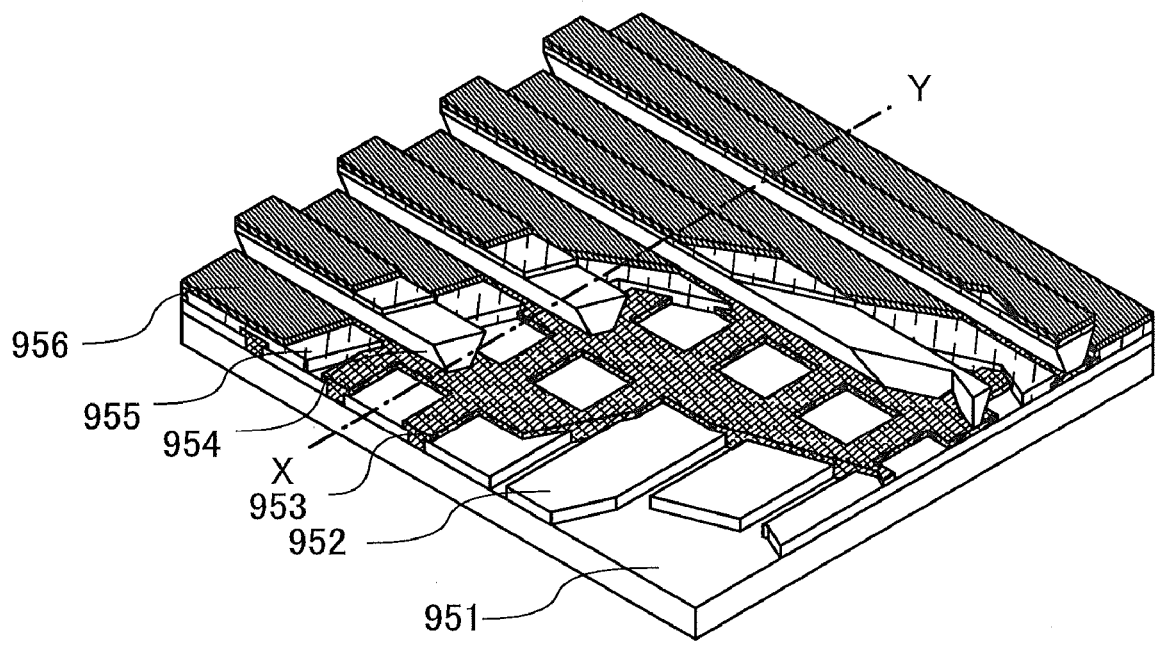
FIGS. 5A and 5B are diagrams illustrating a light emitting device of the present invention.
Figure 5B:
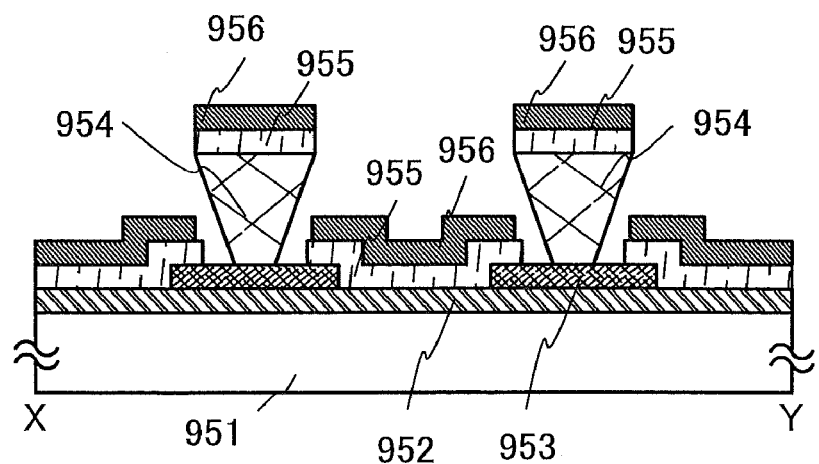

Although an active matrix light emitting device in which the driving of a light emitting element is controlled by a transistor is thus described in this embodiment mode, the present invention may be applied to a passive matrix light emitting device. FIGS. 5A and 5B illustrate a passive matrix light emitting device manufactured by application of the present invention. Note that FIG. 5A is a perspective view of a light emitting device, and FIG. 5B is a cross-sectional view taken along line X-Y of FIG. 5A. In FIGS. 5A and 5B, an EL layer 955 is provided between an electrode 952 and an electrode 956 over a substrate 951. An end portion of the electrode 952 is covered with an insulating layer 953. A partition layer 954 is provided over the insulating layer 953. The sidewalls of the partition layer 954 have such a gradient that the distance between both sidewalls is gradually narrowed toward the surface of the substrate. That is, a cross section in the direction of a short side of the partition layer 954 is a trapezoid, in which a lower side (that faces a surface of the insulating layer 953 and is in contact with the insulating layer 953) is shorter than an upper side (that faces the surface of the insulating layer 953 and is not in contact with the insulating layer 953). By providing the partition layer 953 in such a manner, a cathode can be patterned. In addition, also in the case of the passive matrix light emitting device, a light emitting device with low power consumption can be obtained by providing the light emitting element of the present invention that has a low driving voltage.

Note that this embodiment mode can be combined with other embodiment modes as appropriate.

Embodiment Mode 7

Described in this embodiment mode are electronic appliances of the present invention each including the light emitting device shown in Embodiment Mode 6. The electronic appliances of the present invention each have the light emitting element shown in Embodiment Modes 2 to 5, and thus have a display portion with low power consumption.

As electronic appliances manufactured using the light emitting device of the present invention, there are cameras such as video cameras and digital cameras, goggle type displays, navigation systems, audio reproducing devices (car audio systems, audio component systems, and the like), computers, game machines, portable information terminals (mobile computers, cellular phones, mobile game machines, electronic books, and the like), image reproducing devices provided with a recording medium (specifically, a device that reproduces a recording medium such as a DVD (digital versatile disc) and has a display device capable of displaying the reproduced image), and the like. Specific examples of these electronic appliances are illustrated in FIGS. 6A to 6D.

Figure 6A:
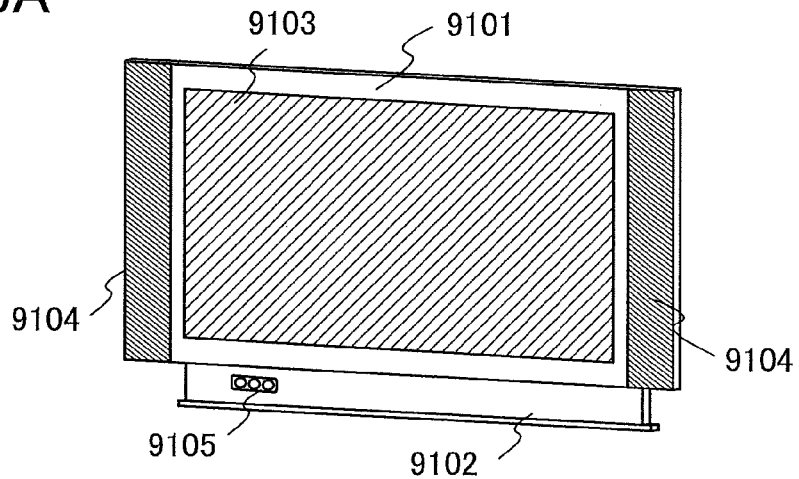
FIGS. 6A to 6D are diagrams each illustrating an electronic appliance of the present invention.

FIG. 6A illustrates a television device in accordance with this embodiment mode, which includes a housing 9101, a supporting base 9102, a display portion 9103, speaker portions 9104, a video input terminal 9105, and the like. In the television device, the display portion 9103 has light emitting elements arranged in matrix that are described in Embodiment Modes 2 to 5. These light emitting elements have characteristics of low driving voltage and low power consumption, and similar characteristics are observed in the display portion 9103 including such light emitting elements. Therefore, the power consumption of this television device can be reduced. Because of such characteristics, the number or scale of power supply circuits in the television device can be drastically reduced, and thus, the size and weight of the housing 9101 and the supporting base 9102 can be reduced. Since the television device in accordance with this embodiment mode has lower power consumption and reduced size and weight, a product suitable for living environment can be provided.

Figure 6B:
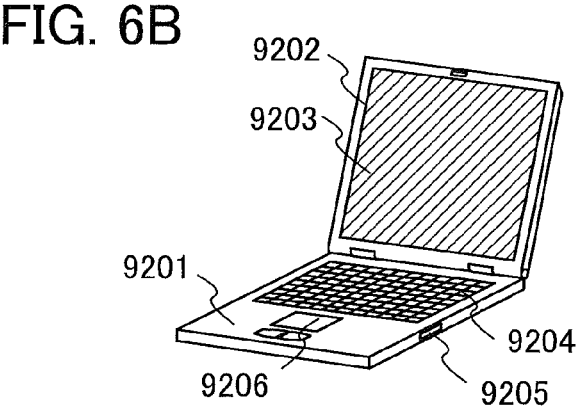

FIG. 6B illustrates a computer in accordance with this embodiment mode, which includes a main body 9201, a housing 9202, a display portion 9203, a keyboard 9204, an external connection port 9205, a pointing device 9206, and the like. In this computer, the display portion 9203 has light emitting elements arranged in matrix that are described in Embodiment Modes 2 to 5. These light emitting elements have characteristics of low driving voltage and low power consumption, and similar characteristics are observed in the display portion 9203 including such light emitting elements. Therefore, the power consumption of this computer can be reduced. Because of such characteristics, the number or scale of power supply circuits in the computer can be drastically reduced, and thus, the size and weight of the main body 9201 and the housing 9202 can be reduced. Since the computer in accordance with this embodiment mode has lower power consumption and reduced size and weight, a product suitable for environment can be provided.

Figure 6C:
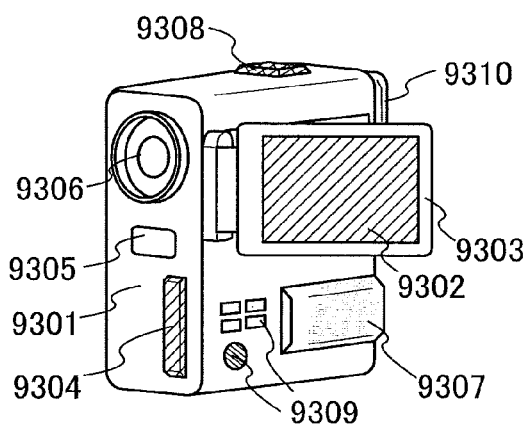

FIG. 6C illustrates a camera including a main body 9301, a display portion 9302, a housing 9303, an external connection port 9304, a remote control receiving portion 9305, an image receiving portion 9306, a battery 9307, an audio input portion 9308, an operation key 9309, an eye piece portion 9310, and the like. In this camera, the display portion 9302 has light emitting elements arranged in matrix that are described in Embodiment Modes 2 to 5. These light emitting elements have characteristics of low driving voltage and low power consumption, and similar characteristics are observed in the display portion 9302 including such light emitting elements. Therefore, the power consumption of this camera can be reduced. Because of such characteristics, the number or scale of power supply circuits in the camera can be drastically reduced, and thus, the size and weight of the main body 9301 can be reduced. Since the camera in accordance with this embodiment mode has lower power consumption and reduced size and weight, a product suitable for carrying around can be provided.

Figure 6D:
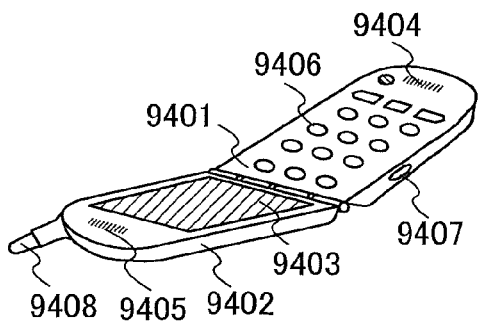

FIG. 6D illustrates a cellular phone in accordance with this embodiment mode, which includes a main body 9401, a housing 9402, a display portion 9403, an audio input portion 9404, an audio output portion 9405, an operation key 9406, an external connection port 9407, an antenna 9408, and the like. In this cellular phone, the display portion 9403 has light emitting elements arranged in matrix that are described in Embodiment Modes 2 to 5. These light emitting elements have characteristics of low driving voltage and low power consumption, and similar characteristics are observed in the display portion 9403 including such light emitting elements. Therefore, the power consumption of this cellular phone can be reduced. Because of such characteristics, the number or scale of power supply circuits in the cellular phone can be drastically reduced, and thus, the size and weight of the main body 9401 and the housing 9402 can be reduced. Since the cellular phone in accordance with this embodiment mode has low power consumption and reduced size and weight, a product suitable for carrying around can be provided.

Figure 12A:
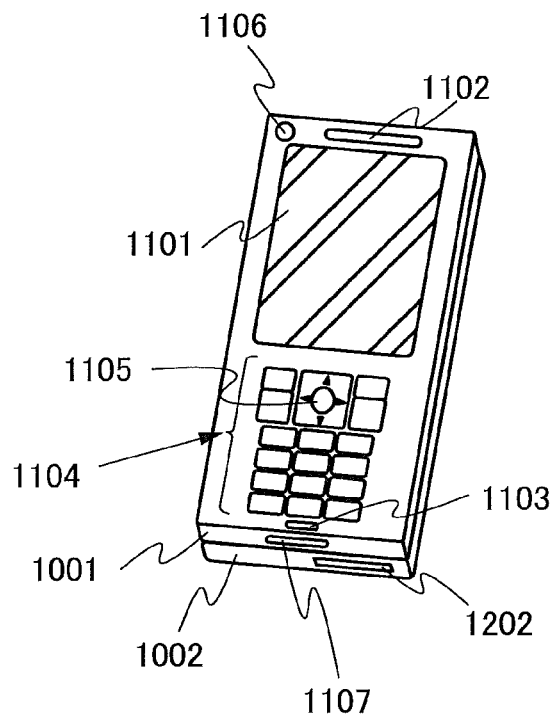
FIGS. 12A to 12C are diagrams each illustrating an electronic appliance of the present invention.
Figure 12B:
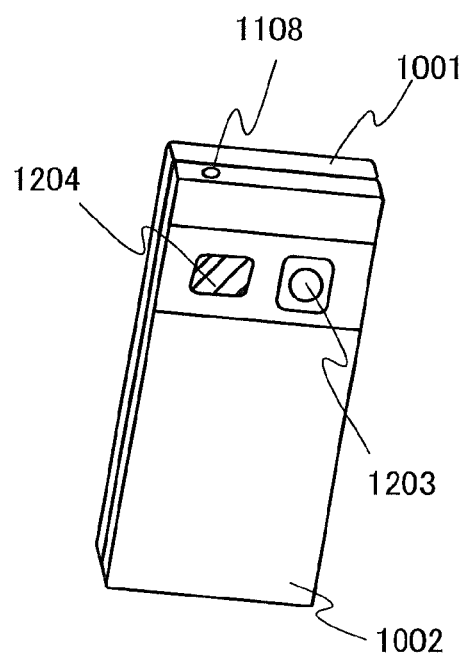
Figure 12C:
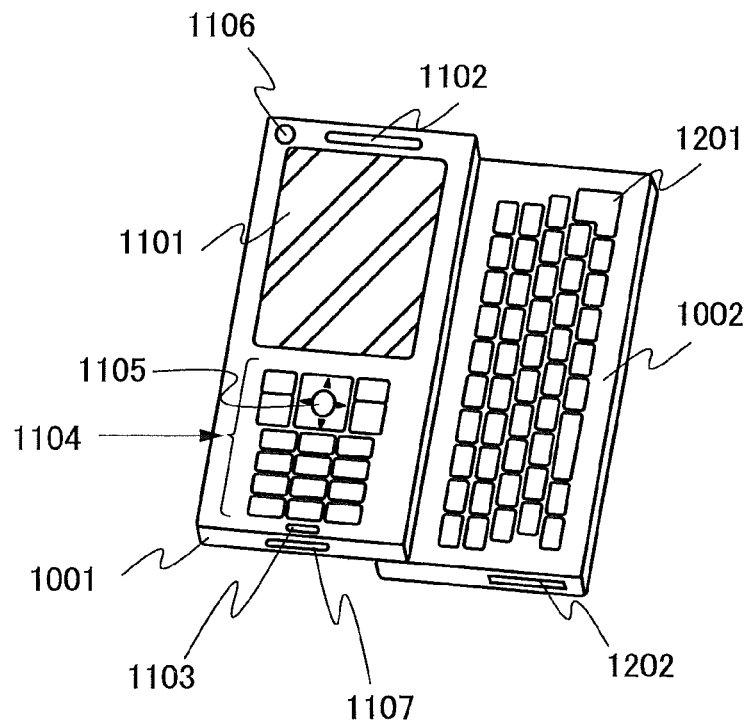

FIGS. 12A to 12C illustrate an example of a cellular phone having a different structure from that of FIG. 6D. FIG. 12A is a front view, FIG. 12B is a back view, and FIG. 12C is a development view. The cellular phone illustrated in FIGS. 12A to 12C is a so-called smartphone that has both functions of a cellular phone and a portable information terminal, incorporates a computer, and conducts a variety of data processing in addition to voice calls.

The cellular phone illustrated in FIGS. 12A to 12C has two housings 1001 and 1002. The housing 1001 includes a display portion 1101, a speaker 1102, a microphone 1103, operation keys 1104, a pointing device 1105, a camera lens 1106, an external connection terminal 1107, and the like, while the housing 1002 includes a keyboard 1201, an external memory slot 1202, a camera lens 1203, a light 1204, an earphone terminal 1108, and the like. In addition, an antenna is incorporated in the housing 1001.

In addition to the above structure, the cellular phone may incorporate a non-contact IC chip, a small size memory device, or the like.

The light emitting device shown in Embodiment Mode 6 can be incorporated in the display portion 1101, and the display orientation can be changed as appropriate depending on usage. Since the cellular phone is provided with the camera lens 1106 on the same surface as the display portion 1101, it can be used as a videophone. Furthermore, still images and moving images can be taken with the camera lens 1203 and the light 1204 by using the display portion 1101 as a viewfinder. The speaker 1102 and the microphone 1103 can be used not only for verbal communication, but also for a videophone, recording, reproduction, and the like. The operation keys 1104 allow incoming and outgoing calls, input of simple information such as e-mails, scrolling of a screen, cursor motion, and the like. Furthermore, the housing 1001 and the housing 1002 that overlap each other (FIG. 12A) slide relative to each other as shown in FIG. 12C, and can be used as a portable information terminal. In this case, operation can be smoothly performed using the keyboard 1201 and the pointing device 1105. The external connection terminal 1107 can be connected to an AC adapter or a variety of cables such as a USB cable, and can be used for the charge of a built-in battery and for data communication with a computer or the like. Furthermore, a larger amount of data can be stored and transferred using a storage medium inserted into the external memory slot 1202.

In addition to the aforementioned functions, the cellular phone may also have an infrared communication function, a television reception function, or the like.

Figure 7:
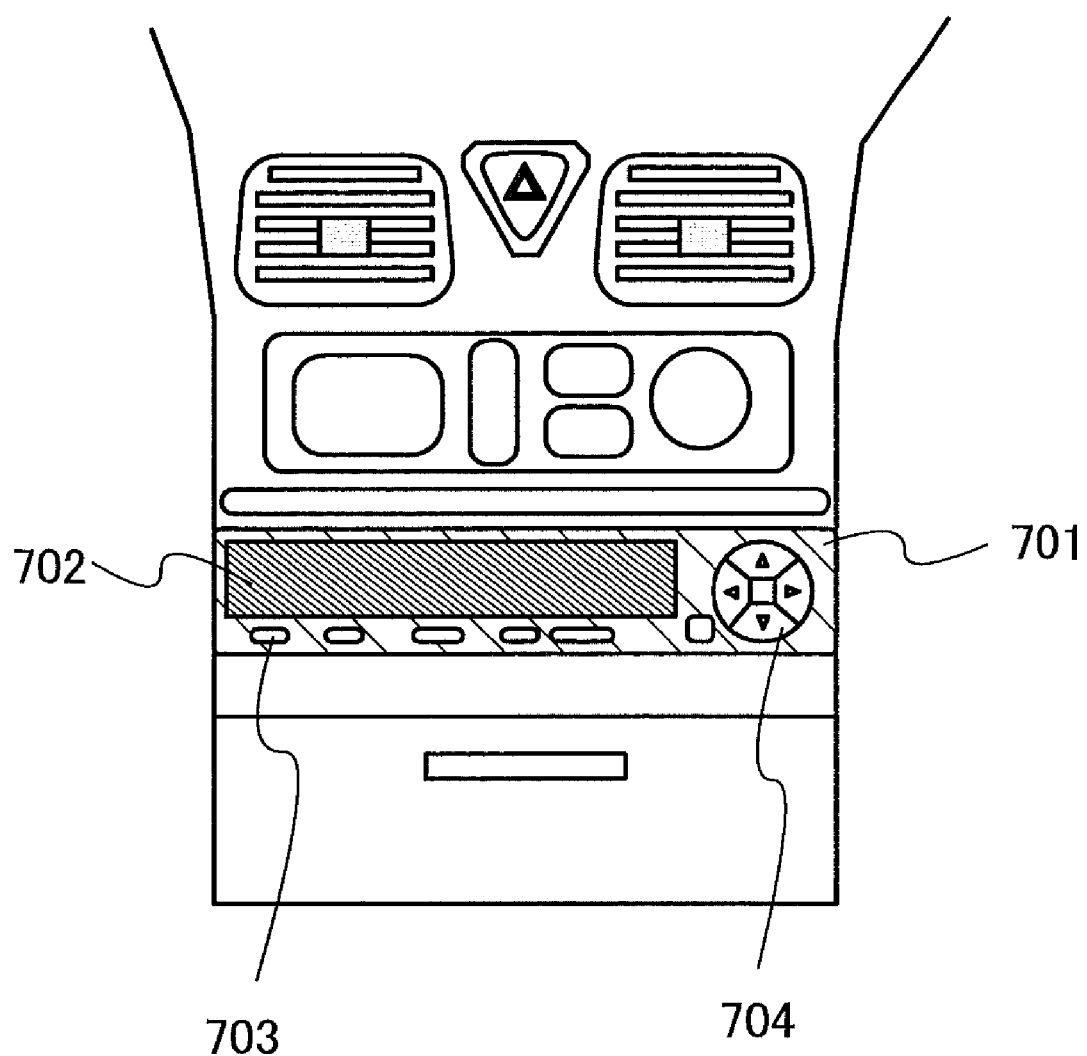
FIG. 7 is a diagram illustrating an electronic appliance of the present invention.

FIG. 7 illustrates an audio reproducing device, specifically, a car audio system that includes a main body 701, a display portion 702, and operation switches 703 and 704. The display portion 702 can be formed using the light emitting device (a passive matrix type or an active matrix type) shown in Embodiment Mode 6. Furthermore, the display portion 702 may employ a segment type light emitting device. In any case, by using the light emitting element of the present invention, a bright display portion with low power consumption can be formed using a vehicle power source (12 V to 42 V). Although an in-car audio system is shown in this embodiment mode, the present invention may be used for a portable audio device or an audio device for household use.

Figure 8:
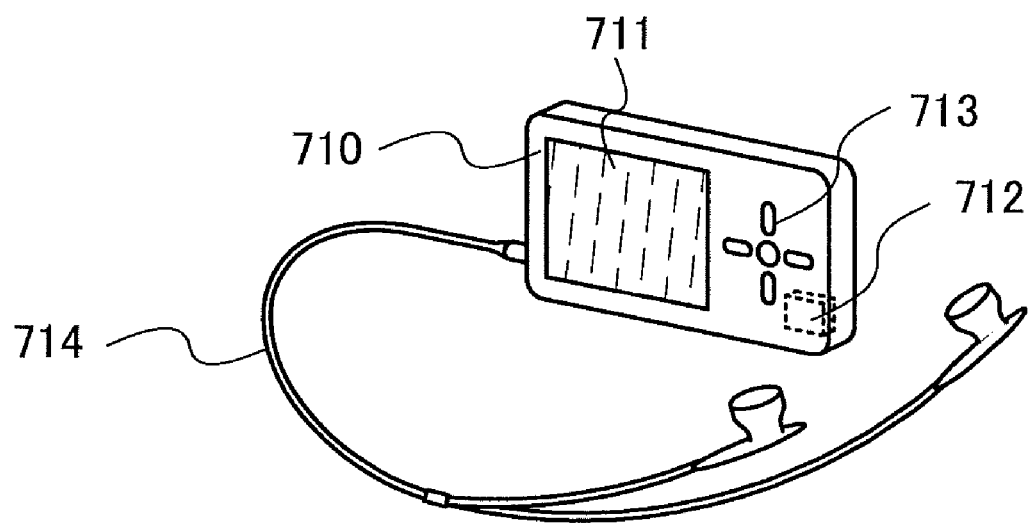
FIG. 8 is a diagram illustrating an electronic appliance of the present invention.

FIG. 8 illustrates a digital player as an example of an audio reproducing device. The digital player illustrated in FIG. 8 includes a main body 710, a display portion 711, a memory portion 712, an operation portion 713, earphones 714, and the like. Note that headphones or wireless earphones may be used instead of the earphones 714. The display portion 711 can be formed using the light emitting device (a passive matrix type or an active matrix type) shown in Embodiment Mode 6. Furthermore, the display portion 711 may employ a segment type light emitting device. In any case, by using the light emitting element of the present invention, a bright display portion with low power consumption can be formed, which is capable of displaying images even when a secondary battery (a nickel-metal hydride battery or the like) is used. As the memory portion 712, a hard disk or a nonvolatile memory is used. For example, by using a NAND-type nonvolatile memory with a storage capacity of 20 to 200 gigabytes (GB), a large amount of image and sound (music) can be recorded and reproduced. Note that the power consumption of the display portions 702 and 711 can be suppressed by displaying white characters on the black background. This is particularly effective for portable audio systems.

As described above, the applicable range of the light emitting device manufactured by using the present invention is extremely wide, which allows the light emitting device to be applied to electronic appliances in various fields. By applying the present invention, an electronic appliance having a display portion with low power consumption can be manufactured.

The light emitting device using the present invention has a light emitting element with high emission efficiency, and can also be used as a lighting device. One mode of a lighting device using the light emitting element of the present invention is described with reference to FIG. 9.

Figure 9:
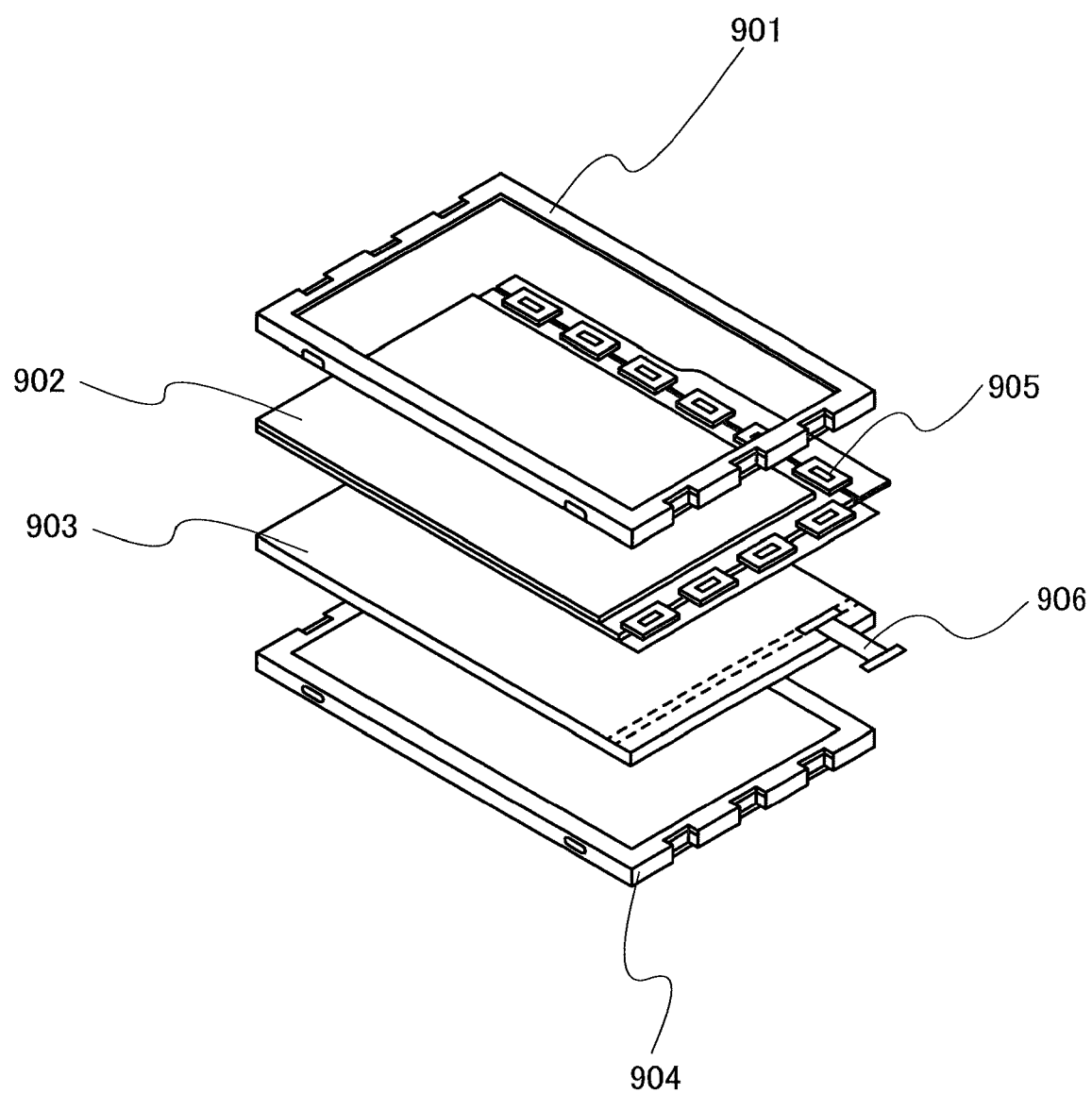
FIG. 9 is a diagram illustrating an electronic appliance of the present invention.

A liquid crystal display device in which the light emitting device of the present invention is used as a backlight is illustrated in FIG. 9 as an example of the electronic appliance using the light emitting device of the present invention as a lighting device. The liquid crystal display device illustrated in FIG. 9 includes a housing 901, a liquid crystal layer 902, a backlight 903, and a housing 904. The liquid crystal layer 902 is connected to a driver IC 905. The light emitting device of the present invention is used as the backlight 903, and supplied with current through a terminal 906.

Since the light emitting device of the present invention has a reduced thickness and low power consumption, the thickness and power consumption of the liquid crystal display device can also be reduced by using the light emitting device of the present invention as the backlight. In addition, the light emitting device of the present invention is a lighting device with planar light emission and can be increased in area. Therefore, the area of the backlight can be increased, resulting in the liquid crystal display device with a larger area.

Figure 10:
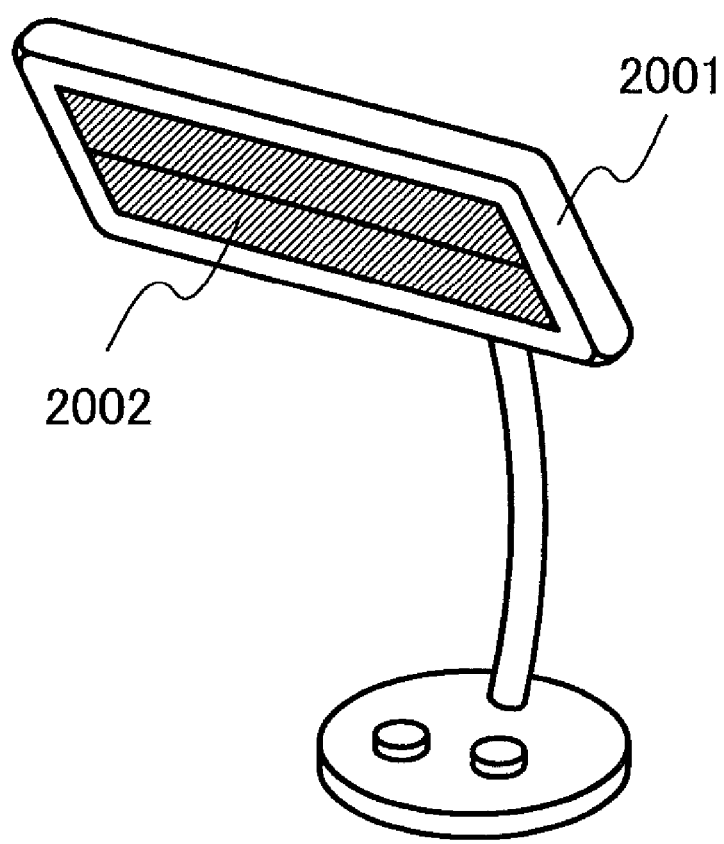
FIG. 10 is a diagram illustrating a lighting device of the present invention.

FIG. 10 illustrates an example of applying the light emitting device of the present invention to a desk lamp as a lighting device. The desk lamp illustrated in FIG. 10 includes a housing 2001 and a light source 2002, and the light emitting device of the present invention is used as the light source 2002. Since the light emitting device of the present invention has low power consumption, the power consumption of the desk lamp can also be reduced.

Figure 11:
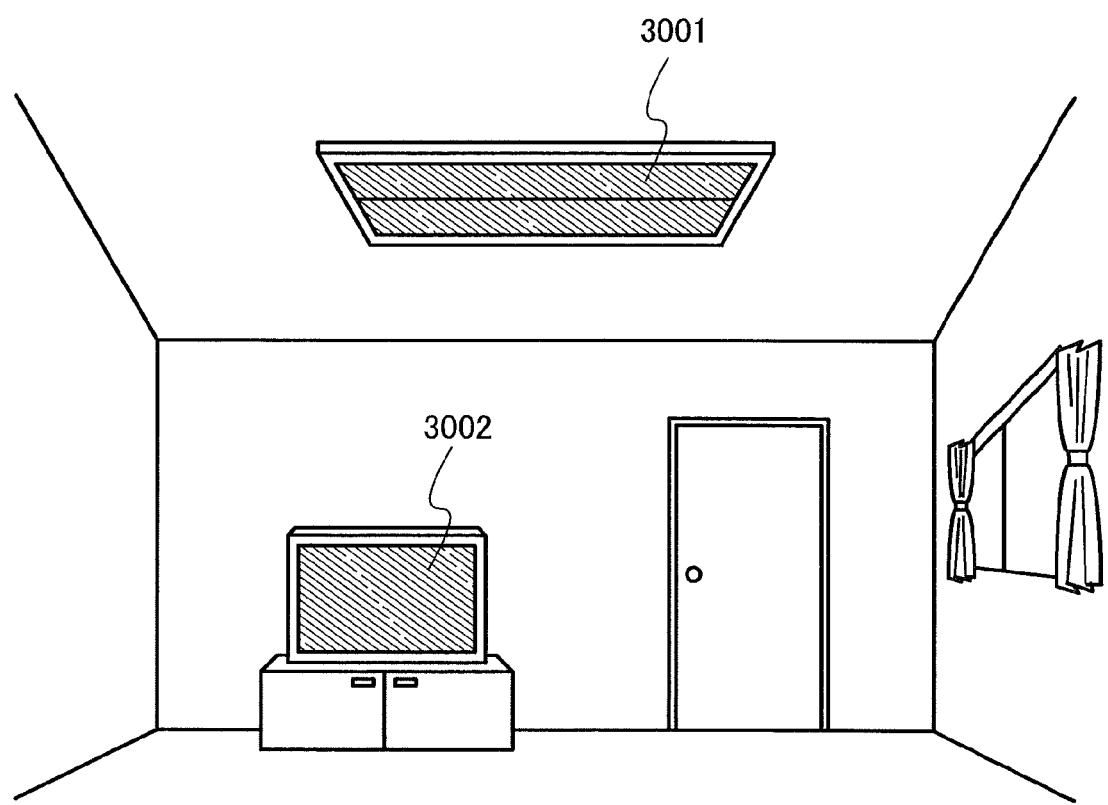
FIG. 11 is a diagram illustrating a lighting device of the present invention.

FIG. 11 illustrates an example of applying the light emitting device of the present invention to an indoor lighting device 3001. Since the light emitting device of the present invention can be increased in area, it can be used as a lighting device with a large area. In addition, the light emitting device of the present invention has low power consumption, and thus it can be used as a lighting device with low power consumption. A television device 3002 in accordance with the present invention as illustrated in FIG. 6A is placed in a room where the light emitting device applying the present invention is used as the indoor lighting device 3001. Thus, public broadcasting and movies can be watched. In such a case, the both devices have low power consumption, which makes it possible to reduce the load on the environment.

Note that this embodiment mode can be combined with other embodiment modes as appropriate.

Embodiment 1

In this embodiment, a synthetic method of 4-(5-phenyl-1,3,4-oxadiazol-2-yl)-4'-(3-phenylquinoxalin-2-yl)triphenylamine (abbreviation: OPA1PQ) represented by the structural formula (101) is described.

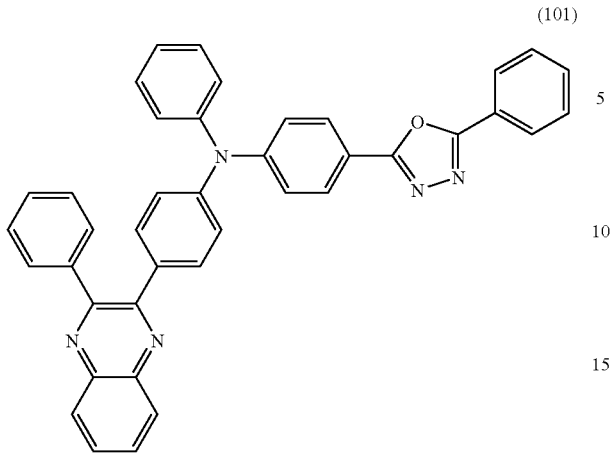

(101)

Step 1: Synthesis of
4-(3-phenylquinoxalin-2-yl)diphenylamine

A synthetic scheme of 4-(3-phenylquinoxalin-2-yl)diphenylamine is shown in (E-1).

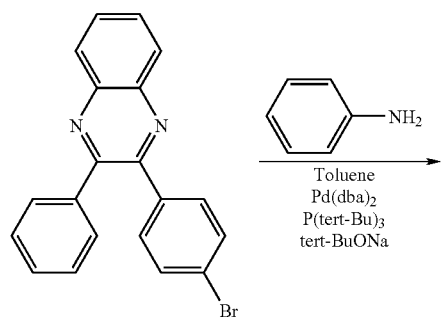

(E-1)

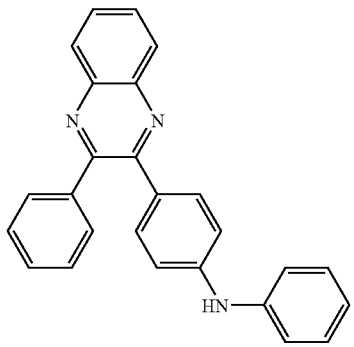

5.0 g (14 mmol) of 2-(4-bromophenyl)-3-phenylquinoxaline, 3.0 g (31 mmol) of sodium tert-butoxide, and 0.20 g (0.35 mmol) of bis(dibenzylideneacetone)palladium(0) were put in a 300 mL three-neck flask, and the air in the flask was replaced with nitrogen. This mixture was added with 50 mL of toluene, 2.0 mL (22 mmol) of aniline, and 0.2 mL of tri(tert-butyl)phosphine (10 wt % hexane solution). This mixture was heated and stirred at 80° C. for three hours, and after the stirring, the mixture was added with chloroform and heated. This suspension was subjected to suction filtration through Celite (manufactured by Wako Pure Chemical Industries, Ltd., Catalog No. 531-16855), whereby the filtrate was obtained. The obtained filtrate was washed with 1M hydrochloric acid, a saturated aqueous solution of sodium bicarbonate, and a brine in this order. The organic layer was dried by adding magnesium sulfate. This mixture was subjected to suction filtration to remove magnesium sulfate, whereby the filtrate was obtained. The obtained filtrate was concentrated, and the resulting solid was washed with methanol, whereby 11 g of the target light yellow solid was obtained in 71% yield.

Step 2: Synthesis of 4-(5-phenyl-1,3,4-oxadiazol-2-yl)-4'-(3-phenylquinoxalin-2-yl)triphenylamine (abbreviation: OPA1PQ)

A synthetic scheme of OPA1PQ is shown in (E-2).

(E-2)

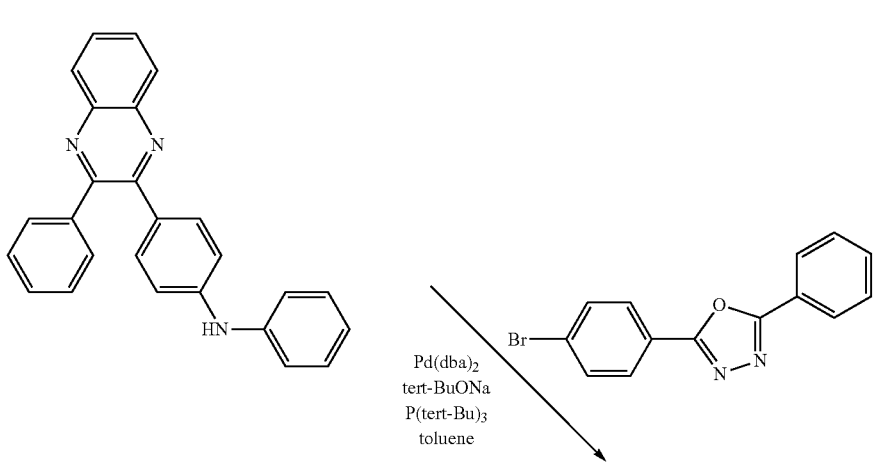

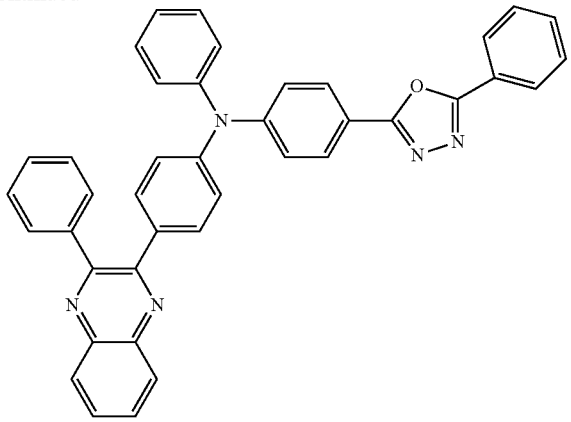

170 mg (0.46 mmol) of 4-(3-phenylquinoxalin-2-yl)diphenylamine, 140 mg (0.46 mmol) of 2-(4-bromophenyl)-5-phenyl-1,3,4-oxadiazole, and 300 mg (3.1 mmol) of sodium tert-butoxide were put in a 50 mL three-neck flask. After the air in the flask was replaced with nitrogen, this mixture was added with 5 mL of toluene and 0.10 mL of tri(tert-butyl)phosphine (10 wt % hexane solution). This mixture was degassed under reduced pressure, and then added with 17 mg (0.02 mmol) of bis(dibenzylideneacetone)palladium(0). This mixture was stirred at 80° C. for three hours. After the stirring, the mixture was added with about 20 mL of toluene and about 20 mL of ethyl acetate, and then filtered through Celite (manufactured by Wako Pure Chemical Industries, Ltd., Catalog No. 531-16855), Florisil (manufactured by Wako Pure Chemical Industries, Ltd., Catalog No. 540-00135), and alumina. The obtained filtrate was concentrated to give a yellow oily substance. This oily substance was purified by silica gel column chromatography (developing solvent: hexane:toluene:ethyl acetate=2:2:1), and the resulting solid was recrystallized with dichloromethane/hexane, whereby 230 mg of the target yellow powdery solid was obtained in 88% yield.

The obtained compound was confirmed to be 4-(5-phenyl-1,3,4-oxadiazole-2-yl)-4'-(3-phenylquinoxaline-2-yl)triphenylamine (abbreviation: OPA1PQ) by the nuclear magnetic resonance (NMR) measurement.

Figure 13A:
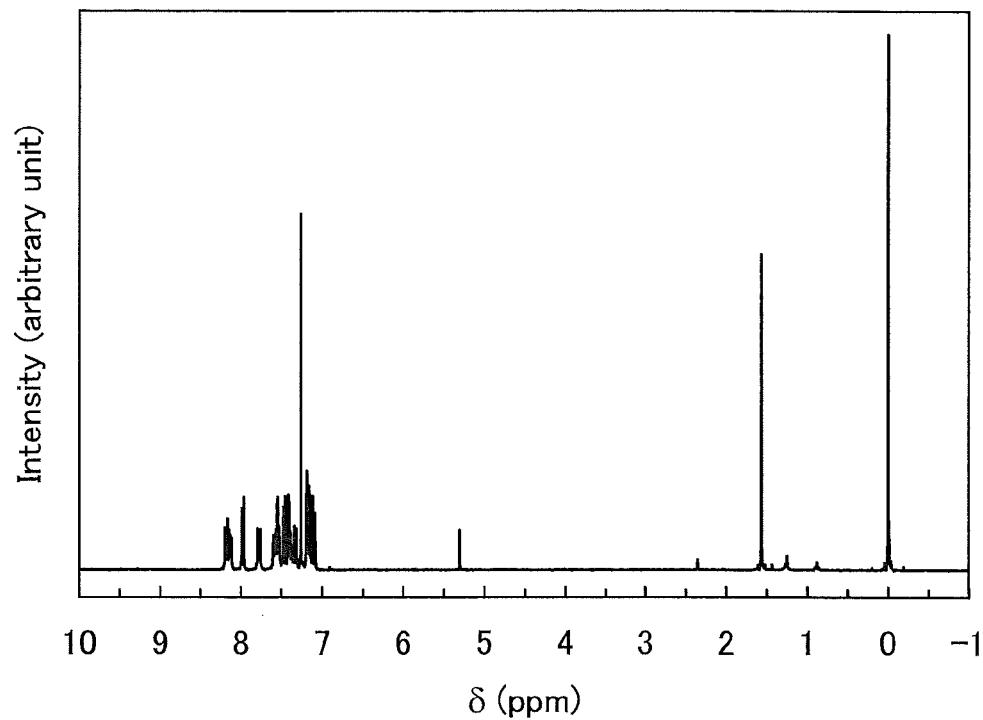
FIGS. 13A and 13B are $^1$H NMR charts of 4-(5-phenyl-1,3,4-oxadiazol-2-yl)-4'-(3-phenylquinoxalin-2-yl)triphenylamine (abbreviation: OPA1PQ)
Figure 13B:
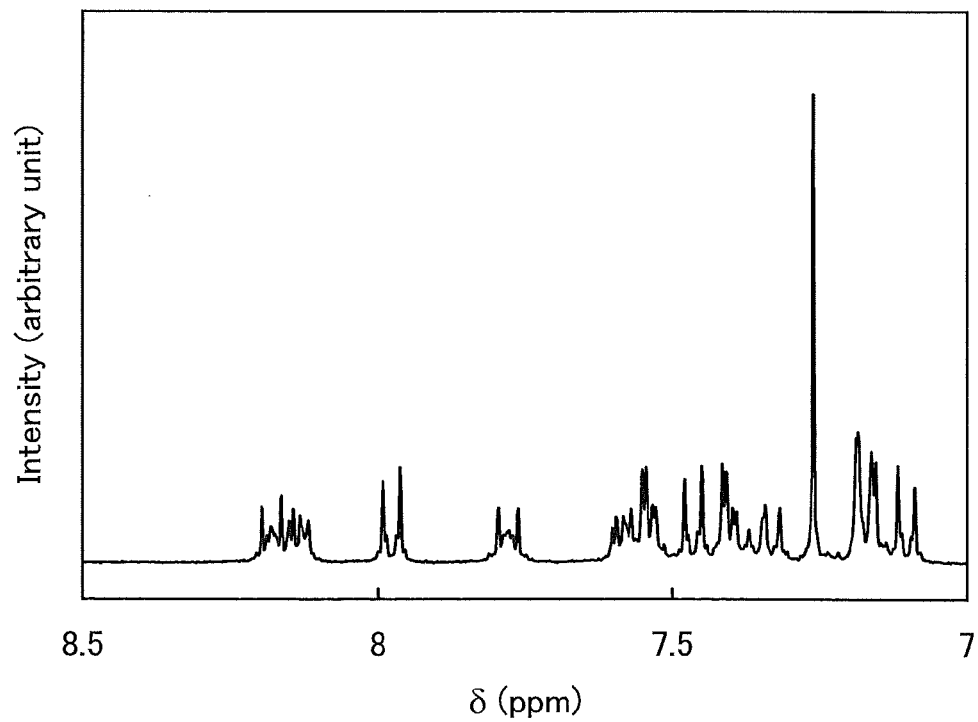

The $^1$H NMR data is shown below. $^1$H NMR (CDCl$_3$, 300 MHz): δ=7.10 (d, J=8.7 Hz, 2H), 7.15-7.19 (m, 5H), 7.33 (d, J=7.2 Hz, 2H), 7.37-7.42 (m, 3H), 7.47 (d, J=8.4 Hz, 2H), 7.53-7.60 (m, 5H), 7.76-7.80 (m, 2H), 7.98 (d, J=8.7 Hz, 2H), 8.12-8.20 (m, 4H). $^1$H NMR charts are shown in FIGS. 13A and 13B. Note that FIG. 13B is a chart in which the range of 7.0 ppm to 8.5 ppm in FIG. 13A is enlarged.

Figure 14A:
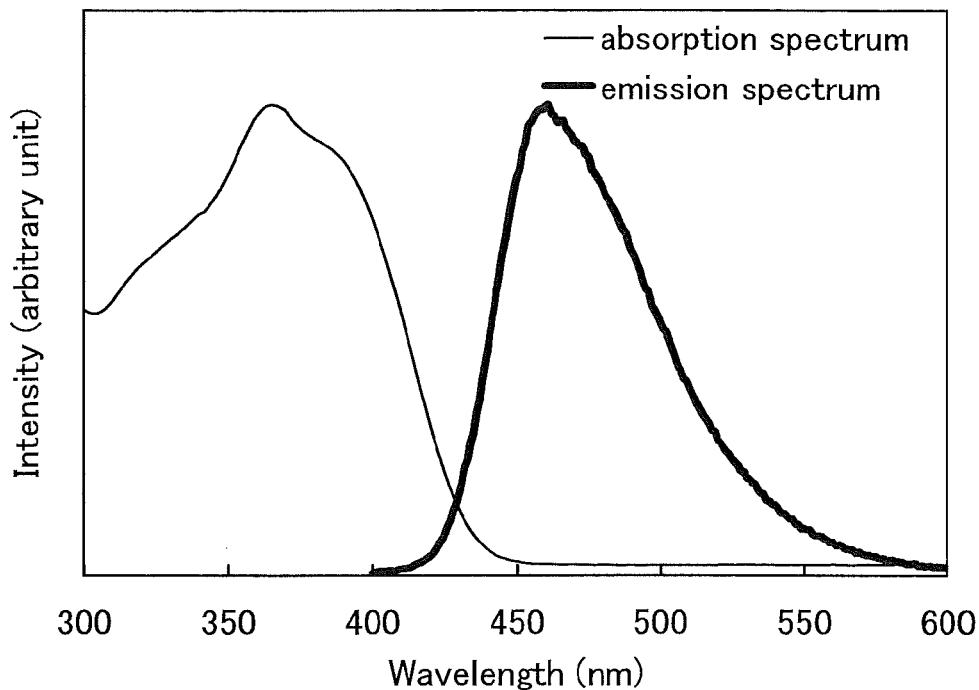
FIGS. 14A and 14B are graphs each showing the absorption spectrum and emission spectrum of 4-(5-phenyl-1,3,4-oxadiazol-2-yl)-4'-(3-phenylquinoxalin-2-yl)triphenylamine (abbreviation: OPA1PQ)

FIG. 14A shows the absorption spectrum and emission spectrum of a toluene solution of OPA1PQ. An ultraviolet-visible spectrophotometer (V-550, manufactured by JASCO Corporation) was used for the measurement. The solution was put into a quartz cell, and the absorption spectrum from which the absorption spectrum of the quartz cell was subtracted is shown in FIG. 14A. In FIG. 14A, the horizontal axis indicates the wavelength (nm) and the longitudinal axis indicates the intensity (arbitrary unit). In the case of the toluene solution, the absorption was observed at around 366 nm. The maximum emission wavelength of the toluene solution was 462 nm (an excitation wavelength of 370 nm).

Figure 14B:
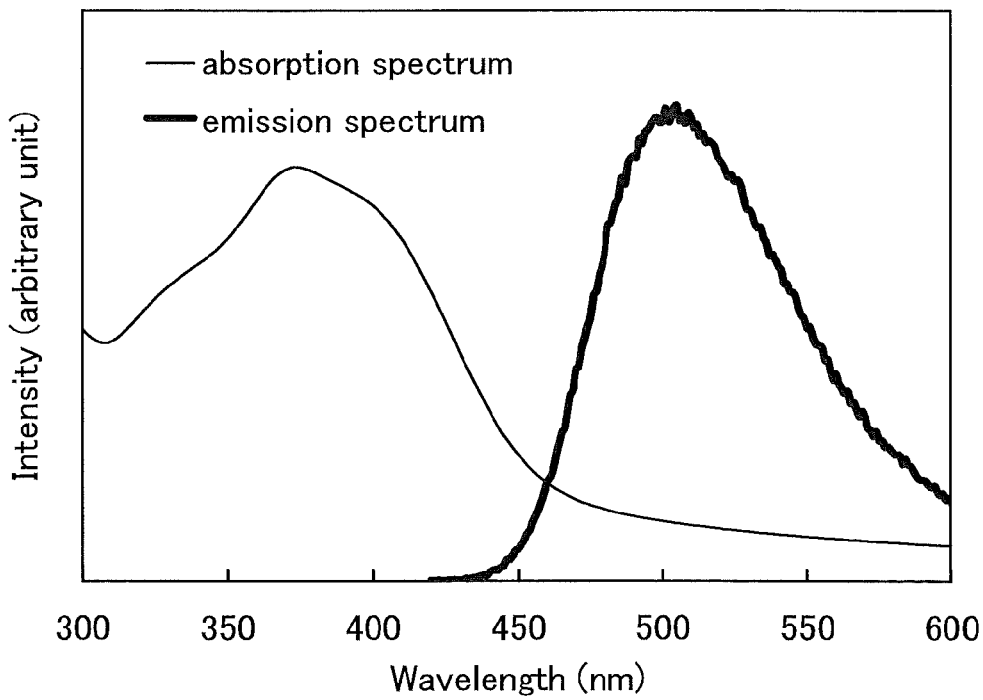

FIG. 14B shows the absorption spectrum and emission spectrum of a thin film of OPA1PQ. An ultraviolet-visible spectrophotometer (V-550, manufactured by JASCO Corporation) was used for the measurement. Samples were formed by evaporation on a quartz substrate, and the absorption spectrum from which the absorption spectrum of the quartz substrate was subtracted is shown in FIG. 14B. In FIG. 14B, the horizontal axis indicates the wavelength (nm) and the longitudinal axis indicates the intensity (arbitrary unit). In the case of the thin film, the absorption was observed at around 374 nm. The maximum emission wavelength of the thin film was 505 nm (an excitation wavelength of 400 nm).

The ionization potential of OPA1PQ in the thin film state, measured using a photoelectron spectrometer (AC-2, manufactured by Riken Keiki Co., Ltd.) in the air, was 5.38 eV. As a result, the HOMO level was found to be −5.38 eV. An absorption edge was obtained from a Tauc plot assuming direct transition with the use of the data of the absorption spectrum of OPA1PQ in the thin film state, and the absorption edge was regarded as an optical energy gap. Then, the energy gap was estimated to be 2.80 eV. A LUMO level of −2.58 eV was obtained from the obtained value of the energy gap and the HOMO level.

Embodiment 2

In this embodiment, a synthetic method of 4-(benzoxazol-2-yl)-4'-(3-phenylquinoxalin-2-yl)triphenylamine (abbreviation: BOxA1PQ) represented by the structural formula (201) is described.

(201)

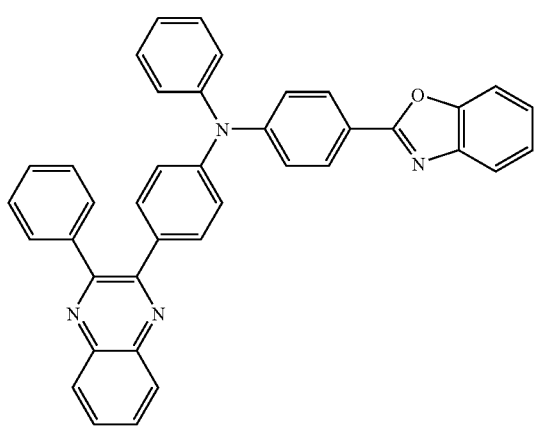

Step 1: Synthesis of 4-bromo-N-(2-hydroxyphenyl)benzamide

A synthetic scheme of 4-bromo-N-(2-hydroxyphenyl)benzamide is shown in (E-3).

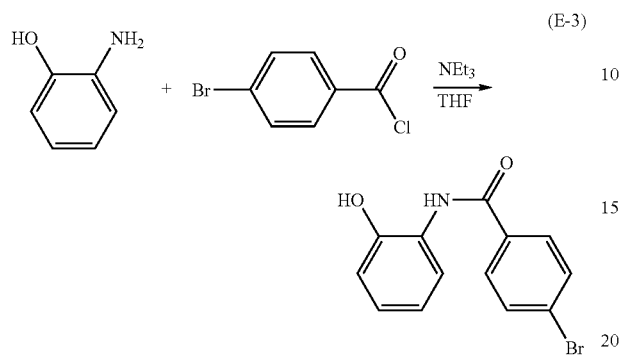

4.5 g (20 mmol) of 2-aminophenol, 3.0 mL (22 mmol) of triethylamine, and 50 mL of tetrahydrofuran (THF) were put in a 200 mL three-neck flask, and cooled to 0° C. After the cooling, 50 mL of THF solution containing 4.5 g (20 mmol) of 4-bromobenzoyl chloride was dropped under a nitrogen atmosphere. This solution was stirred at 0° C. for four hours under a nitrogen atmosphere. Then, water was added to the solution, and an organic layer and an aqueous layer were separated. An organic substance was extracted with ethyl acetate from the aqueous layer. The resulting extracted solution was combined with the organic layer, and the organic layer was washed with 0.2 M hydrochloric acid and a saturated aqueous solution of sodium bicarbonate, and then dried with magnesium sulfate. This mixture was subjected to suction filtration through Celite (manufactured by Wako Pure Chemical Industries, Ltd., Catalog No. 531-16855), and the filtrate was concentrated to give a solid. The obtained solid was recrystallized with ethyl acetate/hexane, whereby 5.3 g of the target white powder was obtained in a yield of 88%.

Step 2: Synthesis of 2-(4-bromophenyl)benzoxazole

A synthetic scheme of 2-(4-bromophenyl)benzoxazole is shown in (E-4).

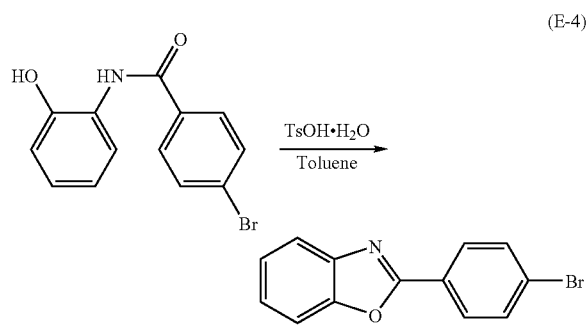

5.3 g (18 mmol) of 4-bromo-N-(2-hydroxyphenyl)benzamide, 8.0 g (46 mmol) of para-toluenesulfonic acid monohydrate, and 200 mL of toluene were put in a 300 mL three-neck flask. This mixture was refluxed for four hours under a nitrogen atmosphere. Then, water was added to the mixture, and an organic layer and an aqueous layer were separated. An organic substance was extracted with ethyl acetate from the aqueous layer. The resulting extracted solution was combined with the organic layer, and the organic layer was washed with a saturated aqueous solution of sodium bicarbonate and then brine, and dried with magnesium sulfate. The obtained mixture was subjected to suction filtration through Celite (manufactured by Wako Pure Chemical Industries, Ltd., Catalog No. 531-16855), and the filtrate was concentrated to give a solid. The obtained solid was recrystallized with ethyl acetate/hexane, whereby 3.1 g of the target white powder was obtained in a yield of 61%.

Step 3: Synthesis of 4-(benzoxazol2-yl)-4'-(3-phenylquinoxalin-2-yl)triphenylamine (abbreviation: BOxA1PQ)

A synthetic scheme of BOxA1PQ is shown in (E-5).

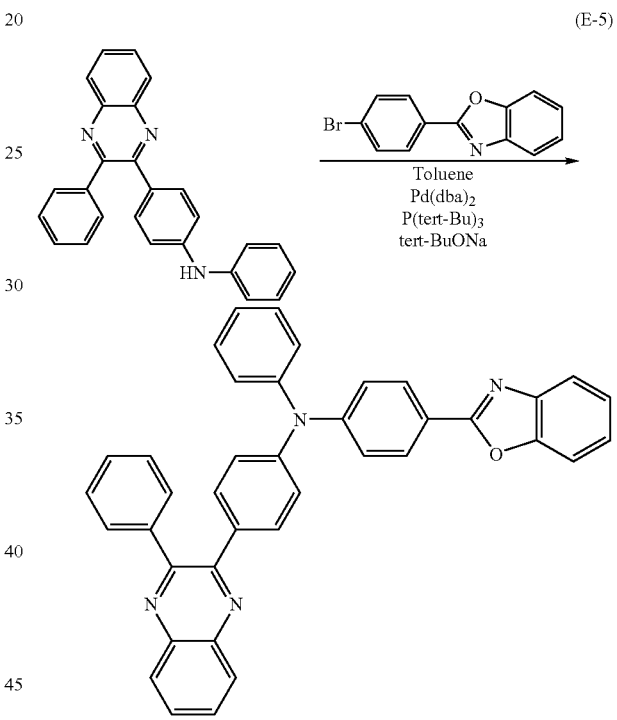

2.0 g (5.4 mmol) of 4-(3-phenylquinoxalin-2-yl)diphenylamine, 1.5 g (5.4 mmol) of 2-(4-bromophenyl)benzoxazole, 1.8 g (19 mmol) of sodium tert-butoxide, and 0.10 g (0.17 mmol) of bis(dibenzylideneacetone)palladium(0) were put in a 100 mL three-neck flask, and the air in the flask was replaced with nitrogen. This mixture was added with 30 mL of toluene and 0.1 mL of tri(tert-butyl)phosphine (10 wt % hexane solution). This mixture was heated and stirred at 80° C. for five hours, and after the stirring, chloroform was added to the mixture. This suspension was subjected to suction filtration through Celite (manufactured by Wako Pure Chemical Industries, Ltd., Catalog No. 531-16855), whereby the filtrate was obtained. The obtained filtrate was washed with a saturated aqueous solution of sodium bicarbonate and brine in this order. The resulting organic layer was dried by adding magnesium sulfate. This mixture was subjected to suction filtration to remove magnesium sulfate, whereby the filtrate was obtained. The obtained filtrate was concentrated, and the resulting solid was dissolved in toluene and purified by silica gel column chromatography using, as a developing solvent, toluene first and then a mixed solvent of toluene:ethyl acetate=9:1. The obtained fraction was concentrated and the resulting solid was recrystallized with a mixed solvent of chloroform and methanol, whereby 2.6 g of yellow powdery solid was obtained in a yield of 85%.

1.0 g of the obtained white solid was purified by sublimation by a train sublimation method. The sublimation purification was performed at 240° C. for 20 hours under a reduced pressure of 7.0 Pa with an argon flow rate of 3 mL/min, whereby 0.74 g of the white solid was obtained in a yield of 74%. This compound was confirmed to be 4-(benzoxazol-2-yl)-4'-(3-phenylquinoxalin-2-yl)triphenylamine (abbreviation: BOxA1PQ) by the nuclear magnetic resonance (NMR) measurement.

Figure 15A:
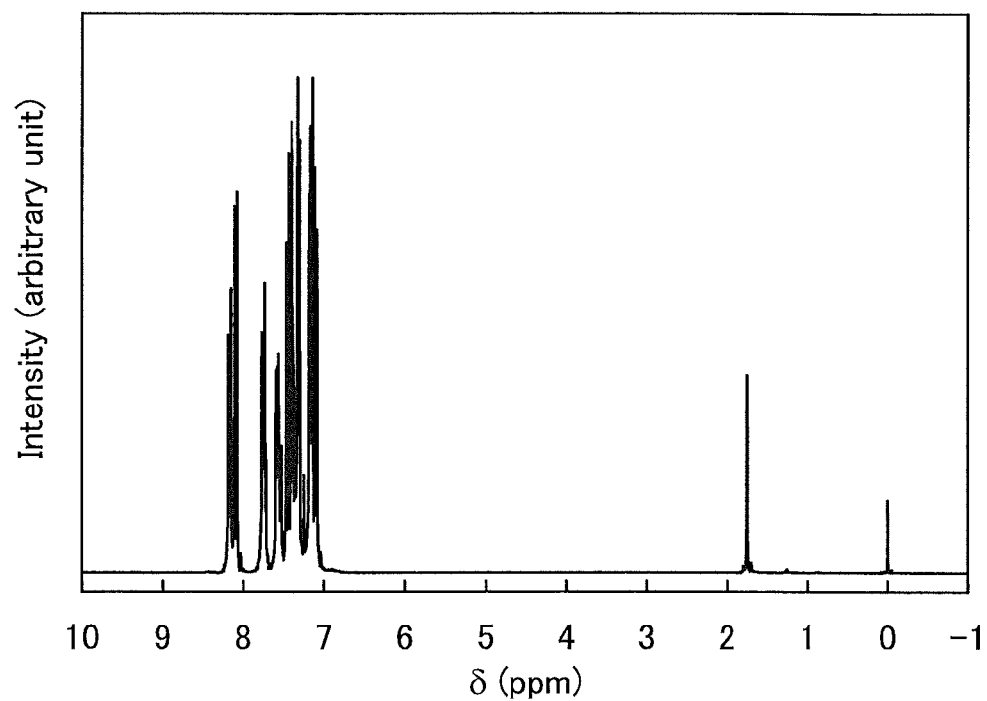
FIGS. 15A and 15B are $^1$H NMR charts of 4-(benzoxazol-2-yl)-4'-(3-phenylquinoxalin-2-yl)triphenylamine (abbreviation: BOxA1PQ)
Figure 15B:
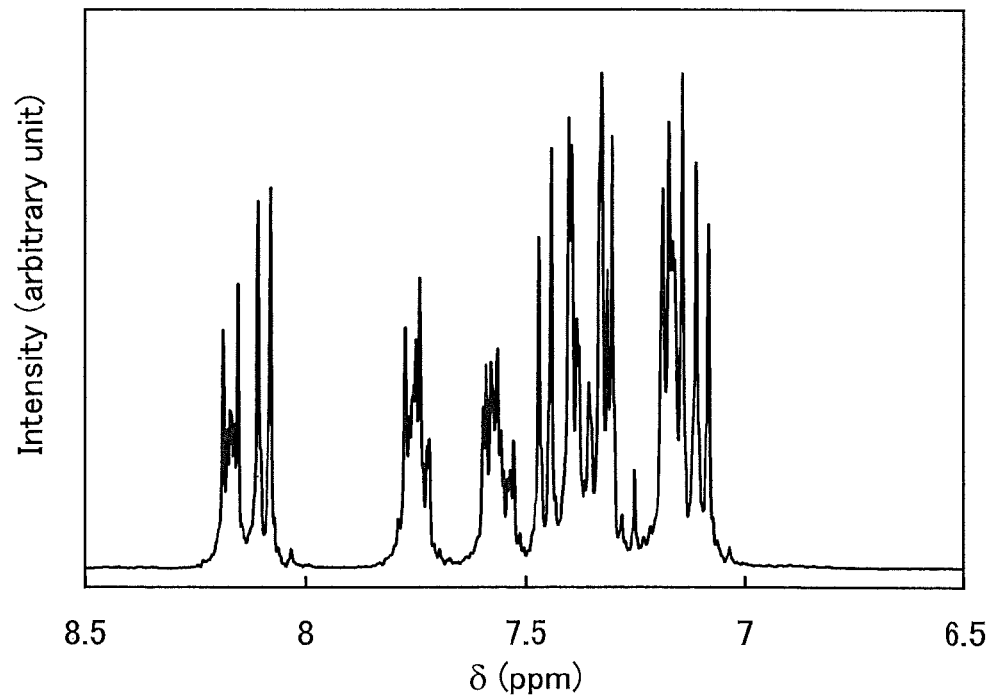

The $^1$H NMR data is shown below. $^1$H NMR (CDCl$_3$, 300 MHz): δ=7.06-7.23 (m, 7H), 7.26-7.43 (m, 7H), 7.46 (d, J=8.8 Hz, 2H), 7.52-7.63 (m, 3H), 7.71-7.81 (m, 3H), 8.09 (d, J=8.8 Hz, 2H), 8.14-8.22 (m, 2H). $^1$H NMR charts are shown in FIGS. 15A and 15B. Note that FIG. 15B is a chart in which the range of 6.5 ppm to 8.5 ppm in FIG. 15A is enlarged.

Figure 16A:
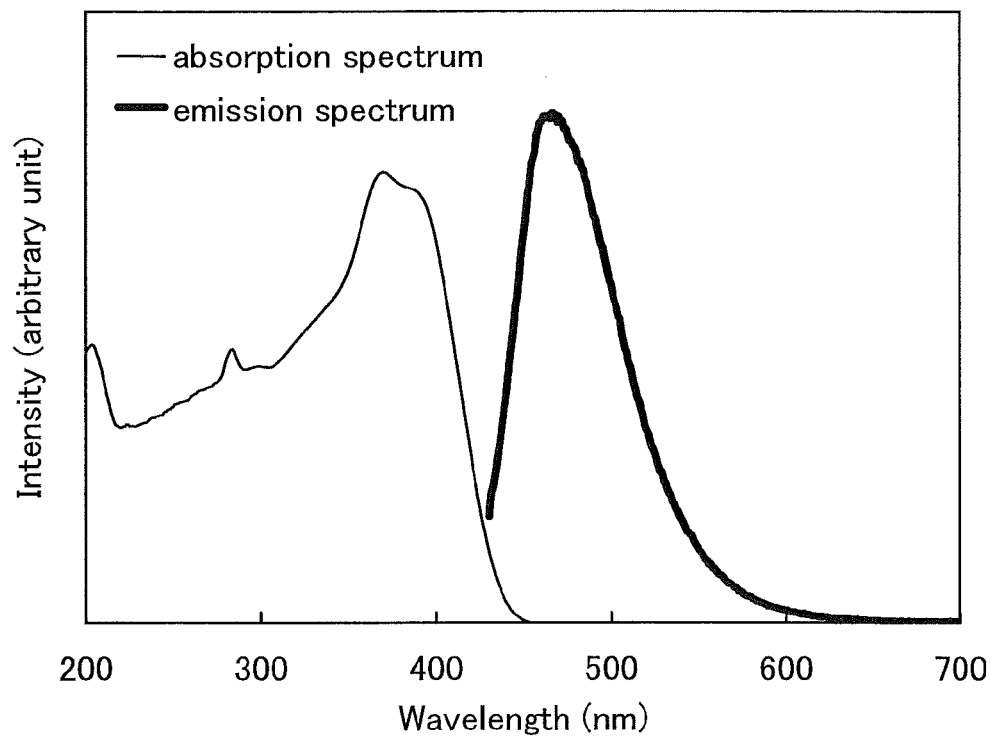
FIGS. 16A and 16B are graphs each showing the absorption spectrum and emission spectrum of 4-(benzoxazol-2-yl)-4'-(3-phenylquinoxalin-2-yl)triphenylamine (abbreviation: BOxA1PQ)

FIG. 16A shows the absorption spectrum and emission spectrum of a toluene solution of BOxA1PQ. An ultraviolet-visible spectrophotometer (V-550, manufactured by JASCO Corporation) was used for the measurement. The solution was put into a quartz cell, and the absorption spectrum from which the absorption spectrum of the quartz cell was subtracted is shown in FIG. 16A. In FIG. 16A, the horizontal axis indicates the wavelength (nm) and the longitudinal axis indicates the intensity (arbitrary unit). In the case of the toluene solution, the absorption was observed at around 386 nm. The maximum emission wavelength of the toluene solution was 468 nm (an excitation wavelength of 386 nm).

Figure 16B:
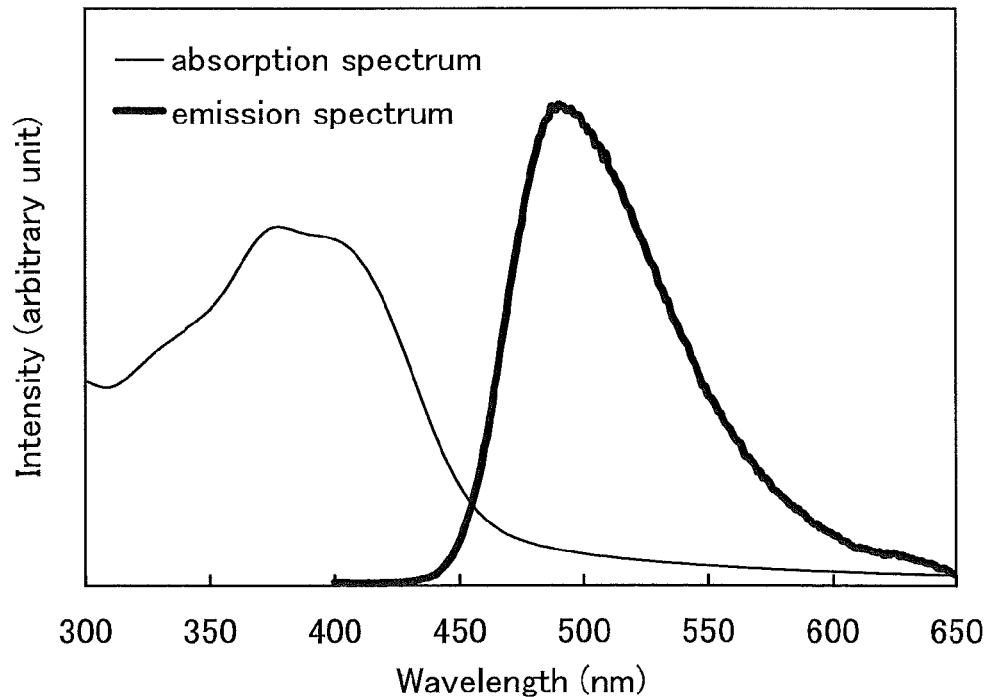

FIG. 16B shows the absorption spectrum and emission spectrum of a thin film of BOxA1PQ. An ultraviolet-visible spectrophotometer (V-550, manufactured by JASCO Corporation) was used for the measurement. Samples were formed by evaporation on a quartz substrate, and the absorption spectrum from which the absorption spectrum of the quartz substrate was subtracted is shown in FIG. 16B. In FIG. 16B, the horizontal axis indicates the wavelength (nm) and the longitudinal axis indicates the intensity (arbitrary unit). In the case of the thin film, the absorption was observed at around 377 nm. The maximum emission wavelength of the thin film was 492 nm (an excitation wavelength of 377 nm).

In addition, the ionization potential of BOxA1PQ in the thin film state, measured by a photoelectron spectrometer (AC-2, manufactured by Riken Keiki Co., Ltd.) in the air, was 5.68 eV. As a result, the HOMO level was found to be −5.68 eV. An absorption edge was obtained from a Tauc plot assuming direct transition with the use of the data of the absorption spectrum of BOxA1PQ in the thin film state, and the absorption edge was regarded as an optical energy gap. Then, the energy gap was determined to be 2.79 eV. A LUMO level of −2.89 eV was obtained from the obtained value of the energy gap and the HOMO level.

Embodiment 3

In this embodiment, a synthetic method of 4-(imidazo[1,2-a]pyridin-2-yl)-4'-(3-phenylquinoxalin-2-yl)triphenylamine (abbreviation: PIMA1PQ) represented by the structural formula (301) is described.

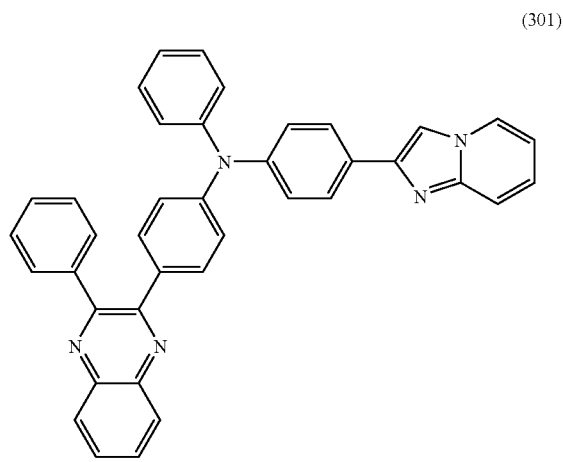

(301)

Step 1: Synthesis of 2-(4-bromophenyl)imidazo[1,2-a]pyridine

A synthetic scheme of 2-(4-bromophenyl)imidazo[1,2-a]pyridine is shown in (E-6).

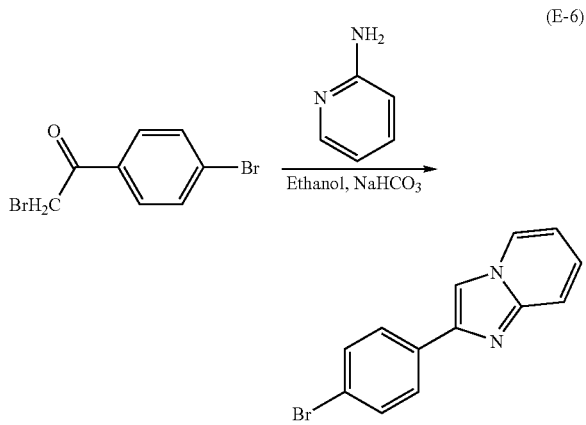

(E-6)

1.0 g (11 mmol) of 2-aminopyridine, 3.0 g (11 mmol) of 4-bromophenacyl bromide, and 1.9 g (14 mmol) of sodium hydrogen carbonate were put in a 50 mL three-neck flask, and the air in the flask was replaced with nitrogen. This mixture was added with 10 mL of ethanol, and then heated and stirred at 80° C. for six hours. After the stirring, the mixture was added with water and subjected to suction filtration to give a solid. The obtained solid was washed with water and methanol in this order, whereby 2.3 g of the target white solid was obtained in a yield of 76%.

Step 2: Synthesis of 4-(imidazo[1,2-a]pyridin-2-yl)-4'-(3-phenylquinoxalin-2-yl)triphenylamine (abbreviation: PIMA1PQ)

A synthetic scheme of PIMA1PQ is shown in (E-7).

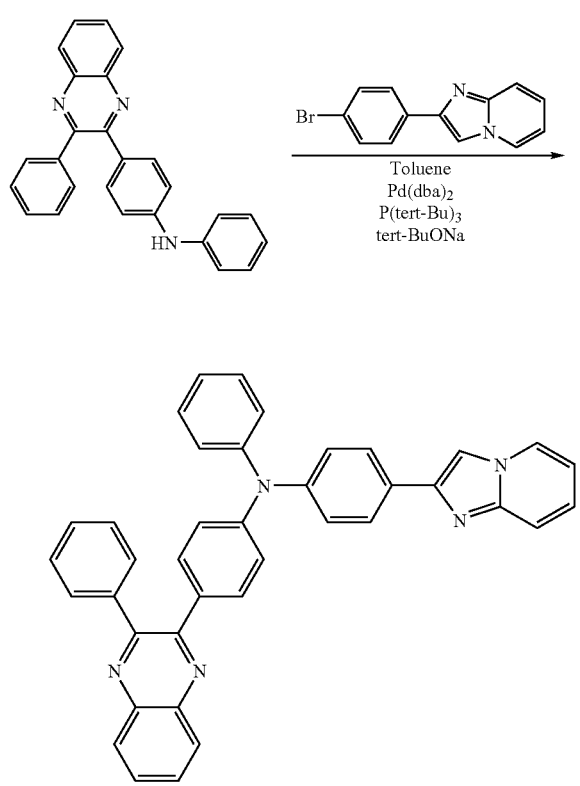

(E-7)

1.5 g (4.0 mmol) of 4-(3-phenylquinoxalin-2-yl)diphenylamine, 1.1 g (4.0 mmol) of 2-(4-bromophenyl)imidazo[1,2-a]pyridine, 1.0 g (10 mmol) of sodium tert-butoxide, and 0.10 g (0.17 mmol) of bis(dibenzylideneacetone)palladium(0) were put in a 100 mL three-neck flask, and the air in the flask was replaced with nitrogen. This mixture was added with 30 mL of toluene and 0.1 mL of tri(tert-butyl)phosphine (10 wt % hexane solution). This mixture was heated and stirred at 80° C. for five hours, and after the stirring, chloroform was added to the mixture. This suspension was subjected to suction filtration through Celite (manufactured by Wako Pure Chemical Industries, Ltd., Catalog No. 531-16855), whereby the filtrate was obtained. The obtained filtrate was washed with a saturated aqueous solution of sodium bicarbonate and brine in this order. The resulting organic layer was dried by adding magnesium sulfate. This mixture was subjected to suction filtration to remove magnesium sulfate, whereby the filtrate was obtained. The obtained filtrate was concentrated, and the resulting solid was dissolved in toluene and purified by silica gel column chromatography using, as a developing solvent, toluene first and then a mixed solvent of toluene:ethyl acetate=5:1. The obtained fraction was concentrated and the resulting solid was recrystallized with a mixed solvent of chloroform and methanol, whereby 1.3 g of yellow powdery solid was obtained in a yield of 59%.

1.3 g of the obtained white solid was purified by sublimation by a train sublimation method. The sublimation purification was performed at 280° C. for 20 hours under a reduced pressure of 7.0 Pa with an argon flow rate of 3 mL/min, whereby 1.2 g of the white solid was obtained in a yield of 92%. Furthermore, this compound was confirmed to be 4-(imidazo[1,2-a]pyridine-2-yl)-4'-(3-phenylquinoxaline-2-yl)triphenylamine (abbreviation: PIMA1PQ) by the nuclear magnetic resonance (NMR) measurement.

Figure 17A:
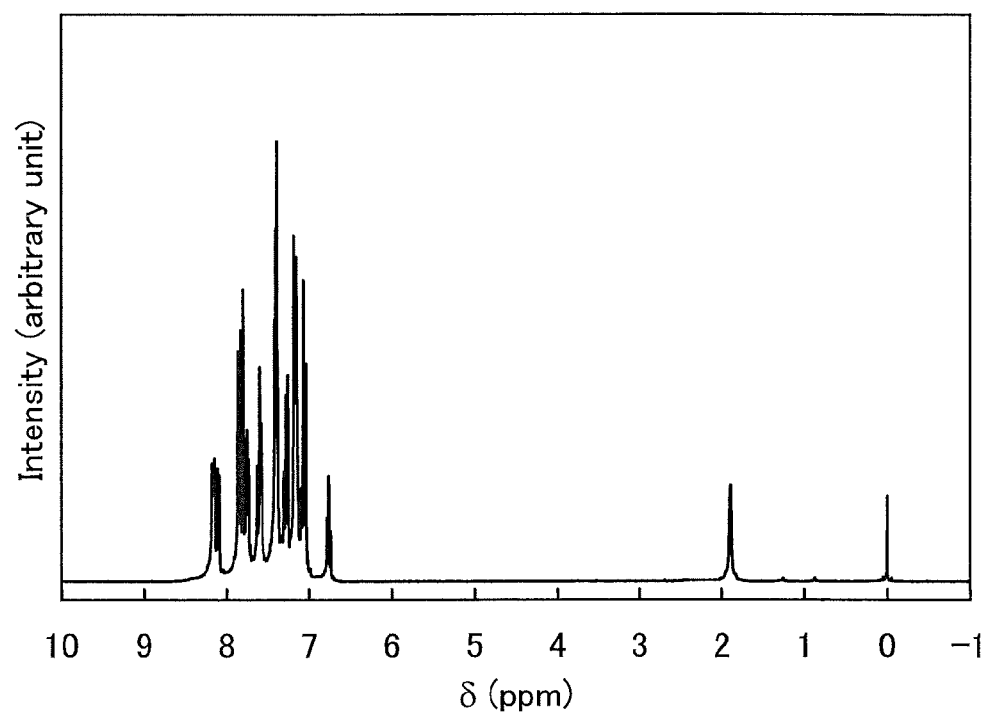
FIGS. 17A and 17B are $^1$H NMR charts of 4-(imidazo[1,2-a]pyridin-2-yl)-4'-(3-phenylquinoxalin-2-yl)triphenylamine (abbreviation: PIMA1PQ)
Figure 17B:
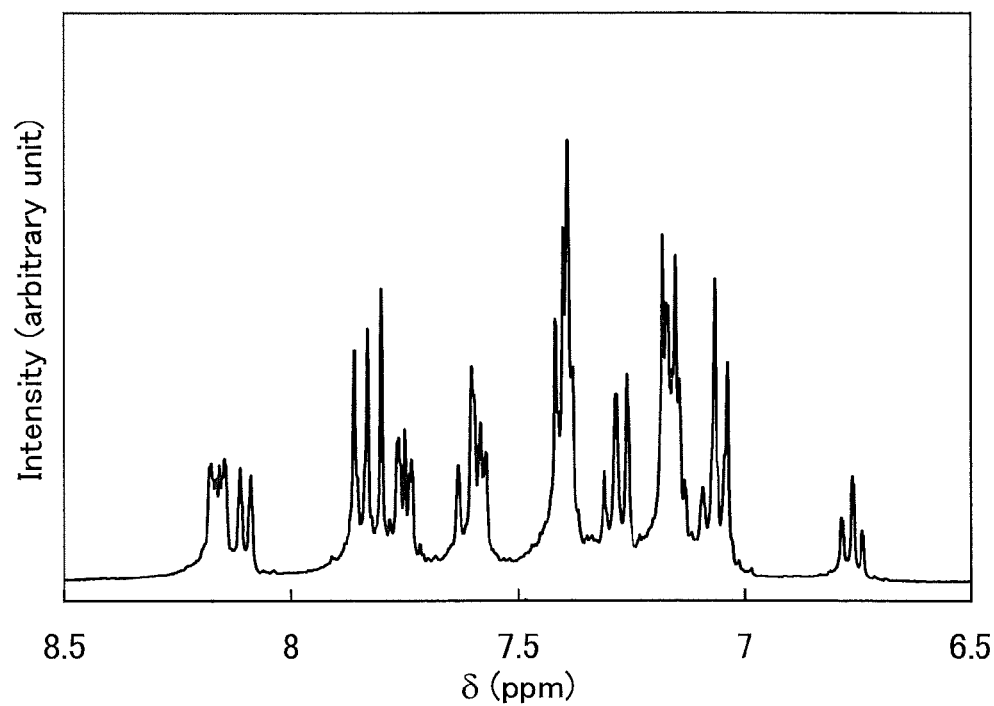

The $^1$H NMR data is shown below. $^1$H NMR (CDCl$_3$, 300 MHz): δ=7.76 (t, J=6.8 Hz, 1H), 7.01-7.51 (m, 15H), 7.53-7.67 (m, 3H), 7.70-7.90 (m, 5H), 8.06-8.22 (m, 3H). $^1$H NMR charts are shown in FIGS. 17A and 17B. Note that FIG. 17B is a chart in which the range of 6.5 ppm to 8.5 ppm in FIG. 17A is enlarged.

Figure 18A:
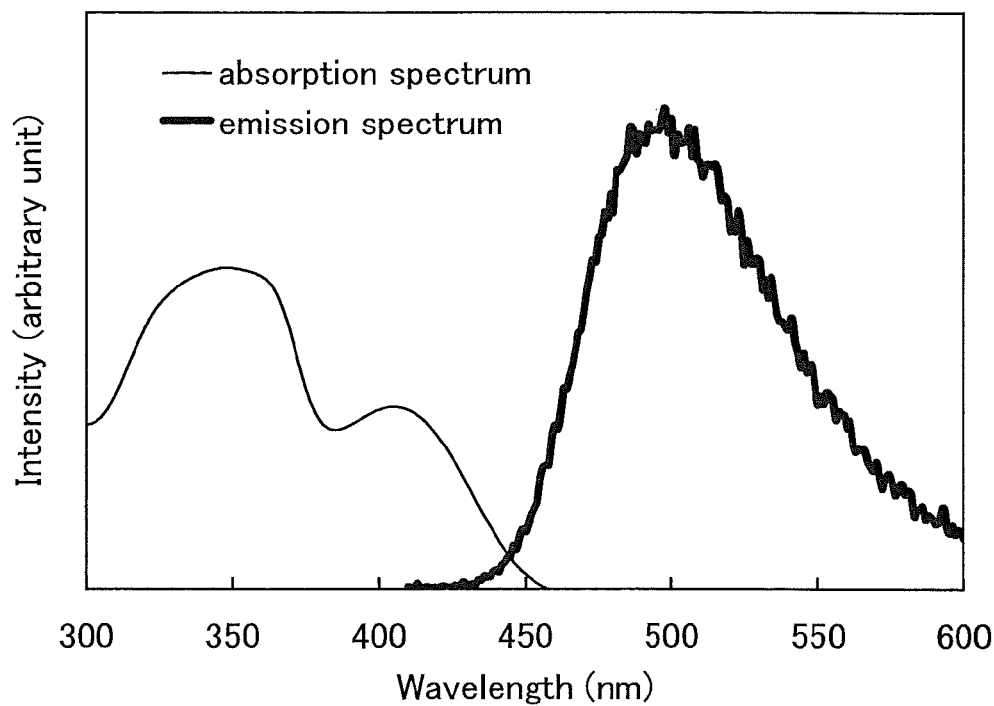
FIGS. 18A and 18B are graphs each showing the absorption spectrum and emission spectrum of 4-(imidazo[1,2-a]pyridin-2-yl)-4'-(3-phenylquinoxalin-2-yl)triphenylamine (abbreviation: PIMA1PQ)

FIG. 18A shows the absorption spectrum and emission spectrum of a toluene solution of PIMA1PQ. An ultraviolet-visible spectrophotometer (V-550, manufactured by JASCO Corporation) was used for the measurement. The solution was put into a quartz cell, and the absorption spectrum from which the absorption spectrum of the quartz cell was subtracted is shown in FIG. 18A. In FIG. 18A, the horizontal axis indicates the wavelength (nm) and the longitudinal axis indicates the intensity (arbitrary unit). In the case of the toluene solution, the absorption was observed at around 406 nm. The maximum emission wavelength of the toluene solution was 497 nm (an excitation wavelength of 406 nm).

Figure 18B:
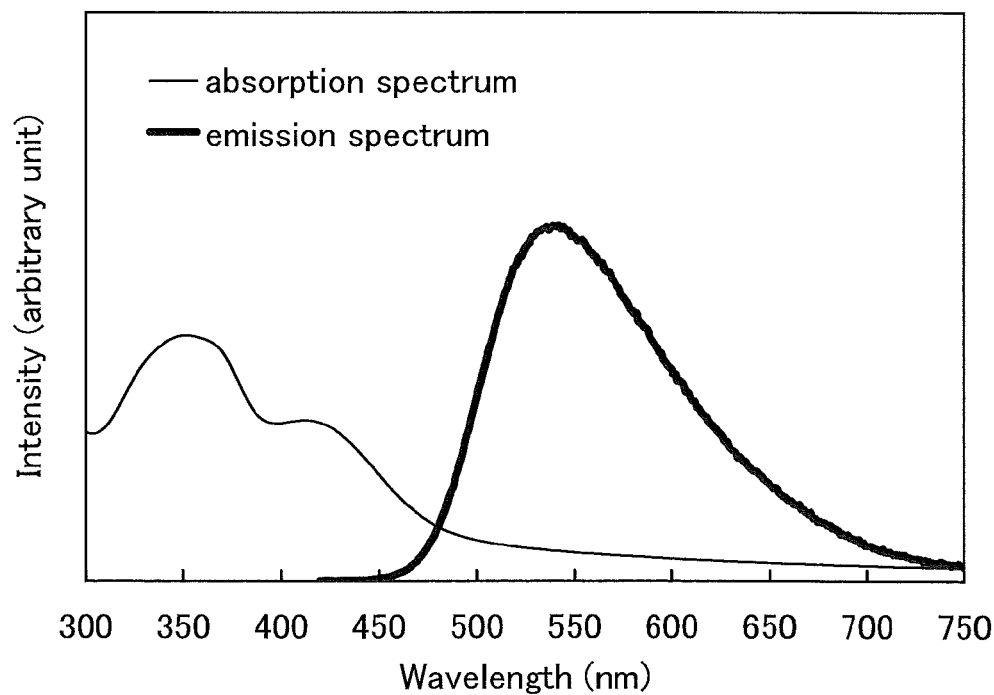

FIG. 18B shows the absorption spectrum and emission spectrum of a thin film of PIMA1PQ. An ultraviolet-visible spectrophotometer (V-550, manufactured by JASCO Corporation) was used for the measurement. Samples were formed by evaporation on a quartz substrate, and the absorption spectrum from which the absorption spectrum of the quartz substrate was subtracted is shown in FIG. 18B. In FIG. 18B, the horizontal axis indicates the wavelength (nm) and the longitudinal axis indicates the intensity (arbitrary unit). In the case of the thin film, the absorption was observed at around 412 nm. The maximum emission wavelength of the thin film was 542 nm (an excitation wavelength of 412 nm).

The ionization potential of PIMA1PQ in the thin film state, measured by a photoelectron spectrometer (AC-2, manufactured by Riken Keiki Co., Ltd.) in the air, was 5.54 eV. As a result, the HOMO level was found to be −5.54 eV. An absorption edge was obtained from a Tauc plot assuming direct transition with the use of the data of the absorption spectrum of PIMA1PQ in the thin film state, and the absorption edge was regarded as an optical energy gap. Then, the energy gap was estimated to be 2.64 eV. A LUMO level of −2.90 eV was obtained from the obtained value of the energy gap and the HOMO level.

Embodiment 4

In this embodiment, a synthetic method of 4,4'-(quinoxaline-2,3-diyl)bis{N-phenyl-N-[4-(5-pheyl-1,3,4-oxadiazol-2-yl)phenyl]aniline} (abbreviation: OPAPQ) represented by the structural formula (401) is described.

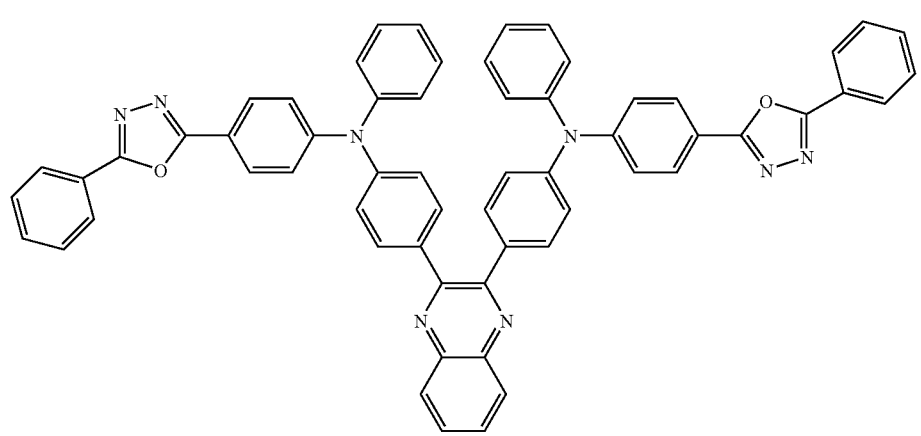

(401)

Step 1: Synthesis of 4-(5-phenyl-1,3,4-oxadiazol-2-yl)diphenylamine

A synthetic scheme of 4-(5-phenyl-1,3,4-oxadiazol-2-yl) diphenylamine is shown in (E-8).

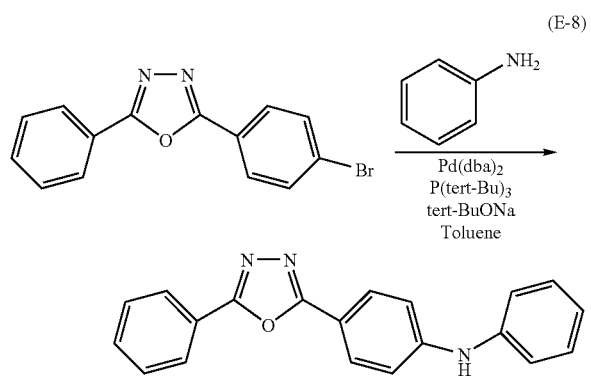

(E-8)

15 g (50 mmol) of 2-(4-bromophenyl)-5-phenyl-1,3,4-oxadiazole, 6.3 g (66 mmol) of sodium tert-butoxide, and 0.20 g (0.35 mmol) of bis(dibenzylideneacetone)palladium (0) were put in a 300 mL three-neck flask, and the air in the flask was replaced with nitrogen. This mixture was added with 100 mL of toluene, 8.0 mL (84 mmol) of aniline, and 0.2 mL of tri(tert-butyl)phosphine (10 wt % hexane solution). This mixture was heated and stirred at 80° C. for three hours, and after the stirring, the mixture was added with chloroform and heated. This suspension was subjected to suction filtration through Celite (manufactured by Wako Pure Chemical Industries, Ltd., Catalog No. 531-16855), whereby the filtrate was obtained. The obtained filtrate was washed with 1M hydrochloric acid, a saturated aqueous sodium of hydrogen bicarbonate, and brine in this order. The resulting organic layer was dried by adding magnesium sulfate. This mixture was subjected to suction filtration to remove magnesium sulfate, whereby the filtrate was obtained. The obtained filtrate was concentrated, and the resulting solid was washed with methanol, whereby 11 g of light yellow solid was obtained in a yield of 71%.

Step 2: Synthesis of 4,4'-(quinoxaline-2,3-diyl) bis{N-phenyl-N-[4-(5-pheyl-1,3,4-oxadiazol-2-yl) phenyl]aniline} (abbreviation: OPAPQ)

A synthetic scheme of OPAPQ is shown in (E-9).

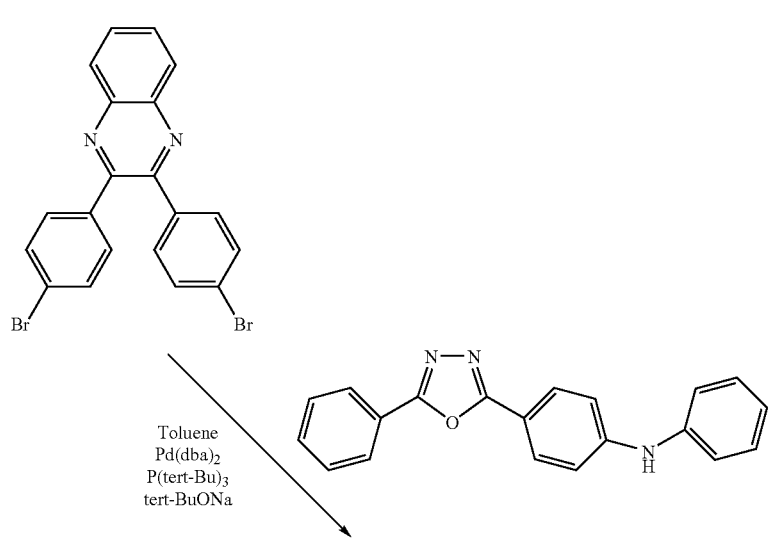

(E-9)

-continued

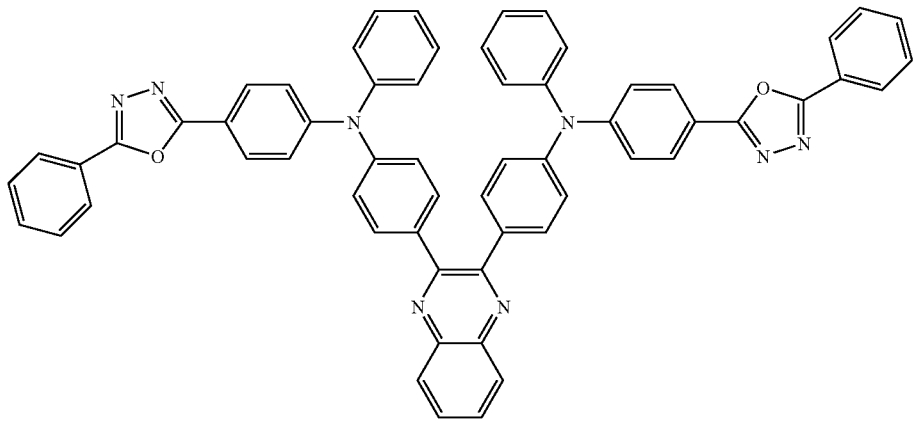

2.0 g (4.5 mmol) of 2,3-bis(4-bromophenyl)quinoxaline, 1.5 g (16 mmol) of sodium tert-butoxide, 0.10 g (0.17 mmol) of bis(dibenzylideneacetone)palladium(0), and 2.8 g (9.1 mmol) of 4-(5-phenyl-1,3,4-oxadiazol-2-yl)diphenylamine synthesized in Embodiment 1 were put in a 100 mL three-neck flask, and the air in the flask was replaced with nitrogen. This mixture was added with 50 mL of toluene and 0.2 mL of tri(tert-butyl)phosphine (10 wt % hexane solution). This mixture was heated and stirred at 80° C. for five hours, and after the stirring, water was added to the mixture, whereby a solid was precipitated. The precipitated solid was subjected to suction filtration to give a solid. The obtained solid was dissolved in chloroform and subjected to suction filtration through Celite (manufactured by Wako Pure Chemical Industries, Ltd., Catalog No. 531-16855), whereby the filtrate was obtained. The obtained filtrate was washed with a saturated aqueous solution of sodium bicarbonate and brine in this order. An organic layer was dried by adding magnesium sulfate. This mixture was subjected to suction filtration to remove magnesium sulfate, whereby the filtrate was obtained. The obtained filtrate was concentrated, and the resulting solid was dissolved in chloroform and purified by silica gel column chromatography using, as a developing solvent, chloroform first and then a mixed solvent of chloroform:ethyl acetate=9:1. The obtained fraction was concentrated and the resulting solid was recrystallized with a mixed solvent of chloroform and methanol, whereby 3.2 g of yellow powdery solid was obtained in a yield of 78%.

The obtained compound was confirmed to be 4,4'-(quinoxaline-2,3-diyl)bis{N-phenyl-N-[4-(5-pheyl-1,3,4-oxadiazol-2-yl)phenyl]aniline} (abbreviation: OPAPQ) by the nuclear magnetic resonance (NMR) measurement.

Figure 19A:
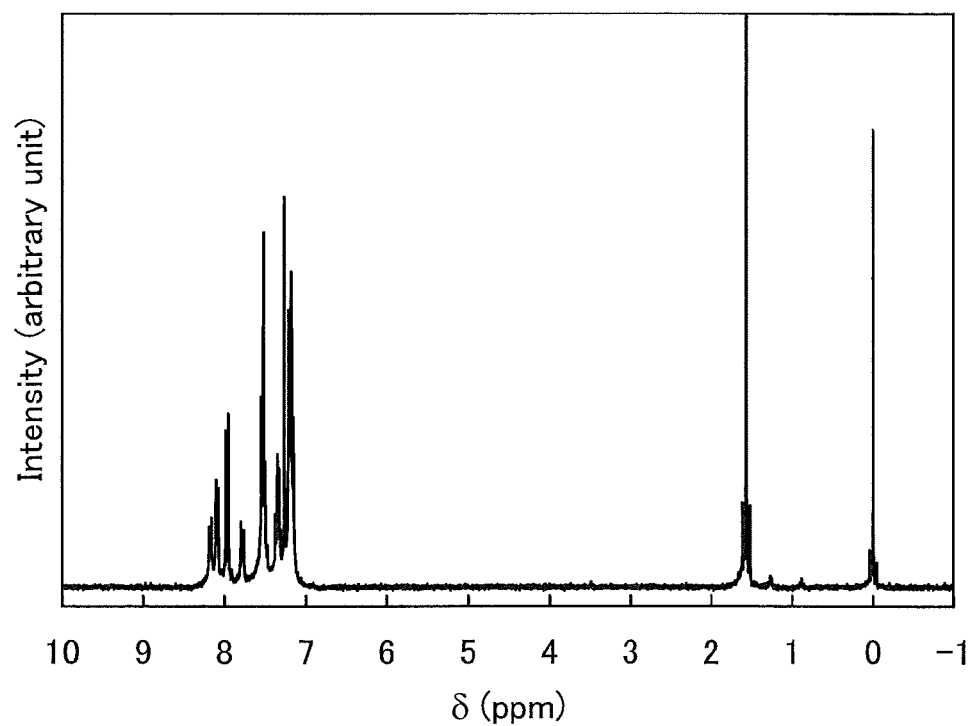
FIGS. 19A and 19B are $^1$H NMR charts of 4,4'-(quinoxaline-2,3-diyl)bis{N-phenyl-N-[4-(5-pheyl-1,3,4-oxadiazol-2-yl)phenyl]aniline} (abbreviation: OPAPQ)
Figure 19B:
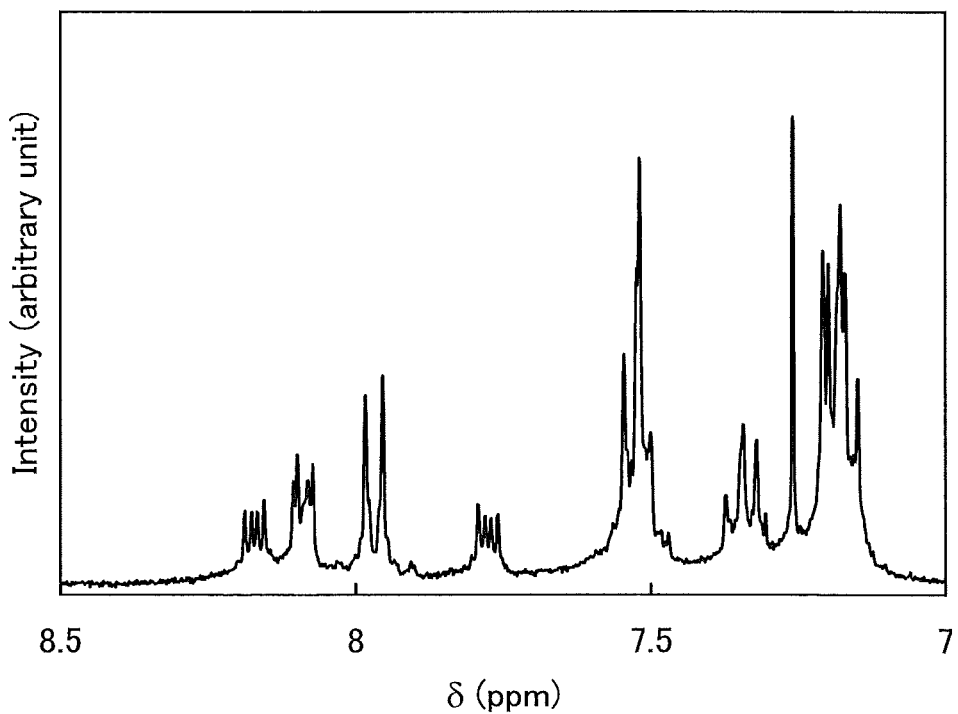

The $^1$H NMR data is shown below. $^1$H NMR (CDCl$_3$, 300 MHz): δ=7.14-7.22 (m, 14H), 7.30-7.38 (m, 5H), 7.49-7.55 (m, 9H), 7.74-7.81 (m, 2H), 7.97 (d, J=8.8 Hz, 4H), 8.06-8.12 (m, 4H), 8.14-8.20 (m, 2H). $^1$H NMR charts are shown in FIGS. 19A and 19B. Note that FIG. 19B is a chart in which the range of 7.0 ppm to 8.5 ppm in FIG. 19A is enlarged.

Figure 20A:
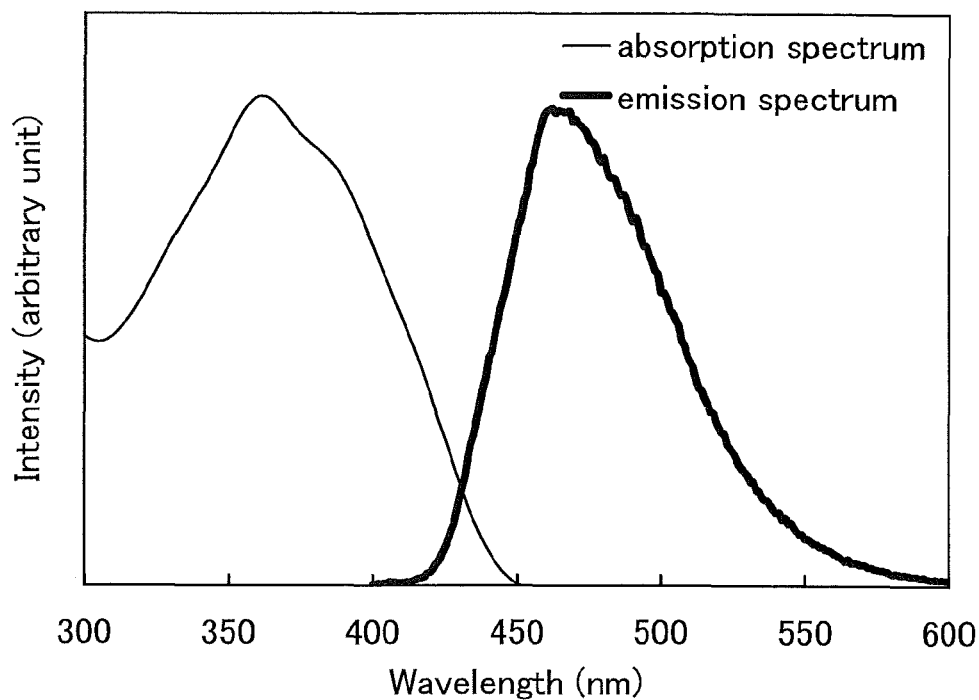
FIGS. 20A and 20B are graphs each showing the absorption spectrum and emission spectrum of 4,4'-(quinoxaline-2,3-diyl)bis{N-phenyl-N-[4-(5-pheyl-1,3,4-oxadiazol-2-yl)phenyl]aniline} (abbreviation: OPAPQ)

FIG. 20A shows the absorption spectrum and emission spectrum of a toluene solution of OPAPQ. An ultraviolet-visible spectrophotometer (V-550, manufactured by JASCO Corporation) was used for the measurement. The solution was put into a quartz cell, and the absorption spectrum from which the absorption spectrum of the quartz cell was subtracted is shown in FIG. 20A. In FIG. 20A, the horizontal axis indicates the wavelength (nm) and the longitudinal axis indicates the intensity (arbitrary unit). In the case of the toluene solution, the absorption was observed at around 362 nm. The maximum emission wavelength of the toluene solution was 466 nm (an excitation wavelength of 362 nm).

Figure 20B:
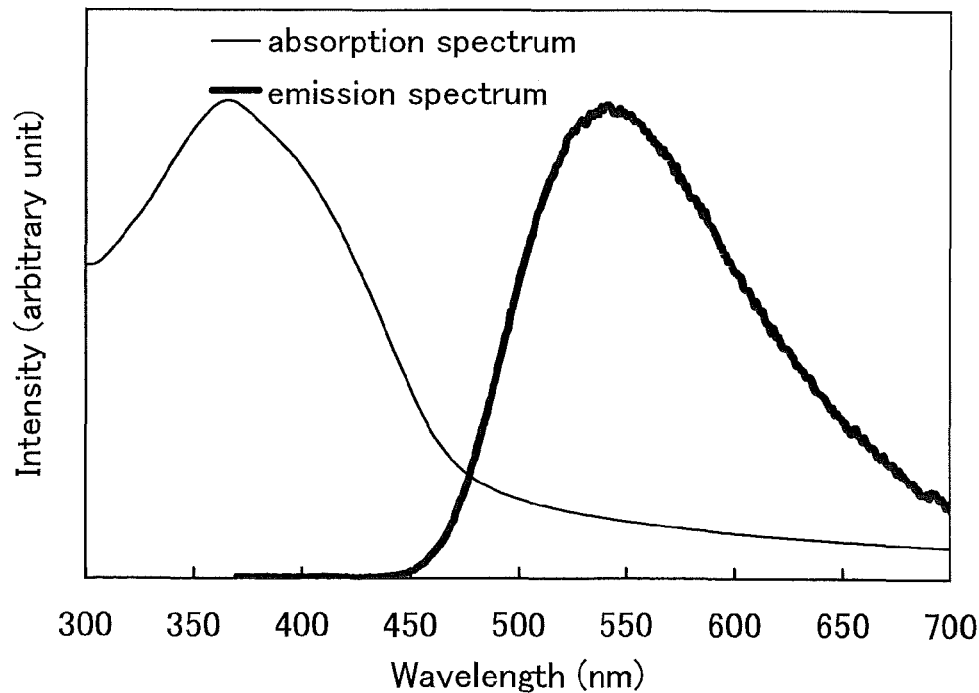

FIG. 20B shows the absorption spectrum and emission spectrum of a thin film of OPAPQ. An ultraviolet-visible spectrophotometer (V-550, manufactured by JASCO Corporation) was used for the measurement. Samples were formed by evaporation on a quartz substrate, and the absorption spectrum from which the absorption spectrum of the quartz substrate was subtracted is shown in FIG. 20B. In FIG. 20B, the horizontal axis indicates the wavelength (nm) and the longitudinal axis indicates the intensity (arbitrary unit). In the case of the thin film, the absorption was observed at around 366 nm. The maximum emission wavelength of the thin film was 541 nm (an excitation wavelength of 366 nm).

The ionization potential of OPAPQ in the thin film state, measured by a photoelectron spectrometer (AC-2, manufactured by Riken Keiki Co., Ltd.) in the air, was 5.40 eV. As a result, the HOMO level was found to be −5.40 eV. An absorption edge was obtained from a Tauc plot assuming direct transition with the use of the data of the absorption spectrum of OPAPQ in the thin film state, and the absorption edge was regarded as an optical energy gap. Then, the energy gap was estimated to be 2.72 eV. A LUMO level of −2.68 eV was obtained from the obtained value of the energy gap and the HOMO level.

Embodiment 5

Figure 21:
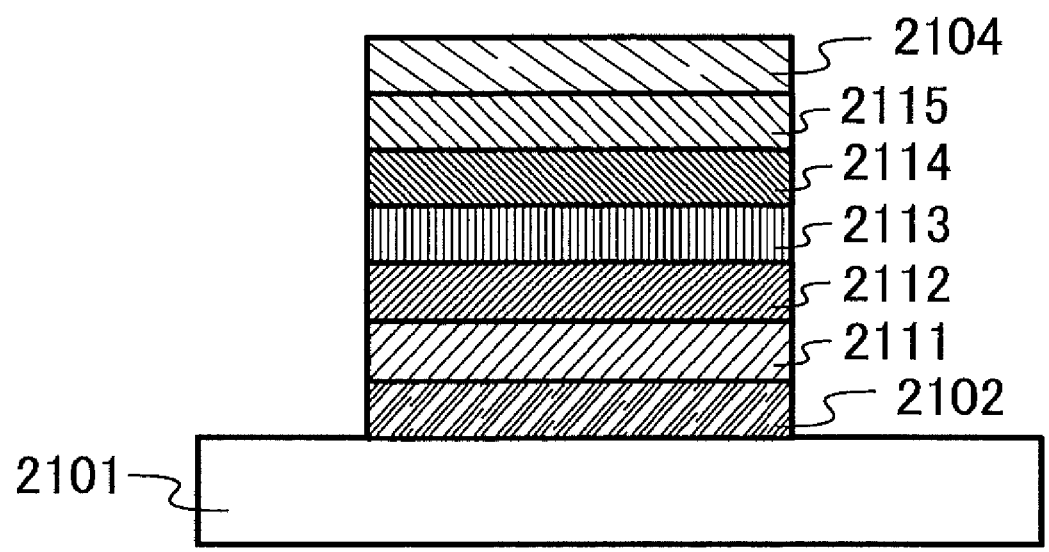
FIG. 21 is a diagram illustrating a light emitting element of an embodiment.

In this embodiment, a light emitting element of the present invention is described with reference to FIG. 21. The structural formula of a material used in this embodiment is shown below. Note that the material, the structural formula of which is shown above, is omitted here.

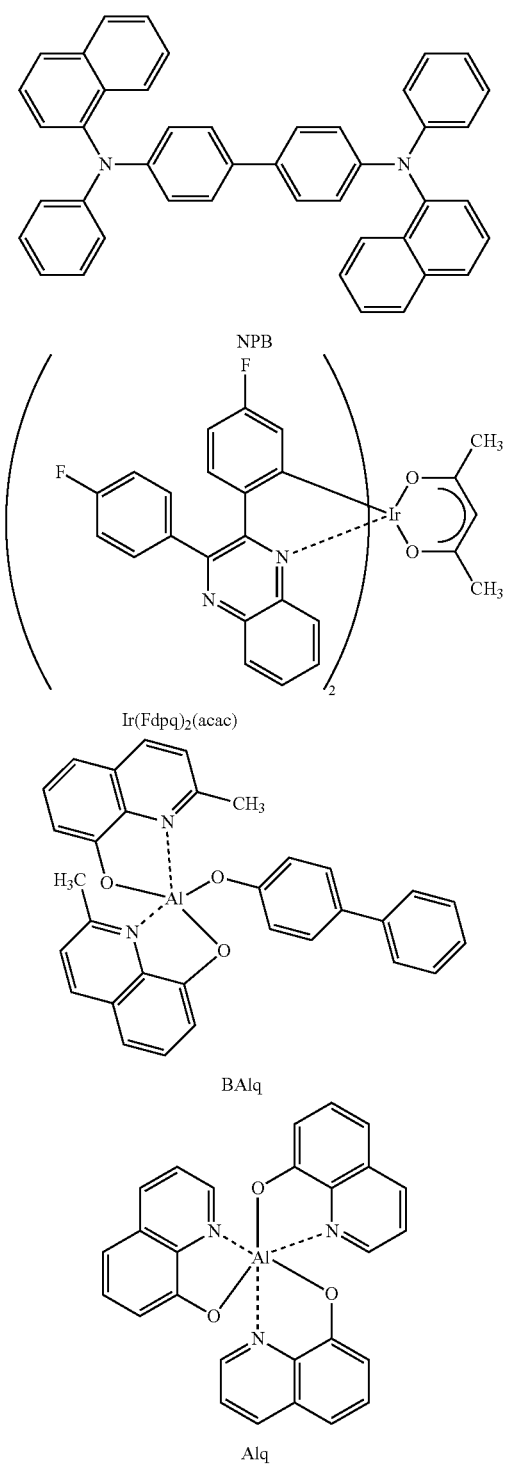

A method for manufacturing the light emitting element of this embodiment is described below.

(Light Emitting Element 1)

First, indium tin oxide containing silicon oxide (ITSO) was deposited on a glass substrate 2101 by sputtering, whereby a first electrode 2102 was formed. Note that the thickness of the first electrode 2102 was set to 110 nm, and the area thereof was set to 2 mm×2 mm.

Next, the substrate provided with the first electrode 2102 was fixed to a substrate holder provided in a vacuum evaporation apparatus so that a surface on which the first electrode 2102 was formed was placed downward. After the pressure of a chamber was reduced to about $10^{-4}$ Pa, 4,4'-bis[N-(1-napthyl)-N-phenylamino]biphenyl (abbreviation: NPB) and molybdenum (VI) oxide were co-evaporated on the first electrode 2102, whereby a layer 2111 containing a composite material of an organic compound and an inorganic compound was formed. The thickness of the layer 2111 was set to 50 nm, and the weight ratio between NPB and molybdenum (VI) oxide was adjusted to 4:1 (=NPB:molybdenum oxide). Note that the co-evaporation is an evaporation method in which evaporation is simultaneously performed from a plurality of evaporation sources in one chamber.

Next, by an evaporation method using resistance heating, 4,4'-bis[N-(1-napthyl)-N-phenylamino]biphenyl (abbreviation: NPB) was deposited on the layer 2111 containing the composite material so as to have a thickness of 10 nm, whereby a hole transporting layer 2112 was formed.

Furthermore, 4-(5-phenyl-1,3,4-oxadiazol-2-yl)-4'-(3-phenylquinoxalin-2-yl)triphenylamine (abbreviation: OPA1PQ) represented by the structural formula (101) and (acetylacetonato)bis[2,3-bis(4-fluorophenyl)quinoxalinato]iridium(III) (abbreviation: Ir(Fdpq)$_2$(acac)) were co-evaporated on the hole transporting layer 2112, whereby a light emitting layer 2113 with a thickness of 30 nm was formed. Here, the weight ratio between OPA1PQ and Ir(Fdpq)$_2$(acac) was adjusted to 1:0.06 (=OPA1PQ:Ir(Fdpq)$_2$(acac)).

Subsequently, with the use of an evaporation method using resistance heating, bis(2-methyl-8-quinolinolato)(4-phenylphenolato)aluminum (abbreviation: BAlq) was deposited on the light emitting layer 2113 so as to have a thickness of 10 nm, whereby an electron transporting layer 2114 was formed. Note that BAlq has a large band gap and a high HOMO level; thus, the electron transporting layer 2114 also functions as a hole blocking layer.

Furthermore, tris(8-quinolinolato)aluminum (abbreviation: Alq) and lithium were co-evaporated on the electron transporting layer 2114, whereby an electron injecting layer 2115 was formed to a thickness of 50 nm. Here, the weight ratio between Alq and lithium was adjusted to 1:0.01 (=Alq:lithium).

Finally, by an evaporation method using resistance heating, aluminum was deposited on the electron injecting layer 2115 so as to have a thickness of 200 nm, whereby a second electrode 2104 was formed. Thus, the light emitting element 1 was completed.

(Light Emitting Element 2)

With the use of the same substrate as that used for the light emitting element 1, the light emitting element 2 was formed in a manner similar to the light emitting element 1. The light emitting element 2 was formed using 4-(imidazo[1,2-a]pyridin-2-yl)-4'-(3-phenylquinoxalin-2-yl)triphenylamine (abbreviation: PIMA1PQ) represented by the structural formula (301) instead of OPA1PQ. That is, PIMA1PQ and Ir(Fdpq)$_2$(acac) were co-evaporated on the hole transporting layer 2112, whereby the light emitting layer 2113 was formed to a thickness of 30 nm. Here, the weight ratio between PIMA1PQ and Ir(Fdpq)$_2$(acac) was adjusted to 1:0.06 (=PIMA1PQ:Ir(Fdpq)$_2$(acac)). The layers other than the light emitting layer 2113 were formed in a manner similar to those of the light emitting element 1.

The thus obtained light emitting element 1 and light emitting element 2 were sealed in a glove box under a nitrogen atmosphere without being exposed to atmospheric air. Then, the operating characteristics of these light emitting elements were measured. Note that the measurement was performed at room temperature (in an atmosphere kept at 25° C.).

Figure 22:
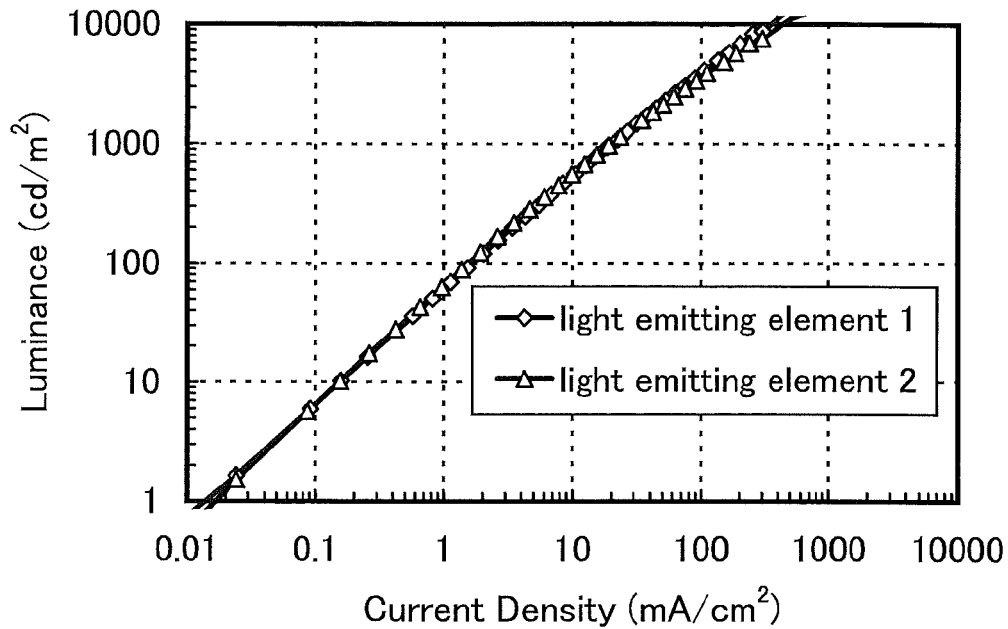
FIG. 22 is a graph showing the current density-luminance characteristics of light emitting elements manufactured in Embodiment 5.
Figure 23:
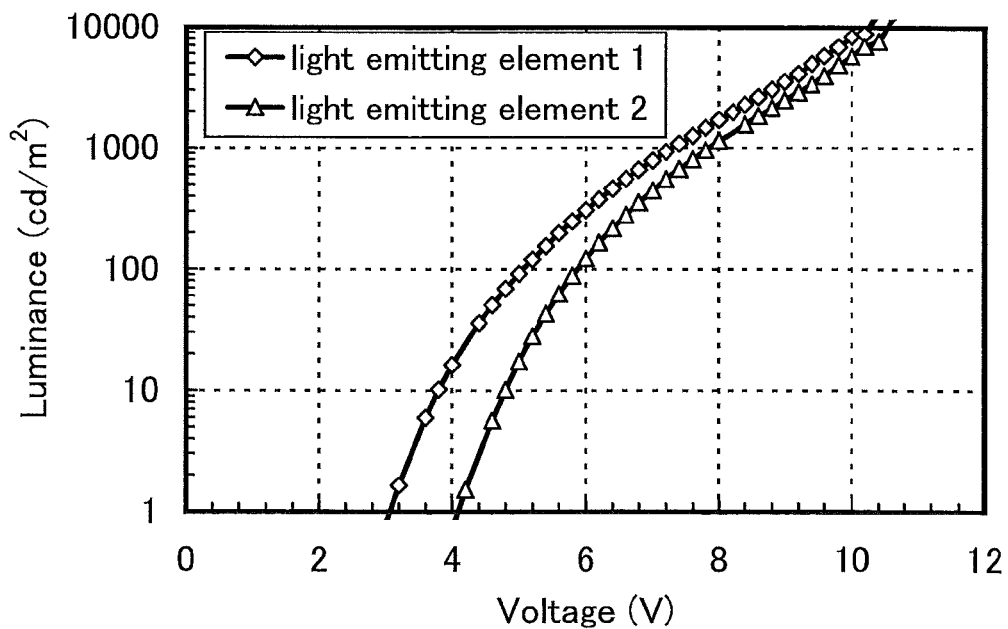
FIG. 23 is a graph showing the voltage-luminance characteristics of the light emitting elements manufactured in Embodiment 5.
Figure 24:
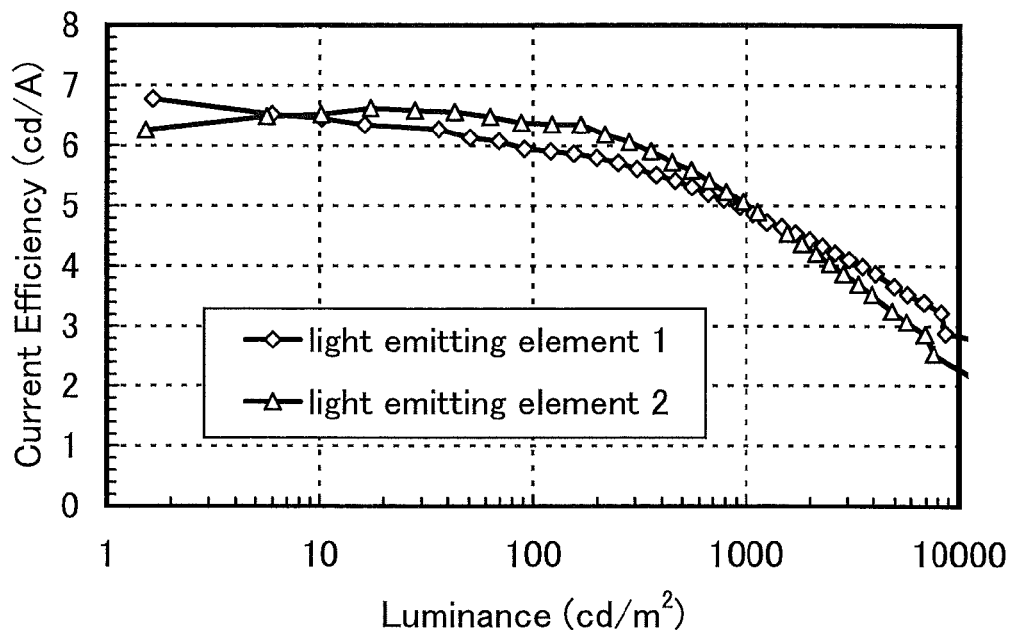
FIG. 24 is a graph showing the luminance-current efficiency characteristics of the light emitting elements manufactured in Embodiment 5.
Figure 25:
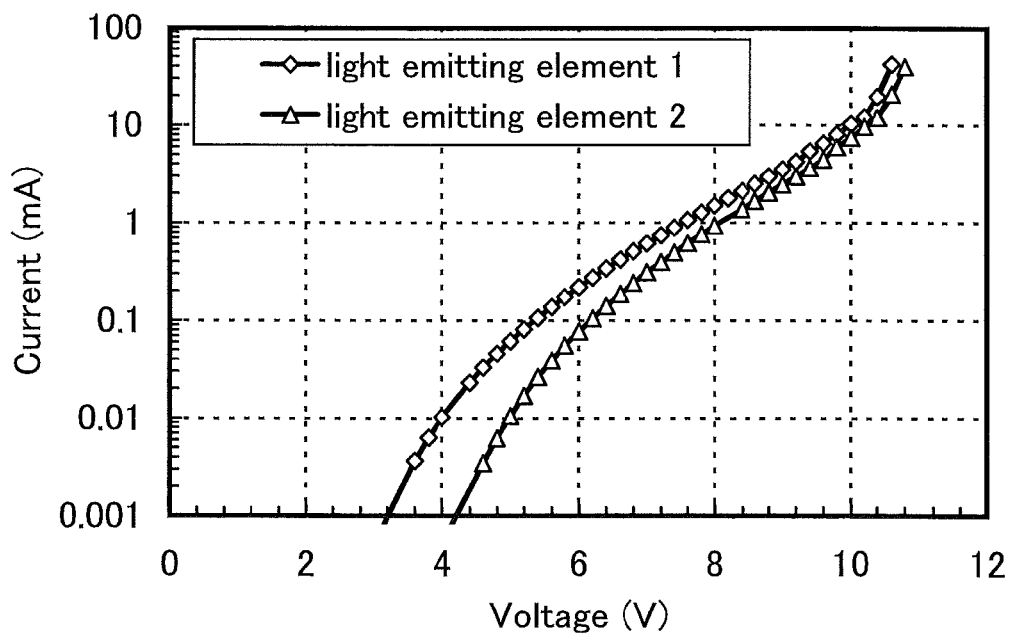
FIG. 25 is a graph showing the voltage-current characteristics of the light emitting elements manufactured in Embodiment 5.

FIG. 22 shows the current density-luminance characteristics of the light emitting elements 1 and 2. FIG. 23 shows the voltage-luminance characteristics of the light emitting elements 1 and 2. FIG. 24 shows the luminance-current efficiency characteristics of the light emitting elements 1 and 2. FIG. 25 shows the voltage-current characteristics of the light emitting elements 1 and 2.

Figure 26:
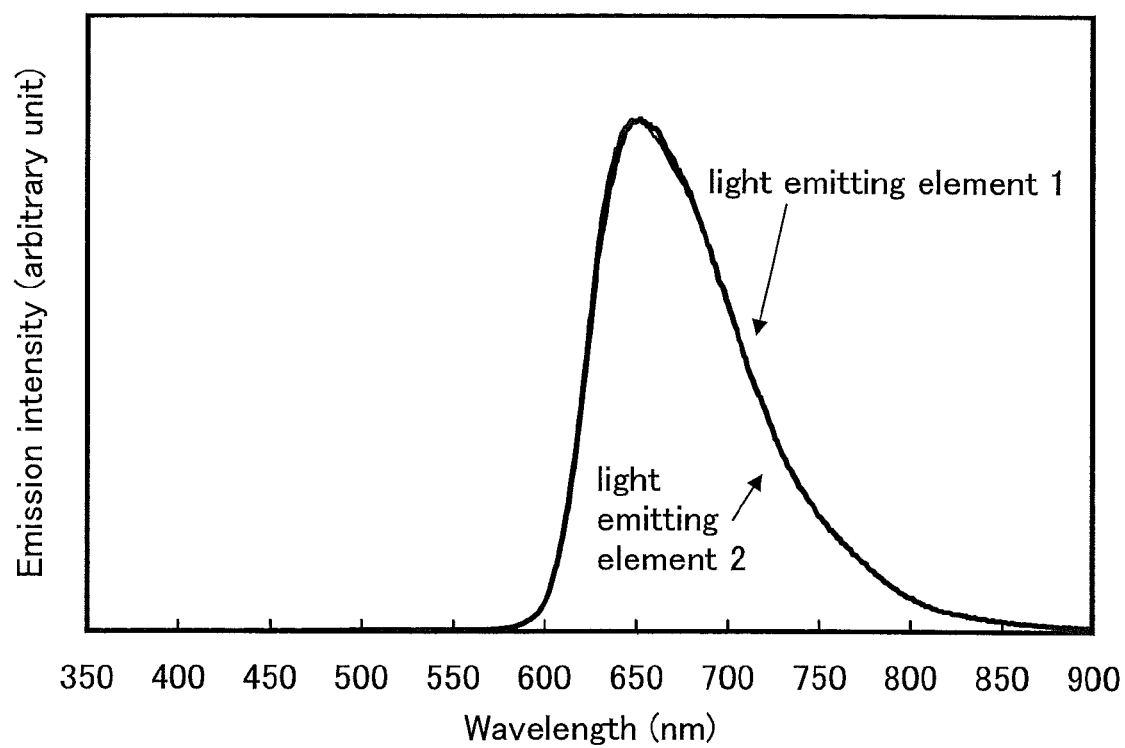
FIG. 26 is a graph showing the emission spectrum of the light emitting elements manufactured in Embodiment 5.

FIG. 26 shows the emission spectrum of the light emitting elements 1 and 2 when a current of 1 mA flows. FIG. 26 shows that the light emission from the light emitting elements 1 and 2 is derived from $Ir(Fdpq)_2(acac)$. Accordingly, it was found that a guest material emitting red phosphorescence is excited by using the quinoxaline derivative shown in Embodiment Mode 1. In addition, it was found that the quinoxaline derivative shown in Embodiment Mode 1 has high triplet excitation energy.

In the light emitting element 1, the CIE chromaticity coordinates were (x=0.71, y=0.29) at a luminance of 930 $cd/m^2$, and deep red emission was obtained. The current efficiency and external quantum efficiency of the light emitting element 1 at a luminance of 930 $cd/m^2$ were 5.0 cd/A and 12.9%, respectively. The voltage, current density, and power efficiency of the light emitting element 1 at a luminance of 930 $cd/m^2$ were 7.2 V, 18.6 $mA/cm^2$, and 2.21 m/W, respectively.

In the light emitting element 2, the CIE chromaticity coordinates were (x=0.71, y=0.29) at a luminance of 960 $cd/m^2$, and deep red emission was obtained. The current efficiency and external quantum efficiency of the light emitting element 2 at a luminance of 960 $cd/m^2$ were 5.1 cd/A and 13.2%, respectively. The voltage, current density, and power efficiency of the light emitting element 2 at a luminance of 960 $cd/m^2$ were 7.8 V, 19.0 $mA/cm^2$, and 2.01 m/W, respectively.

As seen from FIG. 24, T-T annihilation is suppressed in the practical luminance region (100 $cd/m^2$ to 1000 $cd/m^2$) and the light emitting elements 1 and 2 have a high emission efficiency. That is, since the quinoxaline derivative shown in Embodiment Mode 1 is bipolar, the carrier balance in the light emitting region is improved by using the quinoxaline derivative shown in Embodiment Mode 1, which results in suppression of T-T annihilation and high emission efficiency.

In addition, since the quinoxaline derivative shown in Embodiment Mode 1 is bipolar, a light emitting element with a low driving voltage can be obtained in accordance with the present invention. Furthermore, a light emitting element with low power consumption can be obtained.

Embodiment 6

In this embodiment, a light emitting element of the present invention is described with reference to FIG. 21. A method for manufacturing the light emitting element of this embodiment is described below.

(Light Emitting Element 3)

First, indium tin oxide containing silicon oxide (ITSO) was deposited on the glass substrate 2101 by sputtering, whereby the first electrode 2102 was formed. Note that the thickness of the first electrode 2102 was set to 110 nm, and the area thereof was set to 2 mm×2 mm.

Next, the substrate provided with the first electrode 2102 was fixed to a substrate holder provided in a vacuum evaporation apparatus so that a surface on which the first electrode 2102 was formed was placed downward. After the pressure of a chamber was reduced to about $10^{-4}$ Pa, 4,4'-bis[N-(1-napthyl)-N-phenylamino]biphenyl (abbreviation: NPB) and molybdenum (VI) oxide were co-evaporated on the first electrode 2102, whereby the layer 2111 containing a composite material of an organic compound and an inorganic compound was formed. The thickness of the layer 2111 was set to 50 nm, and the weight ratio between NPB and molybdenum (VI) oxide was adjusted to 4:1 (=NPB:molybdenum oxide). Note that the co-evaporation is an evaporation method in which evaporation is simultaneously performed from a plurality of evaporation sources in one chamber.

Next, by an evaporation method using resistance heating, 4,4'-bis[N-(1-napthyl)-N-phenylamino]biphenyl (abbreviation: NPB) was deposited on the layer 2111 containing the composite material so as to have a thickness of 10 nm, whereby the hole transporting layer 2112 was formed.

Furthermore, 4-(benzoxazol-2-yl)-4'-(3-phenylquinoxalin-2-yl)triphenylamine (abbreviation: BOxA1PQ) represented by the structural formula (201) and (acetylacetonato)bis[2,3-bis(4-fluorophenyl)quinoxalinato]iridium(III) (abbreviation: $Ir(Fdpq)_2(acac)$) were co-evaporated on the hole transporting layer 2112, whereby the light emitting layer 2113 with a thickness of 30 nm was formed. Here, the weight ratio between BOxA1PQ and $Ir(Fdpq)_2(acac)$ was adjusted to 1:0.06 (=BOxA1PQ $Ir(Fdpq)_2(acac)$).

Subsequently, with the use of an evaporation method using resistance heating, bis(2-methyl-8-quinolinolato)(4-phenylphenolato)aluminum (abbreviation: BAlq) was deposited on the light emitting layer 2113 so as to have a thickness of 10 nm, whereby the electron transporting layer 2114 was formed. Note that BAlq has a large band gap and a high HOMO level; thus, the electron transporting layer 2114 also functions as a hole blocking layer.

Furthermore, tris(8-quinolinolato)aluminum (abbreviation: Alq) and lithium were co-evaporated on the electron transporting layer 2114, whereby the electron injecting layer 2115 was formed to a thickness of 50 nm. Here, the weight ratio between Alq and lithium was adjusted to 1:0.01 (=Alq:lithium).

Finally, by an evaporation method using resistance heating, aluminum was deposited on the electron injecting layer 2115 so as to have a thickness of 200 nm, whereby the second electrode 2104 was formed. Thus, the light emitting element 3 was completed.

The thus obtained light emitting element 3 was sealed in a glove box under a nitrogen atmosphere without being exposed to atmospheric air. Then, the operating characteristics of this light emitting element were measured. Note that the measurement was performed at room temperature (in an atmosphere kept at 25° C.).

Figure 27:
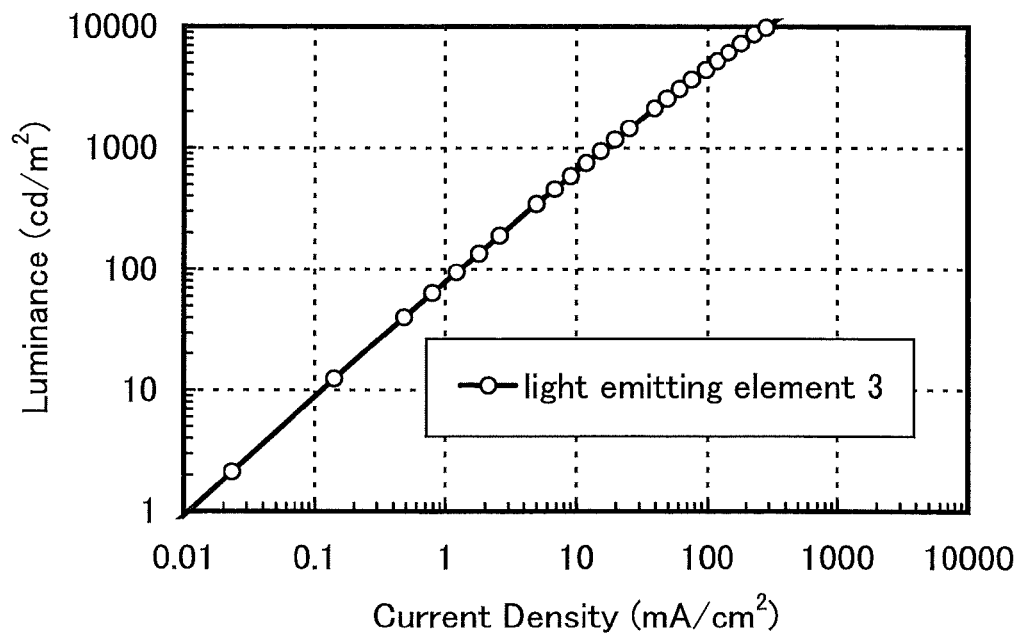
FIG. 27 is a graph showing the current density-luminance characteristics of a light emitting element manufactured in Embodiment 6.
Figure 28:
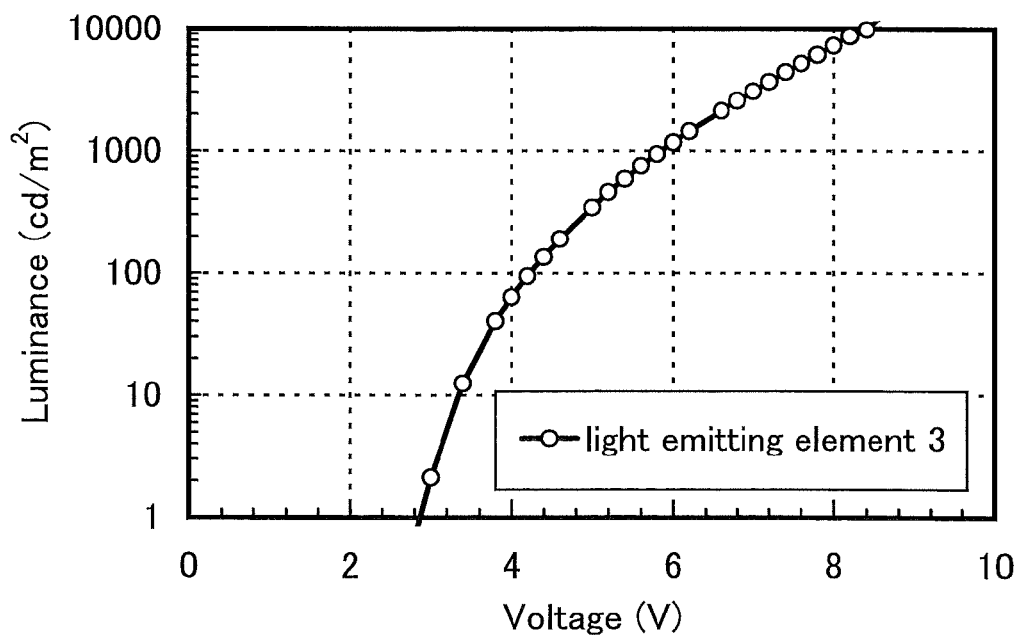
FIG. 28 is a graph showing the voltage-luminance characteristics of the light emitting element manufactured in Embodiment 6.
Figure 29:
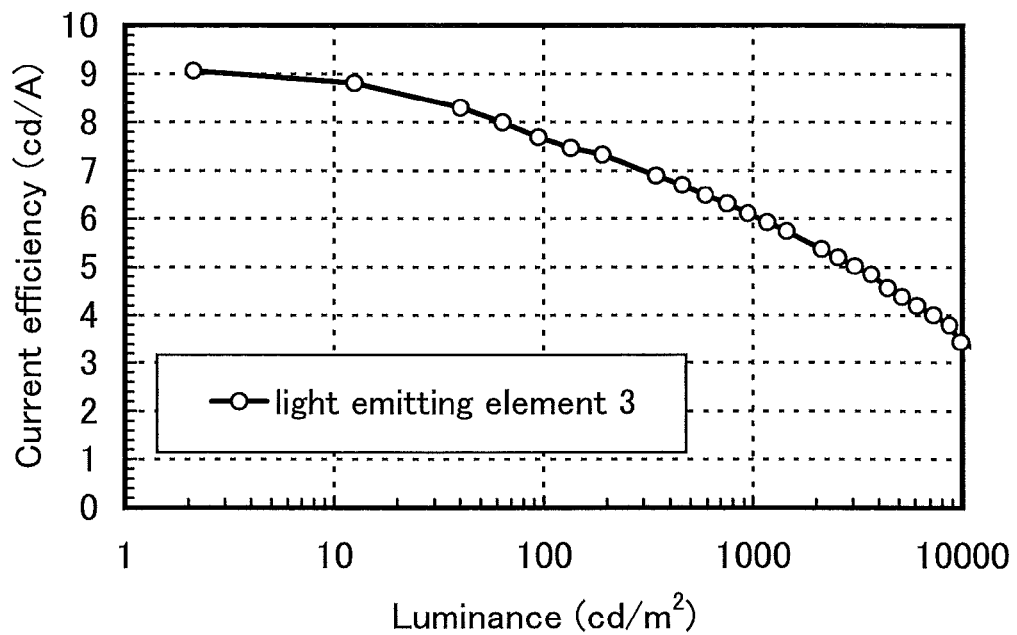
FIG. 29 is a graph showing the luminance-current efficiency characteristics of the light emitting element manufactured in Embodiment 6.
Figure 30:
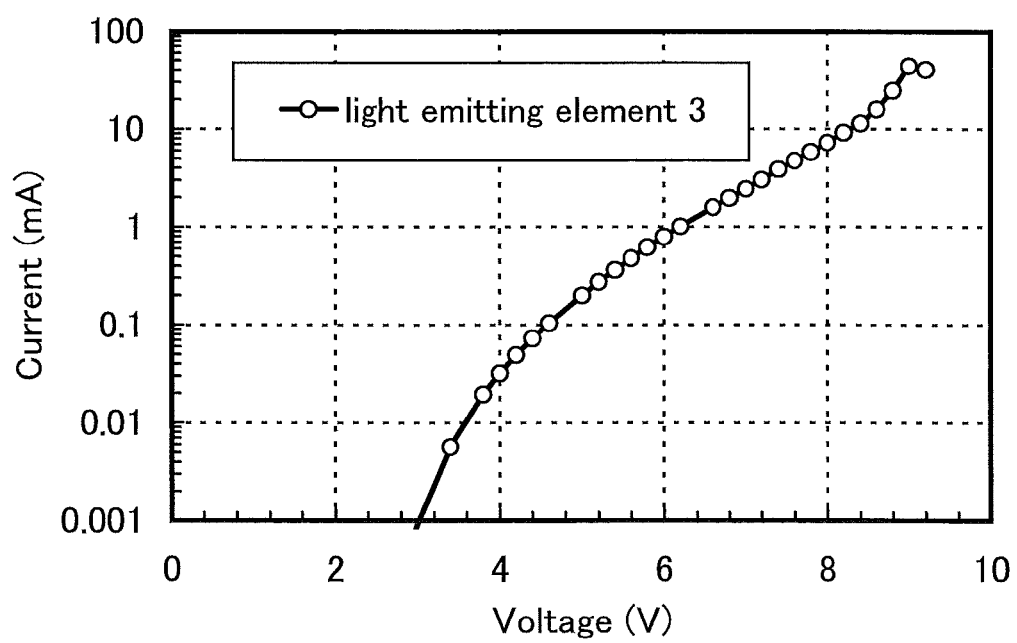
FIG. 30 is a graph showing the voltage-current characteristics of the light emitting element manufactured in Embodiment 6.

FIG. 27 shows the current density-luminance characteristics of the light emitting element 3. FIG. 28 shows the voltage-luminance characteristics of the light emitting element 3. FIG. 29 shows the luminance-current efficiency characteristics of the light emitting element 3. FIG. 30 shows the voltage-current characteristics of the light emitting element 3.

Figure 31:
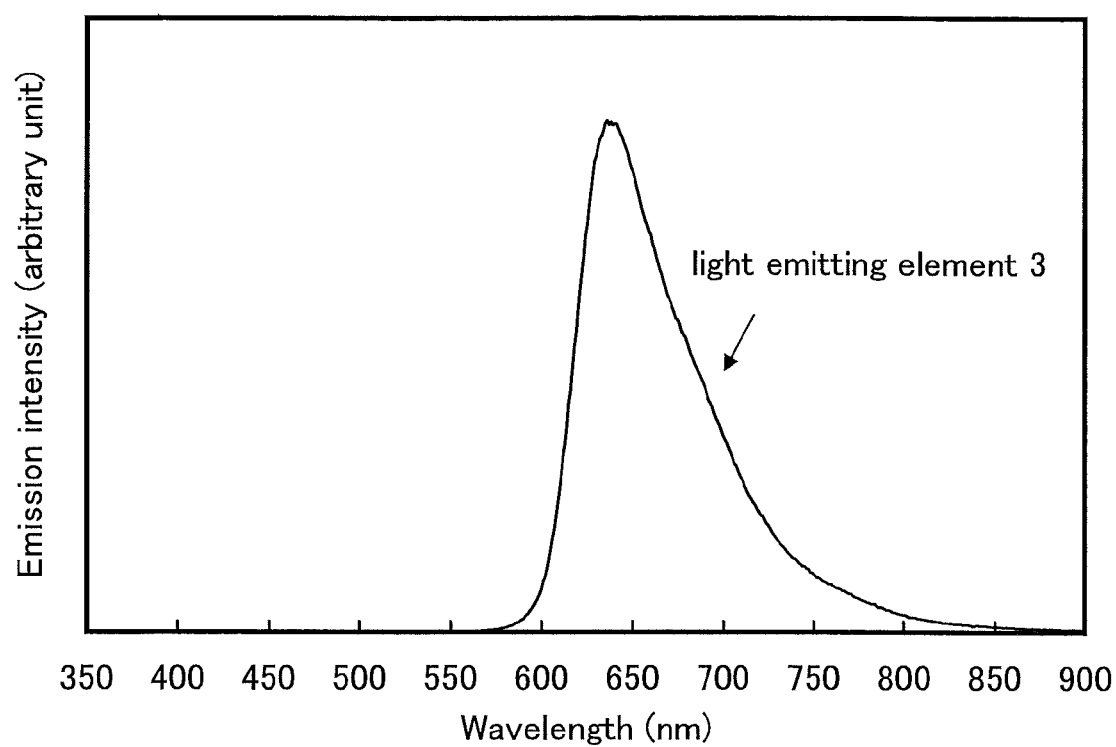
FIG. 31 is a graph showing the emission spectrum of the light emitting element manufactured in Embodiment 6.

FIG. 31 shows the emission spectrum of the light emitting element 3 when a current of 1 mA flows. FIG. 31 shows that the light emission from the light emitting element 3 is derived from $Ir(Fdpq)_2(acac)$. Accordingly, it was found that a guest material emitting red phosphorescence is excited by using the quinoxaline derivative shown in Embodiment Mode 1. In addition, it was found that the quinoxaline derivative shown in Embodiment Mode 1 has high triplet excitation energy.

In the light emitting element 3, the CIE chromaticity coordinates were (x=0.71, y=0.29) at a luminance of 940 $cd/m^2$, and deep red emission was obtained. The current efficiency and external quantum efficiency of the light emitting element 3 at a luminance of 940 $cd/m^2$ were 6.1 cd/A and 10.8%, respectively. Furthermore, the voltage, current density, and power efficiency of the light emitting element 3 at a luminance of 940 cd/m² were 5.8 V, 15.4 mA/cm², and 3.31 m/W, respectively.

As seen from FIG. 29, T-T annihilation is suppressed in the practical luminance region (100 cd/m² to 1000 cd/m²) and the light emitting element 3 has a high emission efficiency. That is, since the quinoxaline derivative shown in Embodiment Mode 1 is bipolar, the carrier balance in the light emitting region is improved by using the quinoxaline derivative shown in Embodiment Mode 1, which results in suppression of T-T annihilation and high emission efficiency.

In addition, since the quinoxaline derivative shown in Embodiment Mode 1 is bipolar, a light emitting element with a low driving voltage can be obtained in accordance with the present invention. Furthermore, a light emitting element with low power consumption can be obtained.

Embodiment 7

In this embodiment, a light emitting element of the present invention is described with reference to FIG. 21. A method for manufacturing the light emitting element of this embodiment is described below.

(Light Emitting Element 4)

First, indium tin oxide containing silicon oxide (ITSO) was deposited on the glass substrate 2101 by sputtering, whereby the first electrode 2102 was formed. Note that the thickness of the first electrode 2102 was set to 110 nm, and the area thereof was set to 2 mm×2 mm.

Next, the substrate provided with the first electrode 2102 was fixed to a substrate holder provided in a vacuum evaporation apparatus so that a surface on which the first electrode 2102 was formed was placed downward. After the pressure of a chamber was reduced to about $10^{-4}$ Pa, 4,4'-bis[N-(1-napthyl)-N-phenylamino]biphenyl (abbreviation: NPB) and molybdenum (VI) oxide were co-evaporated on the first electrode 2102, whereby the layer 2111 containing a composite material of an organic compound and an inorganic compound was formed. The thickness of the layer 2111 was set to 50 nm, and the weight ratio between NPB and molybdenum (VI) oxide was adjusted to 4:1 (=NPB:molybdenum oxide). Note that the co-evaporation is an evaporation method in which evaporation is simultaneously performed from a plurality of evaporation sources in one chamber.

Next, by an evaporation method using resistance heating, 4,4'-bis[N-(1-napthyl)-N-phenylamino]biphenyl (abbreviation: NPB) was deposited on the layer 2111 containing the composite material so as to have a thickness of 10 nm, whereby the hole transporting layer 2112 was formed.

Furthermore, 4-(5-phenyl-1,3,4-oxadiazol-2-yl)-4'-(3-phenylquinoxalin-2-yl)triphenylamine (abbreviation: OPA1PQ) represented by the structural formula (101) and (acetylacetonato)bis[2,3-bis(4-fluorophenyl)quinoxalinato]iridium(III) (abbreviation: Ir(Fdpq)$_2$(acac)) were co-evaporated on the hole transporting layer 2112, whereby the light emitting layer 2113 with a thickness of 30 nm was formed. Here, the weight ratio between OPA1PQ and Ir(Fdpq)$_2$(acac) was adjusted to 1:0.06 (=OPA1PQ:Ir(Fdpq)$_2$(acac)).

Subsequently, with the use of an evaporation method using resistance heating, tris(8-quinolinolato)aluminum (abbreviation: Alq) was deposited on the light emitting layer 2113 so as to have a thickness of 10 nm, whereby the electron transporting layer 2114 was formed.

Furthermore, tris(8-quinolinolato)aluminum (abbreviation: Alq) and lithium were co-evaporated on the electron transporting layer 2114, whereby the electron injecting layer 2115 was formed to a thickness of 50 nm. Here, the weight ratio between Alq and lithium was adjusted to 1:0.01 (=Alq:lithium).

Finally, by an evaporation method using resistance heating, aluminum was deposited on the electron injecting layer 2115 so as to have a thickness of 200 nm, whereby the second electrode 2104 was formed. Thus, the light emitting element 4 was completed.

(Light Emitting Element 5)

With the use of the same substrate as that used for the light emitting element 4, the light emitting element 5 was formed in a manner similar to the light emitting element 4. The light emitting element 5 was formed using 4-(imidazo[1,2-a]pyridin-2-yl)-4'-(3-phenylquinoxalin-2-yl)triphenylamine (abbreviation: PIMA1PQ) represented by the structural formula (301) instead of OPA1PQ. That is, PIMA1PQ and Ir(Fdpq)$_2$(acac) were co-evaporated on the hole transporting layer 2112, whereby the light emitting layer 2113 was formed to a thickness of 30 nm. Here, the weight ratio between PIMA1PQ and Ir(Fdpq)$_2$(acac) was adjusted to 1:0.06 (=PIMA1PQ:Ir(Fdpq)$_2$(acac)). The layers other than the light emitting layer 2113 were formed in a manner similar to those of the light emitting element 4.

The thus obtained light emitting elements 4 and 5 were sealed in a glove box under a nitrogen atmosphere without being exposed to atmospheric air. Then, the operating characteristics of these light emitting elements were measured. Note that the measurement was performed at room temperature (in an atmosphere kept at 25° C.).

Figure 32:
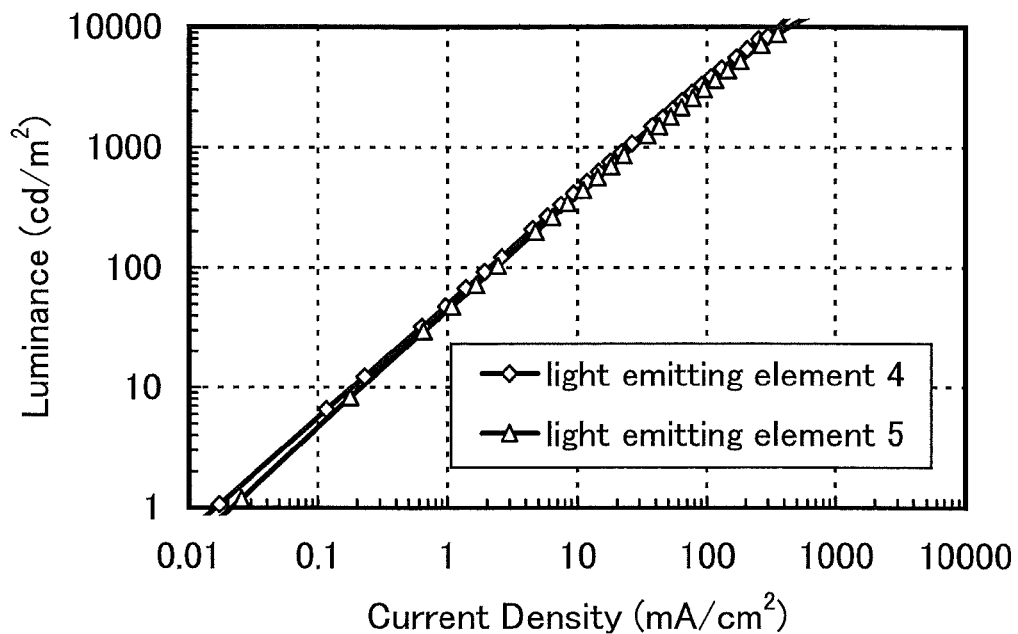
FIG. 32 is a graph showing the current density-luminance characteristics of light emitting elements manufactured in Embodiment 7.
Figure 33:
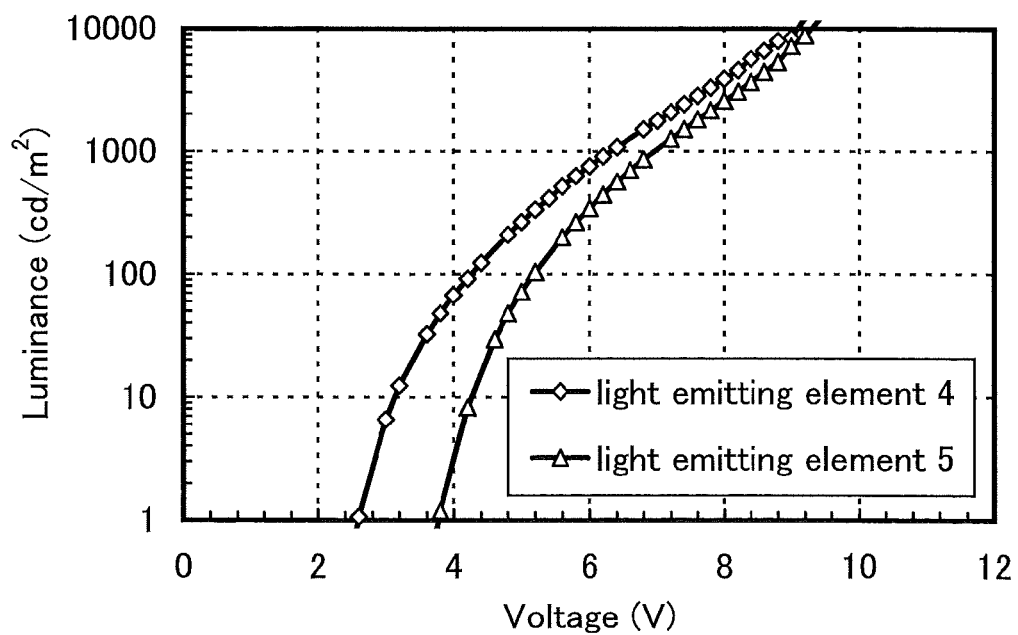
FIG. 33 is a graph showing the voltage-luminance characteristics of the light emitting elements manufactured in Embodiment 7.
Figure 34:
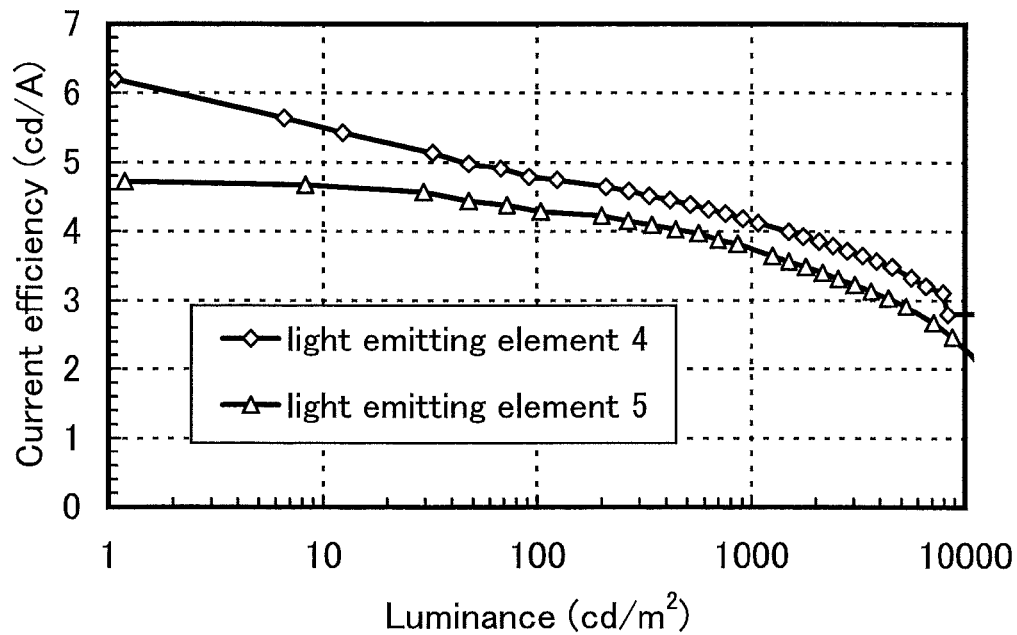
FIG. 34 is a graph showing the luminance-current efficiency characteristics of the light emitting elements manufactured in Embodiment 7.
Figure 35:
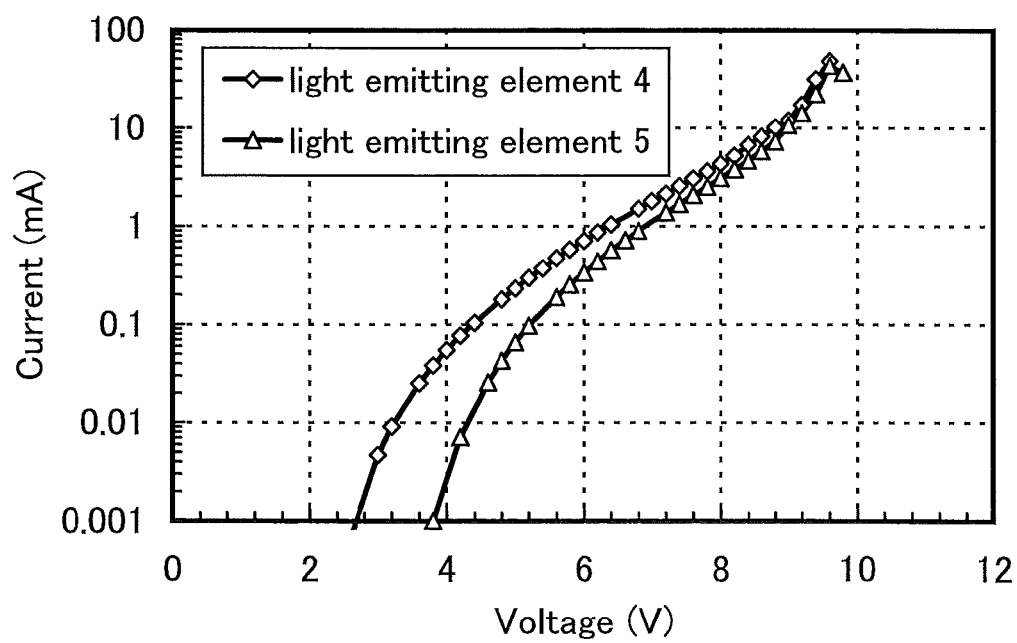
FIG. 35 is a graph showing the voltage-current characteristics of the light emitting elements manufactured in Embodiment 7.

FIG. 32 shows the current density-luminance characteristics of the light emitting elements 4 and 5. FIG. 33 shows the voltage-luminance characteristics of the light emitting elements 4 and 5. FIG. 34 shows the luminance-current efficiency characteristics of the light emitting elements 4 and 5. FIG. 35 shows the voltage-current characteristics of the light emitting elements 4 and 5.

Figure 36:
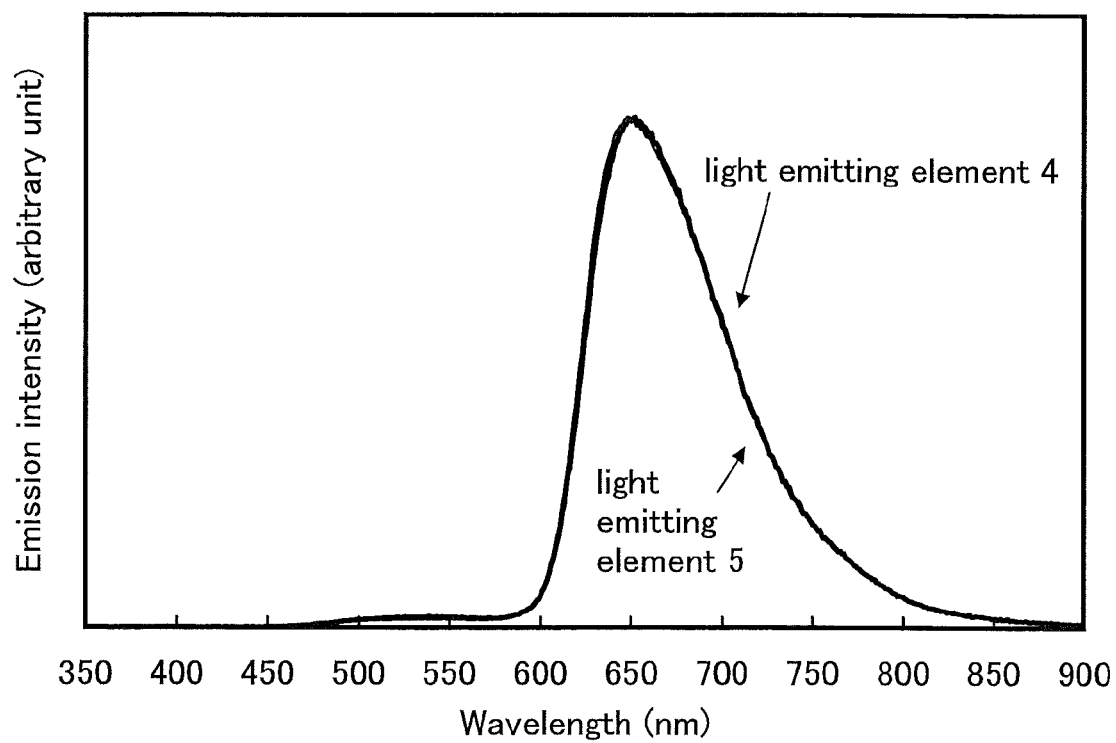
FIG. 36 is a graph showing the emission spectrum of the light emitting elements manufactured in Embodiment 7.

FIG. 36 shows the emission spectrum of the light emitting elements 4 and 5 when a current of 1 mA flows. FIG. 36 shows that the light emission from the light emitting elements 4 and 5 is derived from Ir(Fdpq)$_2$(acac). Accordingly, it was found that a guest material emitting red phosphorescence is excited by using the quinoxaline derivative shown in Embodiment Mode 1. In addition, it was found that the quinoxaline derivative shown in Embodiment Mode 1 has high triplet excitation energy. Furthermore, from the fact that the light emission derived from Ir(Fdpq)$_2$(acac) used for the light emitting layer was efficiently obtained even in the case where the hole blocking layer was not used, it was found that the quinoxaline derivative shown in Embodiment Mode 1 is bipolar and excellent in carrier balance.

In the light emitting element 4, the CIE chromaticity coordinates were (x=0.68, y=0.30) at a luminance of 1080 cd/m², and deep red emission was obtained. The current efficiency and external quantum efficiency of the light emitting element 4 at a luminance of 1080 cd/m² were 4.1 cd/A and 9.1%, respectively. Furthermore, the voltage, current density, and power efficiency of the light emitting element 4 at a luminance of 1080 cd/m² were 6.4 V, 26.2 mA/cm², and 2.01 m/W, respectively.

In the light emitting element 5, the CIE chromaticity coordinates were (x=0.67, y=0.32) at a luminance of 860 cd/m², and deep red emission was obtained. The current efficiency and external quantum efficiency of the light emitting element 5 at a luminance of 860 cd/m² were 3.8 cd/A and 8.4%, respectively. Furthermore, the voltage, current density, and power efficiency of the light emitting element 5 at a luminance of 860 cd/m² were 6.8 V, 22.5 mA/cm², and 1.81 m/W, respectively.

As seen from FIG. 34, T-T annihilation is suppressed in the practical luminance region (100 cd/m² to 1000 cd/m²) and the light emitting elements 4 and 5 have a high emission efficiency. That is, since the quinoxaline derivative shown in Embodiment Mode 1 is bipolar, the carrier balance in the light emitting region is improved by using the quinoxaline derivative shown in Embodiment Mode 1, which results in suppression of T-T annihilation and high emission efficiency.

In addition, since the quinoxaline derivative shown in Embodiment Mode 1 is bipolar, a light emitting element with a low driving voltage can be obtained in accordance with the present invention. Furthermore, a light emitting element with low power consumption can be obtained.

Embodiment 8

In this embodiment, a light emitting element of the present invention is described with reference to FIG. 21. A method for manufacturing the light emitting element of this embodiment is described below.

(Light Emitting Element 6)

First, indium tin oxide containing silicon oxide (ITSO) was deposited on the glass substrate 2101 by sputtering, whereby the first electrode 2102 was formed. Note that the thickness of the first electrode 2102 was set to 110 nm, and the area thereof was set to 2 mm×2 mm.

Next, the substrate provided with the first electrode 2102 was fixed to a substrate holder provided in a vacuum evaporation apparatus so that a surface on which the first electrode 2102 was formed was placed downward. After the pressure of a chamber was reduced to about $10^{-4}$ Pa, 4,4'-bis[N-(1-napthyl)-N-phenylamino]biphenyl (abbreviation: NPB) and molybdenum (VI) oxide were co-evaporated on the first electrode 2102, whereby the layer 2111 containing a composite material of an organic compound and an inorganic compound was formed. The thickness of the layer 2111 was set to 50 nm, and the weight ratio between NPB and molybdenum (VI) oxide was adjusted to 4:1 (=NPB:molybdenum oxide). Note that the co-evaporation is an evaporation method in which evaporation is simultaneously performed from a plurality of evaporation sources in one chamber.

Next, by an evaporation method using resistance heating, 4,4'-bis[N-(1-napthyl)-N-phenylamino]biphenyl (abbreviation: NPB) was deposited on the layer 2111 containing the composite material so as to have a thickness of 10 nm, whereby the hole transporting layer 2112 was formed.

Furthermore, 4-(benzoxazol-2-yl)-4'-(3-phenylquinoxalin-2-yl)triphenylamine (abbreviation: BOxA1PQ) represented by the structural formula (201) and (acetylacetonato)bis[2,3-bis(4-fluorophenyl)quinoxalinato]iridium(III) (abbreviation: Ir(Fdpq)$_2$(acac)) were co-evaporated on the hole transporting layer 2112, whereby the light emitting layer 2113 with a thickness of 30 nm was formed. Here, the weight ratio between BOxA1PQ and Ir(Fdpq)$_2$(acac) was adjusted to 1:0.06 (=BOxA1PQ:Ir(Fdpq)$_2$(acac)).

Subsequently, with the use of an evaporation method using resistance heating, tris(8-quinolinolato)aluminum (abbreviation: Alq) was deposited on the light emitting layer 2113 so as to have a thickness of 10 nm, whereby the electron transporting layer 2114 was formed.

Furthermore, tris(8-quinolinolato)aluminum (abbreviation: Alq) and lithium were co-evaporated on the electron transporting layer 2114, whereby the electron injecting layer 2115 was formed to a thickness of 50 nm. Here, the weight ratio between Alq and lithium was adjusted to 1:0.01 (=Alq:lithium).

Finally, by an evaporation method using resistance heating, aluminum was deposited on the electron injecting layer 2115 so as to have a thickness of 200 nm, whereby the second electrode 2104 was formed. Thus, the light emitting element 6 was completed.

The thus obtained light emitting element 6 was sealed in a glove box under a nitrogen atmosphere without being exposed to atmospheric air. Then, the operating characteristics of this light emitting element were measured. Note that the measurement was performed at room temperature (in an atmosphere kept at 25° C.).

Figure 37:
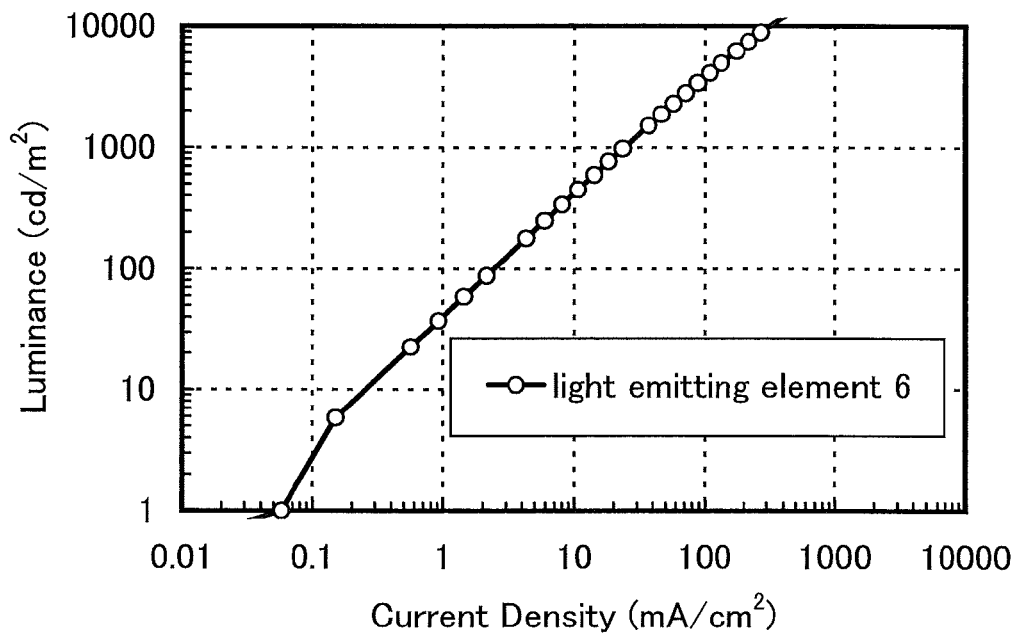
FIG. 37 is a graph showing the current density-luminance characteristics of a light emitting element manufactured in Embodiment 8.
Figure 38:
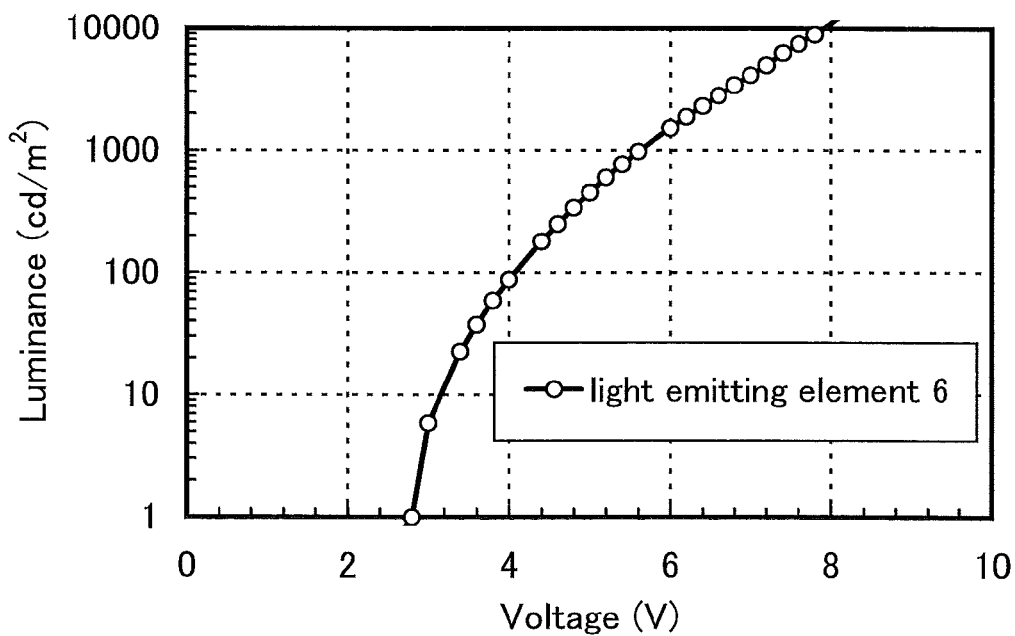
FIG. 38 is a graph showing the voltage-luminance characteristics of the light emitting element manufactured in Embodiment 8.
Figure 39:
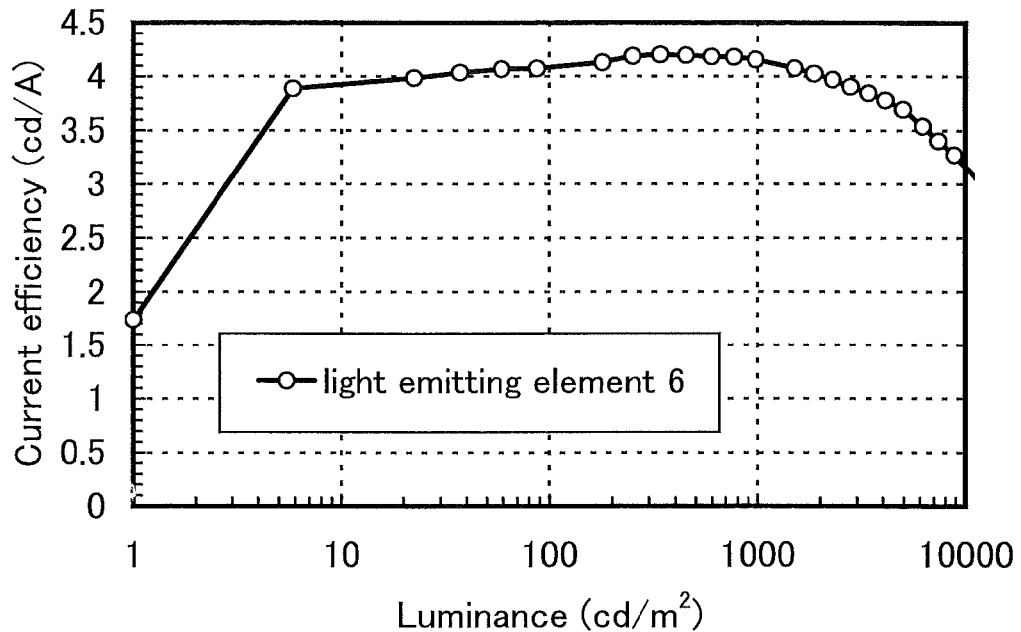
FIG. 39 is a graph showing the luminance-current efficiency characteristics of the light emitting element manufactured in Embodiment 8.
Figure 40:
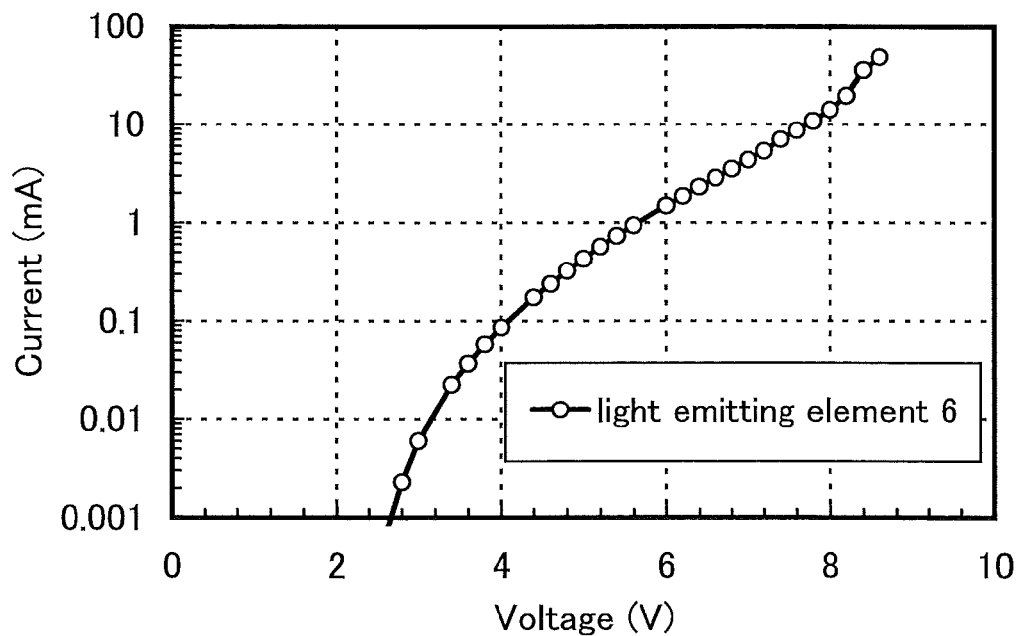
FIG. 40 is a graph showing the voltage-current characteristics of the light emitting element manufactured in Embodiment 8.

FIG. 37 shows the current density-luminance characteristics of the light emitting element 6. FIG. 38 shows the voltage-luminance characteristics of the light emitting element 6. FIG. 39 shows the luminance-current efficiency characteristics of the light emitting element 6. FIG. 40 shows the voltage-current characteristics of the light emitting element 6.

Figure 41:
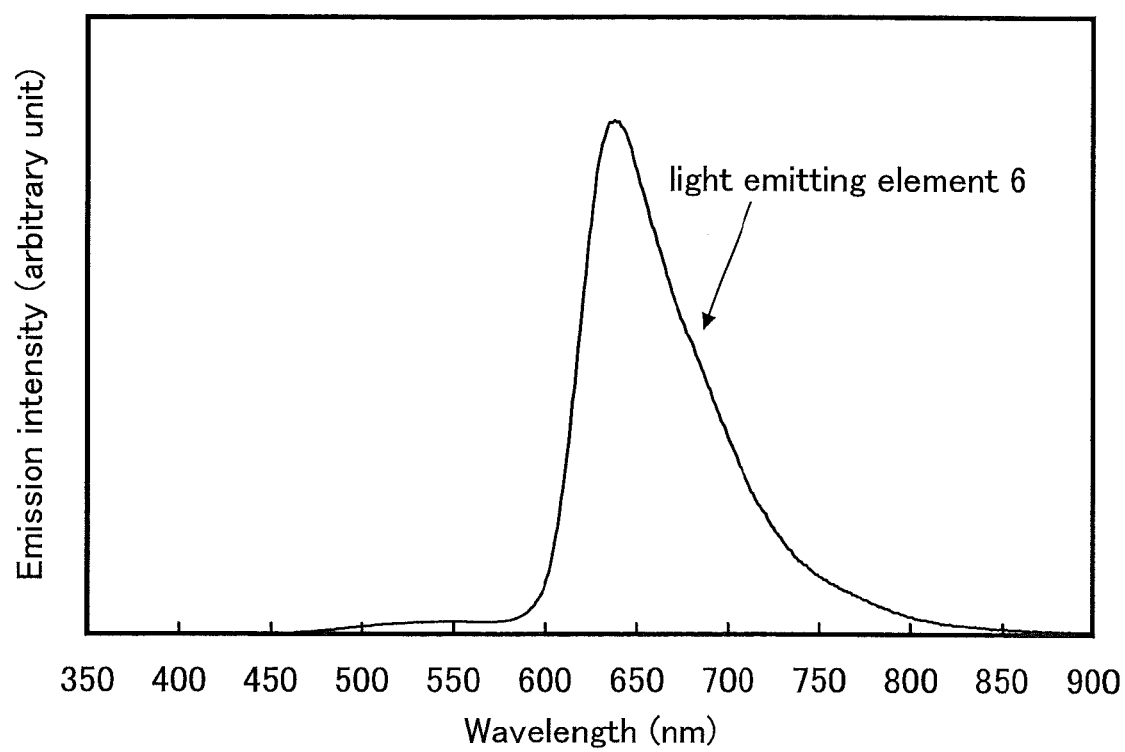
FIG. 41 is a graph showing the emission spectrum of the light emitting element manufactured in Embodiment 8.

FIG. 41 shows the emission spectrum of the light emitting element 6 when a current of 1 mA flows. FIG. 41 shows that the light emission from the light emitting element 6 is derived from Ir(Fdpq)$_2$(acac). Accordingly, it was found that a guest material emitting red phosphorescence is excited by using the quinoxaline derivative shown in Embodiment Mode 1. In addition, it was found that the quinoxaline derivative shown in Embodiment Mode 1 has high triplet excitation energy. Furthermore, from the fact that the light emission derived from Ir(Fdpq)$_2$(acac) used for the light emitting layer was efficiently obtained even in the case where the hole blocking layer was not used, it was found that the quinoxaline derivative shown in Embodiment Mode 1 is bipolar and excellent in carrier balance.

In the light emitting element 6, the CIE chromaticity coordinates were (x=0.67, y=0.32) at a luminance of 980 cd/m², and deep red emission was obtained. The current efficiency and external quantum efficiency of the light emitting element 6 at a luminance of 980 cd/m² were 4.2 cd/A and 6.4%, respectively. Furthermore, the voltage, current density, and power efficiency of the light emitting element 6 at a luminance of 980 cd/m² were 5.6 V, 23.5 mA/cm², and 2.31 m/W, respectively.

As seen from FIG. 39, T-T annihilation is suppressed in the practical luminance region (100 cd/m² to 1000 cd/m²) and the light emitting element 6 has a high emission efficiency. That is, since the quinoxaline derivative shown in Embodiment Mode 1 is bipolar, the carrier balance in the light emitting region is improved by using the quinoxaline derivative shown in Embodiment Mode 1, which results in suppression of T-T annihilation and high emission efficiency.

In addition, since the quinoxaline derivative shown in Embodiment Mode 1 is bipolar, a light emitting element with a low driving voltage can be obtained in accordance with the present invention. Furthermore, a light emitting element with low power consumption can be obtained.

This application is based on Japanese Patent Application serial no. 2007-312354 filed with Japan Patent Office on Dec. 3, 2007, the entire contents of which are hereby incorporated by reference.

What is claimed is:

1. A quinoxaline derivative represented by the general formula (G11):

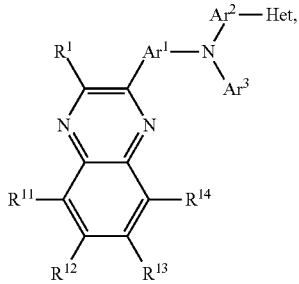

wherein Het is a substituted or unsubstituted 1,3,4-oxadiazole group,
wherein Ar$^1$ and Ar$^2$ each are a substituted or unsubstituted arylene group having 6 to 13 carbon atoms,
wherein Ar$^3$ is a substituted or unsubstituted aryl group having 6 to 13 carbon atoms,
wherein R$^1$ is any of an alkyl group having 1 to 4 carbon atoms and a substituted or unsubstituted aryl group having 6 to 13 carbon atoms, and
wherein R$^{11}$ to R$^{14}$ may be the same or different from one another, each of which represents any of hydrogen, an alkyl group having 1 to 4 carbon atoms, and a substituted or unsubstituted aryl group having 6 to 13 carbon atoms.

2. The quinoxaline derivative according to claim 1, wherein Ar$^2$ is a phenylene group.

3. The quinoxaline derivative according to claim 1, wherein Ar$^2$ is a phenylene group, and
wherein Ar$^3$ is a phenyl group having a substituent which is selected from hydrogen, an alkyl group having 1 to 4 carbon atoms, and a substituted or unsubstituted phenyl group.

4. The quinoxaline derivative according to claim 1,
wherein Ar$^2$ is a phenylene group,
wherein Ar$^3$ is a phenyl group having a substituent which is selected from hydrogen, an alkyl group having 1 to 4 carbon atoms, and a substituted or unsubstituted phenyl group,
wherein R$^1$ is a phenyl group having a substituent which is selected from hydrogen, an alkyl group having 1 to 4 carbon atoms, and a substituted or unsubstituted phenyl group, and
wherein R$^{11}$ to R$^{14}$ each are hydrogen.

5. The quinoxaline derivative according to claim 1,
wherein Ar$^1$ and Ar$^2$ each are a phenylene group,
wherein R$^1$ and Ar$^3$ each are an unsubstituted phenyl group, and
wherein R$^{11}$ to R$^{14}$ each are hydrogen.

6. The quinoxaline derivative according to claim 1, wherein the quinoxaline derivative is represented by the general formula (G16):

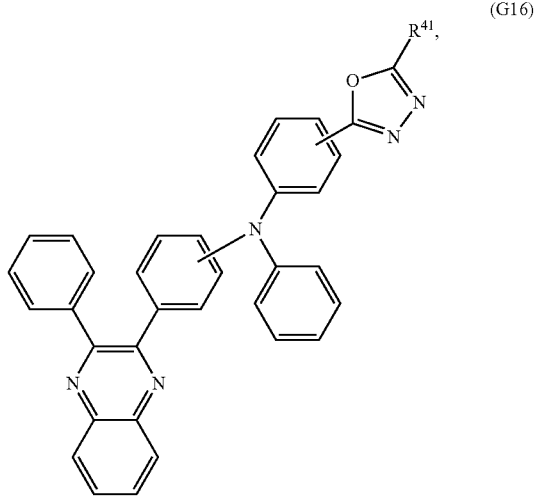

wherein R$^{41}$ is any of a substituted or unsubstituted phenyl group and a substituted or unsubstituted naphthyl group.

7. The quinoxaline derivative according to claim 1, wherein the quinoxaline derivative is represented by the structural formula (101):

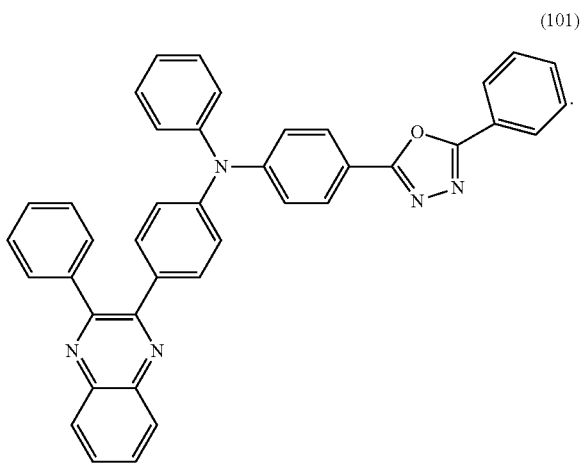

8. A light emitting element comprising the quinoxaline derivative according to claim 1.

9. An electronic appliance comprising a display portion, the display portion comprising the light emitting element according to claim 8.

10. A lighting device comprising the light emitting element according to claim 8.

* * * * *